US007928197B2

(12) United States Patent
Wonderling

(10) Patent No.: US 7,928,197 B2
(45) Date of Patent: Apr. 19, 2011

(54) FELINE IL-18 PROTEINS

(75) Inventor: Ramani S. Wonderling, Mundelein, IL (US)

(73) Assignee: Heska Corporation, Loveland, CO (US)

( * ) Notice: Subject to any disclaimer, the term of this patent is extended or adjusted under 35 U.S.C. 154(b) by 0 days.

(21) Appl. No.: 12/128,440

(22) Filed: May 28, 2008

(65) Prior Publication Data
US 2009/0198043 A1    Aug. 6, 2009

Related U.S. Application Data

(62) Division of application No. 11/514,728, filed on Sep. 1, 2006, now Pat. No. 7,556,963, which is a division of application No. 10/821,670, filed on Apr. 9, 2004, now Pat. No. 7,205,143, which is a division of application No. 09/917,265, filed on Jul. 27, 2001, now Pat. No. 6,818,444.

(60) Provisional application No. 60/223,016, filed on Aug. 4, 2000.

(51) Int. Cl.
*C07K 14/435*    (2006.01)
*C07K 14/46*    (2006.01)
*C07K 14/54*    (2006.01)

(52) U.S. Cl. ...... 530/351; 530/350; 536/23.1; 536/23.5; 435/69.52; 435/69.1

(58) Field of Classification Search .................. None
See application file for complete search history.

(56) References Cited

U.S. PATENT DOCUMENTS

| 5,350,836 | A | * | 9/1994 | Kopchick et al. ............ 530/399 |
| 5,858,778 | A | | 1/1999 | Alnemri et al. |
| 5,912,324 | A | | 6/1999 | Okamura et al. |
| 5,914,253 | A | | 6/1999 | Okamura et al. |
| 5,919,790 | A | | 7/1999 | Allen et al. |
| 5,942,224 | A | | 8/1999 | Miwa et al. |
| 5,945,310 | A | | 8/1999 | Young et al. |
| 5,985,863 | A | | 11/1999 | Su et al. |
| 6,013,268 | A | | 1/2000 | Reed |

FOREIGN PATENT DOCUMENTS

| WO | WO 98/51327 | 11/1998 |
| WO | WO 99/07851 | 2/1999 |
| WO | WO 99/50425 | 10/1999 |
| WO | WO 00/12555 | 3/2000 |

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Ishizaka et al., 2001, Veterinary Immunology and Immunopathology 79:209-218.*
Argyle, et al., Accession No. Y11133, Jul. 7, 1999.
Argyle, et al., *Immunogenetics*, Jun. 1999, vol. 49, No. 6, pp. 541-543.
Belke-Louis, G.F., Accession No. U49085, Mar. 13, 1996.
Belke-Louis, G.F., Accession No. U49100, Mar. 13, 1996.
Carr, et al., *Journal of Virology*, Oct. 1997, vol. 71, No. 10, pp. 7799-7803.
Cerretti, et al., Accession No. M87507, May 18, 1995.
Culhane, et al., Accession No. AJ222813, Aug. 11, 1998.
Johnson, et al., Accession No. AF031351, Nov. 3, 1998.
Keane, et al., Accession U14647, Jan. 27, 1996.
Lee, et al., *Human Gene Therapy*, Mar. 1, 1998, vol. 9, pp. 457-465.
Lieschke, et al., *Nature Biotechnology*, vol. 15, Jan. 1997, pp. 35-40.
Lode, et al., *Proc. Natl. Acad. Sci. USA*, vol. 95, Mar. 1998, pp. 2475-2480.
Molineaux, et al., Accession No. L28095, Jul. 27, 1994.
Mortola, et al., *J Vet Med Sci*, 1998, vol. 60, No. 11, pp. 1181-1185.
Nicolson, L., et al., Accession No. Y11131, Jul. 7, 1999.
Okamura, H., Accession No. D49949, Feb. 10, 1999.
Okano, F., Accession No. E15017, Jul. 28, 1999.
Okano, F., Accession No. E15018, Jul. 28, 1999.
Okano, et al., *Journal of Interferon and Cytokine Research*, 1997, vol. 17, pp. 713-718.
Okano, et al., *Journal of Interferon and Cytokine Research*, 1999, vol. 19, pp. 27-32.
Osaki, et al., *The Journal of Immunology*, 1998, vol. 160, pp. 1742-1749.
Penha-Goncalves, et al., Accession No. Y11132, Jul. 7, 1999.
Pirhonen, et al., *The Journal of Immunology*, 1999, vol. 162, pp. 7322-7329.
Rogerson, et al., *Ann N Y Acad Sci*, Oct. 31, 1996, vol. 795, pp. 354-356.
Sareneva et al., *The Journal of Immunology*, 1998, vol. 160, pp. 6032-6038.
Schijns, V.E.C.J., Accession No. Y07761, May 13, 1997.
Schijns, et al., Accession No. Y07762, May 13, 1997.
Taylor, et al., Accession No. AF135967, Jul. 12, 2000.
Ushio, S., Accession No. D49950, Feb. 10, 1999.
Wardlow, et al., Accession No. AF090119, Aug. 2, 1999. Yoshimoto, et al., *The Journal of Immunology*, 1998, vol. 161, pp. 3400-3407.
Yoshimoto, et al., *Proc. Natl. Acad. Sci. USA*, Apr. 1997, vol. 94, pp. 3948-3953.
Foss, et al., 1999, *Scand. J. Immunol.*, vol. 50, pp. 596-604.
Peng, et al., 1999, *The Journal of Immunology*, vol. 163, pp. 250-258.

* cited by examiner

*Primary Examiner* — Elizabeth C. Kemmerer
(74) *Attorney, Agent, or Firm* — Sheridan Ross P.C.

(57) ABSTRACT

The present invention relates to canine and feline proteins. In particular, the present invention discloses feline interleukin-18, feline caspase-1, feline interleukin-12 single chain and canine interleukin-12 single chain proteins. The present invention also includes feline interleukin-18, feline caspase-1, feline interleukin-12 single chain and canine interleukin-12 single chain nucleic acid molecules encoding such proteins, antibodies raised against such proteins and/or inhibitors of such proteins or nucleic acid molecules. The present invention also includes therapeutic compositions comprising such nucleic acid molecules, proteins, antibodies and/or inhibitors, as well as their use to evaluate and regulate an immune response in an animal.

6 Claims, No Drawings

FELINE IL-18 PROTEINS

CROSS REFERENCE TO RELATED APPLICATION

This application is a divisional of U.S. patent application Ser. No. 11/514,728, filed Sep. 1, 2006, entitled "FELINE IL-18 NUCLEIC ACID MOLECULES", now U.S. Pat. No. 7,556,693 B2;which is a divisional of U.S. patent application Ser. No. 10/821,670, filed Apr. 9, 2004, entitled "FELINE IL-12 SINGLE CHAIN NUCLEIC ACID MOLECULES," now U.S. Pat. No. 7,205,143 B2; which is a divisional of U.S. patent application Ser. No. 09/917,265, filed Jul. 27, 2001, now issued as U.S. Pat. No. 6,818,444 B2, entitled "CANINE AND FELINE PROTEINS, NUCLEIC ACID MOLECULES AND USES THEREOF"; which claims priority to U.S. Provisional Patent Application Ser. No. 60/223,016, filed Aug. 4, 2000, entitled "CANINE AND FELINE PROTEINS, NUCLEIC ACID MOLECULES AND USES THEREOF"; all of which are incorporated herein by reference.

FIELD OF THE INVENTION

The present invention relates to canine and feline proteins. In particular, the present invention relates to feline interleukin-18 (IL-18), feline caspase-1 (casp-1), feline interleukin-12 (IL-12) single chain, and canine interleukin-12 (IL-12) single chain proteins and includes nucleic acid molecules encoding such proteins, antibodies raised against such proteins and/or inhibitors of such proteins or nucleic acid molecules. The present invention also includes therapeutic compositions comprising such nucleic acid molecules, proteins, antibodies and/or inhibitors, as well as their use to evaluate and regulate an immune response in an animal.

BACKGROUND OF THE INVENTION

Regulation of immune and inflammatory responses in animals is important in disease management. Immune responses can be regulated by modifying the activity of immunoregulatory molecules and immune cells. Examples of such immunoregulatory molecules include IL-18, caspase-1 and IL-12. These molecules have been found to play a role in the treatment of several disorders including allergy, cancer, and pathogenic infection.

Monocytes and macrophages represent the first line of defense against disease. Various diseases and infections activate transcriptional and posttranslational events in monocytes and macrophages, which lead to the production of cytokines such as IL-18 and IL-12. These cytokines in turn activate responses in T and B cells helping to eliminate pathogens and/or disease in a animal. Both IL-18 and IL-12 augment cellular immunity by stimulating T cells to produce interferon gamma (IFN-γ) which inhibits the production of IgE formation without compromising B cell proliferation. IL-18, formerly referred to as interferon gamma inducing factor (IGIF), stimulates T cells to produce IFN-γ and has been isolated from humans, dogs, and mice. A cDNA encoding human IL-18 was isolated and used to express recombinant human IL-18 by Ushio et al., 1996, J. Immunol. 156, 4274-4279, GENBANK® accession number D49950. Feline IL-18 cDNA has a 85.8% homology to human IL-18 cDNA and feline IL-18 protein has a 81.7% homology to human IL-18 protein. A cDNA encoding canine IL-18 was isolated and used to express recombinant canine IL-18 by Okano et al., 1999, J. Interferon Cytokine Res. 19, 27-32, GENBANK® accession number Y11133. Feline IL-18 cDNA has a 90.7% homology to canine IL-18 cDNA and feline IL-18 protein has a 88.5% homology to canine IL-18 protein. A cDNA encoding murine IL-18 was isolated and used to express recombinant murine IL-18 by Okamura et al., 1995, Nature 378, 88-91, GENBANK® accession number D49949. Feline IL-18 cDNA has a 73.8% homology to murine IL-18 cDNA and feline IL-18 protein has a 70% homology to murine IL-18 protein. A cDNA encoding rat IL-18 was isolated by Culhane, et al. Mol. Psych. 3, 362-366 (1998), GENBANK® accession number AJ222813. Feline IL-18 cDNA has a 73.4% homology with rat IL-18 cDNA, and feline IL-18 protein has a 70.7% homology with rat IL-18 protein. A cDNA encoding equine IL-18 was isolated by Nicolson, et al. (unpublished, direct submission to GENBANK®, accession number Y11131). Feline IL-18 cDNA has a 92% homology to equine IL-18 cDNA and feline IL-18 protein has a 89% homology to equine IL-18 protein. A cDNA encoding pig IL-18 was isolated by Penha-Goncalves, et al. (unpublished, direct submission to GENBANK®, accession number Y11132. Feline IL-18 cDNA has a 90.2% homology to pig IL-18 cDNA and feline IL-18 protein has a 85.9% homology to pig IL-18 protein. Expression of active IL-18 is controlled by caspase-1 (IL-1β converting enzyme). That is, IL-18 lacks a signal peptide so the precursor form of IL-18 (pro IL-18) is cleaved by caspase-1 resulting in a mature protein that is biologically active.

IL-12 is a heterodimer comprised of two subunits p40 and p35 which are covalently linked by a disulfide bond to form an active molecule. Simultaneous expression of the two subunits is necessary for the production of the biologically active heterodimer. Both human and murine p35 and p40 IL-12 single chain proteins (i.e., a single protein containing both p35 and p40 subunits) have been produced; see e.g., Lieschke et al., 1997, Nature Biotechnology 15, 35-40. Co-expression of the human and murine p35 and p40 cDNA subunits of IL-12 resulting in a biologically active IL-12 heterodimer was achieved by Gubler et al., 1991, Proc. Natl. Acad. Sci. U.S.A., 88, 4143-4147 and Schoenhaut et al., 1992, J. Immunol., 148, 3433-3440, respectively. cDNAs encoding canine IL-12 p35 and p40 subunits were isolated and co-transfected to express canine IL-12 by Okano et al., 1997, J. Interferon Cytokine Res. 17, 713-718. cDNAs encoding feline p35 and p40 subunits have been isolated and expressed; see, for example, Fehr et al., 1997, DNA Seq. 8, 77-82; Schijns et al., 1997, Immunogenetics 45, 462-463; Bush et al., 1994, Molec. Immunol. 31, 1373-1374. At the amino acid level, canine and feline IL-12 p40 subunit share 92.7 percent identity to each other; share 84.8 and 84.2 percent identity to human IL-12 p40, respectively; and share 67.4 and 68.9 percent identity to murine IL-12 p40, respectively. IL-12 shares some biological activities with IL-18 including IFN-γ production in T cells. IL-18 and IL-12 in combination work synergistically to increase IFN-γ production in T cells; as such these cytokines when utilized alone or in combination can be very effective in mediating IgE responses.

Caspase-1 may play a key role in the processing of IL-18 precursor in cells where IL-18 is produced. It may be that coexpression of caspase-1 along with IL-18 may be necessary for the proper processing of the IL-18 precursor and enhanced secretion of the processed IL-18 mature polypeptide. A cDNA encoding equine caspase-1 was isolated by Wardlow, et al. (unpublished; direct submission to GENBANK®, accession number AF090119). Feline caspase-1 cDNA has a 71% homology to equine caspase-1 cDNA and feline caspase-1 protein has a 48.8% homology to equine caspase-1 protein. A cDNA encoding equine caspase-1 was isolated by Cerretti, et al. (Science 256, p 97-100 (1992); GENBANK® accession number M87507). Feline caspase-1 cDNA has a 60% homology to human caspase-1 cDNA and feline caspase-1 protein has a 60% homology to human caspase-1 protein. A cDNA encoding rat caspase-1 (called interleukin-1 beta converting enzyme) was isolated by Keane, et al. (Cytokine 7(2) 105-110 1995); GENBANK® accession number U14647). Feline caspase-1 cDNA has a 55.4% homology to rat caspase-1 cDNA and feline caspase-1 protein has a 40.2% homology to rat caspase-1 protein. A cDNA encoding murine caspase-1 was isolated by Molineaux, et al. (Proc Natl. Acad. Sci. 90, 1809-1813, 1993); GENBANK® accession number L28095). Feline caspase-1 cDNA has a 55.7% homology to murine caspase-1 cDNA and feline caspase-1 protein has a 38.5% homology to murine caspase-1 protein. A cDNA encoding canine caspase-1 was isolated by Taylor, et al. (2000) *DNA Seq*. 10(6), pp 387-394; GENBANK® accession number AF135967). Feline caspase-1 cDNA has a 90% homology to canine caspase-1 cDNA.

To date, however, neither IL-18 nor caspase-1, nor the nucleic acid molecules encoding such proteins, have been isolated from cats. Neither have IL-12 single chain proteins been produced using feline or canine IL-12 subunits. As such there remains a need for compounds and methods to regulate an immune response in cats and dogs through manipulation of IL-18, caspase-1 and IL-12 single chain activities.

SUMMARY OF THE INVENTION

The present invention relates to canine and feline proteins, nucleic acid molecules encoding such proteins, antibodies raised against such proteins and/or inhibitors of such proteins or nucleic acid molecules. In a preferred embodiment, the present invention relates to feline interleukin-18 (IL-18), feline caspase-1 (casp-1), feline interleukin-12 (IL-12) single chain and canine interleukin-12 single chain proteins, nucleic acid molecules, antibodies and inhibitors. The present invention also includes therapeutic compositions comprising such nucleic acid molecules, proteins, antibodies and/or inhibitors, as well as their use to evaluate and regulate an immune response in an animal.

One embodiment of the present invention is an isolated nucleic acid molecule selected from the group consisting of: (a) an isolated nucleic acid molecule selected from the group consisting of (i) a nucleic acid molecule comprising a nucleic acid sequence selected from the group consisting of SEQ ID NO:1, SEQ ID NO:3, SEQ ID NO:4, SEQ ID NO:6, SEQ ID NO:7, SEQ ID NO:10, SEQ ID NO:9, SEQ ID NO:41, SEQ ID NO:11, and SEQ ID NO:13; and (ii) a nucleic acid molecule comprising at least 70 contiguous nucleotides identical in sequence to at least 70 contiguous nucleotides of a nucleic acid sequence selected from the group consisting of SEQ ID NO:1, SEQ ID NO:3, SEQ ID NO:4, SEQ ID NO:6, SEQ ID NO:7, SEQ ID NO:9, SEQ ID NO:10, SEQ ID NO:11, SEQ ID NO:13, and SEQ ID NO:41; (b) an isolated nucleic acid molecule selected from the group consisting of (i) a nucleic acid molecule comprising a nucleic acid sequence selected from the group consisting of SEQ ID NO:14, SEQ ID NO:16, SEQ ID NO:17, SEQ ID NO: 19, SEQ ID NO:20, SEQ ID NO:22, SEQ ID NO:23 and SEQ ID NO:25, and (ii) a nucleic acid molecule comprising at least 70 contiguous nucleotides identical in sequence to at least 70 contiguous nucleotides of a nucleic acid sequence selected from the group consisting of SEQ ID NO:14, SEQ ID NO:16, SEQ ID NO:17, SEQ ID NO:19, SEQ ID NO:20, SEQ ID NO:22, SEQ ID NO:23 and SEQ ID NO:25; (c) an isolated nucleic acid molecule selected from the group consisting of: (i) a nucleic acid molecule comprising ((a)) an isolated nucleic acid molecule comprising a nucleic acid sequence selected from the group consisting of SEQ ID NO:26, SEQ ID NO:29, and a nucleic acid sequence comprising at least 44 contiguous nucleotides identical in sequence to at least 44 contiguous nucleotides of a nucleic acid sequence selected from the group consisting of SEQ ID NO:26 and SEQ ID NO:29; ((b)) a nucleic acid linker of $(XXX)_n$ wherein n=0 to 60; and ((c)) an isolated nucleic acid molecule comprising a nucleic acid sequence selected from the group consisting of SEQ ID NO:32, SEQ ID NO:35, and a nucleic acid molecule comprising at least 44 contiguous nucleotides identical in sequence to at least 44 contiguous nucleotides of a nucleic acid sequence selected from the group consisting of SEQ ID NO:32 and SEQ ID NO:35, such that said nucleic acid molecule of (i) encodes a feline IL-12 single chain protein; and (ii) a nucleic acid molecule comprising a nucleic acid sequence fully complementary to the coding strand of any of said nucleic acid molecules as set forth in (i); (d) an isolated nucleic acid molecule selected from the group consisting of: (i) a nucleic acid molecule comprising ((a)) an isolated nucleic acid molecule comprising a nucleic acid sequence selected from the group consisting of SEQ ID NO:52 and SEQ ID NO:58, and a nucleic acid sequence comprising at least 47 contiguous nucleotides identical in sequence to at least 47 contiguous nucleotides of a nucleic acid sequence selected from the group consisting of SEQ ID NO:46 and SEQ ID NO:49; ((b)) a nucleic acid linker of $(XXX)_n$ wherein n=0 to 60; and ((c)) an isolated nucleic acid molecule comprising a nucleic acid sequence selected from the group consisting of SEQ ID NO:46, SEQ ID NO:49, and a nucleic acid molecule comprising at least 47 contiguous nucleotides identical in sequence to at least 47 contiguous nucleotides of a nucleic acid sequence selected from the group consisting of SEQ ID NO:46 and SEQ ID NO:49, such that said nucleic acid molecule of (i) encodes a canine IL-12 single chain protein; and (ii) a nucleic acid molecule comprising a nucleic acid sequence fully complementary to the coding strand of any of said nucleic acid molecules as set forth in (i); (e) an isolated nucleic acid molecule selected from the group consisting of: (i) a nucleic acid molecule having a nucleic acid sequence that is at least 92 percent identical to a nucleic acid sequence selected from the group consisting of SEQ ID NO:1, SEQ ID NO:3, SEQ ID NO:4, SEQ ID NO:6, SEQ ID NO:7, SEQ ID NO:10, SEQ ID NO:9, SEQ ID NO:41, SEQ ID NO:11, and SEQ ID NO:13; and (ii) a nucleic acid molecule comprising a fragment of a nucleic acid molecule of (i) wherein said fragment is at least 80 nucleotides in length; (f) an isolated nucleic acid molecule selected from the group consisting of (i) a nucleic acid molecule having a nucleic acid sequence that is at least 85 percent identical to a nucleic acid sequence selected from the group consisting of SEQ ID NO:14, SEQ ID NO:16, SEQ ID NO:17, SEQ ID NO:19, SEQ ID NO:20, SEQ ID NO:22, SEQ ID NO:23 and SEQ ID NO:25, and (ii) a nucleic acid molecule comprising a fragment of a nucleic acid molecule of (i) wherein said fragment is at least 85 nucleotides in length; (g) an isolated nucleic acid molecule selected from the group consisting of: (i) a nucleic acid molecule comprising ((a)) a nucleic acid molecule comprising a nucleic acid sequence that is at least 87 percent identical to a nucleic acid sequence selected from the group consisting of SEQ ID NO:26 and SEQ ID NO:29, or a fragment thereof of at least 55 nucleotides in length; ((b)) a nucleic acid linker of $(XXX)_n$ wherein n=0 to 60; and ((c)) nucleic acid molecule comprising a nucleic acid sequence that is at least 87 percent identical to a nucleic acid sequence selected from the group consisting of SEQ ID NO:32 and SEQ ID NO:35, or a fragment thereof of at least 55 nucleotides in length, such that said nucleic acid molecule (i)

encodes a feline IL-12 single chain protein; and (ii) a nucleic acid molecule comprising a nucleic acid sequence fully complementary to the coding strand of a nucleic acid molecule as set forth in (i); and (h) an isolated nucleic acid molecule selected from the group consisting of: (i) a nucleic acid molecule comprising ((a)) an isolated nucleic acid molecule comprising a nucleic acid sequence selected from the group consisting of SEQ ID NO:52 and SEQ ID NO:58, and a nucleic acid sequence comprising at least 55 contiguous nucleotides identical in sequence to at least 55 contiguous nucleotides of a nucleic acid sequence selected from the group consisting of NO:52 and SEQ ID NO:58; ((b)) a nucleic acid linker of (XXX)$_n$, wherein n=0 to 60; and ((c)) an isolated nucleic acid molecule comprising a nucleic acid sequence selected from the group consisting of SEQ ID NO:46, SEQ ID NO:49, and a nucleic acid molecule comprising at least 55 contiguous nucleotides identical in sequence to at least 55 contiguous nucleotides of a nucleic acid sequence selected from the group consisting of SEQ ID NO:32 and SEQ ID NO:35, such that said nucleic acid molecule of (i) encodes a canine IL-12 single chain protein; and (ii) a nucleic acid molecule comprising a nucleic acid sequence fully The present invention also includes recombinant molecules, recombinant viruses and recombinant cells comprising such IL-18, caspase-1, and IL-12 single chain nucleic acid molecules and methods to produce such nucleic acid molecules, recombinant molecules, recombinant viruses and recombinant cells.

Another embodiment of the present invention is an isolated nucleic acid molecule selected from the group consisting of: (a) a nucleic acid molecule having a nucleic acid sequence encoding an IL-18 protein selected from the group consisting of: (i) a protein selected from the group consisting of ((a)) a protein having an amino acid sequence that is at least 92 percent identical to an amino acid sequence selected from the group consisting of SEQ ID NO:2, SEQ ID NO:5, SEQ ID NO:8 and SEQ ID NO:12, and ((b)) a protein comprising a fragment of a protein of ((a)), wherein said fragment is at least 30 amino acids in length; and (ii) a protein comprising at least 25 contiguous amino acids identical in sequence to at least 25 contiguous amino acids of an amino acid sequence selected from the group consisting of SEQ ID NO:2, SEQ ID NO:5, SEQ ID NO:8 and SEQ ID NO:12; (b) a nucleic acid molecule having a nucleic acid sequence encoding a caspase-1 protein selected from the group consisting of: (i) a protein selected from the group consisting of ((a)) a protein having an amino acid sequence that is at least 85 percent identical to an amino acid sequence selected from the group consisting of SEQ ID NO:15, SEQ ID NO:18, SEQ ID NO:21, and SEQ ID NO:24, and ((b)) a protein comprising a fragment of a protein of ((a)), wherein said fragment is at least 30 amino acids in length; and (ii) a protein comprising at least 25 contiguous amino acids identical in sequence to at least 25 contiguous amino acids selected from the group consisting of SEQ ID NO:15, SEQ ID NO:18, SEQ ID NO:21, and SEQ ID NO:24; (c) a nucleic acid molecule having a nucleic acid sequence encoding an IL-12 single chain protein comprising an IL-12 p40 subunit domain linked to a IL-12 p35 subunit domain, wherein said p40 subunit domain is selected from the group consisting of (i) a p40 subunit protein having an amino acid sequence that is at least 84 percent identical to an amino acid sequence selected from the group consisting of SEQ ID NO:27 and SEQ ID NO:30, (ii) a p40 subunit protein comprising a fragment of a protein of (i), wherein said fragment is at least 30 amino acids in length, and (iii) a p40 subunit protein comprising at least 23 contiguous amino acids identical in sequence to at least 23 contiguous amino acids of an amino acid sequence selected from the group consisting of SEQ ID NO:27 and SEQ ID NO:30 and wherein said p35 subunit domain is selected from the group consisting of (i) a p35 subunit protein having an amino acid sequence that is at least 84 percent identical to an amino acid sequence selected from the group consisting of SEQ ID NO:33 and SEQ ID NO:36, (ii) a p35 subunit protein comprising a fragment of a protein of (i), wherein said fragment is at least 30 amino acids in length, and (iii) a p35 subunit protein comprising at least 23 contiguous amino acids identical in sequence to at least 23 contiguous amino acids of an amino acid sequence selected from the group consisting of SEQ ID NO:33 and SEQ ID NO:36; (d) a nucleic acid molecule having a nucleic acid sequence encoding an IL-12 single chain protein comprising an IL-12 p40 subunit domain linked to a IL-12 p35 subunit domain, wherein said p40 subunit domain is selected from the group consisting of (i) a p40 subunit protein having an amino acid sequence that is at least 84 percent identical to an amino acid sequence selected from the group consisting of SEQ ID NO:53 and SEQ ID NO:59, (ii) a p40 subunit protein comprising a fragment of a protein of (i), wherein said fragment is at least 40 amino acids in length, and (iii) a p40 subunit protein comprising at least 31 contiguous amino acids identical in sequence to at least 31 contiguous amino acids of an amino acid sequence selected from the group consisting of SEQ ID NO:53 and SEQ ID NO:59, and wherein said p35 subunit domain is selected from the group consisting of (i) a p35 subunit protein having an amino acid sequence that is at least 84 percent identical to an amino acid sequence selected from the group consisting of SEQ ID NO:47 and SEQ ID NO:50, (ii) a p35 subunit protein comprising a fragment of a protein of (i), wherein said fragment is at least 40 amino acids in length, and (iii) a p35 subunit protein comprising at least 31 contiguous amino acids identical in sequence to at least 31 contiguous amino acids of an amino acid sequence selected from the group consisting of SEQ ID NO:47 and SEQ ID NO:50; (e) a nucleic acid molecule comprising a nucleic acid sequence fully complementary to the coding strand of any of said nucleic acid molecules as set forth in (a), (b), (c), or (d). The present invention also includes recombinant molecules, recombinant viruses and recombinant cells comprising such IL-18, caspase-1, and IL-12 single chain nucleic acid molecules and methods to produce such nucleic acid molecules, recombinant molecules, recombinant viruses and recombinant cells.

Another embodiment of the present invention is an isolated protein selected from the group consisting of: (a) an isolated IL-18 protein selected from the group consisting of: (i) an isolated protein of at least 25 amino acids in length, wherein said protein has an at least 25 contiguous amino acid region identical in sequence to a 25 contiguous amino acid region selected from the group consisting of SEQ ID NO:2, SEQ ID NO:5, SEQ ID NO:8 and SEQ ID NO:12; and (ii) an isolated protein having an amino acid sequence that is at least 92 percent identical to an amino acid sequence selected from the group consisting of SEQ ID NO:2, SEQ ID NO:5, SEQ ID NO:8 and SEQ ID NO:12 and a fragment thereof of at least 30 nucleotides; wherein said isolated protein has a function selected from the group consisting of (i) eliciting an immune response against an IL-18 protein having an amino acid sequence selected from the group consisting of SEQ ID NO:2, SEQ ID NO:5, SEQ ID NO:8 and SEQ ID NO:12, (ii) selectively binding to an antibody raised against an IL-18 protein having an amino acid sequence selected from the group consisting of SEQ ID NO:2, SEQ ID NO:5, SEQ ID NO:8, and SEQ ID NO:12, and (iii) exhibiting IL-18 activity; (b) an isolated caspase-1 protein selected from the group consisting of: (i) an isolated protein of at least about 25 amino acids in length, wherein said protein has an at least 25 contiguous amino acid region identical in sequence to a 25 contiguous amino acid region selected from the group consisting of SEQ ID NO:15, SEQ ID NO:18, SEQ ID NO:21, and SEQ ID NO:24; and (ii) an isolated protein having an amino acid sequence that is at least 85 percent identical to an amino acid sequence selected from the group consisting of SEQ ID NO:15, SEQ ID NO:18, SEQ ID NO:21, and SEQ ID NO:24 and has a nucleic acid fragment thereof of at least 30 nucleotides; wherein said isolated protein has a function selected from the group consisting of (i) eliciting an immune response against a caspase-1 protein having an amino acid sequence selected from the group consisting of SEQ ID NO:15, SEQ ID NO:18, SEQ ID NO:21, and SEQ ID NO:24, (ii) ii) selectively binding to an antibody raised against caspase-1 protein having an amino acid sequence selected from the group consisting of SEQ ID NO:15, SEQ ID NO:18, SEQ ID NO:21, and SEQ ID NO:24, and (iii) exhibiting caspase-1 activity; (c) an isolated IL-12 single chain protein comprising an IL-12 p40 subunit domain linked to an IL-12 p35 subunit domain, wherein said p40 subunit domain is selected from the group consisting of (i) a p40 subunit protein having an amino acid sequence that is at least 84 percent identical to an amino acid sequence selected from the group consisting of SEQ ID NO:27 and SEQ ID NO:30, (ii) a p40 subunit protein comprising a fragment of a protein of (i), wherein said fragment is at least 30 amino acids in length, and (iii) a p40 subunit protein comprising at least 23 contiguous amino acids identical in sequence to at least 23 contiguous amino acids of an amino acid sequence selected from the group consisting of SEQ ID NO:27 and SEQ ID NO:30 and wherein said p35 subunit domain is selected from the group consisting of (i) a p35 subunit protein having an amino acid sequence that is at least 84 percent identical to an amino acid sequence selected from the group consisting of SEQ ID NO:33 and SEQ ID NO:36, (ii) a p35 subunit protein comprising a fragment of a protein of (i), wherein said fragment is at least 30 amino acids in length, and (iii) a p35 subunit protein comprising at least 23 contiguous amino acids identical in sequence to at least 23 contiguous amino acids of an amino acid sequence selected from the group consisting of SEQ ID NO:33 and SEQ ID NO:36; wherein said isolated protein has a function selected from the group consisting of (i) eliciting an immune response against an IL-12 protein having an amino acid sequence selected from the group consisting of SEQ ID NO:39 and SEQ ID NO:44, (ii) selectively binding to an antibody raised against an IL-12 protein having an amino acid sequence selected from the group consisting of SEQ ID NO:27, SEQ ID NO:30, SEQ ID NO:33, SEQ ID NO:36, SEQ ID NO:47, SEQ ID NO:50, SEQ ID NO:53, and SEQ ID NO:59, SEQ ID NO:102, SEQ ID NO:105, SEQ ID NO:108, SEQ ID NO:39, SEQ ID NO:40, SEQ ID NO:62, and/or SEQ ID NO:67, and (iii) exhibiting IL-12 activity; and (d) an isolated IL-12 single chain protein comprising an IL-12 p40 subunit domain linked to an IL-12 p35 subunit domain, wherein said p40 subunit domain is selected from the group consisting of (i) a p40 subunit protein having an amino acid sequence that is at least 84 percent identical to an amino acid sequence selected from the group consisting of SEQ ID NO:53 and SEQ ID NO:59, (ii) a p40 subunit protein comprising a fragment of a protein of (i), wherein said fragment is at least 40 amino acids in length, and (iii) a p40 subunit protein comprising at least 31 contiguous amino acids identical in sequence to at least 31 contiguous amino acids of an amino acid sequence selected from the group consisting of SEQ ID NO:53 and SEQ ID NO:59; wherein said p35 subunit domain is selected from the group consisting of (i) a p35 subunit protein having an amino acid sequence that is at least 84 percent identical to an amino acid sequence selected from the group consisting of SEQ ID NO:47 and SEQ ID NO:50, (ii) a p35 subunit protein comprising a fragment of a protein of (i), wherein said fragment is at least 40 amino acids in length, and (iii) a p35 subunit protein comprising at least 31 contiguous amino acids identical in sequence to at least 31 contiguous amino acids of an amino acid sequence selected from the group consisting of SEQ ID NO:47 and SEQ ID NO:50; and wherein said isolated protein has a function selected from the group consisting of (i) eliciting an immune response against an IL-12 protein having an amino acid sequence selected from the group consisting of SEQ ID NO:39, SEQ ID NO:44, SEQ ID NO:62, and SEQ ID NO:67, (ii) selectively binding to an antibody raised against an IL-12 protein having an amino acid sequence selected from the group consisting of SEQ ID NO:27, SEQ ID NO:30, SEQ ID NO:33, SEQ ID NO:36, SEQ ID NO:47, SEQ ID NO:50, SEQ ID NO:53, and SEQ ID NO:59, SEQ ID NO:102, SEQ ID NO:105, SEQ ID NO:108, SEQ ID NO:39, SEQ ID NO:40, SEQ ID NO:62, and/or SEQ ID NO:67, and (iii) exhibiting IL-12 activity. The present invention also includes recombinant molecules, recombinant viruses and recombinant cells comprising such IL-18, caspase-1, and IL-12 single chain nucleic acid molecules and methods to produce such nucleic acid molecules, recombinant molecules, recombinant viruses and recombinant cells.

The present invention also includes an antibody that selectively binds to a protein of the present invention as well as methods to produce and use such proteins or antibodies. By selectively is meant an antibody that binds to a protein of the present invention, but does not bind a similar protein of another species.

One aspect of the present invention is a therapeutic composition that, when administered to an animal, regulates an immune response in the animal. Such a therapeutic composition includes at least one of the following protective compounds: an IL-18, caspase-1, or IL-12 single chain protein of the present invention, a mimetope of any of the proteins, a multimeric form of any of the proteins, an isolated nucleic acid molecule of the present invention, an antibody that selectively binds any of the proteins, and/or an inhibitor of a protein activity identified by its ability to inhibit the activity of any of the proteins. Also included is a method to regulate an immune response by administering such a therapeutic composition to an animal.

The present invention also includes a method to produce a protein of the present invention; such a method includes the step of culturing a recombinant cell capable of expressing a protein being encoded by a nucleic acid molecule of the present invention.

Another embodiment of the present invention is a method to identify a compound capable of regulating an immune response in an animal, a method selected from the group consisting of: (a) contacting an isolated feline IL-18 protein with a putative inhibitory compound under conditions in which, in the absence of the compound, the protein has T cell stimulating activity inducing T cells to make interferon gamma, and determining if the putative inhibitory compound inhibits that activity; (b) contacting an isolated feline caspase-1 protein with a putative inhibitory compound under conditions in which, in the absence of the compound, the protein cleaves precursor form of IL-18 resulting in biologically active IL-18, and determining if the putative inhibitory compound inhibits that activity; and (c) contacting an isolated IL-12 single chain protein with a putative inhibitory compound under conditions in which, in the absence of the compound, the protein has T cell proliferation stimulating activity, and determining if the putative inhibitory compound inhibits that activity.

DETAILED DESCRIPTION OF THE INVENTION

The present invention provides for isolated feline and canine proteins, nucleic acid molecules encoding such proteins, antibodies raised against such proteins and/or inhibitors of such proteins or nucleic acid molecules. Specifically, the present invention provides for isolated feline IL-18, feline caspase-1, and feline and canine IL-12 single chain proteins and nucleic acid molecules as well as antibodies raised against such proteins, and/or inhibitors of such proteins or nucleic acid molecules. Also included in the present invention is the use of these proteins, nucleic acid molecules, antibodies, inhibitors and/or other compounds derived therefrom as therapeutic compositions to regulate the immune response of an animal as well as in other applications, such as those disclosed below.

One embodiment of the present invention is an isolated protein that includes a feline IL-18 protein, a feline caspase-1 protein, a feline IL-12 single chain protein and/or a canine IL-12 single chain protein. As used herein, a feline and/or canine protein refers to a protein. As used herein, a protein of the present invention is a protein that is isolated from a felid or a canid or is derived therefrom and can be produced by methods known in the art, such as, for example, using recombinant DNA technology or by chemical synthesis. As such, a feline or canine protein of the present invention includes natural forms as well as any variants thereof, such as a feline or canine protein that has been altered in a manner known to those skilled in the art, such as those methods disclosed herein. As used herein, a feline or canine protein does not refer to a mouse or human protein.

Similarly, a feline or canine nucleic acid molecule of the present invention includes a feline IL-18 nucleic acid molecule, a feline caspase-1 nucleic acid molecule, a feline IL-12 single chain nucleic acid molecule and/or canine IL-12 single chain nucleic acid molecule. As used herein a feline or canine nucleic acid molecule of the present invention refers to a nucleic acid molecule that includes a nucleic acid molecule that encodes a protein of the present invention and/or a complement thereof. As such, a feline IL-18 nucleic acid molecule, a feline caspase-1 nucleic acid molecule, a feline IL-12 single chain nucleic acid molecule or a canine IL-12 single chain nucleic acid molecule of the present invention is a nucleic acid molecule that encodes a feline IL-18 protein, a feline caspase-1 protein, a feline IL-12 single chain protein or a canine IL-12 single chain protein, respectively, and/or that is a complement thereof. As used herein, a feline or canine nucleic acid molecule of the present invention is a nucleic acid molecule that is isolated from a felid or canid or is derived therefrom and can be produced using methods known in the art, such as, for example, recombinant DNA technology, or by chemical synthesis. As such, a feline or canine nucleic acid molecule of the present invention includes natural forms as well as any variants thereof, such as a feline or canine nucleic acid molecule that has been altered in a manner known to those skilled in the art, such as those methods disclosed herein. As used herein, a feline or canine nucleic acid molecule does not refer to a mouse or human nucleic acid molecule.

According to the present invention, an isolated, or biologically pure, nucleic acid molecule or protein, is a nucleic acid molecule or protein that has been removed from its natural milieu. As such, "isolated" and/or "biologically pure" do not necessarily reflect the extent to which the nucleic acid molecule or protein has been purified. "Proteins" are defined as any compounds which comprise amino acids, including peptides, polypeptides and fusion proteins. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. Furthermore, an item "selected from the group consisting of" refers to one or more of the items in that group, including combinations thereof. The term "fragment" refers to any subset of the referent nucleic acid molecule. Furthermore, the term "linked in frame" refers to nucleic acid fragment joined to another nucleic acid fragment in a manner such that the molecule is able to be expressed when transformed into a host cell.

As used herein, a felid refers to any member of the felid family (i.e. the family Felidae), including, but not limited to, domestic cats, and wild cats such as tigers, lions, and lynx. Similarly, the term feline refers to "of the family Felidae".

As used herein, a canid refers to any member of the canid family (i.e. the family Canidae), including, but not limited to, domestic dogs, and wild canids such as wolves, foxes, and coyotes. Similarly, the term canine refers to "of the family Canidae".

Nucleic acid molecules of the present invention of known length isolated from *Felis catus* are denoted as follows: a feline IL-18 nucleic acid molecule is denoted as nFeIL-18$_x$, wherein "x" refers to the number of nucleotides in that molecule; for example, nFeIL-18$_{607}$ refers to a feline IL-18 nucleic acid molecule of 607 nucleotides in length; and in a similar fashion, a feline Casp-1 nucleic acid molecule of length "x" is referred to as nFeCasp-1$_x$, a feline IL-12 single chain nucleic acid molecule of length "x" is referred to as nFeIL-12$_x$, a feline IL-12p35 subunit nucleic acid molecule of length "x" is referred to as nFeIL-12p35$_x$ and a feline IL-12p40 subunit nucleic acid molecule of length "x" is referred to as nFeIL-12p40$_x$, Similarly, *Felis catus* IL-18, Casp-1, IL-12 single chain, IL-12p35 subunit, and IL-12p40 subunit proteins of the present invention of known length are denoted PFeIL-18$_x$, PFeCasp-1$_x$, PFeIL-12$_x$, PFeIL-12p35$_x$, and PFeIL-12p40$_x$ respectively.

Nucleic acid molecules of the present invention of known length isolated from *Canis familiaris* are denoted as follows: a canine IL-12 single chain is denoted as nCaIL-12$_x$, wherein "x" refers to the number of nucleotides in that molecule; for example, nCaIL-12$_{1602}$ refers to a canine IL-12 single chain nucleic acid molecule of 1602 nucleotides in length and in a similar fashion, a canine IL-12 single chain nucleic acid molecule of length "x" is referred to as nCaIL-12p35$_x$ and a canine IL-12p40 subunit nucleic acid molecule of length "x" is referred to as nCaIL-12p40$_x$. Similarly, *Canis familiaris* IL-12 single chain proteins of the present invention of known length isolated from are denoted PCaIL-12$_x$, PCaIL-12p35$_x$, or PCaIL-12p40$_x$ respectively. The present invention includes nucleic acid molecules selected from the group consisting of nCaIL-12p35$_{591}$, nCaIL-12p40$_{2267}$, nCaIL-12p40$_{1002}$, nCaIL-12p40$_{987}$, nCaIL-12$_{1599}$, and nCaIL-12$_{1533}$.

The present invention includes nucleic acid molecules that include one or more of the following nucleic acid sequences: SEQ ID NO:1, SEQ ID NO:4, SEQ ID NO:7, SEQ ID NO:9, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, SEQ ID NO:43, SEQ ID NO:46, SEQ ID NO:49, SEQ ID NO:52, SEQ ID NO:58, SEQ ID NO:61, SEQ ID NO:64 and/or SEQ ID NO:66, and/or a complements of these nucleic acid sequences, i.e. SEQ ID NO:3, SEQ ID NO:6, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, SEQ ID NO:45, SEQ ID NO:48, SEQ ID NO:51, SEQ ID NO:54, SEQ ID NO:60, SEQ ID NO:63, and/or SEQ ID NO:68, respectively. Complements are defined as two single strands of nucleic acid in which the nucleotide sequences are such that the strands will hybridize as a result of base pairing throughout their full length; i.e., these sequences are fully complementary. Such nucleic acid sequences are further described herein and can be easily be determined by those skilled in the art. It should be noted that since nucleic acid sequencing technology is not entirely error-free, nucleic acid and protein sequences presented herein represent apparent nucleic acid and amino acid sequences of the isolated nucleic acid molecules and proteins, respectively, of the present invention.

As used herein, an isolated feline IL-18, feline caspase-1, feline IL-12p40 subunit, feline IL-12p35 subunit, feline IL-12 single chain, canine IL-12p40 subunit, canine IL-12p35, and/or canine IL-12 single chain protein of the present invention can be a full-length protein or any homolog of such a protein, including truncated forms of the protein. An isolated IL-18 protein of the present invention, including a homolog, can be identified in a straight-forward manner by the protein's ability to elicit an immune response against, (or to) an IL-18 protein, whether the protein has IL-18 activity, such as T cell stimulating activity, or selectively binding to an antibody raised against an IL-18 protein. An isolated caspase-1 protein of the present invention may be identified in a straight-forward manner by the protein's ability to elicit an immune response against, (or to) a caspase-1 protein, whether the protein has caspase-1 activity, such as cleaving the precursor form of IL-18 resulting in a biologically active IL-18, or selectively binding to an antibody raised against a caspase-1 protein. A IL-12 single chain protein of the present invention may be identified in a straight-forward manner by the protein's ability to elicit an immune response against, (or to) an IL-12 protein, including the p35 or p40 subunits, whether the protein has IL-12 activity, such as T cell stimulating activity, or selectively binding to an antibody raised against an IL-12 protein, including the p35 or p40 subunits. Examples of protein homologs of the present invention includes proteins of the present invention in which amino acids have been deleted (e.g. a truncated version of the protein, such as a peptide), inserted, inverted, substituted and/or derivatized (e.g. by glycosylation, phosphorylation, acetylation, myristoylation, prenylation, palmitoylation, amidation and/or addition of glycerophosphatidyl inositol) such that the protein homolog include at least one epitope capable of eliciting an immune response against the parent protein, where the term parent refers to the longer and/or full-length protein that the homolog is derived from. The ability of a protein to effect an immune response can be measured using techniques known to those skilled in the art. As used herein, the term "epitope" refers to the smallest portion of a protein capable of selectively binding to the antigen binding site of an antibody. It is well accepted by those skilled in the art that the minimal size of a protein epitope capable of selectively binding to the antigen binding site of an antibody is about five or six to seven amino acids.

Proteins of the present invention include variants of a full-length protein of the present invention. Such variants include proteins that are less than full-length. As used herein, variants of the present invention refer to nucleic acid molecules that are naturally-occurring a defined below, and may result from alternative RNA splicing, alternative termination of an amino acid sequence or DNA recombination. Examples of variants include allelic variants as defined below. It is to be noted that a variant is an example of a homolog of the present invention.

Proteins of the present invention are encoded by nucleic acid molecules of the present invention. As used herein, an IL-18 nucleic acid molecule includes sequences related to a natural feline IL-18 gene. As used herein, a caspase-1 protein includes nucleic acid sequences related to a natural feline caspase-1 gene. As used herein, an IL-12 single chain nucleic acid molecule includes sequences related to a natural canine or feline IL-12 gene, IL-12p35 gene, and/or IL-12p40 gene. As used herein, a feline IL-18, a feline caspase-1, and or a feline or canine IL-12 single chain refers to the natural genomic elements that encode a feline IL-18, a feline caspase-1, and or a feline or canine IL-12 single chain, and includes all regions such as regulatory regions that control production of the protein encoded by the gene) such as, but not limited to, transcription, translation or post-translation control regions) as well as the coding region itself, and any introns or non-translated coding regions. As used herein, a gene that "includes" or "comprises" a sequence may include that sequence in one continuous array, or may include the sequence of fragmented exons. As used herein, the term "coding region" refers to a continuous linear array of nucleotides that translates into a protein. A full-length coding region is that region that is translated into a full-length, i.e., a complete protein as would be initially translated in its natural milieu, prior to any post-translational modifications.

In one embodiment of the present invention, isolated proteins are encoded by nucleic acid molecules that hybridize under stringent hybridization conditions to the non-coding strand of nucleic acid molecules encoding proteins. The minimal size of a protein of the present invention (4-6 amino acids) is a size sufficient to be encoded by a nucleic acid molecule capable of forming a stable hybrid, i.e., hybridizing under stringent hybridization conditions, with the complementary sequence of a nucleic acid molecule encoding the corresponding natural protein. The size of a nucleic acid molecule encoding such a protein is dependent on the nucleic acid composition and the percent homology between the nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered, i.e. localized, in distinct regions on a given nucleic acid molecule.

The minimal size of a feline IL-18, feline caspase-1, and/or canine or feline IL-12 single chain protein homolog/portion/fragment of the present invention is a size sufficient to be encoded by a nucleic acid molecule capable of forming a stable hybrid (i.e. hybridize under stringent hybridization conditions) with the complementary sequence of a nucleic acid molecule encoding the corresponding natural protein. Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al, 1989, *Molecular Cloning. A Laboratory Manual*, Cold Spring Harbor Labs Press, and Meinkoth, et al, 1984, *Anal. Biochem.* 138, 267-284, each of which is incorporated herein by this reference. As explained in detail in the cited references, the determination of hybridization conditions involves the manipulation of a set of variables including the ionic strength (M, in moles/liter), the hybridization temperature (° C.), the concentration of nucleic acid helix destabilizing agents, such as formamide, the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m=81.5° C.+16.6 \log M+0.41(\% G+C)-500/n-0.61(\% \text{ formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d=4(G+C)+2(A+T).$$

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions, by altering, for example, the salt concentration, the formamide concentration or the temperature, so that only nucleic acid hybrids with greater than a specified % base pair mismatch will hybridize. Stringent hybridization conditions are commonly understood by those skilled in the art to be those experimental conditions that will allow about 30% or less base pair mismatch, i.e., at least about 85% identity. Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene or specified nucleic acid molecule under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

In one embodiment, an IL-18 gene of the present invention includes the nucleic acid molecule SEQ ID NO:1, as well as the complement of SEQ ID NO:1. Nucleic acid sequence SEQ ID NO:1 represents the deduced sequence of the coding strand of a cDNA (complementary DNA) denoted herein as nucleic acid molecule nFeIL-18-$N_{514}$, the production of which is disclosed in the Examples. SEQ ID NO:1 comprises an apparent partial coding region of nFeIL-18, coding for the N-terminal portion of feline IL-18 protein. The complement of SEQ ID NO:1 (represented herein by SEQ ID NO:3) refers to the nucleic acid sequence of the strand fully complementary to the strand having SEQ ID NO:1, which can easily be determined by those skilled in the art. Likewise, a nucleic acid sequence complement of any nucleic acid sequence of the present invention refers to the nucleic acid sequence complement of any nucleic acid sequence of the present invention that is fully complementary (i.e. can form a double helix with) the strand for which the sequence is cited. It should be noted that since nucleic acid sequencing technology is not entirely error-free, SEQ ID NO:1 (as well as other nucleic acid and protein sequences presented herein) represents an apparent nucleic acid sequence of the nucleic acid molecule encoding an immunoregulatory protein of the present invention.

Another IL-18 gene of the present invention includes the nucleic acid molecule SEQ ID NO:4, as well as the complement represented by SEQ ID NO:6. Nucleic acid sequence SEQ ID NO:4 represents the deduced sequence of the coding strand of a cDNA denoted herein as nucleic acid molecule nFeIL-18-$C_{502}$, the production of which is disclosed in the examples. Nucleic acid nFeIL-18-$C_{502}$ represents an apparent partial coding region of FeIL-18, encoding a partial C-terminal region of the feline IL-18 protein. Another IL-18 gene of the present invention includes the nucleic acid molecule SEQ ID NO:7, as well as the complement represented by SEQ ID NO:10. Nucleic acid sequence SEQ ID NO:7 represents the deduced sequence of the coding strand of a cDNA denoted herein as nucleic acid molecule nFeIL-$18_{607}$, the production of which is disclosed in the examples. Nucleic acid nFeIL-$18_{607}$ represents an apparent full-length coding region of the feline IL-18 protein. Another IL-18 gene of the present invention includes the nucleic acid molecule SEQ ID NO:9, as well as the complement represented by SEQ ID NO:41. Nucleic acid sequence SEQ ID NO:9 represents the deduced sequence of the coding strand of a cDNA denoted herein as nucleic acid molecule nFe IL-$18_{576}$, the production of which is disclosed in the examples. Nucleic acid molecule nFe IL-$18_{576}$ represents the coding region for an apparent precursor protein to a mature feline IL-18 protein. Another IL-18 gene of the present invention includes the nucleic acid molecule SEQ ID NO:11, as well as the complement represented by SEQ ID NO:13. Nucleic acid sequence SEQ ID NO:11 represents the deduced sequence of the coding strand of a cDNA denoted herein as nucleic acid molecule nFe IL-$18_{471}$, the production of which is disclosed in the Examples. Nucleic acid molecule nFe IL-$18_{471}$ represents the coding region for an apparent mature IL-18 protein. The putative cleavage site for the mature IL-18 protein is between amino acid positions 35 and 36 of SEQ ID NO:8, representing PFeIL-$18_{192}$, which is the predicted amino acid sequence of the full-length IL-18 protein (i.e., containing signal, or leader, peptide). SEQ ID NO:12 represents the predicted amino acid sequence of the mature IL-18 protein (i.e., without the signal, or leader, sequence), also denoted as PFeIL-18$_{157}$.

In another embodiment, a caspase-1 gene of the present invention includes the nucleic acid sequence SEQ ID NO:14, as well as the complement represented by SEQ ID NO:16. Nucleic acid sequence SEQ ID NO:14 represents the deduced sequence of the coding strand of a cDNA denoted herein as nucleic acid molecule nFeCasp-1$_{1233}$, the production of which is disclosed in the Examples. Nucleic acid molecule nFeCasp-1$_{1233}$ represents the coding region for an apparent full-length feline caspase-1 protein and includes a human primer sequence. Another caspase-1 protein of the present invention includes the nucleic acid sequence SEQ ID NO:17, as well as the complement represented by SEQ ID NO:19. Nucleic acid sequence SEQ ID NO:17 represents the deduced sequence of the coding strand of a cDNA denoted herein as nucleic acid molecule nFeCasp-1-N$_{526}$, the production of which is disclosed in the Examples. Nucleic acid molecule nFeCasp-1-N$_{526}$ represents the coding region for the apparent N-terminal region of the feline caspase-1 protein. Another caspase-1 protein of the present invention includes the nucleic acid molecule SEQ ID NO:20, as well as the complement represented by SEQ ID NO:22. Nucleic acid sequence SEQ ID NO:20 represents the deduced sequence of a coding strand of a cDNA denoted herein as nucleic acid molecule nFeCasp-1-C$_{500}$, the production of which is disclosed in the Examples. Nucleic acid molecule nFeCasp-1-C$_{500}$ represents the coding region for the apparent C-terminal region of the feline caspase-1 protein. Another caspase-1 protein of the present invention includes the nucleic acid molecule SEQ ID NO:23, as well as the complement represented by SEQ ID NO:25. Nucleic acid sequence SEQ ID NO:23 represents the deduced sequence of a coding strand of a cDNA denoted herein as nucleic acid molecule nFeCasp-1$_{1230}$, the production of which is disclosed in the examples. Nucleic acid molecule nFeCasp-1$_{1230}$ represents the coding region for the apparent full-length feline caspase-1 protein, denoted herein as PFeCasp-1$_{410}$, represented herein as SEQ ID NO:24.

In another embodiment, feline IL-12 single chain proteins of the present invention contain both a mature IL-12 p35 subunit and a full-length IL-12 p40 subunit, joined by a linker. An IL-12 single chain gene of the present invention includes the nucleic acid sequence SEQ ID NO:38, as well as the complement represented by SEQ ID NO:40. Nucleic acid sequence SEQ ID NO:38 represents the deduced sequence of the coding strand of a cDNA denoted herein as nucleic acid molecule nFeIL-12$_{1599}$, the production of which is disclosed in the Examples. Nucleic acid molecule nFeIL-12$_{1599}$ represents the coding region encoding a single chain full-length feline IL-12 protein, which includes the coding region for a full-length (i.e. containing signal, or leader, sequence) IL-12 p40 subunit, a linker of the present invention, and the coding region for a mature (i.e. not containing signal, or leader, sequence) IL-12 p35 subunit. SEQ ID NO:38 comprises a sequence that includes both the nucleic acid sequence SEQ ID NO:29 (nucleic acid sequence SEQ ID NO:29 represents the deduced sequence of the coding strand of a cDNA denoted herein as nucleic acid molecule nFeIL-12p40$_{987}$, which represents the coding region encoding the full-length feline IL-12 p40 subunit, whereas SEQ ID NO:31 represents the complement of SEQ ID NO:29) and SEQ ID NO:35 (nucleic acid sequence SEQ ID NO:35 represents the deduced sequence of the coding strand of a cDNA denoted herein as nucleic acid molecule nFeIL-12p35$_{591}$, which represents the coding region encoding the mature feline IL-12 p35 subunit, whereas SEQ ID NO:37 represents the complement of SEQ ID NO:35). Translation of SEQ ID NO:38 yields a predicted protein denoted herein as PFeIL-12$_{533}$, also denoted as SEQ ID NO:39.

In another embodiment, feline IL-12 single chain proteins of the present invention contain both a mature IL-12 p35 subunit and an mature IL-12 p40 subunit, joined by a linker. An IL-12 single chain gene of the present invention includes the nucleic acid sequence SEQ ID NO:43, as well as the complement represented by SEQ ID NO:45. Nucleic acid sequence SEQ ID NO:43 represents the deduced sequence of the coding strand of a cDNA denoted herein as nucleic acid molecule nFeIL-12$_{1533}$, the production of which is disclosed in the Examples. Nucleic acid molecule nFeIL-12$_{1533}$ represents the coding region encoding a single chain mature feline IL-12 protein. SEQ ID NO:33 comprises a sequence that includes both the nucleic acid sequence SEQ ID NO:26 (nucleic acid sequence SEQ ID NO:26 represents the deduced sequence of the coding strand of a cDNA denoted herein as nucleic acid molecule nFeIL-12p40$_{985}$, which represents the coding region encoding the mature feline IL-12 p40 subunit, whereas SEQ ID NO:28 represents the complement of SEQ ID NO:26) and SEQ ID NO:35 (nucleic acid sequence SEQ ID NO:35 represents the deduced sequence of the coding strand of a cDNA denoted herein as nucleic acid molecule nFeIL-12p35$_{591}$, which represents the coding region encoding the mature feline IL-12 p35 subunit, whereas SEQ ID NO:37 represents the complement of SEQ ID NO:35). Translation of SEQ ID NO:43 yields a predicted protein denoted herein as PFeIL-12$_{511}$, also denoted as SEQ ID NO:44.

In another embodiment, canine IL-12 single chain proteins and nucleic acid molecules of the present invention contain both a mature IL-12 p35 subunit and a full-length IL-12 p40 subunit, joined by a linker. An IL-12 single chain gene of the present invention includes the nucleic acid sequence SEQ ID NO:61, as well as the complement represented by SEQ ID NO:63. Nucleic acid sequence SEQ ID NO:61 represents the deduced sequence of the coding strand of a cDNA denoted herein as nucleic acid molecule nCaIL-12$_{1599}$, the production of which is disclosed in the Examples. Nucleic acid molecule nCaIL-12$_{1599}$ represents the coding region encoding a single chain full-length canine IL-12 protein, which includes the coding region for a full-length (i.e. containing signal, or leader, sequence), IL-14 p40 subunit, a linker of the present invention, and the coding region for a mature, (i.e., not containing signal, or leader, sequence) IL-12 p35 subunit. SEQ ID NO:61 comprises a nucleic acid sequence that includes both the nucleic acid sequence SEQ ID NO:58 (nucleic acid SEQ ID NO:58 represents the deduced sequence of the coding strand of a cDNA denoted herein as nucleic acid molecule nCaIL-12$_{987}$, which represents the coding region encoding the full-length canine IL-12 p40 subunit, whereas SEQ ID NO:60 represents the complement of SEQ ID NO:58) and SEQ ID NO:49 (nucleic acid sequence SEQ ID NO:49 represents the deduced sequence of the coding strand of a cDNA denoted herein as nucleic acid molecule nFeIL-12p35$_{591}$, which represents the coding region encoding the mature canine IL-12 subunit, whereas SEQ ID NO:51 represents the complement of SEQ ID NO:49. Translation of SEQ ID NO:61 yields a predicted protein denoted herein as PCaIL-12$_{533}$, also denoted as SEQ ID NO:62.

In another embodiment, canine IL-12 single chain proteins and nucleic acid molecules of the present invention contain both a mature IL-12 p35 subunit and a mature IL-12 p40 subunit, joined by a linker. An IL-12 single chain gene of the present invention includes the nucleic acid sequence SEQ ID NO:66, as well as the complement represented by SEQ ID NO:68. Nucleic acid sequence SEQ ID NO:66 represents the deduced sequence of the coding strand of a cDNA denoted herein as nucleic acid molecule nCaIL-12$_{1533}$, the production of which is disclosed in the Examples. Nucleic acid molecule nCaIL-12$_{1533}$ represents the coding region encoding a single chain full-length canine IL-12 protein, which includes the coding region for a full-length (i.e. containing signal, or leader, sequence), IL-14 p40 subunit, a linker of the present invention, and the coding region for a mature, (i.e., not containing signal, or leader, sequence) IL-12 p35 subunit. SEQ ID NO:66 comprises a nucleic acid sequence that includes both the nucleic acid sequence SEQ ID NO:52 (nucleic acid SEQ ID NO:52 represents the deduced sequence of the coding strand of a cDNA denoted herein as nucleic acid molecule nCaIL-12$_{921}$, which represents the coding region encoding the mature canine IL-12 p40 subunit, whereas SEQ ID NO:54 represents the complement of SEQ ID NO:52) and SEQ ID NO:49 (nucleic acid sequence SEQ ID NO:49 represents the deduced sequence of the coding strand of a cDNA denoted herein as nucleic acid molecule nFeIL-12p35$_{591}$, which represents the coding region encoding the mature canine IL-12 subunit, whereas SEQ ID NO:51 represents the complement of SEQ ID NO:49. Translation of SEQ ID NO:66 yields a predicted protein denoted herein as PCaIL-12$_{511}$, also denoted as SEQ ID NO:67.

Nucleic acid molecules and proteins of the present invention having specific sequence identifiers are described in Table 1.

TABLE 1

Sequence identification numbers (SEQ ID NOs) and their corresponding nucleic acid molecule or proteins.

| SEQ ID NO: | description |
|---|---|
| 1 | nFeIL-18-N$_{514}$ coding strand |
| 2 | PFeIL-18-N$_{133}$ |
| 3 | nFeIL-18-N$_{514}$ complementary strand |
| 4 | nFeIL-18-C$_{502}$ coding strand |
| 5 | PFeIL-18-C$_{154}$ |
| 6 | nFeIL-18-C$_{502}$ complementary strand |
| 7 | nFeIL-18$_{607}$ coding strand |
| 8 | PFeIL-18$_{192}$ |
| 9 | nFeIL-18$_{576}$ coding strand: coding sequence for full-length feline IL-18 protein |
| 10 | nFeIL-18$_{607}$ complementary strand to SEQ ID NO: 7 |
| 11 | nFeIL-18$_{471}$ coding strand: coding sequence for mature feline IL-18 protein |
| 12 | PFeIL-18$_{157}$ |
| 13 | nFeIL-18$_{471}$ complementary strand |
| 14 | nFeCasp-1$_{1233}$ coding strand |
| 15 | PFeCasp-1$_{410}$ |
| 16 | nFeCasp-1$_{1233}$ complementary strand |
| 17 | nFeCasp-1-N$_{526}$ coding strand |
| 18 | PFeCasp-1-N$_{169}$ |
| 19 | nFeCasp-1-N$_{526}$ complementary strand |
| 20 | nFeCasp-1-C$_{500}$ coding strand |
| 21 | PFeCasp-1-C$_{120}$ |
| 22 | nFeCasp-1-C$_{500}$ complementary strand |
| 23 | nFeCasp-1$_{1230}$ coding strand: coding sequence for feline caspase-1 protein |
| 24 | PFeCasp-1$_{410}$ |
| 25 | nFeCasp-1$_{1230}$ complementary strand |
| 26 | nFeIL-12p40$_{921}$ coding strand: coding sequence for feline mature IL-12p40 subunit |
| 27 | PFeIL-12p40$_{307}$ |
| 28 | nFeIL-12p40$_{921}$ complementary strand |
| 29 | nFeIL-12p40$_{987}$ coding strand: coding sequence for feline full-length IL-12p40 subunit |
| 30 | PFeIL-12p40$_{329}$ |
| 31 | nFeIL-12p40$_{987}$ complementary strand |
| 32 | nFeIL-12p35$_{666}$ coding strand: coding sequence for feline full-length IL-12p35 subunit |
| 33 | PFeIL-12p35$_{222}$ |

TABLE 1-continued

Sequence identification numbers (SEQ ID NOs) and their corresponding nucleic acid molecule or proteins.

| SEQ ID NO: | description |
|---|---|
| 34 | nFeIL-12p35$_{666}$ complementary strand |
| 35 | nFeIL-12p35$_{591}$ coding strand: coding sequence for feline mature IL-12p35 subunit |
| 36 | PFeIL-12p35-N$_{187}$ |
| 37 | nFeIL-12p35$_{591}$ complementary strand |
| 38 | nFeIL-12$_{1599}$ coding strand |
| 39 | PFeIL-12$_{533}$ |
| 40 | nFeIL-12$_{1599}$ complementary strand |
| 41 | nFeIL-18$_{576}$ complementary strand to SEQ ID NO: 9 |
| 42 | not used--inactive |
| 43 | nFeIL-12$_{1533}$ coding strand |
| 44 | PFeIL-12$_{511}$ |
| 45 | nFeIL-12$_{1533}$ complementary strand |
| 46 | nCaIL-12p35$_{666}$ coding strand: coding strand for canine full-length IL-12p35 subunit |
| 47 | PCaIL-12p35$_{222}$ |
| 48 | nCaIL-12p35$_{666}$ complementary strand |
| 49 | nCaIL-12p35$_{591}$ coding strand |
| 50 | PCaIL-12p35$_{197}$ |
| 51 | nCaIL-12p35$_{591}$ complementary strand |
| 52 | nCaIL-12p40$_{921}$ coding strand: coding sequence for mature form canine IL-12 p40 subunit |
| 53 | PCaIL-12p40$_{307}$ |
| 54 | nCaIL-12p40$_{921}$ reverse complement |
| 55 | nFeIL-12p40-N$_{985}$ coding sequence |
| 56 | PCaIL-12p40-N$_{328}$ |
| 57 | nFeIL-12p40-N$_{985}$ complementary strand |
| 58 | nCaIL-12p40$_{987}$ coding strand: coding sequence for full-length canine IL-12 p40 subunit |
| 59 | PCaIL-12p40$_{329}$ |
| 60 | nCaIL-12p40$_{987}$ complementary strand |
| 61 | nCaIL-12$_{1599}$ coding strand |
| 62 | PCaIL-12$_{533}$ |
| 63 | nCaIL-12$_{1599}$ complementary strand |
| 64 | not used-inactive |
| 65 | not used-inactive |
| 66 | nCaIL-12$_{1533}$ coding strand |
| 67 | PCaIL-12$_{511}$ |
| 68 | nCaIL-12$_{1533}$ complementary strand |
| 101 | nFeIL-12p35-N$_{561}$ coding strand |
| 102 | PFeIL-12p35-N$_{187}$ |
| 103 | nFeIL-12p35-N$_{561}$ complementary strand |
| 104 | nCaIL-12p35$_{1455}$ coding strand |
| 105 | PCaIL-12p35$_{222}$ |
| 106 | nCaIL-12p35$_{1455}$ complementary strand |
| 107 | nCaIL-12p40$_{2267}$ coding strand |
| 108 | PcaIL-12p40$_{329}$ |
| 109 | nCaIL-12p40$_{2267}$ complementary strand |

Particularly preferred nucleic acid molecules encoding feline IL-18 proteins are nFeIL-18-N$_{514}$, nFeIL-18-C$_{502}$ nFeIL-18$_{607}$, nFeIL-18$_{576}$, and nFeIL-18$_{471}$, the coding strands of which are represented by SEQ ID NO:1, SEQ ID NO:4, SEQ ID NO:7, SEQ ID NO:9 and SEQ ID NO:11, respectively.

Particularly preferred nucleic acid molecules encoding feline caspase-1 proteins are nFeCasp-1$_{1233}$, nFeCasp-1-N$_{526}$, nFeCasp-1-C$_{500}$ and nFeCasp-1$_{1230}$, the coding strands of which are represented by SEQ ID NO:14, SEQ ID NO:17, SEQ ID NO:20, and SEQ ID NO:23 respectively.

Particularly preferred nucleic acid molecules encoding canine and feline IL-12 p35 and p40 subunit proteins are nFeIL-12p40-N$_{985}$, nFeIL-12p40$_{987}$, nFeIL-12p40$_{921}$, nFeIL-12p35$_{666}$, nFeIL-12p35-N$_{561}$, nFeIL-12p35$_{591}$, nCaIL-12p35$_{666}$, nCaIL-12p35$_{1455}$, nCaIL-12p35$_{591}$, nCaIL-12p40$_{2267}$, nCaIL-12p40$_{921}$, and nCaIL-12p40$_{987}$, Coding strands of which are represented by SEQ ID NO:28, SEQ ID NO:31, SEQ ID NO:32, SEQ ID NO:35, SEQ ID NO:46, SEQ ID NO:49, SEQ ID NO:52, SEQ ID NO:55, SEQ ID NO:58, SEQ ID NO:101, SEQ ID NO:104, and SEQ ID NO:107.

Additional preferred nucleic acid molecules encoding canine and feline IL-12 single chain proteins are nFeIL-$12_{1533}$, nFeIL-$12_{1599}$, nCaIL-$12_{2533}$, nCaIL-$12_{1599}$, the coding strands of which are represented by SEQ ID NO:43, SEQ ID NO:38, SEQ ID NO:61, and SEQ ID NO:66.

One embodiment of the present invention includes an isolated nucleic acid molecule that is selected from a group of nucleic acid molecules. One member of this group includes an isolated nucleic acid molecule that is selected from the group consisting of SEQ ID NO:1, SEQ ID NO:3, SEQ ID NO:4, SEQ ID NO:6, SEQ ID NO:7, SEQ ID NO:10, SEQ ID NO:9, SEQ ID NO:41, SEQ ID NO:11, and SEQ ID NO:13; and a nucleic acid molecule comprising at least 70 contiguous nucleotides identical in sequence to at least 70 contiguous nucleotides of a nucleic acid sequence selected from the group consisting of SEQ ID NO:1, SEQ ID NO:3, SEQ ID NO:4, SEQ ID NO:6, SEQ ID NO:7, SEQ ID NO:10, SEQ ID NO:9, SEQ ID NO:41, SEQ ID NO:11, and SEQ ID NO:13. Another member of this group of nucleic acid molecules includes an isolated nucleic acid molecule that is selected from the group consisting of SEQ ID NO:14, SEQ ID NO:16, SEQ ID NO:17, SEQ ID NO:19, SEQ ID NO:20, SEQ ID NO:22, SEQ ID NO:23, and SEQ ID NO:25; and a nucleic acid molecule comprising at least 70 contiguous nucleotides identical in sequence to at least 70 contiguous nucleotides of a nucleic acid sequence selected from the group consisting of SEQ ID NO:14, SEQ ID NO:16, SEQ ID NO:17, SEQ ID NO:19, SEQ ID NO:20, SEQ ID NO:22, SEQ ID NO:23, and SEQ ID NO:25. Another member of this group of nucleic acid molecules includes an isolated nucleic acid molecule that is selected from the group consisting of a nucleic acid molecule comprising (a) an isolated nucleic acid molecule comprising a nucleic acid sequence selected from the group consisting of SEQ ID NO:26, SEQ ID NO:29, and a nucleic acid sequence comprising at least 44 contiguous nucleotides identical in sequence to at least 44 contiguous nucleotides of a nucleic acid sequence selected from the group consisting of SEQ ID NO:26 and SEQ ID NO:9; (b) a nucleic acid linker of $(XXX)_n$ wherein n=0 to 60; and (c) an isolated nucleic acid molecule comprising a nucleic acid sequence selected from the group consisting of SEQ ID NO:32, SEQ ID NO:35, and a nucleic acid molecule comprising at least 44 contiguous nucleotides identical in sequence to at least 44 contiguous nucleotides of a nucleic acid sequence selected from the group consisting of SEQ ID NO:32 and SEQ ID NO:35, such that a nucleic acid molecule of this particular group encodes a feline IL-12 protein. Another member of this group of nucleic acid molecules includes an isolate nucleic acid molecule selected from the group consisting of a nucleic acid molecule comprising (a) an isolated nucleic acid molecule comprising a nucleic acid sequence selected from the group consisting of SEQ ID NO:52 and SEQ ID NO:58, and a nucleic acid sequence comprising at least 47 contiguous nucleotides identical in sequence to at least 47 contiguous nucleotides of a nucleic acid sequence selected from the group consisting of SEQ ID NO:46 and SEQ ID NO:49; (b) a nucleic acid linker of $(XXX)_n$ wherein n=0 to 60; and (c) an isolated nucleic acid molecule comprising a nucleic acid sequence selected from the group consisting of SEQ ID NO:46, SEQ ID NO:49, and a nucleic acid molecule comprising at least 47 contiguous nucleotides identical in sequence to at least 47 contiguous nucleotides of a nucleic acid sequence selected from the group consisting of SEQ ID NO:46 and SEQ ID NO:49, such that a nucleic acid molecule of this particular group encodes a canine IL-12 single chain protein.

The phrase, a nucleic acid molecule comprising at least "x" contiguous nucleotides identical in sequence to at least "x" contiguous nucleotides of a nucleic acid molecule selected from the group consisting of SEQ ID NO:"y", refers to an "x"-nucleotide in length nucleic acid molecule that is identical in sequence to an "x"-nucleotide portion of SEQ ID NO:"y", as well as to nucleic acid molecules that are longer in length than "x". The additional length may be in the form of nucleotides that extend from either the 5' or the 3' end(s) of the contiguous identical "x"-nucleotide portion. The 5' and/or 3' extensions can include one or more extensions that have no identity to an immunoregulatory molecule of the present invention, as well as extensions that show similarity or identity to cited nucleic acids sequences or portions thereof.

Preferred portions, or lengths, for feline IL-18, feline caspase-1, feline IL-12 single chain, and canine IL-12 single chain nucleic acid molecules of the present invention include nucleic acid molecules of at least 40 nucleotides in length, at least 43 nucleotides in length, at least 44 nucleotides in length, at least 47 nucleotides in length, at least 50 nucleotides in length, at least 55 nucleotides in length, at least 60 nucleotides in length, at least 65 nucleotides in length, at least 70 nucleotides in length, at least 75 nucleotides in length, at least 80 nucleotides in length, at least 85 nucleotides in length, at least 90 nucleotides in length, at least 95 nucleotides in length, at least 100 nucleotides in length, at least 120 nucleotides in length, at least 140 nucleotides in length, at least 160 nucleotides in length, at least 180 nucleotides in length, at least 200 nucleotides in length, at least 250 nucleotides in length, at least 300 nucleotides in length, at least 350 nucleotides in length, at least 400 nucleotides in length, at least 450 nucleotides in length, at least 500 nucleotides in length, at least 600 nucleotides in length, at least 700 nucleotides in length, at least 800 nucleotides in length, at least 900 nucleotides in length, and a full-length molecule. Particularly preferred portions, or lengths, of the nucleic acid molecules of the present invention include nucleic acids of at least 43 nucleotides, 44 nucleotides, 47 nucleotides, 70 nucleotides, and a full length molecule.

One embodiment of a protein and/or nucleic acid molecule of the present invention is a fusion nucleic acid and/or protein that includes either a feline IL-18, caspase-1, feline IL-12 single chain, and canine IL-12 single chain nucleic acid molecule and/or protein of the present invention domain, each attached to one or more fusion segments. Suitable fusion segments for use with the present invention include, but are not limited to, segments that can: link two or more nucleic acids and/or proteins of the present invention, to form multimeric forms of a nucleic acids and/or protein of the present invention; enhance a nucleic acid molecules or protein's stability; enhance the biological activity of a nucleic acid molecule and/or protein of the present invention; and/or assist in purification a molecule of the present invention (e.g., by affinity chromatography). A suitable fusion segment can be a domain of any size that has the desired function (e.g., imparts increased stability, enhanced activity, and/or simplifies purification of a protein). Fusion segments can be joined to amino and/or carboxyl termini of the IL-18-containing domain, or the caspase-1 ligand-containing domain, or the IL-12 p40-containing domain, or the IL-12 p35-containing domain, or the IL-12 single chain-containing domain, of a protein and/or nucleic acid and can be susceptible to cleavage in order to enable straight-forward recovery of the protein and/or nucleic acid molecule. Fusion proteins are preferably produced by culturing a recombinant cell transformed with a fusion nucleic acid molecule that encodes a protein including the fusion segment attached to either the carboxyl and/or amino terminal end of a feline IL-18, feline caspase-1, feline IL-12 p35 subunit, feline IL-12 p40 subunit, feline IL-12 single chain, canine IL-12 p35 subunit, canine IL-12 p40 subunit, and/or canine IL-12 single chain-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a FLAGS peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

The phrase, a nucleic acid linker, is a term known to those skilled in the art, and refers to a nucleic acid linker that can link, or attach, nucleic acid molecules, in such a manner that expression of the nucleic acid molecules produces one fusion protein as expression product. A linker can be any nucleotide sequence that directs expression of a single fusion polypeptide from a nucleotide molecule which includes two or more nucleic acid molecules of the present invention, wherein the fusion polypeptide has appropriate biological activity. Preferably, a nucleic acid linker of the present invention comprises nucleotides arranged in codons, (i.e., 3 nucleotides that, when transcribed, code for an amino acid residue), and the linker does not contain any stop codons in frame. A linker is represented herein as $(XXX)_n$, where X is the designation of a variable nucleotide and n refers to the number of codons. The length of the nucleic acid linker may be of any length that permits expression of the fusion protein. More preferably, the length of the nucleic acid linker is from about 0 codons to about 60 codons, or from about 0 nucleotides to about 180 nucleotides. A particularly preferred linker includes SEQ ID NO:83. Appropriate biological activity includes the ability of such a fusion protein to elicit an immune response against a protein of the present invention, selectively binding an antibody raised against a protein of the present invention, and exhibiting the immunoregulatory activity of a protein of the present invention.

A single chain IL-12 protein of the present invention includes single chain IL-12 proteins comprising an IL-12 p35 subunit of the present invention at the N-terminus of the single chain protein and an IL-12 p40 subunit of the present invention at the C-terminus of the single chain protein, with the linker between the p35 subunit and the p40 subunit. Preferred single chain IL-12 proteins comprise an IL-12 p40 of the present invention at the N-terminus of the single chain protein and an IL-12 p40 subunit of the present invention at the C-terminus of the single chain protein, with the linker in between the subunits.

Another embodiment of the present invention includes an isolated nucleic acid molecule that is selected from the group consisting of: (i) a nucleic acid molecule having a nucleic acid sequence that is at least 92 percent identical to a nucleic acid sequence selected from the group consisting of SEQ ID NO:1, SEQ ID NO:3, SEQ ID NO:4, SEQ ID NO:6, SEQ ID NO:7, SEQ ID NO:10, SEQ ID NO:9, SEQ ID NO:41, SEQ ID NO:11, and SEQ ID NO:13; and (ii) a nucleic acid molecule comprising a fragment of a nucleic acid molecule of (i) wherein said fragment is at least 80 nucleotides in length. Preferred nucleic acid molecules include nucleic acid sequences that are at least 92%, at least 93%, at least 94%, more preferably at least 95% identical, and even more preferably at least about 98% identical to SEQ ID NO:1, SEQ ID NO:3, SEQ ID NO:4, SEQ ID NO:6, SEQ ID NO:7, SEQ ID NO:10, SEQ ID NO:9, SEQ ID NO:41, SEQ ID NO:11, and SEQ ID NO:13. Preferred fragment lengths include fragments of SEQ ID NO:1, SEQ ID NO:3, SEQ ID NO:4, SEQ ID NO:6, SEQ ID NO:7, SEQ ID NO:10, SEQ ID NO:9, SEQ ID NO:41, SEQ ID NO:11, and SEQ ID NO:13 which are at least 75 nucleotides in length, which are at least 80 nucleotides in length, which are at least 85 nucleotides in length, which are at least 90 nucleotides in length, which are at least 100 nucleotides in length, which are at least 120 nucleotides in length, which are at least 150 nucleotides in length, which are at least 200 nucleotides in length, which are at least 300 nucleotides in length, which are at least 400 nucleotides in length, which are at least 500 nucleotides in length, which are at least 600 nucleotides in length, and which preferably are full-length.

Another embodiment of the present invention includes an isolated nucleic acid molecule that is selected from the group consisting of: (i) a nucleic acid molecule having a nucleic acid sequence that is at least 85 percent identical to a nucleic acid sequence selected from the group consisting of SEQ ID NO:14, SEQ ID NO:16, SEQ ID NO:17, SEQ ID NO:19, SEQ ID NO:20, SEQ ID NO:22, SEQ ID NO:23, and SEQ ID NO:25; and (ii) a nucleic acid molecule comprising a fragment of a nucleic acid molecule of (i) wherein said fragment is at least 85 nucleotides in length. Preferred nucleic acid molecules include nucleic acid sequences that are at least 85%, preferably at least 87%, more preferably at least 90%, even more preferably at least 95% identical to SEQ ID NO:14, SEQ ID NO:16, SEQ ID NO:17, SEQ ID NO:19, SEQ ID NO:20, SEQ ID NO:22, SEQ ID NO:23, and SEQ ID NO:25. Preferred fragment lengths include fragments of SEQ ID NO:14, SEQ ID NO:16, SEQ ID NO:17, SEQ ID NO:19, SEQ ID NO:20, SEQ ID NO:22, SEQ ID NO:23, and SEQ ID NO:25 which are at least 70 nucleotides in length, which are at least 80 nucleotides in length, which are at least 85 nucleotides in length, which are at least 90 nucleotides in length, which are at least 100 nucleotides in length, which are at least 200 nucleotides in length, which are at least 300 nucleotides in length, which are at least 400 nucleotides in length, which are at least 500 nucleotides in length, which are at least 600 nucleotides in length, or which preferably are full-length.

Another embodiment of the present invention is an isolated nucleic acid molecule selected from the group consisting of: (i) a nucleic acid molecule comprising (a) a nucleic acid molecule comprising a nucleic acid sequence that is at least 87 percent identical to a nucleic acid sequence selected from the group consisting of SEQ ID NO:26 and SEQ ID NO:29, or a fragment thereof of at least 55 nucleotides in length; (b) a nucleic acid linker of $(XXX)_n$ wherein n=0 to 60, and (c) a nucleic acid molecule comprising a nucleic acid sequence that is at least 87 percent identical to a nucleic acid sequence selected from the group consisting of SEQ ID NO:32 and SEQ ID NO:35, or a fragment thereof of at least 55 nucleotides in length, such that said nucleic acid molecule of (i) encodes a feline IL-12 single chain protein; and a nucleic acid molecule fully complementary to the coding strand of a nucleic acid molecule as set forth in (i). Preferred nucleic acid molecules include nucleic acid sequences that are at least 87%, at least 88%, at least 89%, more preferably at least 90%, even more preferably at least 95% identical to SEQ ID NO:26, SEQ ID NO:29, SEQ ID NO:32, and SEQ ID NO:35. Preferred fragment lengths include fragments of SEQ ID NO:26, SEQ ID NO:29, SEQ ID NO:32, and SEQ ID NO:35, which are at least 55 nucleotides in length, which are at least 60 nucleotides in length, which are at least about 65 nucleotides in length, which are at least 70 nucleotides in length, which are at least 80 nucleotides in length, which are at least 90 nucleotides in length, which are at least 100 nucleotides in length, which are at least 200 nucleotides in length, which are at least 300 nucleotides in length, which are at least 400 nucleotides in length, which are at least 500 nucleotides in length, which are at least 600 nucleotides in length, or which preferably are full-length.

Another embodiment of the present invention is an isolated nucleic acid molecule selected from the group consisting of: (i) a nucleic acid molecule comprising (a) a nucleic acid molecule comprising a nucleic acid sequence that is at least 87 percent identical to a nucleic acid sequence selected from the group consisting of SEQ ID NO:52 and SEQ ID NO:58, or a fragment thereof of at least 55 nucleotides in length; (b) a nucleic acid linker of $(XXX)_n$ wherein n=0 to 60; and (c) a nucleic acid molecule comprising a nucleic acid sequence that is at least 87 percent identical to a nucleic acid sequence selected from the group consisting of SEQ ID NO:46 and SEQ ID NO:49, or a fragment thereof of at least 55 nucleotides in length, such that said nucleic acid molecule of (i) encodes a canine IL-12 single chain protein; and a nucleic acid molecule fully complementary to the coding strand of a nucleic acid molecule as set forth in (i). Preferred nucleic acid molecules include nucleic acid sequences that are at least 87%, at least 88%, at least 89%, more preferably at least 90%, even more preferably at least 95% identical to SEQ ID NO:52, SEQ ID NO:58, SEQ ID NO:46, and SEQ ID NO:49. Preferred fragment lengths include fragments of SEQ ID NO:52, SEQ ID NO:58, SEQ ID NO:46, and SEQ ID NO:49, which are at least 55 nucleotides in length, which are at least 60 nucleotides in length, which are at least about 65 nucleotides in length, which are at least 70 nucleotides in length, which are at least 80 nucleotides in length, which are at least 90 nucleotides in length, which are at least 100 nucleotides in length, which are at least 200 nucleotides in length, which are at least 300 nucleotides in length, which are at least 400 nucleotides in length, which are at least 500 nucleotides in length, which are at least 600 nucleotides in length, or which preferably are full-length.

Preferred portions, or fragments, of a feline IL-18, feline caspase-1, canine or feline IL-12 single chain protein of the present invention include at least 15 amino acids, at least 20 amino acids, at least 25 amino acids, at least 30 amino acids, at least 35 amino acids, at least 40 amino acids, at least 45 amino acids, at least 50 amino acids, at least 60 amino acids, at least 75 amino acids or at least 100 amino acids. An IL-18 or IL-12 single chain protein of the present invention can include at least a portion of an IL-18 or IL-12 single chain protein that is capable of binding to an IL-18 or IL-12 receptor, respectively. These receptors are known to those of skill in the art, and are described in Janeway et al., in *Immunobiology, the Immune System in Health and Disease*, Garland Publishing, Inc., NY, 1996 (which is incorporated herein by this reference in its entirety). The IL-18 or IL-12 receptor-binding portion of an IL-18 or IL-12 protein, respectively, can be determined by incubating the protein with an isolated IL-18 or IL-12 receptor, as appropriate, or a cell having an IL-18 or IL-12 receptor on its surface, as appropriate. IL-18 or IL-12 protein binding to purified IL-18 or IL-12 receptor, respectively, can be determined using methods known in the art including BIACORE® screening, confocal immunofluorescent microscopy, immunoprecipitation, gel chromatography, determination of inhibition of binding of antibodies that bind specifically to the IL-18 or IL-12 binding domain of an IL-18 or IL-12 receptor, ELISA using an IL-18 or IL-12 receptor, respectively, labeled with a detectable tag such as an enzyme or chemiluminescent tag or yeast-2 hybrid technology. A caspase-1 protein of the present invention can include at least a portion of a caspase-1 protein that is capable cleaving pro-IL-18 to mature IL-18. The ability of the caspase-1 protein to cleave IL-18 can be determined by methods known in the art, including methods such as BIACORE® screening, confocal immunofluorescent microscopy, immunoprecipitation, gel chromatography, determination of inhibition of cleavage upon binding of antibodies that bind specifically to either IL-18 or caspase-1, and enzymatic assays.

The present invention also includes mimetopes of feline IL-18, feline caspase-1, and canine and/or feline IL-12 single chain proteins of the present invention. As used herein, a mimetope of an immunoregulatory protein of the present invention refers to any compound that is able to mimic the activity of such a feline IL-18, feline caspase-1, and canine and/or feline IL-12 single chain protein, respectively, often because the mimetope has a structure that mimics the particular protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and/or synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

Furthermore, it is known in the art that there are commercially available computer programs for determining the degree of similarity between two nucleic acid or protein sequences. These computer programs include various known methods to determine the percentage identity and the number and length of gaps between hybrid nucleic acid molecules or proteins. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, the SEQLAB® WISCONSIN PACKAGE® Version 10.0-UNIX sequence analysis software, available from Genetics Computer Group, Madison, Wis.; and DNASIS® sequence analysis software, version 2.0 (hereinafter "DNAsis"), available from Hitachi Software, San Bruno, Calif. Such software programs represent a collection of algorithms paired with a graphical user interface for using the algorithms. The DNAsis version 2.0 software and SEQLAB® WISCONSIN PACKAGE® Version 10.0-UNIX software, for example, employ a particular algorithm, the Needleman-Wunsch algorithm to perform pair-wise comparisons between two sequences to yield a percentage identity score, see Needleman, S. B. and Wunsch, C. D., 1970, *J. Mol. Biol.*, 48, 443, which is incorporated herein by reference in its entirety. Such algorithms, including the Needleman-Wunsch algorithm, are commonly used by those skilled in the nucleic acid and amino acid sequencing art to compare sequences. A preferred method to determine percent identity among amino acid sequences and also among nucleic acid sequences includes using the Needleman-Wunsch algorithm, available in the SEQLAB® WISCONSIN PACKAGE® Version 10.0-UNIX software (hereinafter "SeqLab"), using the Pairwise Comparison/Gap function with the nwsgapdna.cmp scoring matrix, the gap creation penalty and the gap extension penalties set at default values, and the gap shift limits set at maximum (hereinafter referred to as "SeqLab default parameters"). An additional preferred method to determine percent identity among amino acid sequences and also among nucleic acid sequences includes using the Higgins-Sharp algorithm, available in the DNAsis version 2.0 software, with the gap penalty set at 5, the number of top diagonals set at 5, the fixed gap penalty set at 10, the k-tuple set at 2, the window size set at 5, and the floating gap penalty set at 10. A particularly preferred method to determine percent identity among amino acid sequences and also among nucleic acid sequences includes using the Needleman-Wunsch algorithm available in the DNAsis version 2.0 software, using the GCG default parameter function.

Another embodiment of the present invention includes a nucleic acid molecule that is selected from the group consisting of: SEQ ID NO:1, SEQ ID NO:3, SEQ ID NO:4, SEQ ID NO:6, SEQ ID NO:7, SEQ ID NO:10, SEQ ID NO:9, SEQ ID NO:41, SEQ ID NO:11, SEQ ID NO:13, SEQ ID NO:14, SEQ ID NO:16, SEQ ID NO:17, SEQ ID NO:19, SEQ ID NO:20, SEQ ID NO:22, SEQ ID NO:23, SEQ ID NO:25, SEQ ID NO:38, SEQ ID NO:40, SEQ ID NO:43, SEQ ID NO:45, SEQ ID NO:61, SEQ ID NO:63, SEQ ID NO:66, and SEQ ID NO:68, and a nucleic acid molecule comprising an allelic variant of a nucleic acid molecule comprising any of said nucleic acid sequences. An allelic variant of a feline and/or canine nucleic acid molecule of the present invention, including the particular SEQ ID NO's cited herein, is a gene that occurs at essentially the same locus (or loci) in the genome as the gene including the particular SEQ ID NO's cited herein, but which, due to natural variations caused by, for example, mutation or recombination, has a similar but not identical sequence. Also included in the term allelic variant are allelic variants of cDNAs derived from such genes. Because natural selection typically selects against alterations that affect function, allelic variants usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to be found within a given animal, since the respective genomes are diploid, and sexual reproduction will result in the reassortment of alleles. As such, a nucleic acid molecule of the present invention can be an allelic variant that includes a similar but not identical sequence to SEQ ID NO:1, SEQ ID NO:3, SEQ ID NO:4, SEQ ID NO:6, SEQ ID NO:7, SEQ ID NO:10, SEQ ID NO:9, SEQ ID NO:41, SEQ ID NO:11, SEQ ID NO:13, SEQ ID NO:14, SEQ ID NO:16, SEQ ID NO:17, SEQ ID NO:19, SEQ ID NO:20, SEQ ID NO:22, SEQ ID NO:23, SEQ ID NO:25, SEQ ID NO:38, SEQ ID NO:40, SEQ ID NO:43, SEQ ID NO:45, SEQ ID NO:61, SEQ ID NO:63, SEQ ID NO:66, and SEQ ID NO:68, and/or any other nucleic acid molecule cited herein.

In another embodiment of the present invention, a nucleic acid molecule of the invention is selected from the group consisting of (a) a nucleic acid molecule comprising a nucleic acid sequence that encodes a protein having an amino acid sequence selected from the group consisting of SEQ ID NO:2, SEQ ID NO:5, SEQ ID NO:8, SEQ ID NO:12, SEQ ID NO:15, SEQ ID NO:18, SEQ ID NO:21, SEQ ID NO:24, SEQ ID NO:39, SEQ ID NO:44, SEQ ID NO:62, and SEQ ID NO:67, and (b) a nucleic acid molecule comprising an allelic variant of a nucleic acid molecule encoding a protein having any of said amino acid sequences of (a).

Another embodiment of the present invention includes feline IL-18 nucleic acid molecules of the present invention, wherein said nucleic acid molecules encode a protein having a function selected from the group consisting of (i) eliciting an immune response against an IL-18 protein having an amino acid sequence selected from the group consisting of SEQ ID NO:2, SEQ ID NO:5, SEQ ID NO:8, and SEQ ID NO:12; (ii) selectively binding to an antibody raised against an IL-18 protein having an amino acid sequence selected from the group consisting of SEQ ID NO:2, SEQ ID NO:5, SEQ ID NO:8, and SEQ ID NO:12, and (iii) exhibiting IL-18 activity. Methods to elicit an immune response and to determine whether an antibody can selectively bind to a particular protein or antigen are known in the art, see, for example, Harlow, et al. (1988) Antibodies, a Laboratory Manual, Cold Spring Harbor Labs Press; Harlow, et al. is incorporated by reference herein in its entirety. Methods to determine whether an IL-18 protein has IL-18 activity are known in the art, and include determining whether IL-18 has the activity of stimulating T cells to produce interferon gamma (IFN-γ).

Another embodiment of the present invention includes caspase-1 nucleic acid molecules of the present invention that encode a protein having a function selected from the group consisting of (i) eliciting an immune response against a caspase-1 protein having an amino acid sequence selected from the group consisting of SEQ ID NO:15, SEQ ID NO:18, SEQ ID NO:21, and SEQ ID NO:24, (ii) selectively binding to an antibody raised against caspase-1 protein having an amino acid sequence selected from the group consisting of SEQ ID NO:15, SEQ ID NO:18, SEQ ID NO:21, and SEQ ID NO:24, and (iii) exhibiting caspase-1 activity. Methods to elicit an immune response and to determine whether an antibody can selectively bind to a particular protein or antigen are known in the art, see, for example, Harlow, et al. (1988) Antibodies, a Laboratory Manual, Cold Spring Harbor Labs Press; Harlow, et al. is incorporated by reference herein in its entirety. Methods to determine whether a caspase-1 protein has caspase-1 activity are known in the art, and include, for example, determining if the caspase-1 protein has the ability to cleave the precursor form of IL-18 resulting in a biologically active IL-18.

Another embodiment of the present invention includes canine and feline IL-12 single chain nucleic acid molecules of the present invention, wherein a said nucleic acid molecule encodes a protein having a function selected from the group consisting of (i) eliciting an immune response against an IL-12 protein having an amino acid selected from the group consisting of SEQ ID NO:39, SEQ ID NO:44, SEQ ID NO:62, and SEQ ID NO:67, (ii) selectively binding to an antibody raised against an IL-12 protein having an amino acid sequence selected from the group consisting from the group of SEQ ID NO:27, SEQ ID NO:30, SEQ ID NO:33, SEQ ID NO:36, SEQ ID NO:47, SEQ ID NO:50, SEQ ID NO:53, and SEQ ID NO:59, SEQ ID NO:102, SEQ ID NO:105, SEQ ID NO:108, SEQ ID NO:39, SEQ ID NO:40, SEQ ID NO:62, and/or SEQ ID NO:67, and (iii) exhibiting IL-12 activity. Methods to elicit an immune response and to determine whether an antibody can selectively bind to a particular protein or antigen are known in the art, see, for example, Harlow, et al. (1988) Antibodies, a Laboratory Manual, Cold Spring Harbor Labs Press; Harlow, et al. is incorporated by reference herein in its entirety. Methods to determine whether an IL-12 protein has IL-12 activity are known in the art, and include determining if IL-12 has the activity of stimulating T cells to produce interferon gamma (IFN-γ).

A preferred nucleic acid molecule of the present invention includes a nucleic acid molecule selected from the group consisting of nFeIL-12p40-$N_{985}$, nFeIL-12p40$_{987}$, nFeIL-12p40$_{921}$, nFeIL-12p35$_{666}$, nFeIL-12p35-$N_{561}$, nFeIL- 12p35$_{591}$, nCaIL-12p35$_{666}$, nCaIL-12p35$_{1455}$, nCaIL-12p35$_{591}$, nCaIL-12p40$_{2267}$, nCaIL-12p40$_{921}$, nCaIL-12p40$_{98}$, nFeIL-12$_{1599}$, nFeIL-12$_{1533}$ nCaIL-12$_{1599}$, and nCaIL-12$_{1533}$.

Another embodiment of the present invention includes an isolated nucleic acid molecule selected from the group consisting of: a nucleic acid molecule having a nucleic acid sequence encoding an IL-18 protein selected from the group consisting of: a protein selected from the group consisting of (a) a protein having an amino acid sequence that is at least 92 percent identical to an amino acid sequence selected from the group consisting of SEQ ID NO:2, SEQ ID NO:5, SEQ ID NO:8, and SEQ ID NO:12, and (b) a protein comprising a fragment of a protein of (a), wherein said fragment is at least 30 amino acids in length; and a protein comprising at least 25 contiguous amino acids identical in sequence to at least 25 contiguous amino acids of an amino acid sequence selected from the group consisting of SEQ ID NO:2, SEQ ID NO:5, SEQ ID NO:8, and SEQ ID NO:12. Preferred IL-18 proteins include proteins that are at least about 90 percent identical, preferably at least about 92 percent identical, preferably at least about 94 percent identical, preferably at least about 96 percent identical, and even more preferably at least about 98 percent identical to SEQ ID NO:2, SEQ ID NO:5, SEQ ID NO:8, and SEQ ID NO:12 or fragments thereof. Preferred fragments of IL-18 proteins include fragments of SEQ ID NO:2, SEQ ID NO:5, SEQ ID NO:8, and SEQ ID NO:12 that are at least about 20 amino acids in length, at least about 30 amino acids in length, at least about 40 amino acids in length, at least about 50 amino acids in length, preferably at least about 75 amino acids in length, preferably at least about 100 amino acids in length, and more preferably are full-length. Preferred IL-18 proteins also include proteins that comprise at least 15 contiguous amino acids identical in sequence to at least 15 contiguous amino acids; at least 20 contiguous amino acids identical in sequence to at least 20 contiguous amino acids, preferably about 30 contiguous amino acids identical in sequence to at least 30 contiguous amino acids, preferably about 50 contiguous amino acids identical in sequence to at least 50 contiguous amino acids, preferably about 75 contiguous amino acids identical in sequence to at least 75 contiguous amino acids, preferably about 100 contiguous amino acids identical in sequence to at least 100 contiguous amino acids, and most preferably a full-length protein identical in sequence to a full-length protein of an amino acid sequence selected from the group consisting of SEQ ID NO:2, SEQ ID NO:5, SEQ ID NO:8, and SEQ ID NO:12.

Another embodiment of the present invention includes an isolated nucleic acid molecule selected from the group consisting of: a nucleic acid molecule having a nucleic acid sequence encoding caspase protein selected from the group consisting of: a protein selected from the group consisting of (a) a protein having an amino acid sequence that is at least 85 percent identical to an amino acid sequence selected from the group consisting of SEQ ID NO:15, SEQ ID NO:18, SEQ ID NO:21, and SEQ ID NO:24, and (b) a protein comprising a fragment of a protein of (a), wherein said fragment is at least 30 amino acids in length; and a protein comprising at least 25 contiguous amino acids identical in sequence to at least 25 contiguous amino acids of an amino acid sequence selected from the group consisting of SEQ ID NO:2, SEQ ID NO:5, SEQ ID NO:8, and SEQ ID NO:12. Preferred caspase-1 proteins include proteins that are at least about 85 percent identical, at least about 87 percent identical, preferably at least about 90 percent identical, preferably at least about 93 percent identical, more preferably at least about 95 percent identical, and even more preferably about 98 percent identical to SEQ ID NO:15, SEQ ID NO:18, SEQ ID NO:21, and SEQ ID NO:24 or fragments thereof. Preferred fragments of caspase-1 proteins include fragments of SEQ ID NO:15, SEQ ID NO:18, SEQ ID NO:21, and SEQ ID NO:24 include fragments that are at least about 20 amino acids in length, at least about 30 amino acids in length, at least about 40 amino acids in length, at least about 50 amino acids in length, at least about 60 amino acids in length, preferably at least about 75 amino acids in length, preferably at least about 100 amino acids in length, and more preferably are full-length. Preferred caspase-1 proteins also include proteins that comprise at least 25 contiguous amino acids identical in sequence to at least 25 contiguous amino acids; at least 20 contiguous amino acids identical in sequence to at least 20 contiguous amino acids, preferably about 30 contiguous amino acids identical in sequence to at least 30 contiguous amino acids, preferably about 50 contiguous amino acids identical in sequence to at least 50 contiguous amino acids, preferably about 75 contiguous amino acids identical in sequence to at least 75 contiguous amino acids, preferably about 100 contiguous amino acids identical in sequence to at least 100 contiguous amino acids, and most preferably a full-length protein identical in sequence to a full-length protein of an amino acid sequence selected from the group consisting of SEQ ID NO:15, SEQ ID NO:18, SEQ ID NO:21, and SEQ ID NO:24.

Another embodiment of the present invention includes a nucleic acid molecule having a nucleic acid sequence encoding an IL-12 single chain protein comprising an IL-12 p40 subunit domain linked to a IL-12 p35 subunit domain, wherein said p40 subunit domain is selected from the group consisting of: (i) a p40 subunit protein having an amino acid sequence that is at least 84 percent identical to an amino acid sequence selected from the group consisting of SEQ ID NO:27 and SEQ ID NO:30, (ii) a p40 subunit protein comprising a fragment of a protein of (i), wherein said fragment is at least 30 amino acids in length, and (iii) a p40 subunit protein comprising at least 23 contiguous amino acids identical in sequence to at least 23 contiguous amino acids of an amino acid sequence selected from the group consisting of SEQ ID NO:27 and SEQ ID NO:30, and wherein said p35 domain is selected from the group consisting of (i) a p35 subunit protein having an amino acid sequence that is at least 84 percent identical to an amino acid sequence selected from the group consisting of SEQ ID NO:33 and SEQ ID NO:36, (ii) a p35 subunit protein comprising a fragment of a protein of (i), wherein said fragment is at least 30 amino acids in length, and (iii) a p35 subunit protein comprising at least 23 contiguous amino acids identical in sequence to at least 23 contiguous amino acids of an amino acid sequence selected from the group consisting of SEQ ID NO:33 and SEQ ID NO:36. Preferred p40 subunit proteins and/or p35 subunit proteins include proteins that are at least about 84 percent identical, preferably at least about 87 percent identical, preferably at least about 90 percent identical, and even more preferably at least about 95 percent identical to SEQ ID NO:27, SEQ ID NO:30, SEQ ID NO:33, and SEQ ID NO:36 or fragments thereof. Preferred fragments of IL-12 single chain proteins include fragments of SEQ ID NO:27, SEQ ID NO:30, SEQ ID NO:33, and SEQ ID NO:36 include fragments that are at least about 30 amino acids in length, at least about 40 amino acids in length, at least about 50 amino acids in length, at least about 60 amino acids in length, preferably at least about 75 amino acids in length, preferably at least about 100 amino acids in length, and more preferably are full-length. Preferred IL-12 single chain proteins also include proteins that comprise at least 23 contiguous amino acids identical in sequence to at least 23 contiguous amino acids, preferably about 30 contiguous amino acids identical in sequence to at least 30 contiguous amino acids, preferably about 50 contiguous amino acids identical in sequence to at least 50 contiguous amino acids, preferably about 75 contiguous amino acids identical in sequence to at least 75 contiguous amino acids, preferably about 100 contiguous amino acids identical in sequence to at least 100 contiguous amino acids, and most preferably a full-length protein identical in sequence to a full-length protein of an amino acid sequence selected from the group consisting of SEQ ID NO:27, SEQ ID NO:30, SEQ ID NO:33, and SEQ ID NO:36.

Another embodiment of the present invention includes a nucleic acid molecule having a nucleic acid sequence encoding an IL-12 single chain protein comprising an IL-12 p40 subunit domain linked to a IL-12 p35 subunit domain, wherein said p40 subunit domain is selected from the group consisting of: (i) a p40 subunit protein having an amino acid sequence that is at least 84 percent identical to an amino acid sequence selected from the group consisting of SEQ ID NO:53 and SEQ ID NO:59, (ii) a p40 subunit protein comprising a fragment of a protein of (i), wherein said fragment is at least 40 amino acids in length, and (iii) a p40 subunit protein comprising at least 31 contiguous amino acids identical in sequence to at least 31 contiguous amino acids of an amino acid sequence selected from the group consisting of SEQ ID NO:53 and SEQ ID NO:59, and wherein said p35 domain is selected from the group consisting of (i) a p35 subunit protein having an amino acid sequence that is at least 84 percent identical to an amino acid sequence selected from the group consisting of SEQ ID NO:47 and SEQ ID NO:50, (ii) a p35 subunit protein comprising a fragment of a protein of (i), wherein said fragment is at least 40 amino acids in length, and (iii) a p35 subunit protein comprising at least 31 contiguous amino acids identical in sequence to at least 31 contiguous amino acids of an amino acid sequence selected from the group consisting of SEQ ID NO:47 and SEQ ID NO:50. Preferred p40 subunit proteins and/or p35 subunit proteins include proteins that are at least about 84 percent identical, preferably at least about 87 percent identical, preferably at least about 90 percent identical, and even more preferably at least about 95 percent identical to SEQ ID NO:47, SEQ ID NO:50, SEQ ID NO:53, and SEQ ID NO:59 or fragments thereof. Preferred fragments of IL-12 single chain proteins include fragments of SEQ ID NO:27, SEQ ID NO:30, SEQ ID NO:33, and SEQ ID NO:36 include fragments that are at least about 40 amino acids in length, at least about 50 amino acids in length, at least about 60 amino acids in length, at least about 70 amino acids in length, preferably at least about 80 amino acids in length, preferably at least about 100 amino acids in length, and more preferably are full-length. Preferred IL-12 single chain proteins also include proteins that comprise at least 31 contiguous amino acids identical in sequence to at least 31 contiguous amino acids, preferably about 35 contiguous amino acids identical in sequence to at least 35 contiguous amino acids, preferably about 50 contiguous amino acids identical in sequence to at least 50 contiguous amino acids, preferably about 75 contiguous amino acids identical in sequence to at least 75 contiguous amino acids, preferably about 100 contiguous amino acids identical in sequence to at least 100 contiguous amino acids, and most preferably a full-length protein identical in sequence to a full-length protein of an amino acid sequence selected from the group consisting of SEQ ID NO:47, SEQ ID NO:50, SEQ ID NO:53, and SEQ ID NO:59.

Another embodiment of the present invention includes a nucleic acid molecule comprising a nucleic acid sequence fully complementary to the coding strand of any of the nucleic acid molecules of the present invention. Another embodiment of the present invention includes a nucleic acid molecule that comprises a nucleic acid sequence that encodes a protein selected from the group consisting of an IL-18 protein, a caspase-1 protein, and an IL-12 single chain protein.

Another embodiment of the present invention includes a nucleic acid molecule that is selected from the group consisting of a nucleic acid molecule comprising a nucleic acid sequence encoding a protein comprising an amino acid sequence selected from the group consisting of SEQ ID NO:2, SEQ ID NO:5, SEQ ID NO:8, SEQ ID NO:12, SEQ ID NO:15, SEQ ID NO;18, SEQ ID NO:21, SEQ ID NO:24, SEQ ID NO:39, SEQ ID NO:44, SEQ ID NO:62, and SEQ ID NO:67; and a nucleic acid molecule comprising an allelic variant of a nucleic acid molecule encoding a protein having any of said nucleic acid molecules set forth in this paragraph. In another embodiment, a nucleic acid molecule encoding an IL-12 single chain protein of the present invention further comprises a nucleic acid molecule encoding a linker.

The present invention also includes oligonucleotides, recombinant molecules, recombinant viruses and recombinant cells comprising such nucleic acid molecules and methods to produce such nucleic acid molecules, oligonucleotides, recombinant molecules, recombinant viruses and recombinant cells.

Knowing the nucleic acid sequences of certain nucleic acid molecules of the present invention allows one skilled in the art to, for example, (a) make copies of those nucleic acid molecules, (b) obtain nucleic acid molecules including at least a portion of such nucleic acid molecules, e.g., nucleic acid molecules including full-length genes, full-length coding regions, regulatory control sequences, truncated coding regions, and (c) obtain other nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. A preferred library to screen or from which to amplify nucleic acid molecules is a feline or canine mast library or a feline or canine peripheral blood mononuclear cell library. Techniques to clone and amplify genes are disclosed, for example, in Sambrook et al., ibid.

Oligonucleotides of the present invention can be RNA, DNA, or derivatives of either. The minimum size of such oligonucleotides is the size required for formation of a stable hybrid between an oligonucleotide and a complementary sequence on a larger nucleic acid molecule of the present invention, typically from about 12 to 15 to about 17 to 18 nucleotides depending on the GC/AT content. The present invention includes oligonucleotides that can be used as, for example, probes to identify nucleic acid molecules, primers to produce nucleic acid molecules, or therapeutic reagents to inhibit protein production or activity, e.g., as antisense-, triplex formation-, ribozyme- and/or RNA drug-based reagents. The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of the nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the nucleic acid molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function, i.e., direct gene expression, in recombinant cells of the present invention, including in bacterial, fungal, insect, other animal, and plant cells. Preferred expression vectors of the present invention can direct gene expression in bacterial, yeast, insect and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences that control the initiation, elongation, and termination of transcription. Particularly important transcription control sequences are those that control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, or insect and mammalian cells, such as, but not limited to, tac, lac, trp, trc, oxy-pro, omp/lpp, rrnB, bacteriophage lambda, such as lambda $p_L$ and lambda $p_R$ and fusions that include such promoters, bacteriophage T7, T7lac, bacteriophage T3, bacteriophage SP6, bacteriophage SP01, metallothionein, alpha-mating factor, *Pichia* alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus, such as immediate early promoter, simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters, e.g., promoters inducible by interferons or interleukins.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein. A recombinant cell is preferably produced by transforming a host cell with one or more recombinant molecules, each comprising one or more nucleic acid molecules of the present invention operatively linked to an expression vector containing one or more transcription control sequences, examples of which are disclosed herein.

Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. It is to be noted that a cell line refers to any recombinant cell of the present invention that is not a transgenic animal. Transformed nucleic acid molecules of the present invention can remain extrachromosomal or can integrate into one or more sites within a chromosome of the transformed, i.e., recombinant, cell in such a manner that their ability to be expressed is retained. Preferred nucleic acid molecules with which to transform a cell include nucleic acid molecules disclosed herein. Particularly preferred nucleic acid molecules with which to transform a cell include nFeIL-18-$N_{514}$, nFeIL-18-$C_{502}$, nFeIL-$18_{607}$, nFeIL-$18_{576}$, nFeIL-$18_{471}$, nFeCasp-$1_{1233}$, nFeCasp-1-$N_{526}$, nFeCasp-1-$C_{500}$, nFeCasp-$1_{1230}$, nFeIL-12p40-$N_{985}$, nFeIL-12p$40_{987}$, nFeIL-12p$40_{921}$, nFeIL-12p$35_{666}$, nFeIL-12p35-$N_{561}$, nFeIL-12p$35_{591}$, nCaIL-12p$35_{666}$, nCaIL-12p$35_{1455}$, nCaIL-12p$35_{591}$, nCaIL-12p$40_{2267}$, nCaIL-12p$40_{921}$, and nCaIL-12p$40_{987}$, nCaIL-$12_{1599}$, nCaIL-$12_{1533}$, nFeIL-$12_{1599}$, and nFeIL-$12_{1533}$.

Recombinant molecules of the present invention may also (a) contain secretory signals, i.e., signal segment nucleic acid sequences, to enable an expressed protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Suitable host cells to transform include any cell that can be transformed with a nucleic acid molecule of the present invention. Host cells can be either untransformed cells or cells that are already transformed with at least one nucleic acid molecule, e.g., nucleic acid molecules encoding one or more proteins of the present invention and/or other proteins. Host cells of the present invention either can be endogenously, i.e., naturally, capable of producing proteins of the present invention or can be capable of producing such proteins after being transformed with at least one nucleic acid molecule of the present invention. Host cells of the present invention can be any cell capable of producing at least one protein of the present invention, and include bacterial, fungal, including yeast, insect, and other animal and plant cells. Preferred host cells include bacterial, mycobacterial, yeast, insect and mammalian cells. More preferred host cells include *Salmonella, Escherichia, Bacillus, Listeria, Saccharomyces, Pichia, Spodoptera, Mycobacteria, Trichoplusia,* BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia coli,* including *E. coli* K-12 derivatives; *Salmonella typhi; Salmonella typhimurium,* including attenuated strains such as UK-1 $\chi$3987 and SR-1 $\chi$4072; *Pichia; Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines, e.g., human, murine or chicken embryo fibroblast cell lines, myeloma cell lines, Chinese hamster ovary cells, mouse NIH/3T3 cells, LMTK$^{31}$ cells and/or HeLa cells.

Recombinant cells of the present invention can also be co-transformed with one or more recombinant molecules including IL-18, caspase-1, IL-12 single chain nucleic acid molecules encoding one or more proteins of the present invention and one or more other nucleic acid molecules encoding other compounds.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals, e.g., promoters, operators, enhancers, substitutions or modifications of translational control signals, e.g., ribosome binding sites, Shine-Dalgarno sequences, modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated feline IL-18, feline caspase-1, feline and/or canine IL-12 single chain proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a protein of the present invention. Such a medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane. The phrase recovering the protein, as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in substantially pure form. As used herein, substantially pure refers to a purity that allows for the effective use of the protein as a therapeutic composition or diagnostic. A therapeutic composition for animals, for example, should exhibit no substantial toxicity.

The present invention also includes isolated, i.e., removed from their natural milieu, antibodies that selectively bind to proteins of the present invention or a mimetope thereof, e.g., anti-feline IL-18, feline caspase-1, feline and canine IL-12 single antibodies. As used herein, the term selectively binds to a protein refers to the ability of antibodies of the present invention to preferentially bind to specified proteins and mimetopes thereof of the present invention. Binding can be measured using a variety of methods standard in the art including enzyme immunoassays, e.g., ELISA, immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated herein by reference in its entirety. For example, an anti-feline IL-18 antibody of the present invention preferably selectively binds to a feline IL-18 protein in such a way as to inhibit the function of that protein.

The antibodies of the present invention bind to the proteins of the present invention, but not to similar proteins of other species. For instance, the antibodies that specifically bind feline IL-18 do not bind canine IL-18.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope of the present invention to produce the antibodies and (b) recovering the antibodies. In another method, antibodies of the present invention are produced recombinantly using techniques as heretofore disclosed to produce proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) to evaluate the immune status in felids and canids with diseases such as allergy, cancer and pathogen infections. Furthermore, antibodies of the present invention can be used to target cytotoxic agents to cells. Targeting can be accomplished by conjugating, i.e., stably joining, such antibodies to the cytotoxic agents using techniques known to those skilled in the art. Suitable cytotoxic agents are known to those skilled in the art. Furthermore, antibodies of the present invention can be used to detect for example, feline IL-18, caspase-1, canine IL-12 single chain, and/or feline IL-12 single chain in a putative IL-18, caspase-1, canine IL-12 single chain, and/or feline IL-12 single chain containing biological sample, by contacting the putative IL-18, caspase-1, canine IL-12 single chain, and/or feline IL-12 single chain containing biological sample with the appropriate anti-IL-18, caspase-1, canine IL-12 single chain, and/or feline IL-12 single chain antibodies under conditions suitable for formation of an antigen-antibody complex, and then detecting said complex. Methods to detect said method are known to those skilled in the art and are contained herein.

The present invention includes proteins comprising SEQ ID NO:2, SEQ ID NO:5, SEQ ID NO:8, SEQ ID NO:12, SEQ ID NO:15, SEQ ID NO:18, SEQ ID NO:21, SEQ ID NO:24, SEQ ID NO:27, SEQ ID NO:30, SEQ ID NO:33, SEQ ID NO:36, SEQ ID NO:39, SEQ ID NO:44, SEQ ID NO:47, SEQ ID NO:50, SEQ ID NO:53, SEQ ID NO:59, SEQ ID NO:62, and SEQ ID NO:67 as well as nucleic acid molecules encoding such proteins.

Preferred feline IL-18 proteins of the present invention include PFeIL-18-$N_{133}$ PFeIL-18-$C_{154}$ PFeIL-18$_{192}$, and/or PFeIL-18$_{157}$. In one embodiment, a preferred feline IL-18 protein of the present invention has an amino acid sequence that includes SEQ ID NO:2, SEQ ID NO:5, SEQ ID NO:8, and/or SEQ ID NO:12 and is preferably encoded by a nucleic acid molecule having nucleic acid sequences SEQ ID NO:1, SEQ ID NO:4, SEQ ID NO:7, SEQ ID NO:9 and/or SEQ ID NO:11. Such proteins are preferably encoded by a nucleic acid molecule comprising nFeIL-18-$N_{514}$, nFeIL-18-$C_{502}$, nFeIL-18$_{607}$, nFeIL-18$_{576}$, and/or nFeIL-18$_{471}$.

Preferred feline caspase-1 proteins of the present invention include proteins encoded by a nucleic acid molecule comprising nFeCasp-1$_{1233}$, nFeCasp-1-$N_{526}$, nFeCasp-1-$C_{500}$, and/or nFeCasp-1$_{1230}$. Preferred feline caspase-1 proteins are PFeCasp-1$_{410}$, PFeCasp-1-$N_{169}$, and/or PFeCasp-1-$C_{120}$. In one embodiment, a preferred feline caspase-1 protein of the present invention is encoded by SEQ ID NO:14, SEQ ID NO:17, SEQ ID NO:20, and/or SEQ ID NO:23, and, as such, has an amino acid sequence that includes SEQ ID NO:15, SEQ ID NO:18, SEQ ID NO:21 and/or SEQ ID NO:24.

Preferred canine and feline IL-12 proteins of the present invention include proteins encoded by a nucleic acid molecule comprising nFeIL-12$_{1599}$, nFeIL-12$_{1533}$, nCaIL-12$_{1599}$, and/or nCaIL-12$_{1533}$. Preferred feline and canine IL-12 proteins are nFeIL-12p40-$N_{985}$, nFeIL-12p40$_{987}$, nFeIL-12p40$_{921}$, nFeIL-12p35$_{666}$, nFeIL-12p35-$N_{561}$, nFeIL-12p35$_{591}$, nCaIL-12p35$_{666}$, nCaIL-12p35$_{1455}$, nCaIL-12p35$_{591}$, nCaIL-12p40$_{2267}$, nCaIL-12p40$_{921}$ and nCaIL-12p40$_{987}$. In one embodiment, a preferred canine and feline IL-12 single chain protein of the present invention is encoded by SEQ ID NO:38, SEQ ID NO:43, SEQ ID NO:61, and/or SEQ ID NO:66, and, as such, has an amino acid sequence that includes SEQ ID NO:39, SEQ ID NO:44, SEQ ID NO:62, and/or SEQ ID NO:67.

More preferred canine and feline IL-12 single chain proteins of the present invention include proteins encoded by a nucleic acid molecule comprising nFeIL-12p40-$N_{985}$, nFeIL-12p40$_{987}$, nFeIL-12p40$_{921}$, nFeIL-12p35$_{666}$, nFeIL-12p35-$N_{561}$, nFeIL-12p35$_{591}$, nCaIL-12p35$_{666}$, nCaIL-12p35$_{1455}$, nCaIL-12p35$_{591}$, nCaIL-12p40$_{2267}$, nCaIL-12p40$_{921}$, nCaIL-12p40$_{987}$, nCaIL-12$_{1533}$, nCaIL-12$_{1599}$, nFeIL-12$_{1533}$, and nFeIL-12$_{1599}$. Preferred feline and canine IL-12 single chain proteins comprise PFeIL-12p40-$N_{328}$, PFeIL-12p40$_{329}$, PFeIL-12p40$_{307}$, PFeIL-12p35$_{222}$, PFeIL-12p35-$N_{187}$, PFeIL-12p35$_{197}$, PCaIL-12p35$_{222}$, PCaIL-12p35$_{197}$, PCaIL-12p40$_{307}$, PCaIL-12p40$_{329}$, PFeIL-12$_{533}$, PFeIL-12$_{511}$, PCaIL-12$_{533}$, and PCaIL-12$_{511}$. In one embodiment, a preferred canine and feline IL-12 single chain protein of the present invention is encoded by a nucleic acid comprising SEQ ID NO:28, SEQ ID NO:31, SEQ ID NO:32, SEQ ID NO:35, SEQ ID NO:46, SEQ ID NO:49, SEQ ID NO:52, SEQ ID NO:55, SEQ ID NO:58, SEQ ID NO: 101, SEQ ID NO:104, SEQ ID NO:107, SEQ ID NO:38, SEQ ID NO:43, SEQ ID NO:61, SEQ ID NO:66, and, as such, has an amino acid sequence that includes SEQ ID NO:27, SEQ ID NO:30, SEQ ID NO:33, SEQ ID NO:36, SEQ ID NO:47, SEQ ID NO:50, SEQ ID NO:53, and SEQ ID NO:59, SEQ ID NO:102, SEQ ID NO:105, SEQ ID NO:108, SEQ ID NO:39, SEQ ID NO:40, SEQ ID NO:62, and/or SEQ ID NO:67.

As used herein, an isolated protein of the present invention can be a full-length protein or any homolog of such a protein. An isolated protein of the present invention, including a homolog, can be identified in a straight-forward manner by the protein's ability to bind to a receptor or a protein. Examples of protein homologs of the present invention include proteins of the present invention in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the protein homolog includes at least one epitope capable of eliciting an immune response against the parent protein, of binding to an antibody directed against the parent protein and/or of binding to the parent's receptor, where the term parent refers to the longer and/or full-length protein that the homolog is derived from. That is, when the homolog is administered to an animal as an immunogen, using techniques known to those skilled in the art, the animal will produce an immune response against at least one epitope of an immunoregulatory protein of the present invention, depending upon which protein is administered to an animal. The ability of a protein to effect an immune response can be measured using techniques known to those skilled in the art.

Homologs of proteins of the present invention can be the result of natural allelic variation, including natural mutation. Protein homologs of the present invention can also be produced using techniques known in the art including, but not limited to, direct modifications to the protein and/or modifications to the gene encoding the protein using, for example, classic or recombinant DNA techniques to effect random or targeted mutagenesis.

One embodiment of the present invention is an IL-18 protein selected from the group consisting of: (i) a protein having an amino acid sequence selected from the group consisting of SEQ ID NO:2, SEQ ID NO:5, SEQ ID NO:8 and SEQ ID NO:12; and (ii) a protein encoded by an allelic variant of a nucleic acid molecule encoding a protein selected from the group consisting of SEQ ID NO:2, SEQ ID NO:5, SEQ ID NO:8 and SEQ ID NO:12. Another embodiment is a caspase-1 protein selected from the group consisting of: (i) a protein having an amino acid sequence selected from the group consisting of SEQ ID NO:15, SEQ ID NO:18, SEQ ID NO:21, and SEQ ID NO:24; and (ii) a protein encoded by an allelic variant of a nucleic acid molecule encoding a protein selected from the group consisting of SEQ ID NO:15, SEQ ID NO:18, SEQ ID NO:21, and SEQ ID NO:24. Yet another embodiment is a feline IL-12 single chain protein selected from the group consisting of: (i) a protein having an amino acid sequence selected from the group consisting of SEQ ID NO:38, and SEQ ID NO:44; and (ii) a protein encoded by an allelic variant of a nucleic acid molecule encoding a protein selected from the group consisting of SEQ ID NO:38, and SEQ ID NO:44; or a canine II-12 single chain protein selected from the group consisting of: (i) a protein having an amino acid sequence selected from the group consisting of SEQ ID NO:62 and SEQ ID NO:67; and (ii) a protein encoded by an allelic variant of a nucleic acid molecule encoding a protein selected from the group consisting of SEQ ID NO:62 and SEQ ID NO:67.

One embodiment of the present invention includes an isolated IL-18 protein selected from the group consisting of (i) an isolated protein of at least 25 amino acids in length, wherein said protein has an at least 25 contiguous amino acid region identical in sequence to a 25 contiguous amino acid region selected from the group consisting of SEQ ID NO:2, SEQ ID NO:5, SEQ ID NO:8, and SEQ ID NO:12; and (ii) an isolated protein having an amino acid sequence that is at least 92 percent identical to an amino acid sequence selected from the group consisting of SEQ ID NO:2, SEQ ID NO:5, SEQ ID NO:8, and SEQ ID NO:12, and a fragment thereof of at least 30 nucleotides. Preferred proteins have an at least 15 contiguous amino acid region identical with a 15 contiguous amino acid region, an at least 20 contiguous amino acid region identical with a 20 contiguous amino acid region, an at least 30 contiguous amino acid region identical with a 30 contiguous amino acid region, an at least 40 contiguous amino acid region identical with a 40 contiguous amino acid region, an at least 50 contiguous amino acid region contiguous with a 50 contiguous amino acid region, an at least 75 contiguous amino acid region contiguous with a 75 contiguous amino acid region, preferably an at least 100 contiguous amino acid region contiguous with a 100 contiguous amino acid region, and most preferably a full-length protein identical in sequence to a full-length protein of an amino acid sequence selected from the group consisting of SEQ ID NO:2, SEQ ID NO:5, SEQ ID NO:8, and SEQ ID NO:12. In another embodiment, preferred proteins have an amino acid sequence that is at least 90 percent identical, at least 92 percent identical, preferably at least 94 percent identical, preferably at least 96 percent identical, and even more preferably at least about 98 percent identical to an amino acid sequence selected from the group consisting of SEQ ID NO:2, SEQ ID NO:5, SEQ ID NO:8, and SEQ ID NO:12, and a fragment thereof of at least 20 amino acids, at least 30 amino acids, at least 50 amino acids, at least 75 amino acids, preferably at least 100 amino acids, and more preferably a full-length protein.

In a preferred embodiment, IL-18 proteins of the present invention has a function selected from the group consisting of: (i) eliciting an immune response against an IL-18 protein having an amino acid sequence selected from the group consisting of SEQ ID NO:2, SEQ ID NO:5, SEQ ID NO:8, and SEQ ID NO:12, (ii) selectively binding to an antibody raised against an IL-18 protein having an amino acid sequence selected from the group consisting of SEQ ID NO:2, SEQ ID NO:5, SEQ ID NO:8, and SEQ ID NO:12, and (iii) exhibiting IL-18 activity.

One embodiment of the present invention includes an isolated caspase-1 protein selected from the group consisting of (i) an isolated protein of at least 25 amino acids in length, wherein said protein has an at least 25 contiguous amino acid region identical in sequence to a 25 contiguous amino acid region selected from the group consisting of SEQ ID NO:15, SEQ ID NO:18, SEQ ID NO:21, and SEQ ID NO:24; and (ii) an isolated protein having an amino acid sequence that is at least 85 percent identical to an amino acid sequence selected from the group consisting of SEQ ID NO:15, SEQ ID NO:18, SEQ ID NO:21, and SEQ ID NO:24, and a fragment thereof of at least 30 nucleotides. Preferred proteins have an at least 25 contiguous amino acid region identical with a 25 contiguous amino acid region, an at least 20 contiguous amino acid region identical with a 20 contiguous amino acid region, an at least 30 contiguous amino acid region identical with a 30 contiguous amino acid region, an at least 40 contiguous amino acid region identical with a 40 contiguous amino acid region, an at least 50 contiguous amino acid region contiguous with a 50 contiguous amino acid region, an at least 75 contiguous amino acid region contiguous with a 75 contiguous amino acid region, preferably an at least 100 contiguous amino acid region contiguous with a 100 contiguous amino acid region, and most preferably a full-length protein identical in sequence to a full-length protein of an amino acid sequence selected from the group consisting of SEQ ID NO:15, SEQ ID NO:18, SEQ ID NO:21, and SEQ ID NO:24. In another embodiment, preferred proteins have an amino acid sequence that is at least 85 percent identical, at least 88 percent identical, preferably at least 90 percent identical, and more preferably at least about 95 percent identical to an amino acid sequence selected from the group consisting of SEQ ID NO:15, SEQ ID NO:18, SEQ ID NO:21, and SEQ ID NO:24, and a fragment thereof of at least 30 amino acids, at least 50 amino acids, at least 75 amino acids, preferably at least 100 amino acids, and more preferably a full-length protein.

In a preferred embodiment, a caspase protein of the present invention has a function selected from the group consisting of: (i) eliciting an immune response against a caspase-1 protein having an amino acid sequence selected from the group consisting of SEQ ID NO:15, SEQ ID NO:18, SEQ ID NO:21, and SEQ ID NO:24, (ii) selectively binding to an antibody raised against a caspase-1 protein having an amino acid sequence selected from the group consisting of SEQ ID NO:15, SEQ ID NO:18, SEQ ID NO:21, and SEQ ID NO:24, and (iii) exhibiting caspase-1 activity.

One embodiment of the present invention includes an isolated IL-12 single chain protein comprising an IL-12 p40 subunit domain linked to an IL-12 p35 subunit domain, wherein said p40 subunit domain is selected from the group consisting of (i) a p40 subunit protein having an amino acid sequence that is at least 84 percent identical to an amino acid sequence selected from the group consisting of SEQ ID NO:27 and SEQ ID NO:30, (ii) a p40 subunit protein comprising a fragment of a protein of (i), wherein said fragment is at least 30 amino acids in length, and (iii) a p40 subunit protein comprising at least 23 contiguous amino acids identical in sequence to at least 23 contiguous amino acids of an amino acid sequence selected from the group consisting of SEQ ID NO:27 and SEQ ID NO:30. The p35 subunit is preferably selected from the group consisting of (i) a p35 subunit protein having an amino acid sequence that is at least 84 percent identical to an amino acid sequence selected from the group consisting of SEQ ID NO:33 and SEQ ID NO:36, (ii) a p35 subunit protein comprising a fragment of a protein of (i), wherein said fragment is at least 30 amino acids in length, and (iii) a p35 subunit protein comprising at least 23 contiguous amino acids identical in sequence to at least 23 contiguous amino acids of an amino acid sequence selected from the group consisting of SEQ ID NO:33 and SEQ ID NO:36. Preferred amino acid sequences have an at least 23 contiguous amino acid region identical with a 23 contiguous amino acid region, an at least 30 contiguous amino acid region identical with a 30 contiguous amino acid region, an at least 40 contiguous amino acid region identical with a 40 contiguous amino acid region, an at least 50 contiguous amino acid region contiguous with a 50 contiguous amino acid region, an at least 75 contiguous amino acid region contiguous with a 75 contiguous amino acid region, preferably an at least 100 contiguous amino acid region contiguous with a 100 contiguous amino acid region, and most preferably a full-length protein identical in sequence to a full-length protein of an amino acid sequence selected from the group consisting of SEQ ID NO:27 and SEQ ID NO:30 In another embodiment, preferred proteins have an amino acid sequence that is at least 84 percent identical, at least 86 percent identical, at least 88 percent identical, preferably at least 90 percent identical, and more preferably at least about 95 percent identical to an amino acid sequence selected from the group consisting of SEQ ID NO:27, SEQ ID NO:30, and a fragment thereof of at least 30 amino acids, at least 50 amino acids, at least 75 amino acids, preferably at least 100 amino acids, and more preferably a full-length protein.

In a preferred embodiment, an IL-12 single chain protein of the present invention has a function selected from the group consisting of: (i) eliciting an immune response against an IL-12 protein having an amino acid sequence selected from the group consisting of SEQ ID NO:27, SEQ ID NO:30, SEQ ID NO:33, SEQ ID NO:36, SEQ ID NO:47, SEQ ID NO:50, SEQ ID NO:53, and SEQ ID NO:59, SEQ ID NO:102, SEQ ID NO:105, SEQ ID NO:108, SEQ ID NO:39, SEQ ID NO:40, SEQ ID NO:62, and/or SEQ ID NO:67; (ii) selectively binding to an antibody raised against an IL-12 protein having an amino acid sequence selected from the group consisting of SEQ ID NO:27, SEQ ID NO:30, SEQ ID NO:33, SEQ ID NO:36, SEQ ID NO:47, SEQ ID NO:50, SEQ ID NO:53, and SEQ ID NO:59, SEQ ID NO:102, SEQ ID NO:105, SEQ ID NO:108, SEQ ID NO:39, SEQ ID NO:40, SEQ ID NO:62, and/or SEQ ID NO:67; and (iii) exhibiting IL-12 activity.

One embodiment of the present invention includes an isolated IL-12 single chain protein comprising an IL-12 p40 subunit domain linked to an IL-12 p35 subunit domain, wherein said p40 subunit domain is selected from the group consisting of (i) a p40 subunit protein having an amino acid sequence that is at least 84 percent identical to an amino acid sequence selected from the group consisting of SEQ ID NO:53 and SEQ ID NO:59, (ii) a p40 subunit protein comprising a fragment of a protein of (i), wherein said fragment is at least 40 amino acids in length, and (iii) a p40 subunit protein comprising at least 31 contiguous amino acids identical in sequence to at least 31 contiguous amino acids of an amino acid sequence selected from the group consisting of SEQ ID NO:53 and SEQ ID NO:59. The p35 subunit is preferably selected from the group consisting of (i) a p35 subunit protein having an amino acid sequence that is at least 84 percent identical to an amino acid sequence selected from the group consisting of SEQ ID NO:47 and SEQ ID NO:50, (ii) a p35 subunit protein comprising a fragment of a protein of (i), wherein said fragment is at least 40 amino acids in length, and (iii) a p35 subunit protein comprising at least 31 contiguous amino acids identical in sequence to at least 31 contiguous amino acids of an amino acid sequence selected from the group consisting of SEQ ID NO:47 and SEQ ID NO:50. Preferred amino acid sequences have an at least 23 contiguous amino acid region identical with a 23 contiguous amino acid region, an at least 30 contiguous amino acid region identical with a 30 contiguous amino acid region, an at least 40 contiguous amino acid region identical with a 40 contiguous amino acid region, an at least 50 contiguous amino acid region contiguous with a 50 contiguous amino acid region, an at least 75 contiguous amino acid region contiguous with a 75 contiguous amino acid region, preferably an at least 100 contiguous amino acid region contiguous with a 100 contiguous amino acid region, and most preferably a full-length protein identical in sequence to a full-length protein of an amino acid sequence selected from the group consisting of SEQ ID NO:47, SEQ ID NO:50, SEQ ID NO:53, and SEQ ID NO:59. In another embodiment, preferred proteins have an amino acid sequence that is at least 84 percent identical, at least 86 percent identical, at least 88 percent identical, preferably at least 90 percent identical, and more preferably at least about 95 percent identical to an amino acid sequence selected from the group consisting of SEQ ID NO:47, SEQ ID NO:50, SEQ ID NO:53, and SEQ ID NO:59, and a fragment thereof of at least 30 amino acids, at least 50 amino acids, at least 75 amino acids, preferably at least 100 amino acids, and more preferably a full-length protein.

In a preferred embodiment, an IL-12 single chain protein of the present invention has a function selected from the group consisting of: (i) eliciting an immune response against an IL-12 protein having an amino acid sequence selected from the group consisting of SEQ ID NO:62 and SEQ ID NO:67, (ii) selectively binding to an antibody raised against an IL-12 protein having an amino acid sequence selected from the group consisting of SEQ ID NO:27, SEQ ID NO:30, SEQ ID NO:33, SEQ ID NO:36, SEQ ID NO:47, SEQ ID NO:50, SEQ ID NO:53, and SEQ ID NO:59, SEQ ID NO:102, SEQ ID NO:105, SEQ ID NO:108, SEQ ID NO:39, SEQ ID NO:40, SEQ ID NO:62, and/or SEQ ID NO:67, and (iii) exhibiting IL-12 activity.

One embodiment of the present invention is a therapeutic composition that, when administered to a animal in an effective manner, is capable of protecting that animal from a disease such as, for example, allergy, cancer or inflammation. Therapeutic compositions of the present invention include protective compounds that are capable of regulating feline IL-18, feline caspase-1, or feline or canine IL-12 protein amounts and/or activity. A protective compound of the present invention is capable of regulating feline IL-18, feline caspase-1, or feline or canine IL-12 activity and/or availability. Examples of protective compounds related to feline and canine proteins of the present invention include an isolated antibody that selectively binds to either feline IL-18, feline caspase-1, or feline or canine IL-12 or other inhibitors or activators of feline IL-18, feline caspase-1, or feline or canine IL-12 activity or amount. Other examples of protective compounds include an isolated nucleic acid molecule of the present invention; an isolated protein of the present invention; a mimetope of a protein of the present invention, a multimeric form of any of said proteins, or an inhibitor identified by its ability to inhibit the activity of any of said proteins; such an inhibitor can inhibit binding of the respective protein with its receptor, or inhibit the activity of the respective protein. Methods to perform such assays to measure binding and/or activity of protein of the present invention are known to those of skill in the art, and are described, for example, in Janeway et al., ibid. As such, these protective compounds may include antibodies, peptides, substrate analogs, and other large or small molecules which can be organic or inorganic. As used herein, a protective compound refers to a compound, that when administered to an animal in an effective manner, is able to treat, ameliorate, and/or prevent a disease due to allergy, cancer or infection. Examples of proteins, nucleic acid molecules, antibodies and/or inhibitors of the present invention are disclosed herein.

The present invention also includes a therapeutic composition comprising at least one compound of the present invention in combination with at least one additional therapeutic compound. Examples of such compounds are disclosed herein.

The efficacy of a therapeutic composition of the present invention to protect an animal from a disease mediated by feline IL-18, feline caspase-1, or feline or canine IL-12 can be tested in a variety of ways including, but not limited to, detection of protective antibodies (using, for example, proteins or mimetopes of the present invention), detection of the amount of feline IL-18, feline caspase-1, or feline or canine IL-12, or detection of cellular immunity within the treated animal. Therapeutic compositions can be tested in animal models such as mice. Such techniques are known to those skilled in the art.

Therapeutic compounds of the present invention can be administered to any animal susceptible to such therapy, preferably to mammals, and more preferably to dogs, cats, humans, ferrets, horses, cattle, sheep and/or other pets, economic food animals, and/or zoo animals. Preferred animals include dogs and cats.

A therapeutic composition of the present invention is administered to an animal in an effective manner such that the composition is capable of regulating an immune response in that animal. Therapeutic compositions of the present invention can be administered to animals prior to the onset of a disease (i.e. as a preventative vaccine) and/or can be administered to animals after onset of a disease in order to treat the disease (i.e. as a therapeutic vaccine). Preferred diseases to prevent and/or treat include autoimmune diseases, allergic reactions, infectious diseases, tumor development, inflammatory diseases and/or graft rejection. In one embodiment, a therapeutic composition of the present invention is administered with an antigen to enhance an immune response against that antigen. Such administration can include, but is not limited to, oral, intravenous, intramuscular, intra ocular, mucosal, intranasal, subcutaneous, topical or transdermal application. In order to protect an animal from disease, a therapeutic composition of the present invention is administered to the animal in an effective manner such that the composition is capable of protecting that animal from a disease. Therapeutic compositions of the present invention can be administered to animals prior to disease in order to prevent disease and/or can be administered to animals after disease occurs. The exact dose, administration regimen, and administration route of therapeutic compositions of the present invention can be determined by one skilled in the art. A suitable single dose is a dose that is capable of regulating the immune response in an animal when administered one or more times over a suitable time period. For example, a preferred single dose of a protein, mimetope or antibody therapeutic composition is from about 1 microgram (μg) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 μg to about 1 mg of the therapeutic composition per kg body weight of the animal is administered from about one to about two times over a time period of from about 2 weeks to about 12 months.

A therapeutic composition of the present invention can include at least one of the following: excipient, an adjuvant and a carrier. Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

Therapeutic compositions of the present invention can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interferon gamma, transforming growth factor beta, RANTES (regulated upon activation, normal T cell expressed and presumably secreted), macrophage inflammatory proteins (e.g., MIP-1 alpha and MIP-1 beta), and *Leishmania* elongation initiating factor (LEIF); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's TITERMAX® adjuvant (Vaxcel, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

Therapeutic compositions of the present invention can include a carrier. Carriers include compounds that increase the half-life of a protective compound in the treated animal. Suitable carriers include, but are not limited to, polymeric controlled release vehicles, biodegradable implants, liposomes, other lipid or lipid containing formulations, including cationic lipids or lipid mixtures including cationic lipids, bacteria, viruses, other cells, oils, esters, and glycols.

A therapeutic composition can be a controlled release formulation that is capable of slowly releasing a protective compound of the present invention into an animal. As used herein, a controlled release formulation comprises a composition or protective compound of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, other lipids or lipid-containing formulations and transdermal delivery systems. Other controlled release formulations of the present invention include liquids that, upon administration to an animal, form a solid or a gel in situ. Preferred controlled release formulations are biodegradable, i.e., bioerodible.

A preferred controlled release formulation of the present invention is capable of releasing a composition of the present invention into the blood of the treated animal at a constant rate sufficient to attain therapeutic dose levels of the composition to regulate an immune response in an animal. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

According to one embodiment, a nucleic acid molecule of the present invention can be administered to an animal in a fashion to enable expression of that nucleic acid molecule into a therapeutic protein or therapeutic RNA (e.g. antisense RNA, ribozyme, triple helix forms or RNA drug) in the animal. Nucleic acid molecules can be delivered to an animal in a variety of methods including, but not limited to, (a) administering a naked (i.e. not packaged in a viral coat or cellular membrane) nucleic acid as a genetic vaccine (e.g. as naked DNA or RNA molecules, such is taught, for example, in Wolff et al., 1990, Science 247, p 1465-68) or (b) administering a nucleic acid molecule packaged as a recombinant virus vaccine or as a recombinant cell vaccine (i.e. the nucleic acid molecule is delivered by a viral or cellular vehicle).

One embodiment of a therapeutic composition of the present invention is a naked nucleic acid, a recombinant virus or a recombinant cell vaccine or therapy. Naked nucleic acid molecules of the present invention can be administered by a variety of methods. Suitable delivery methods include, for example, intramuscular injection, subcutaneous injection, intradermal injection, intradermal scarification, particle bombardment, oral application, topical application and nasal application, with intramuscular injection, intradermal injection, intradermal scarification and particle bombardment being preferred. A preferred single dose of a naked nucleic acid molecule ranges from about 1 nanogram (ng) to about 1 milligram (mg), depending on the route of administration and/or method of delivery, as can be determined by those skilled in the art. Examples of administration methods are disclosed, for example, in U.S. Pat. No. 5,204,253, by Bruner, et al., issued Apr. 20, 1993, PCT Publication No. WO 95/19799, published Jul. 27, 1995, by McCabe, and PCT Publication No. WO 95/05853, published Mar. 2, 1995, by Carson, et al. Naked nucleic acid molecules of the present invention can be contained in an aqueous excipient (e.g., phosphate buffered saline) and/or with a carrier (e.g., lipid-based vehicles), or it can be bound to microparticles (e.g., gold particles).

According to one embodiment, a nucleic acid molecule of the present invention can be administered to an animal in a fashion to enable expression of that nucleic acid molecule into a protective protein or protective RNA, e.g., antisense RNA, ribozyme, triple helix form or RNA drug, in the animal. Nucleic acid molecules can be delivered to an animal in a variety of methods including, but not limited to, (a) administering a naked, i.e., not packaged in a viral coat or cellular membrane, nucleic acid as a genetic therapy or vaccine, e.g., as naked DNA or RNA molecules, such as is taught, for example in Wolff et al., 1990, Science 247, 1465-1468, or (b) administering a nucleic acid molecule packaged as a recombinant virus therapy or vaccine or as a recombinant cell therapy or vaccine, i.e., the nucleic acid molecule is delivered by a viral or cellular vehicle.

A genetic, i.e., naked nucleic acid, therapy vaccine of the present invention includes a nucleic acid molecule of the present invention and preferably includes a recombinant molecule of the present invention that preferably is replication or otherwise amplification, competent. A genetic therapy or vaccine of the present invention can comprise one or more nucleic acid molecules of the present invention operatively linked to a transcriptional control sequence in the form of, for example, a dicistronic recombinant molecule. Preferred viral vectors include those based on alphaviruses, poxviruses, adenoviruses, herpesviruses, picornaviruses, and/or retroviruses, with those based on alphaviruses (such as sindbis or Semliki forest virus) species-specific herpesviruses and/or poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic therapies and vaccines of the present invention can be administered in a variety of ways, with intramuscular, subcutaneous, intradermal, transdermal, intranasal, topical and oral routes of administration being preferred. A preferred single dose of a genetic therapy or vaccine ranges from about 1 nanogram (ng) to about 600 µg, depending on the route of administration and/or method of delivery, as can be determined by those skilled in the art. Suitable delivery methods include, for example, by injection, as drops, aerosolized and/or topically. Genetic therapies or vaccines of the present invention can be contained in an aqueous excipient, e.g., phosphate buffered saline, alone or in a carrier, e.g., lipid-based vehicles. One embodiment is a nucleic acid-lipid complex, preferably a nucleic acid-cationic lipid complex.

A recombinant virus therapy or vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses, such as Sindbis virus, raccoon poxviruses, species-specific herpesviruses and species-specific poxviruses. An example of methods to produce and use recombinant virus therapies and vaccines is disclosed in U.S. Pat. No. 5,766,602, Xiong et al., issued Jun. 16, 1998; U.S. Pat. No. 5,753,235, Haanes et al., issued May 19, 1998; and U.S. Pat. No. 5,804,197, Haanes et al., issued Sep. 8, 1998, all of which are incorporated by reference herein in their entireties.

When administered to an animal, a recombinant virus therapy or vaccine of the present invention infects cells within the immunized animal and directs the production of a protective protein or RNA nucleic acid molecule that is capable of protecting the animal from a disease. For example, a recombinant virus vaccine comprising a feline IL-18 nucleic acid molecule of the present invention can be administered according to a protocol that results in the animal producing a sufficient immune response to protect itself from a disease mediated by IL-18. In another embodiment of the present invention a feline IL-18 nucleic acid molecule can be used as therapy to treat a disease. A recombinant virus vaccine comprising a feline IL-18 nucleic acid molecule can be administered to an animal with clinical signs of disease according to a protocol that results in reduction and/or termination of clinical signs of disease. A preferred single dose of a recombinant virus therapy or vaccine of the present invention is from about $1 \times 10^4$ to about $1 \times 10^8$ virus plaque forming units (pfu) per kilogram body weight of the animal. Administration protocols are similar to those described herein for protein-based vaccines, with subcutaneous, intramuscular, intranasal, topical and oral administration routes being preferred.

A recombinant cell therapy or vaccine of the present invention includes recombinant cells of the present invention that express at least one protein of the present invention. Preferred recombinant cells for this embodiment include *Salmonella, E. coli, Listeria, Mycobacterium, S. frugiperda*, yeast, (including *Saccharomyces cerevisiae* and *Pichia pastoris*), BHK, CV-1, myoblast G8, COS, e.g., COS-7, Vero, MDCK and CRFK recombinant cells. Recombinant cell therapy or vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

In one embodiment of the present invention, a method to regulate an immune response in an animal by administering the therapeutic compound to an animal preferably a canine or feline, wherein the composition comprises a component selected from the group consisting of an excipient, an adjuvant and a carrier.

Proteins of the present invention can be used to develop regulatory compounds including inhibitors and activators that, when administered to an animal in an effective manner, are capable of protecting that animal from disease mediated by IL-18, caspase-1 or IL-12. Preferred regulatory compounds derived from the present invention include inhibitors and activators. In accordance with the present invention, the ability of a regulatory compound, including an inhibitor or activator, of the present invention to protect a felid or canid from disease mediated by IL-18, caspase-1 or IL-12 refers to the ability of that compound to, for example, treat, ameliorate or prevent a disease mediated by IL-18, caspase-1 or IL-12 in that animal.

An IL-18, caspase-1 or IL-12 single chain inhibitor of the present invention is identified by its ability to bind to, modify, or otherwise interact with, an IL-18, caspase-1 or IL-12 single chain protein of the present invention, thereby inhibiting the activity of the protein. Suitable inhibitors of activity are compounds that inhibit the activity of the proteins of the present invention in at least one of a variety of ways: (1) by binding to or otherwise interacting with or otherwise modifying the protein binding, (2) by interacting with other regions of the protein to inhibit activity, for example, by allosteric interaction, and (3) by binding to or otherwise interacting with or otherwise modifying a protein receptor binding site such that the protein is less likely to bind to the protein receptor binding site. Inhibitors of IL-18, caspase-1 and IL-12 single chain proteins are preferably relatively small compounds.

An embodiment of the present invention includes use of one of the following methods to identify a compound capable of regulating an immune response in an animal: (a) contacting an isolated feline IL-18 protein with a putative inhibitory compound under conditions in which, in the absence of the compound, the protein has T cell stimulating activity; and determining if the putative inhibitory compound inhibits the activity; (b) contacting an isolated feline caspase-1 protein with a putative inhibitory compound under conditions in which, in the absence of the compound, the protein cleaves precursor IL-18 resulting in a biologically active mature IL-18; and determining if the putative inhibitory compound inhibits the activity; and (c) contacting an isolated IL-12 single chain protein with a putative inhibitory compound under conditions in which, in the absence of the compound, the protein has T cell proliferation stimulating activity; and determining if the putative inhibitory compound inhibits the activity.

A variety of methods are known to one skilled in the art to detect binding of an IL-18, caspase-1 or IL-12 protein to its binding partner (e.g., an antibody or receptor, as appropriate). Such methods can be used to detect IL-12, casp-1, or IL-18, or Abs or other binding partners thereof in a biological sample or to produce inhibitors of such interactions. Such methods include, but are not limited to an assay in which, for example, IL-18 and an IL-18 binding partner can interact and/or bind to each other, using, for example, the yeast two-hybrid system, see for example, Luban, et al. 1995, *Curr. Opin. Biotechnol.*, 6, 59-64; and identifying those proteins that specifically bind to the IL-18 protein binding domain. Additional methods to identify protein-protein interactions include BIACORE® screening, confocal immunofluorescent microscopy, UV cross-linking, and immunoprecipitations. An example of a protein binding domain is an IL-18-binding domain, and a protein that would bind to an IL-18-binding domain would be IL-18. Additional teachings of general characteristics of reagents for use in the detection of binding between two moieties (e.g., between IL-18 and its receptor) as well as methods to produce and use such reagents are disclosed, for example, in U.S. Pat. No. 5,958,880, issued Sep. 28, 1999, by Frank et al.; and PCT International Publication No. WO 99/54349, published Oct. 28, 1999, by McCall et al.; each of these references is incorporated by reference herein in its entirety; furthermore, the disclosed reagents and methods are incorporated by reference herein in their entireties. It is to be noted that although the reagents and methods disclosed in each of the citations do not relate to the proteins, nucleic acid molecules, antibodies and inhibitors of the present invention per se, the disclosed reagents and methods are applicable by those skilled in the art to reagents, kits and detection methods of the present invention. Furthermore, proteins of the present invention can be used to develop regulatory compounds including inhibitors and activators that, when administered to a canid or felid in an effective manner are capable of protecting and treating that felid or canid from disease mediated by IL-18, caspase-1 or IL-12.

The following examples are provided for the purposes of illustration and are not intended to limit the scope of the present invention. The following examples include a number of recombinant DNA and protein chemistry techniques known to those skilled in the art; see, for example, Sambrook et al., ibid.

Example 1

Identification of the nucleic acid molecules of the feline IL-18 is unexpected because initial attempts to isolate feline IL-18 nucleic acid molecules using standard cDNA screening techniques were unsuccessful.

This example describes the isolation, sequencing and expression of nucleic acid molecules encoding feline IL-18 proteins of the present invention.

A. Feline IL-18 nucleic acid molecules were isolated as follows: A cDNA mitogen library was prepared from cat peripheral blood lymphocytes stimulated with ConA for 4 hours as previously described in Example 2 of PCT Publication No. WO 99/61618, entitled "Canine and Feline Immunoregulatory Proteins, Nucleic Acid Molecules, and Uses Thereof," inventors Gek-Kee Sim, Shumin Yang, Matthew Dreitz, and Ramani Wonderling, filed May 28, 1999, which is incorporated by reference herein in its entirety. An aliquot of this library was used as a template to isolate a feline IL-18 nucleic acid molecule by polymerase chain reaction (PCR). PCR amplification was performed using Amplitaq DNA POLYMERASE™ (available from PE Applied Biosystems Inc, Foster City, Calif.). Two overlapping nucleic acid molecules encoding partial length feline IL-18 proteins were obtained by using IL-18 specific primers in combination with cDNA library vector specific primers. All primers came from Life Technologies, Gaithersburg, Md. The sequence of the vector forward primer (T3 primer) was 5' GCCAAGCTCG AAATTAACCC TCACTAAAGG 3' (SEQ ID NO:69), and that of the vector reverse primer (T7 primer) was 5 CGACG- GCCAG TGAATTGTAA TACGACTC 3' (SEQ ID NO:70). The sequence of the IL-18-specific forward primer (IL-18 Forward 85) was 5' AGTGATGAAG GCCTGGAATC AGATTACTTT G 3' (SEQ ID NO:71) and the sequence of the IL-18-specific reverse primer (IL-18 Reverse 435) was 5' ATGGCCTGGA ACACTTCTCT GAAAGAATAT GA 3' (SEQ ID NO:72). The first PCR amplification was done using T3 primer and IL-18 Reverse 435 primer and the second PCR amplification was done using IL-18 Forward 85 primer and T7 primer. The PCR profile for both reactions were as follows: one initial denaturation step at 94° C. for 5 minutes; then 43 cycles of the following: 94° C. for 30 seconds, then 59° C. for 30 seconds, then 72° C. for 2 minutes; followed by a final extension at 72° C. for 7 minutes. The PCR products from both reactions were cloned into the TA CLONING® vector (available from Invitrogen, San Diego, Calif.) and the nucleic acid molecules were sequenced using an ABI PRISM® Model 377 Automatic DNA Sequencer (available from PE Applied Biosystems Inc.). DNA sequencing reactions were performed using PRISM® dRhodamine Terminator Cycle Sequencing Ready Reaction kits (available from PE Applied Biosystems Inc.). The PCR product from the first PCR amplification was sequenced and found to contain 514 nucleotides and was denoted herein as nFeIL-$18_{514}$ (5'-end partial clone) with a coding strand of SEQ ID NO:1, and a complementary strand of SEQ ID NO:3. The PCR product from the second PCR amplification was sequenced and found to contain 502 nucleotides and was denoted herein as nFeIL-$18_{502}$ (3'-end partial clone) with a coding strand of SEQ ID NO:4, and a complementary strand of SEQ ID NO:6. These two nucleic acid molecules shared more than 280 base pairs (bp) and together provided the sequence for the complete feline IL-18 open reading frame. Translation of SEQ ID NO:1 suggests that nucleic acid molecule nFeIL-18-$N_{514}$ encodes an N-terminal portion of PFeIL-18-N protein, of about 133 amino acids, denoted herein as PFe IL-18-$N_{133}$, the amino acid sequence of which is presented in SEQ ID NO:2, assuming an open reading frame having an initiation codon spanning from nucleotide 114 through nucleotide 116 of SEQ ID NO:1 and a stop codon spanning from nucleotide 510 through nucleotide 512 of SEQ ID NO:1. Translation of SEQ ID NO:4 suggests that nucleic acid molecule nFeIL-18-$C_{502}$ encodes an C-terminal portion of PFeIL-18-C protein, of about 154 amino acids, denoted herein as PFe IL-18-$C_{154}$, the amino acid sequence of which is presented in SEQ ID NO:5, assuming an open reading frame having an initiation codon spanning from nucleotide 3 through nucleotide 5 of SEQ ID NO:4 and a stop codon spanning from nucleotide 462 through nucleotide 464 of SEQ ID NO:4.

Based on the sequence data obtained from these two nucleic acid molecules two new primers were made to isolate a cDNA encoding full-length feline IL-18. The IL-18 Full Forward primer sequence was 5' AACTATTGAG CACAGG- GATA AAGATGACTG 3' (SEQ ID NO:73) and IL-18 Full Reverse primer sequence was 5' AATATCTAAT TCT- TGTTTTG AACAGTGAAC ATT 3' (SEQ ID NO:74). The PCR amplification was performed using these two primers and Amplitaq DNA POLYMERASE™ (available from PE Applied Biosystems Inc.) and an aliquot of the cDNA library prepared from cat peripheral blood lymphocytes stimulated with ConA for 4 hours. The PCR profile was as follows: one initial denaturation step at 94° C. for 5 minutes; then 43 cycles of the following: 94° C. for 30 seconds, then 53° C. for 30 seconds, then 72° C. for 90 seconds; followed by a final extension at 72° C. for 7 minutes. The PCR product was cloned into the TA CLONING® vector (available from Invitrogen, San Diego, Calif.) and the nucleic acid molecule insert was sequenced using an ABI PRISM® Model 377 Automatic DNA Sequencer (available from PE Applied Biosystems Inc.). DNA sequencing reactions were performed using PRISM® dRhodamine Terminator Cycle Sequencing Ready Reaction kits (available from PE Applied Biosystems Inc.). This PCR product the FeIL-18 containing region of which is denoted nFeIL-$18_{607}$ was found to encode a full-length FeIL-18 protein. The nucleotide sequence of the coding strand of nFeIL-$18_{607}$ is represented herein as SEQ ID NO:7, and its complement is denoted by SEQ ID NO:10. Translation of the open reading frame in SEQ ID NO:7, denoted herein as nFeIL-$18_{576}$, the coding strand of which is denoted SEQ ID NO: 9, and the complementary strand denoted SEQ ID NO:41 suggests that feline IL-18 encodes a protein containing 192 amino acids, referred to herein as PFeIL-$18_{192}$, with a SEQ ID NO:8. The nucleic acid sequence encoding feline IL-18 protein assumes an open reading frame in which the first codon spans from nucleotide 24 through 26 of SEQ ID NO:7, and the last codon spans from nucleotide 597 through nucleotide 599 of SEQ ID NO:7. The encoded protein has a predicted molecular weight of about 21.3 kiloDaltons (kDa) for the precursor protein. The IL-18 precursor protein does not contain a signal sequence; in order for IL-18 to be biologically active the precursor is cleaved by caspase-1. The putative caspase-1 cleavage site is between amino acid positions 35 and 36 of the feline IL-18 precursor protein. Nucleic acid molecule nFeIL-1847, which encodes the mature protein contains a coding strand with SEQ ID NO:11, and a complementary strand with SEQ ID NO:13. The amino acid sequence of the mature protein, denoted herein as PFeIL-$18_{157}$ is SEQ ID NO:12 and the mature protein has a predicted molecular weight of about 17.4 kDa. Sequence analysis was performed using DNAsis, available from Hitachi Software, San Bruno, Calif. using the alignment settings of: gap penalty set at 5, k-tuple set at 3, number of top diagonals set at 5, window size set at 5, fixed gap penalty set at 10 and floating gap penalty set at 10.

B. In an attempt to express a mature feline IL-18 protein in a mammalian cell line, the region encoding only the mature IL-18 protein (SEQ ID NO:11) was isolated from the feline cDNA library described in Example 1A using the following primers: IL-18 MatNgo Forward primer which has the sequence 5' TATGCCGGCT ACTTTGGCAA GCTTGAA-CAT AAACTC 3' (SEQ ID NO:75) and IL-18 MatXho Reverse primer which has the sequence 5' GGCCTCGAGC TAATTCTTGT TTTGAACAGT GAACATT 3' (SEQ ID NO:76). The PCR amplification was performed using these two primers and Amplitaq DNA POLYMERASE™ (available from PE Applied Biosystems Inc.) and an aliquot of the cDNA library prepared from cat peripheral blood lymphocytes stimulated with ConA for 4 hours. The PCR profile was as follows: one initial denaturation step at 94° C. for 5 minutes; then 43 cycles of the following: 94° C. for 30 seconds, then 53° C. for 30 seconds, then 72° C. for 90 seconds; followed by a final extension at 72° C. for 7 minutes. The PCR products were digested with Ngo MI and Xho I restriction enzymes (available from New England Biolabs, Beverly, Mass.) and ligated downstream of nucleotides encoding a tissue plasminogen activator (tPA) signal sequence contained in the CMV-IntronA-tPA vector (available from Invitrogen). The construct was sequenced using an ABI PRISM® Model 377 Automatic DNA Sequencer (available from PE Applied Biosystems Inc.). DNA sequencing reactions were performed using PRISM® dRhodamine Terminator Cycle Sequencing Ready Reaction kits (available from PE Applied Biosystems Inc.). This construct encoded the mature feline IL-18 protein with the tPA signal sequence. When Chinese hamster ovary (CHO) cells (available from ATCC, Rockville, Md.) were transiently transfected with this construct, using techniques known to those skilled in the art and cell pellets and supernatants were harvested after 48 hrs. Western analysis was performed on the cell pellets and supernatant samples using a polyclonal antibody against human IL-18 (available from Biosource International, Camarillo, Calif.). A faint band of the expected size (about 17.4 kDa) was detected in the cell pellet and not in the supernatant, indicating that IL-18 is produced by this construct but it is not exported out of the cell at detectable levels. While not being bound by theory, it is believed that caspase-1 plays a key role in the processing of native IL-18 precursor in cells where IL-18 is produced, co-expression of full-length feline IL-18 along with the feline caspase-1 may be necessary for the proper processing of the IL-18 precursor and enhanced secretion of the processed IL-18 mature polypeptide.

Example 2

This example describes the isolation and sequencing of nucleic acid molecules encoding feline caspase-1 proteins of the present invention.

Feline caspase-1 nucleic acid molecules were isolated as follows: A cDNA mitogen library was prepared from cat peripheral blood lymphocytes stimulated with ConA for 4 hours as described in Example 1. An aliquot of this library was used as a template to isolate a feline caspase-1 by polymerase chain reaction (PCR). PCR amplification was performed using Amplitaq DNA POLYMERASE™ (available from PE Applied Biosystems Inc.). The forward and reverse primers were designed based on human caspase-1 sequences. The forward primer (Casp-1 For) had a sequence of 5' ATG-GCCGACA AGGTCCTGAA GGAGAAGA 3' (SEQ ID NO:77) and the reverse primer (Casp-1 Rev) had a sequence of 5' TTAATGTCCT GGGAAGAGGT AGAAACATCT TGT 3' (SEQ ID NO:78). The PCR profile was as follows: one initial denaturation step at 94° C. for 5 minutes; then 43 cycles of the following: 94° C. for 45 seconds, then 53° C. for 45 seconds, then 72° C. for 2 minutes; followed by a final extension at 72° C. for 7 minutes. The PCR product was cloned into the TA CLONING® vector (available from Invitrogen, San Diego, Calif.) and sequenced using an ABI PRISM® Model 377 Automatic DNA Sequencer (available from PE Applied Biosystems Inc.). DNA sequencing reactions were performed using PRISM® dRhodamine Terminator Cycle Sequencing Ready Reaction kits (available from PE Applied Biosystems Inc.). The PCR product was found to contain the complete full-length feline caspase-1 except for the primer region which was based on the human caspase-1 sequence. The nucleotide sequence of the coding strand of this PCR product is represented herein as nFeCasp-$1_{1233}$ with a SEQ ID NO:14, and its complement is denoted by SEQ ID NO:16. Translation of SEQ ID NO:14 suggests that nucleic acid molecule nFeCasp-$1_{1233}$ encodes a full-length nFeCasp-$1_{1233}$ protein, of about 410 amino acids, denoted herein as PFeCasp-$1_{410}$, the amino acid sequence of which is presented in SEQ ID NO:15, assuming an open reading frame having an initiation codon spanning from nucleotide 1 through nucleotide 3 of SEQ ID NO:14 and a stop codon spanning from nucleotide 408 through nucleotide 410 of SEQ ID NO:14.

Additional primers were made based on the feline caspase-1 sequence of nFeCasp-$1_{1233}$ in order to obtain two nucleic acid molecules spanning the 5' and 3' end of the feline caspase-1 open reading frame. Two feline caspase-1 nucleic acid molecules were generated using feline caspase-1 specific primers in combination with cDNA library vector specific primers. The sequence of the vector forward primer (T3 primer) was 5' GCCAAGCTCG AAATTAACCC TCAC-TAAAGG 3' (SEQ ID NO:69), and that of the vector reverse primer (T7 primer) was 5'CGACGGCCAG TGAATTGTAA TACGACTC 3' (SEQ ID NO:70). The sequence of the feline caspase-1-specific forward primer (Casp 271 Forward) was 5' TCAAGCCCAC AATCTGGAAA TTCTCA 3' (SEQ ID NO:79) and the sequence of the feline caspase-1-specific reverse primer (Casp 895 Reverse) was 5' CTGGAGAGTC ACTGATCAAC AGTTCC 3' (SEQ ID NO:80). The first PCR amplification was done using T3 primer and Casp 895 Reverse primer and the second PCR amplification was done using Casp 271 Forward primer and T7 primer. The PCR profile for both reactions was as follows: one initial denaturation step at 94° C. for 5 minutes; then 43 cycles of the following: 94° C. for 45 seconds, then 52° C. for 45 seconds, then 72° C. for 2 minutes; followed by a final extension at 72° C. for 7 minutes. The PCR products from both reactions that were greater than or equal to 1 kb were gel purified and cloned into the TA CLONING® vector (available from Invitrogen) and the nucleic acid molecules were sequenced using an ABI PRISM® Model 377 Automatic DNA Sequencer (available from PE Applied Biosystems Inc.). DNA sequencing reactions were performed using PRISM® dRhodamine Terminator Cycle Sequencing Ready Reaction kits (available from PE Applied Biosystems Inc.). The nucleic acid molecules obtained from these two PCR products represented two nucleic acid molecules of feline caspase-1. The region of the first PCR amplification was sequenced and found to contain 527 nucleotides denoted herein as nFeCasp-1-$N_{527}$ (5'-end partial clone) with a coding strand of SEQ ID NO:17, and a complementary strand of SEQ ID NO:19. The region of the second PCR amplification was sequenced and found to contain 500 nucleotides denoted here as nFeCasp-1-$C_{500}$ (3'-end partial clone) with a coding strand of SEQ ID NO: 20, and a complementary strand of SEQ ID NO: 22. Translation of SEQ ID NO:17 suggests that nucleic acid molecule nFeCasp-1-

$N_{526}$ encodes an N-terminal portion of PFeCasp-1-N protein, of about 169 amino acids, denoted herein as PFeCasp-1-$N_{169}$, the amino acid sequence of which is presented in SEQ ID NO:18, assuming an open reading frame having an initiation codon spanning from nucleotide 18 through nucleotide 20 of SEQ ID NO:17 and a stop codon spanning from nucleotide 522 through nucleotide 524 of SEQ ID NO:17. Translation of SEQ ID NO:20 suggests that nucleic acid molecule nFeCasp-1-$C_{500}$ encodes an C-terminal portion of PFeCasp-1-C protein, of about 120 amino acids, denoted herein as PFeCasp-1-$C_{120}$, the amino acid sequence of which is presented in SEQ ID NO:21, assuming an open reading frame having an initiation codon spanning from nucleotide 3 through nucleotide 5 of SEQ ID NO:20 and a stop codon spanning from nucleotide 360 through nucleotide 362 of SEQ ID NO:20

Based on the sequence data obtained from nucleic acid molecules nFeCasp-1-$N_{527}$ and nFeCasp-1-$C_{500}$, two new primers were made to isolate a cDNA encoding full-length feline caspase-1. The feline caspase-1 full-length forward primer (CaspBamKozFor) sequence was 5' ACAAGGATCC ACCATGGCCG ACAAGGATCT GAAGGG 3' (SEQ ID NO:81) and feline caspase-1 full-length reverse primer (CaspXbaRev) sequence was 5' CGCCTCTAGA CCTCAAT-TGC CAGGGAAGAG ATAGAAGTA 3' (SEQ ID NO:82). The PCR amplification was performed using these two primers and Amplitaq DNA POLYMERASE™ (available from PE Applied Biosystems Inc.) and an aliquot of the cDNA mitogen library prepared from cat peripheral blood lymphocytes stimulated with ConA for 4 hours. The PCR profile was as follows: one initial denaturation step at 94° C. for 5 minutes; then 43 cycles of the following: 94° C. for 45 seconds, then 52° C. for 45 seconds, then 72° C. for 2 minutes; followed by a final extension at 72° C. for 7 minutes. The PCR product was cloned into the TA CLONING® vector (available from Invitrogen) and the nucleic acid molecule inserts were sequenced using an ABI PRISM® Model 377 Automatic DNA Sequencer (available from PE Applied Biosystems Inc.). DNA sequencing reactions were performed using PRISM® dRhodamine Terminator Cycle Sequencing Ready Reaction kits (available from PE Applied Biosystems Inc.). This PCR product the FeCaspase-1 containing region of which is denoted nFeCasp-$1_{1230}$ was found to encode the a full-length feline caspase-1 protein. The nucleotide sequence of the coding strand of nFeCasp-$1_{1230}$ is represented herein as SEQ ID NO 23, and its complement is denoted by SEQ ID NO:25. Translation of the open reading frame in SEQ ID NO:23, denoted here as nFeCasp-$1_{1230}$, the coding strand of which is denoted SEQ ID NO:25 suggests that feline caspase-1 encodes a protein containing 410 amino acids, referred to herein as PFeCasp-$1_{410}$, with a SEQ ID NO:24. The nucleic acid sequence encoding the protein assumes an open reading frame in which the first codon spans from nucleotide 1 through 3 of SEQ ID NO:23, and the last codon spans from nucleotide 1228 nucleotide 1230 of SEQ ID NO:23. The encoded protein has a predicted molecular weight of about 45.5 kDa. The feline caspase-1 protein is 9 amino acids longer than mouse and rat caspase-1 proteins, 6 amino acids longer than dog and human caspase-1 proteins, and 5 amino acids longer than horse caspase-1 proteins. Sequence analysis was performed using DNAsis, available from Hitachi Software, San Bruno, Calif. using the alignment settings of: gap penalty set at 5, k-tuple set at 3, number of top diagonals set at 5, window size set at 5, fixed gap penalty set at 10 and floating gap penalty set at 10.

Example 3

This example describes the isolation and sequencing of nucleic acid molecules encoding feline IL-12 single chain proteins of the present invention.

A. A PBLUESCRIPT®-Linker plasmid was constructed as follows: Two complementary oligonucleotides, 60 nucleotides in length were synthesized. The oligonucleotides were allowed to hybridize to each other in solution producing a double stranded DNA fragment that would serve as a linker between the cDNAs encoding the p40 and p35 subunits of feline IL-12. The sequence of the sense linker was 5' CTG-CAGTGGT GGCGGTGGCG GCGGATCTAG AAACT-TGCCA ACCCCTACTC CATCCCCGGG 3' (SEQ ID NO:83) and the sequence of the antisense linker was 5' CCCGGGGATG GAGTAGGGGT TGGCAAGTTT CTA-GATCCGC CGCCACCGCC ACCACTGCAG 3' (SEQ ID NO:84). Equimolar amounts of sense linker and antisense linker were mixed and heated to 95° C. for 10 minutes in a heat block. The heat block containing the samples was removed from the heat source and allowed to cool to room temperature slowly, over a period of 4 hours. Then the hybridized oligonucleotides were digested with PstI and SmaI restriction enzymes (available from New England Biolabs, Beverly, Mass.) and ligated into PBLUESCRIPT® SK$^+$ vector (available from Stratagene, La Jolla, Calif.) digested with the same restriction enzymes to produce PBLUESCRIPT®-Linker plasmid. The presence of the linker in the ligated PBLUESCRIPT®-Linker plasmid was confirmed by sequencing conducted as described in Example 1. The PBLUESCRIPT®-Linker plasmid contained DNA coding for the following elements: (1) the last two C-terminal amino acid residues of the p40 subunit (i.e. C,S); (2) the seven amino acid residues of the linker (i.e. GGGGGGS) (SEQ ID NO:110); and (3) the first ten N-terminal amino acid residues of the mature p35 subunit mature protein (i.e. RNLPTPTPSP) (SEQ ID NO:111).

B. Feline IL-12 p40 nucleic acid molecule subunit was isolated as follows: A cDNA mitogen library was prepared from cat peripheral blood lymphocytes stimulated with ConA for 4 hours as previously described in Example 1. An aliquot of this library was used as a template to isolate a feline IL-12 p40 nucleic acid molecule subunit by polymerase chain reaction (PCR). The PCR amplification was performed using Amplitaq DNA POLYMERASE™ (available from PE Applied Biosystems Inc.). The sequence of the forward primer was 5' ATGCATCCTC AGCAGTTGGT CATCGCCT 3' (SEQ ID NO:85), and that of the reverse primer was 5' TGCAGGACAC GGATGCCCAG TTGCT 3' (SEQ ID NO:86). The PCR profile was as follows: one initial denaturation step at 94° C. for 5 minutes; then 43 cycles of the following: 94° C. for 45 seconds, then 50° C. for 45 seconds, then 72° C. for 2 minutes; followed by a final extension at 72° C. for 7 minutes. PCR products were cloned into the TA CLONING® vector (available from Invitrogen) and the nucleic acid molecule inserts were sequenced as described in Example 1. One of the sequenced PCR products contained 985 nucleotides and was denoted herein as nFeIL-12 p40-$N_{985}$ with a coding strand of SEQ ID NO:55, and a complementary strand of SEQ ID NO:57. Translation of SEQ ID NO:55 suggests that nucleic acid molecule nFeIL-12p40-$N_{985}$ encodes an N-terminal portion of PFeIL-12p40-N protein, of about 328 amino acids, denoted herein as PFe IL-12p40-$N_{328}$, the amino acid sequence of which is presented in SEQ ID NO:56, assuming an open reading frame having an initiation codon spanning from nucleotide 1 through nucleotide 3 of SEQ ID NO:55 and a stop codon spanning from nucleotide 982 through nucleotide 984 of SEQ ID NO:55.

This nucleic acid molecule was used as a template for a subsequent PCR reaction to obtain a full-length nucleic acid molecule. The PCR amplification was performed using Amplitaq DNA POLYMERASE™ (PE Applied Biosystems Inc, Foster City, Calif.). The sequence of the forward primer was 5' ACAGGTACCA TGCATCCTCA GCAGTTGGTC ATCGCCT 3' (SEQ ID NO:87), and that of the reverse primer was 5' CTAACTGCAG GACACGGATG CCCAG 3' (SEQ ID NO:88). The PCR profile was as follows: one initial denaturation step at 94° C. for 5 minutes; then 35 cycles of the following: 94° C. for 30 seconds, then 50° C. for 30 seconds, then 72° C. for 90 seconds; followed by a final extension at 72° C. for 7 minutes. This PCR product, the Fe IL-12p40 single chain subunit containing region of which is denoted nFeIL-12 p40$_{987}$ was found to encode a full-length feline IL-12 p40 single chain subunit protein. The nucleotide sequence of the coding strand of nFeIL-12 p40$_{987}$ is represented herein as SEQ ID NO:29, and its complementary strand is denoted by SEQ ID NO:31. Translation of SEQ ID NO:29 suggests that nucleic acid molecule nFeIL-12p40$_{987}$ encodes a full-length PFeIL-12p40 protein of about 329 amino acids, denoted herein as PFe IL-12p40$_{329}$, the amino acid sequence of which is presented in SEQ ID NO:30, assuming an open reading frame having an initiation codon spanning from nucleotide 1 through nucleotide 3 of SEQ ID NO:29 and a stop codon spanning from nucleotide 985 through nucleotide 987 of SEQ ID NO:29. This PCR product was digested with Kpn I and Pst I restriction enzymes (available from New England Biolabs) and cloned into the PBLUESCRIPT®-Linker plasmid described in Example 3A. The resultant recombinant molecule is referred to as fep40-linker plasmid. There is a putative cleavage site on SEQ ID NO:30, yielding the coding region for a mature (i.e. lacking a signal or leader sequence)$_n$FeIL-12p40$_{921}$, denoted herein as SEQ ID NO:26, with the complement denoted SEQ ID NO:28. Translation of SEQ ID NO:26 yields a mature IL-12 p40 protein denoted PFeIL-12p40$_{307}$, also denoted herein as SEQ ID NO:27.

C. A Feline IL-12 p35 nucleic acid molecule subunit was isolated as follows: A cDNA mitogen library was prepared from cat peripheral blood lymphocytes stimulated with ConA for 4 hours as previously described in Example 1. An aliquot of this library was used as a template to isolate feline IL-12 p35 subunit by polymerase chain reaction (PCR). The PCR amplification was performed using Amplitaq DNA POLYMERASE™ (PE Applied Biosystems Inc, Foster City, Calif.). The sequence of the forward primer was 5' ATGTGC-CCGC CGCGTGGCC 3' (SEQ ID NO:89), and that of the reverse primer was 5' CTAGGAAGCA TTCAGATAGC TCATCAT 3' (SEQ ID NO:90). The PCR profile was as follows: one initial denaturation step at 94° C. for 5 minutes; then 43 cycles of the following: 94° C. for 45 seconds, then 50° C. for 45 seconds, then 72° C. for 2 minutes; followed by a final extension at 72° C. for 7 minutes. PCR products were cloned into the TA CLONING® vector (available from Invitrogen) and the nucleic acid molecules were sequenced as described in Example 1. One of the sequenced PCR products contained 666 nucleotides and was denoted herein as nFeIL-12-p35$_{666}$ with a coding strand of SEQ ID NO:32, and a complementary strand of SEQ ID NO:34. Translation of SEQ ID NO:32 suggests that nucleic acid molecule nFeIL-12p35$_{666}$ encodes a full-length PFeIL-12p35 protein of about 222 amino acids, denoted herein as PFe IL-12p35$_{222}$, the amino acid sequence of which is presented in SEQ ID NO:33, assuming an open reading frame having an initiation codon spanning from nucleotide 1 through nucleotide 3 of SEQ ID NO:32 and a stop codon spanning from nucleotide 664 through nucleotide 666 of SEQ ID NO:32. There is a putative cleavage site on SEQ ID NO:33, yielding the coding region for a mature (i.e. lacking a signal or leader sequence) nFeIL-12p35$_{591}$, denoted herein as SEQ ID NO:35, with the complement denoted SEQ ID NO:37. Translation of SEQ ID NO:26 yields a mature IL-12 p35 protein denoted PFeIL-12p35$_{197}$, also denoted herein as SEQ ID NO:36. SEQ ID NO:26 was digested with Sma I and Not I restriction enzymes (available from New England Biolabs) and cloned into the fep40-linker plasmid described in Example 3B digested with the same enzymes. The resultant recombinant molecule is referred to as fep40-linker-p35mature plasmid.

D. The fep40-linker-p35mature plasmid contained a nucleic acid molecule encoding a feline IL-12 single chain protein of the present invention inserted into the Kpn I and Not I sites of the PBLUESCRIPT® backbone. Nucleic acid molecule nFeIL-12$_{1599}$ was sequenced as described in Example 1. The nucleotide sequence of the coding strand of nFeIL-12$_{1599}$ is represented herein as SEQ ID NO:38, and that of the complementary strand is SEQ ID NO:40. Translation of the open reading frame in SEQ ID NO:38, suggests that nFeIL-12$_{1599}$ encodes a protein containing 533 amino acids, referred to herein as pFeIL-12$_{533}$, with an amino acid sequence denoted by SEQ ID NO:39. The nucleic acid sequence encoding the protein assumes an open reading frame in which the first codon spans from nucleotide 1 through 3 of SEQ ID NO:38 and the last codon spans from nucleotide 1597 through nucleotide 1599 of SEQ ID NO:38. The encoded protein has a predicted molecular weight of about 59.2 kDa. The putative signal peptide cleavage site is between amino acid positions 22 and 23 of the p40 subunit. Nucleic acid molecule nFeIL-12$_{1533}$, which encodes the mature protein contains a coding strand with SEQ ID NO:43, and a complementary strand with SEQ ID NO:45. The amino acid sequence of the mature protein, denoted herein as PFeIL-12$_{511}$ is SEQ ID NO:44 and the mature protein has a predicted molecular weight of about 56.8 kDa.

Chinese hamster ovary (CHO) cells (available from ATCC, Rockville, Md.) were transiently transfected with fep40-linker-p35mature plasmid (containing SEQ ID NO:38) using techniques known to those skilled in the art, cell pellets and supernatants were harvested after 48 hrs. Western analysis was performed on the cell pellets and supernatant samples using a polyclonal antibody against human IL-12 (available from Biosource International, Camarillo, Calif.). A faint band of the expected size (about 59.2 kDa) was detected in the cell pellet and in the supernatant, indicating that IL-12 is produced by this construct at detectable levels.

Example 4

This example describes the isolation and sequencing of nucleic acid molecules encoding canine IL-12 single chain proteins of the present invention.

A. A canine IL-12 p35 nucleic acid molecule subunit was isolated as follows: A cDNA mitogen library was prepared from canine peripheral blood lymphocytes (PBLs) stimulated with ConA for 4 hours as described in Example 1. Recombinant phage containing DNA encoding the p35 subunit were identified by nucleic acid hybridization using a $P^{32}$ radiolabeled probe. The p35 probe (nCaIL-12p35TA) was generated by PCR of total RNA, prepared from ConA-stimulated PBLs in the following manner. The sequence of the forward primer was 5' CCATCCTGGT CCTGCTAAG C 3' (SEQ ID NO:93) and the sequence of the reverse primer was 5' CCATCTGGTA CATCTTCAAG TC 3' (SEQ ID NO:94). PCR amplification was performed using Amplitaq DNA POLYMERASE™ (available from PE Applied Biosystems Inc.) using the following profile: 95° C. for 2 minutes; then 30 cycles of 95° C. for 1 minute, 55° C. for 1 minute, and 72° C. for 1 minute; and a final extension at 72° C. for 10 minutes. The amplified DNA fragment was purified with Qiagen gel purification kit, available from Qiagen, La Jolla, Calif.) and PCR products were cloned into the TA CLONING® vector (available from Invitrogen Corporation, Carlsbad, Calif.), and the resulting clones were sequenced using an ABI PRISM® Model 377 Automatic DNA Sequencer (available from Perkin-Elmer Applied Biosystems Inc., Foster City, Calif.). DNA sequencing reactions were performed using PRISM® dRhodamine Terminator Cycle Sequencing Ready Reaction kits (available from PE Applied Biosystems Inc.). Phage DNA was permanently cross-linked to the nitrocellulose sheets using a STRATALINKER® UV crosslinker (available from Stratagene). The plaque lifts were pre-hybridized in a solution of 6×SSC (20×SSC is 3.0 M NaCl and 0.3 M sodium citrate), 5×Denhardt's solution (50×SSC is 0.01 grams/milliliter Ficoll, type 400; 0.0 µg/ml polyvinylpyrrolidone; and 0.0 µg/ml bovine serum albumin, fraction V, all available from Sigma, St. Louis, Mo.), 0.5% sodium dodecyl sulfate (SDS), and 100 micrograms/ml denatured salmon sperm for 2 hours at 68° C. Denatured, radiolabeled probe was added to the pre-hybridization solution at a concentration of $1 \times 10^6$ cpm/ml and the hybridization continued for 18-24 hours at 68° C. Nonspecifically bound and unbound probe was removed by washing two times in 2×SSC with 0.1% SDS, 30 minutes each at 68° C. and one time in 1×SSC with 0.1% SDS, 60 minutes at 68° C. The hybridized plaque lifts were exposed to Kodak x-ray film for approximately 18 hours. Positive phage were plaque purified three times using the following hybridization protocol: phage plaques grown in solid top agar were lifted onto pure nitrocellulose sheets (available from Schleicher & Schuell, Keene, N.H.) then denatured and neutralized by soaking the sheets in 0.5 N NaOH/1.5 M NaCl, followed by 0.5 M Tris-HCl pH7.4/1.5 M NaCl. PBLUESCRIPT® plasmid, containing a cDNA encoding the full-length canine IL-12 p35 subunit, was excised from plaque purified phage using the EXASSIST® helper phage (available from Stratagene) following the manufacturers' instructions. The nucleotide sequence of that cDNA, denoted herein as nCa IL-12 $P35_{1455}$ was verified by sequencing as described in Example 1. The nucleic acid sequence of the coding strand of nCaIL-$12p35_{1455}$ represented as SEQ ID NO:104, and its complementary strand is SEQ ID NO:106. Translation of SEQ ID NO:104 suggests that nucleic acid molecule nCaIL-$12p35_{1455}$ encodes an N-terminal portion of PCaIL-12p35 protein, of about 222 amino acids, denoted herein as PCa IL-$12p35_{222}$, the amino acid sequence of which is presented in SEQ ID NO:105, assuming an open reading frame having an initiation codon spanning from nucleotide 232 through nucleotide 234 of SEQ ID NO:104 and a stop codon spanning from nucleotide 895 through nucleotide 897 of SEQ ID NO:104.

Nucleic acid molecule nCaIL-$12p35_{1455}$ was used as the template in PCR to obtain the coding region of the full-length form of canine IL-12 p35 subunit. The sequence of the forward primer was 5' AAAAAACCCG GGTATGTTCC AAT-GTTTCAA CCACTCCC 3' (SEQ ID NO:95) and the sequence of the reverse primer was 5' GCGGCCGCTC GAGTTAGGAA GAGTTCAAGT AGGACATCAT TCTAT-TGATG G 3' (SEQ ID NO:96). PCR was performed using Pfu DNA POLYMERASE™ (available from Stratagene) as follows: 95° C. for 45 seconds; then 25 cycles of 95° C. for 45 seconds, 55° C. for 45 seconds, 72° C. for 1 minute; followed by a final extension at 72° C. for 10 minutes. The PCR product contains the nucleic acid sequence of canine IL-12 p35 subunit which encodes a full-length canine IL-12 p35 subunit protein. The nucleotide sequence of the coding strand of nCaIL-$12p35_{666}$ is represented herein as SEQ ID NO:46 and its complementary strand is denoted SEQ ID NO:48. Translation of SEQ ID NO:46 suggests that nucleic acid molecule nCaIL-$12p35_{666}$ encodes a mature PCaIL-12p35 single chain protein of about 222 amino acids, denoted herein as PCaIL-$12p35_{222}$, the amino acid sequence of which is presented in SEQ ID NO:47, assuming an open reading frame having an initiation codon spanning from nucleotide 1 through nucleotide 3 of SEQ ID NO:46 and a stop codon spanning from nucleotide 589 through nucleotide 591 of SEQ ID NO:46. The coding sequence for the mature polypeptide is encoded by SEQ ID NO:46, the coding region for a mature (i.e. lacking a signal or leader sequence) nCaIL-$12p35_{591}$, denoted herein as SEQ ID NO:49, with the complement denoted SEQ ID NO:51. Translation of SEQ ID NO:49 yields a mature IL-12 p35 protein denoted PCaIL-$12p35_{197}$, also denoted herein as SEQ ID NO:50. nCaIL-$12p35_{591}$, was digested with SmaI and XhoI restriction endonucleases (available from New England Biolabs) and ligated into the PBLUESCRIPT®-Linker plasmid described in Example 3A digested with the same enzymes. The resultant recombinant molecule is referred to as calinker-p35mature plasmid.

B. Canine IL-12 p40 nucleic acid molecule subunit was isolated as follows: A cDNA mitogen library was prepared from canine peripheral blood lymphocytes stimulated with ConA for 4 hours as described in Example 1. Recombinant phage containing DNA encoding the p40 subunit were identified by nucleic acid hybridization using a $P^{32}$ radiolabeled probe. The p40 probe (nCaIL-12p40TA) was generated by PCR of total RNA, prepared from ConA stimulated PBLs in the following manner. The sequence of the forward primer was 5' CTTAAAGGAA CAGAAAGAAT CC 3' (SEQ ID NO:97) and the sequence of the reverse primer was 5' GGTATTCCCA GCTGACCTC 3' (SEQ ID NO:98). PCR amplification was performed using Amplitaq DNA POLYMERASE™ (available from PE Applied Biosystems Inc.) using the following profile: 95° C. for 2 minutes; then 30 cycles of 95° C. for 1 minute, 55° C. for 1 minute, and 72° C. for 1 minute; and a final extension at 72° C. for 10 minutes. The amplified DNA fragment was purified with Qiagen gel purification kit, available from Qiagen, La Jolla, Calif.) and PCR products were cloned into the TA CLONING® vector (available from Invitrogen Corporation, Carlsbad, Calif.), and the resulting clones were sequenced using an ABI PRISM® Model 377 Automatic DNA Sequencer (available from Perkin-Elmer Applied Biosystems Inc., Foster City, Calif.). DNA sequencing reactions were performed using PRISM® dRhodamine Terminator Cycle Sequencing Ready Reaction kits (available from PE Applied Biosystems Inc.). Phage DNA was permanently cross-linked to the nitrocellulose sheets using a STRATALINKER® UV crosslinker (available from Stratagene). The plaque lifts were pre-hybridized in a solution of 6×SSC (20×SSC is 3.0 M NaCl and 0.3 M sodium citrate), 5×Denhardt's solution (50×SSC is 0.01 grams/milliliter Ficoll, type 400; 0.01 g/ml polyvinylpyrrolidone; and 0.01 g/ml bovine serum albumin, fraction V, all available from Sigma, St. Louis, Mo.), 0.5% sodium dodecyl sulfate (SDS), and 100 micrograms/ml denatured salmon sperm for 2 hours at 68° C. Denatured, radiolabeled probe was added to the pre-hybridization solution at a concentration of $1 \times 10^6$ cpm/ml and the hybridization continued for 18-24 hours at 68° C. Nonspecifically bound and unbound probe was removed by washing two times in 2×SSC with 0.1% SDS, 30 minutes each at 68° C. and one time in 1×SSC with 0.1% SDS, 60 minutes at 68° C. The hybridized plaque lifts were exposed to Kodak x-ray film for approximately 18 hours. Positive phage were plaque purified three times using the following hybridization protocol: phage plaques grown in solid top agar were lifted onto pure nitrocellulose sheets (available from Schleicher & Schuell, Keene, N.H.) then denatured and neutralized by soaking the sheets in 0.5 N NaOH/1.5 M NaCl, followed by 0.5 M Tris-HCl pH7.4/1.5 M NaCl. PBLUESCRIPT® plasmid, containing a cDNA encoding the full-length canine IL-12 p40 subunit, was excised from plaque purified phage using the EXASSIST® helper phage (available from Stratagene) following the manufacturers' instructions. The nucleotide sequence of that cDNA, denoted herein as nCaIL-12p40$_{2267}$ was verified by sequencing as described in Example 1. The nucleic acid sequence of the coding strand of nCaIL-12p40$_{2267}$ represented as SEQ ID NO:107, and its complementary strand is SEQ ID NO:109. Translation of SEQ ID NO:107 suggests that nucleic acid molecule nCaIL-12p40$_{2267}$ encodes an PCaIL-12p40 protein, of about 329 amino acids, denoted herein as PCa IL-12p40$_{329}$, the amino acid sequence of which is presented in SEQ ID NO:108, assuming an open reading frame having an initiation codon spanning from nucleotide 154 through nucleotide 156 of SEQ ID NO:107 and a stop codon spanning from nucleotide 1138 through nucleotide 1140 of SEQ ID NO:107.

Full length canine IL-12 p40 nucleic acid molecule was isolated as follows: A plasmid containing full-length canine IL-12 p40 nucleic acid molecule subunit (pCaIL-12p40) was used as a template to sub-clone canine IL-12 p40 subunit by polymerase chain reaction (PCR). PCR amplification was performed using Amplitaq DNA POLYMERASE™ (available from PE Applied Biosystems Inc.). The sequence of the forward primer (Dog p40 KpnFor) was 5' CATAGGTACC ATGCACCCTC AGCAGTTGGT CATCTCC 3' (SEQ ID NO:99), and that of the reverse primer (Dog p40 NsiRev) was 5' ATCTAAATGC ATGACACAGA TGCCCAGTC 3' (SEQ ID NO:100). The PCR profile was as follows: one initial denaturation step at 94° C. for 5 minutes; then 35 cycles of the following: 94° C. for 30 seconds, then 55° C. for 30 seconds, then 72° C. for 2 minutes; followed by a final extension at 72° C. for 7 minutes. The PCR product contains the nucleic acid sequence of canine IL-12 p40 subunit along with its native signal sequence which encodes a canine full-length IL-12 p40 subunit protein. The nucleotide sequence of the coding strand of nCaIL-12 p40$_{987}$ is represented herein as SEQ ID NO:58 and its complementary strand is denoted SEQ ID NO:60. Translation of the open reading frame in SEQ ID NO:58, suggests that canine IL-12 p40 subunit encodes a protein containing 329 amino acids, referred to herein as PCaIL-12 p40$_{329}$ with an amino acid sequence denoted by SEQ ID NO:59. The resulting recombinant molecule is referred to as cap40-linker plasmid. The cap40-linker plasmid was digested with Kpn I and Pst I restriction enzymes (available from New England Biolabs) to remove the region encoding canine p40 mature protein. The PCR product containing the full-length canine p40 subunit (nCaIL-12 p40$_{987}$) was digested with Kpn I and Nsi I restriction enzymes (available from New England Biolabs) and cloned into this digested plasmid. The coding sequence for the mature canine IL-12 p40 polypeptide is encoded by SEQ ID NO:52, the coding region for a mature (i.e. lacking a signal or leader sequence) nCaIL-12p40$_{921}$, with the complement denoted SEQ ID NO:53. Translation of SEQ ID NO:52 yields a mature IL-12 p40 protein denoted PCaIL-12p35$_{307}$, also denoted herein as SEQ ID NO:53. nCaIL-12p40$_{921}$, was digested with SmaI and XhoI restriction endonucleases (available from New England Biolabs) and ligated into the PBLUESCRIPT®-Linker plasmid described in Example 3A digested with the same enzymes.

The resulting plasmid contains a nucleic acid molecule encoding a canine IL-12 single chain cloned at the Kpn I and Not I site into the PBLUESCRIPT® backbone. The complete canine IL-12 single chain insert was sequenced as described in Example 1. The nucleotide sequence of the coding strand of nCaIL-12-single chain$_{1599}$ is represented herein as SEQ ID NO:61, and its complement is denoted by SEQ ID NO:63. Translation of the open reading frame in SEQ ID NO:61, denoted here as nCaIL-12$_{1599}$ with a SEQ ID NO:64 suggests that canine IL-12-single chain encodes a protein containing 533 amino acids, referred to herein as PCaIL-12$_{533}$, with an amino acid sequence denoted by SEQ ID NO:62, assuming an open reading frame in which the first codon spans from nucleotide 1 through 3 of SEQ ID NO:61 and the last codon spans from nucleotide 1597 nucleotide 1599 of SEQ ID NO:61. The encoded protein has a predicted molecular weight of about 59.2 kDa for the precursor protein, and about 56.8 kDa for the mature protein. The putative signal peptide cleavage site is between amino acid positions 22 and 23 of the canine p40 subunit protein. Nucleic acid molecule nCaIL-12$_{1533}$, which encodes the mature protein contains a coding strand with SEQ ID NO:66, and a complementary strand with SEQ ID NO:68. The amino acid sequence of the mature protein, denoted herein as pCaIL-12$_{511}$, is SEQ ID NO:67 and the mature protein has a predicted molecular weight of about 56.8 kDa.

Chinese hamster ovary (CHO) cells (available from ATCC, Rockville, Md.) were transiently transfected with cap40-linker-p35mature plasmid using techniques known to those skilled in the art and cell pellets and supernatants were harvested after 48 hrs. Western analysis was performed on the cell pellets and supernatant samples using a polyclonal antibody against human IL-12 (available from Biosource International, Camarillo, Calif.). A faint band of the expected size (about 59.2 kDa) was detected in the cell pellet and in the supernatant, indicating that IL-12 is produced by this construct at detectable levels.

What is claimed is:

1. An isolated protein comprising an amino acid sequence at least 95% identical to a polypeptide sequence selected from the group consisting of SEQ ID NO:2, SEQ ID NO:5, SEQ ID NO:8 and SEQ ID NO:12, wherein said protein has IL-18 activity.

2. The isolated protein of claim 1, wherein said protein comprises SEQ ID NO:2, SEQ ID NO:5, SEQ ID NO:8 or SEQ ID NO:12.

3. An isolated protein encoded by a nucleic acid sequence at least 95% identical to SEQ ID NO:1, SEQ ID NO:4, SEQ ID NO:7, SEQ ID NO:9, SEQ ID NO:11, and SEQ ID NO:41, wherein said isolated protein has IL-18 activity.

4. The isolated protein of claim 3, wherein said protein is encoded by a nucleic acid sequence selected from the group consisting of SEQ ID NO:1, SEQ ID NO:4, SEQ ID NO:7, SEQ ID NO:9, SEQ ID NO:11, and SEQ ID NO:41.

5. An isolated protein consisting of an amino acid sequence at least 95% identical to a polypeptide sequence selected from the group consisting of SEQ ID NO:2, SEQ ID NO:5, SEQ ID NO:8 and SEQ ID NO:12, wherein said protein has IL-18 activity.

6. The isolated protein of claim 5, wherein the protein consists of an amino acid sequence selected from the group consisting of SEQ ID NO:2, SEQ ID NO:5, SEQ ID NO:8 and SEQ ID NO:12.

* * * * *

SEQUENCE LISTING

```
<160> NUMBER OF SEQ ID NOS: 111

<210> SEQ ID NO 1
<211> LENGTH: 514
<212> TYPE: DNA
<213> ORGANISM: Felis catus
<220> FEATURE:
<221> NAME/KEY: CDS
<222> LOCATION: (114)..(512)
<220> FEATURE:
<221> NAME/KEY: misc_feature
<222> LOCATION: (470)..(470)
```

<223> OTHER INFORMATION: n = unknown

<400> SEQUENCE: 1

```
gctaaaggcg ctcctgccac cttctgccat ctacacagct caggaaaaga aagggacctc    60
aaaccttcca gatcccttcc tctcttagga aactattgag cacagggata aag atg     116
                                                            Met
                                                            1
```

| | | | | | | | | | | | | | | | | |
|---|---|---|---|---|---|---|---|---|---|---|---|---|---|---|---|---|
| act | gct | ata | cca | gta | gat | gat | tgc | atc | aac | ttt | gtg | gga | atg | aaa | ttt | 164 |
| Thr | Ala | Ile | Pro | Val | Asp | Asp | Cys | Ile | Asn | Phe | Val | Gly | Met | Lys | Phe | |
| | | 5 | | | | | 10 | | | | | 15 | | | | |

| | | | | | | | | | | | | | | | | |
|---|---|---|---|---|---|---|---|---|---|---|---|---|---|---|---|---|
| att | gac | aat | aca | ctt | tac | ttt | gta | gct | gac | agt | gat | gaa | aac | ctg | gaa | 212 |
| Ile | Asp | Asn | Thr | Leu | Tyr | Phe | Val | Ala | Asp | Ser | Asp | Glu | Asn | Leu | Glu | |
| | | | 20 | | | | | 25 | | | | | 30 | | | |

| | | | | | | | | | | | | | | | | |
|---|---|---|---|---|---|---|---|---|---|---|---|---|---|---|---|---|
| aca | gat | tac | ttt | ggc | aag | ctt | gaa | cat | aaa | ctc | tca | atc | tta | cga | aac | 260 |
| Thr | Asp | Tyr | Phe | Gly | Lys | Leu | Glu | His | Lys | Leu | Ser | Ile | Leu | Arg | Asn | |
| | | 35 | | | | | 40 | | | | | 45 | | | | |

| | | | | | | | | | | | | | | | | |
|---|---|---|---|---|---|---|---|---|---|---|---|---|---|---|---|---|
| ttg | aac | gac | caa | gtt | ctc | ttc | att | aac | cag | gga | gat | caa | cct | gtg | ttt | 308 |
| Leu | Asn | Asp | Gln | Val | Leu | Phe | Ile | Asn | Gln | Gly | Asp | Gln | Pro | Val | Phe | |
| 50 | | | | | 55 | | | | | 60 | | | | | 65 | |

| | | | | | | | | | | | | | | | | |
|---|---|---|---|---|---|---|---|---|---|---|---|---|---|---|---|---|
| gag | gat | atg | cct | gat | tct | gac | tgt | aca | gat | aat | gca | ccc | cgg | act | gaa | 356 |
| Glu | Asp | Met | Pro | Asp | Ser | Asp | Cys | Thr | Asp | Asn | Ala | Pro | Arg | Thr | Glu | |
| | | | 70 | | | | | 75 | | | | | 80 | | | |

| | | | | | | | | | | | | | | | | |
|---|---|---|---|---|---|---|---|---|---|---|---|---|---|---|---|---|
| ttt | atc | ata | tat | atg | tat | aaa | gat | agc | ctc | act | aga | ggt | ctg | gca | gta | 404 |
| Phe | Ile | Ile | Tyr | Met | Tyr | Lys | Asp | Ser | Leu | Thr | Arg | Gly | Leu | Ala | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| acc | atc | tct | gtg | aat | tat | aag | acc | atg | tct | act | ctc | tcc | tgt | gag | aac | 452 |
| Thr | Ile | Ser | Val | Asn | Tyr | Lys | Thr | Met | Ser | Thr | Leu | Ser | Cys | Glu | Asn | |
| | | | 100 | | | | | 105 | | | | | 110 | | | |

| | | | | | | | | | | | | | | | | |
|---|---|---|---|---|---|---|---|---|---|---|---|---|---|---|---|---|
| aaa | att | att | tcc | ttt | aan | gga | atg | agt | cct | cct | gag | agt | atc | aat | gat | 500 |
| Lys | Ile | Ile | Ser | Phe | Xaa | Gly | Met | Ser | Pro | Pro | Glu | Ser | Ile | Asn | Asp | |
| | | 115 | | | | | 120 | | | | | 125 | | | | |

```
gaa gga aat gac at                                                  514
Glu Gly Asn Asp
130
```

<210> SEQ ID NO 2
<211> LENGTH: 133
<212> TYPE: PRT
<213> ORGANISM: Felis catus
<220> FEATURE:
<221> NAME/KEY: misc_feature
<222> LOCATION: (119)..(119)
<223> OTHER INFORMATION: The 'Xaa' at location 119 stands for Lys, or Asn.

<400> SEQUENCE: 2

```
Met Thr Ala Ile Pro Val Asp Asp Cys Ile Asn Phe Val Gly Met Lys
1               5                   10                  15

Phe Ile Asp Asn Thr Leu Tyr Phe Val Ala Asp Ser Asp Glu Asn Leu
            20                  25                  30

Glu Thr Asp Tyr Phe Gly Lys Leu Glu His Lys Leu Ser Ile Leu Arg
        35                  40                  45

Asn Leu Asn Asp Gln Val Leu Phe Ile Asn Gln Gly Asp Gln Pro Val
    50                  55                  60

Phe Glu Asp Met Pro Asp Ser Asp Cys Thr Asp Asn Ala Pro Arg Thr
65                  70                  75                  80

Glu Phe Ile Ile Tyr Met Tyr Lys Asp Ser Leu Thr Arg Gly Leu Ala
                85                  90                  95

Val Thr Ile Ser Val Asn Tyr Lys Thr Met Ser Thr Leu Ser Cys Glu
            100                 105                 110
```

```
        Asn Lys Ile Ile Ser Phe Xaa Gly Met Ser Pro Glu Ser Ile Asn
            115                 120                 125

Asp Glu Gly Asn Asp
            130

<210> SEQ ID NO 3
<211> LENGTH: 514
<212> TYPE: DNA
<213> ORGANISM: Felis catus
<220> FEATURE:
<221> NAME/KEY: misc_feature
<222> LOCATION: (45)..(45)
<223> OTHER INFORMATION: n = unknown at position 45

<400> SEQUENCE: 3
atgtcatttc cttcatcatt gatactctca ggaggactca ttccnttaaa ggaaataatt      60
ttgttctcac aggagagagt agacatggtc ttataattca cagagatggt tactgccaga    120
cctctagtga ggctatcttt atacatatat atgataaatt cagtccgggg tgcattatct    180
gtacagtcag aatcaggcat atcctcaaac acaggttgat ctccctggtt aatgaagaga    240
acttggtcgt tcaagtttcg taagattgag agtttatgtt caagcttgcc aaagtaatct    300
gtttccaggt tttcatcact gtcagctaca aagtaaagtg tattgtcaat aaatttcatt    360
cccacaaagt tgatgcaatc atctactggt atagcagtca tctttatccc tgtgctcaat    420
agtttcctaa gagaggaagg gatctggaag gtttgaggtc cctttctttt cctgagctgt    480
gtagatggca gaaggtggca ggagcgcctt tagc                               514

<210> SEQ ID NO 4
<211> LENGTH: 502
<212> TYPE: DNA
<213> ORGANISM: Felis catus
<220> FEATURE:
<221> NAME/KEY: CDS
<222> LOCATION: (3)..(464)
<220> FEATURE:
<221> NAME/KEY: misc_feature
<222> LOCATION: (126)..(126)
<223> OTHER INFORMATION: n = unknown at position 126

<400> SEQUENCE: 4 gc aag ctt gaa cat aaa ctc tca atc tta cga aac ttg aac gac caa       47
   Lys Leu Glu His Lys Leu Ser Ile Leu Arg Asn Leu Asn Asp Gln
    1               5                   10                  15 gtt ctc ttc att aac cag gga gat caa cct gtg ttt gag gat atg cct      95
Val Leu Phe Ile Asn Gln Gly Asp Gln Pro Val Phe Glu Asp Met Pro
                20                  25                  30 gat tct gac tgt aca gat aat gca ccc cgg nct gaa ttt atc ata tat     143
Asp Ser Asp Cys Thr Asp Asn Ala Pro Arg Xaa Glu Phe Ile Ile Tyr
        35                  40                  45 atg tat aaa gat agc ctc act aga ggt ctg gca gta acc atc tct gtg     191
Met Tyr Lys Asp Ser Leu Thr Arg Gly Leu Ala Val Thr Ile Ser Val
    50                  55                  60 aat tat aag acc atg tct act ctc tcc tgt gag aac aaa att att tcc     239
Asn Tyr Lys Thr Met Ser Thr Leu Ser Cys Glu Asn Lys Ile Ile Ser
65                  70                  75 ttt aag gaa atg agt cct cct gag agt atc aat gat gaa gga aat gac     287
Phe Lys Glu Met Ser Pro Pro Glu Ser Ile Asn Asp Glu Gly Asn Asp
80                  85                  90                  95 atc ata ttc ttt cag aga agt gtt cca gga cat gat gat aag ata caa     335
Ile Ile Phe Phe Gln Arg Ser Val Pro Gly His Asp Asp Lys Ile Gln
                100                 105                 110 ttt gag tct tca ttg tac aag ggg tac ttt cta gct tgt gaa aaa gag     383
Phe Glu Ser Ser Leu Tyr Lys Gly Tyr Phe Leu Ala Cys Glu Lys Glu
```

```
                Phe Glu Ser Ser Leu Tyr Lys Gly Tyr Phe Leu Ala Cys Glu Lys Glu
                        115                 120                 125 aaa gat ctt ttc aaa ctc att ttg aaa aaa aag gat gaa aat ggg gat           431
Lys Asp Leu Phe Lys Leu Ile Leu Lys Lys Lys Asp Glu Asn Gly Asp
        130                 135                 140 aag tcc ata atg ttc act gtt caa aac aag aat tagatattaa aattgcataa         484
Lys Ser Ile Met Phe Thr Val Gln Asn Lys Asn
        145                 150 tttgaaaaaa aaaaaaaa                                                       502

<210> SEQ ID NO 5
<211> LENGTH: 154
<212> TYPE: PRT
<213> ORGANISM: Felis catus
<220> FEATURE:
<221> NAME/KEY: misc_feature
<222> LOCATION: (42)..(42)
<223> OTHER INFORMATION: The 'Xaa' at location 42 stands for Thr, Ala,
      Pro, or Ser.

<400> SEQUENCE: 5

Lys Leu Glu His Lys Leu Ser Ile Leu Arg Asn Leu Asn Asp Gln Val
1               5                   10                  15

Leu Phe Ile Asn Gln Gly Asp Gln Pro Val Phe Glu Asp Met Pro Asp
            20                  25                  30

Ser Asp Cys Thr Asp Asn Ala Pro Arg Xaa Glu Phe Ile Ile Tyr Met
        35                  40                  45

Tyr Lys Asp Ser Leu Thr Arg Gly Leu Ala Val Thr Ile Ser Val Asn
50                  55                  60

Tyr Lys Thr Met Ser Thr Leu Ser Cys Glu Asn Lys Ile Ile Ser Phe
65                  70                  75                  80

Lys Glu Met Ser Pro Pro Glu Ser Ile Asn Asp Glu Gly Asn Asp Ile
                85                  90                  95

Ile Phe Phe Gln Arg Ser Val Pro Gly His Asp Asp Lys Ile Gln Phe
            100                 105                 110

Glu Ser Ser Leu Tyr Lys Gly Tyr Phe Leu Ala Cys Glu Lys Glu Lys
        115                 120                 125

Asp Leu Phe Lys Leu Ile Leu Lys Lys Lys Asp Glu Asn Gly Asp Lys
    130                 135                 140

Ser Ile Met Phe Thr Val Gln Asn Lys Asn
145                 150

<210> SEQ ID NO 6
<211> LENGTH: 502
<212> TYPE: DNA
<213> ORGANISM: Felis catus
<220> FEATURE:
<221> NAME/KEY: misc_feature
<222> LOCATION: (377)..(377)
<223> OTHER INFORMATION: n = unknown

<400> SEQUENCE: 6
tttttttttt ttttcaaatt atgcaatttt aatatctaat tcttgttttg aacagtgaac         60
attatggact tatccccatt ttcatccttt tttttcaaaa tgagtttgaa aagatctttc         120 tcttttcac aagctagaaa gtaccccttg tacaatgaag actcaaattg tatcttatca         180
tcatgtcctg gaacacttct ctgaaagaat atgatgtcat ttccttcatc attgatactc        240
tcaggaggac tcatttcctt aaaggaaata attttgttct cacaggagag agtagacatg        300
gtcttataat tcacagagat ggttactgcc agacctctag tgaggctatc tttatacata        360
```

```
tatatgataa attcagnccg gggtgcatta tctgtacagt cagaatcagg catatcctca      420
aacacaggtt gatctccctg gttaatgaag agaacttggt cgttcaagtt tcgtaagatt      480
gagagtttat gttcaagctt gc                                               502
```

<210> SEQ ID NO 7
<211> LENGTH: 607
<212> TYPE: DNA
<213> ORGANISM: Felis catus
<220> FEATURE:
<221> NAME/KEY: CDS
<222> LOCATION: (24)..(599)

<400> SEQUENCE: 7

```
aactattgag cacagggata aag atg act gct ata cca gta gat gat tgc atc        53
                         Met Thr Ala Ile Pro Val Asp Asp Cys Ile
                          1               5                  10 aac ttt gtg gga atg aaa ttt att gac aat aca ctt tac ttt gta gct         101
Asn Phe Val Gly Met Lys Phe Ile Asp Asn Thr Leu Tyr Phe Val Ala
             15                  20                  25 gac agt gat gaa aac ctg gaa aca gat tac ttt ggc aag ctt gaa cat         149
Asp Ser Asp Glu Asn Leu Glu Thr Asp Tyr Phe Gly Lys Leu Glu His
         30                  35                  40 aaa ctc tca atc tta cga aac ttg aac gac caa gtt ctc ttc att aac         197
Lys Leu Ser Ile Leu Arg Asn Leu Asn Asp Gln Val Leu Phe Ile Asn
     45                  50                  55 cag gga gat caa cct gtg ttt gag gat atg cct gat tct gac tgt aca         245
Gln Gly Asp Gln Pro Val Phe Glu Asp Met Pro Asp Ser Asp Cys Thr
 60                  65                  70 gat aat gca ccc cgg act gaa ttt atc ata tat atg tat aaa gat agc         293
Asp Asn Ala Pro Arg Thr Glu Phe Ile Ile Tyr Met Tyr Lys Asp Ser
 75                  80                  85                  90 ctc act aga ggt ctg gca gta acc atc tct gtg aat tat aag acc atg         341
Leu Thr Arg Gly Leu Ala Val Thr Ile Ser Val Asn Tyr Lys Thr Met
                 95                 100                 105 tct act ctc tcc tgt gag aac aaa att att tcc ttt aag gaa atg agt         389
Ser Thr Leu Ser Cys Glu Asn Lys Ile Ile Ser Phe Lys Glu Met Ser
            110                 115                 120 cct cct gag agt atc aat gat gaa gga aat gac atc ata ttc ttt cag         437
Pro Pro Glu Ser Ile Asn Asp Glu Gly Asn Asp Ile Ile Phe Phe Gln
        125                 130                 135 aga agt gtt cca gga cat gat gat aag ata caa ttt gag tct tca ttg         485
Arg Ser Val Pro Gly His Asp Asp Lys Ile Gln Phe Glu Ser Ser Leu
    140                 145                 150 tac aag ggg tac ttt cta gct tgt gaa aaa gag aaa gat ctt ttc aaa         533
Tyr Lys Gly Tyr Phe Leu Ala Cys Glu Lys Glu Lys Asp Leu Phe Lys
155                 160                 165                 170 ctc att ttg aaa aaa aag gat gaa aat ggg gat aag tcc ata atg ttc         581
Leu Ile Leu Lys Lys Lys Asp Glu Asn Gly Asp Lys Ser Ile Met Phe
                175                 180                 185 act gtt caa aac aag aat tagatatt                                        607
Thr Val Gln Asn Lys Asn
            190
```

<210> SEQ ID NO 8
<211> LENGTH: 192
<212> TYPE: PRT
<213> ORGANISM: Felis catus

<400> SEQUENCE: 8

```
Met Thr Ala Ile Pro Val Asp Asp Cys Ile Asn Phe Val Gly Met Lys
 1               5                  10                  15
```

```
Phe Ile Asp Asn Thr Leu Tyr Phe Val Ala Asp Ser Asp Glu Asn Leu
         20                  25                  30

Glu Thr Asp Tyr Phe Gly Lys Leu Glu His Lys Leu Ser Ile Leu Arg
         35                  40                  45

Asn Leu Asn Asp Gln Val Leu Phe Ile Asn Gln Gly Asp Gln Pro Val
 50                  55                  60

Phe Glu Asp Met Pro Asp Ser Asp Cys Thr Asp Asn Ala Pro Arg Thr
 65                  70                  75                  80

Glu Phe Ile Ile Tyr Met Tyr Lys Asp Ser Leu Thr Arg Gly Leu Ala
                 85                  90                  95

Val Thr Ile Ser Val Asn Tyr Lys Thr Met Ser Thr Leu Ser Cys Glu
                100                 105                 110

Asn Lys Ile Ile Ser Phe Lys Glu Met Ser Pro Pro Glu Ser Ile Asn
            115                 120                 125

Asp Glu Gly Asn Asp Ile Ile Phe Phe Gln Arg Ser Val Pro Gly His
        130                 135                 140

Asp Asp Lys Ile Gln Phe Glu Ser Ser Leu Tyr Lys Gly Tyr Phe Leu
145                 150                 155                 160

Ala Cys Glu Lys Glu Lys Asp Leu Phe Lys Leu Ile Leu Lys Lys Lys
                165                 170                 175

Asp Glu Asn Gly Asp Lys Ser Ile Met Phe Thr Val Gln Asn Lys Asn
            180                 185                 190

<210> SEQ ID NO 9
<211> LENGTH: 576
<212> TYPE: DNA
<213> ORGANISM: Felis catus

<400> SEQUENCE: 9
atgactgcta taccagtaga tgattgcatc aactttgtgg gaatgaaatt tattgacaat      60
acactttact tgtagctga cagtgatgaa aacctggaaa cagattactt tggcaagctt     120
gaacataaac tctcaatctt acgaaacttg aacgaccaag ttctcttcat taaccaggga     180
gatcaacctg tgtttgagga tatgcctgat tctgactgta cagataatgc accccggact     240
gaatttatca tatatatgta taagatagc ctcactagag gtctggcagt aaccatctct     300
gtgaattata agaccatgtc tactctctcc tgtgagaaca aaattattc ctttaaggaa      360 atgagtcctc ctgagagtat caatgatgaa ggaaatgaca tcatattctt tcagagaagt     420
gttccaggac atgatgataa gatcaaattt gagtcttcat tgtacaaggg gtactttcta     480
gcttgtgaaa aagagaaaga tctttttcaaa ctcatttga aaaaaaagga tgaaaatggg     540
gataagtcca taatgttcac tgttcaaaac aagaat                              576

<210> SEQ ID NO 10
<211> LENGTH: 607
<212> TYPE: DNA
<213> ORGANISM: Felis catus

<400> SEQUENCE: 10
aatatctaat tcttgttttg aacagtgaac attatggact tatccccatt ttcatccttt      60
tttttcaaaa tgagtttgaa aagatctttc tcttttttcac aagctagaaa gtaccccttg     120
tacaatgaag actcaaattg tatcttatca tcatgtcctg aacacttct ctgaaagaat       180 atgatgtcat ttccttcatc attgatactc tcaggaggac tcatttcctt aaaggaaata     240 atttgttct cacaggagag agtagacatg gtccttataa tcacagagat ggttactgcc       300
agacctctag tgaggctatc tttatacata tatatgataa attcagtccg ggtgcatta      360
```

```
tctgtacagt cagaatcagg catatcctca aacacaggtt gatctccctg gttaatgaag    420
agaacttggt cgttcaagtt tcgtaagatt gagagtttat gttcaagctt gccaaagtaa    480 tctgttttcca ggttttcatc actgtcagct acaaagtaaa gtgtattgtc aataaatttc   540
attcccacaa agttgatgca atcatctact ggtatagcag tcatctttat ccctgtgctc    600
aatagtt                                                              607
```

<210> SEQ ID NO 11
<211> LENGTH: 471
<212> TYPE: DNA
<213> ORGANISM: Felis catus
<220> FEATURE:
<221> NAME/KEY: CDS
<222> LOCATION: (1)..(471)

<400> SEQUENCE: 11

```
tac ttt ggc aag ctt gaa cat aaa ctc tca atc tta cga aac ttg aac     48
Tyr Phe Gly Lys Leu Glu His Lys Leu Ser Ile Leu Arg Asn Leu Asn
1               5                   10                  15 gac caa gtt ctc ttc att aac cag gga gat caa cct gtg ttt gag gat     96
Asp Gln Val Leu Phe Ile Asn Gln Gly Asp Gln Pro Val Phe Glu Asp
            20                  25                  30 atg cct gat tct gac tgt aca gat aat gca ccc cgg act gaa ttt atc    144
Met Pro Asp Ser Asp Cys Thr Asp Asn Ala Pro Arg Thr Glu Phe Ile
        35                  40                  45 ata tat atg tat aaa gat agc ctc act aga ggt ctg gca gta acc atc    192
Ile Tyr Met Tyr Lys Asp Ser Leu Thr Arg Gly Leu Ala Val Thr Ile
    50                  55                  60 tct gtg aat tat aag acc atg tct act ctc tcc tgt gag aac aaa att    240
Ser Val Asn Tyr Lys Thr Met Ser Thr Leu Ser Cys Glu Asn Lys Ile
65                  70                  75                  80 att tcc ttt aag gaa atg agt cct cct gag agt atc aat gat gaa gga    288
Ile Ser Phe Lys Glu Met Ser Pro Pro Glu Ser Ile Asn Asp Glu Gly
                85                  90                  95 aat gac atc ata ttc ttt cag aga agt gtt cca gga cat gat gat aag    336
Asn Asp Ile Ile Phe Phe Gln Arg Ser Val Pro Gly His Asp Asp Lys
            100                 105                 110 ata caa ttt gag tct tca ttg tac aag ggg tac ttt cta gct tgt gaa    384
Ile Gln Phe Glu Ser Ser Leu Tyr Lys Gly Tyr Phe Leu Ala Cys Glu
        115                 120                 125 aaa gag aaa gat ctt ttc aaa ctc att ttg aaa aaa aag gat gaa aat    432
Lys Glu Lys Asp Leu Phe Lys Leu Ile Leu Lys Lys Lys Asp Glu Asn
    130                 135                 140 ggg gat aag tcc ata atg ttc act gtt caa aac aag aat                471
Gly Asp Lys Ser Ile Met Phe Thr Val Gln Asn Lys Asn
145                 150                 155
```

<210> SEQ ID NO 12
<211> LENGTH: 157
<212> TYPE: PRT
<213> ORGANISM: Felis catus

<400> SEQUENCE: 12

```
Tyr Phe Gly Lys Leu Glu His Lys Leu Ser Ile Leu Arg Asn Leu Asn
1               5                   10                  15

Asp Gln Val Leu Phe Ile Asn Gln Gly Asp Gln Pro Val Phe Glu Asp
            20                  25                  30

Met Pro Asp Ser Asp Cys Thr Asp Asn Ala Pro Arg Thr Glu Phe Ile
        35                  40                  45

Ile Tyr Met Tyr Lys Asp Ser Leu Thr Arg Gly Leu Ala Val Thr Ile
```

```
                    50                  55                  60
Ser Val Asn Tyr Lys Thr Met Ser Thr Leu Ser Cys Glu Asn Lys Ile
 65                  70                  75                  80

Ile Ser Phe Lys Glu Met Ser Pro Pro Glu Ser Ile Asn Asp Glu Gly
                 85                  90                  95

Asn Asp Ile Ile Phe Phe Gln Arg Ser Val Pro Gly His Asp Asp Lys
            100                 105                 110

Ile Gln Phe Glu Ser Ser Leu Tyr Lys Gly Tyr Phe Leu Ala Cys Glu
        115                 120                 125

Lys Glu Lys Asp Leu Phe Lys Leu Ile Leu Lys Lys Asp Glu Asn
    130                 135                 140

Gly Asp Lys Ser Ile Met Phe Thr Val Gln Asn Lys Asn
145                 150                 155

<210> SEQ ID NO 13
<211> LENGTH: 471
<212> TYPE: DNA
<213> ORGANISM: Felis catus

<400> SEQUENCE: 13
attcttgttt tgaacagtga acattatgga cttatcccca ttttcatcct ttttttcaa       60 aatgagtttg aaaagatctt tctctttttc acaagctaga aagtacccct tgtacaatga     120
agactcaaat tgtatcttat catcatgtcc tggaacactt ctctgaaaga atatgatgtc     180
atttccttca tcattgatac tctcaggagg actcatttcc ttaaaggaaa taattttgtt     240
ctcacaggag agagtagaca tggtcttata attcacagag atggttactg ccagacctct     300
agtgaggcta tctttataca tatatatgat aaattcagtc cggggtgcat tatctgtaca     360
gtcagaatca ggcatatcct caaacacagg ttgatctccc tggttaatga agagaacttg     420
gtcgttcaag tttcgtaaga ttgagagttt atgttcaagc ttgccaaagt a              471

<210> SEQ ID NO 14
<211> LENGTH: 1233
<212> TYPE: DNA
<213> ORGANISM: Felis catus
<220> FEATURE:
<221> NAME/KEY: CDS
<222> LOCATION: (1)..(1230)

<400> SEQUENCE: 14 atg gcc gac aag gtc ctg aag gag aag agg aag cag ttc atc aac tca        48
Met Ala Asp Lys Val Leu Lys Glu Lys Arg Lys Gln Phe Ile Asn Ser
  1               5                  10                  15 gtc ggc atg ggg acg gtc aac ggc ttg ctg gat gaa ctc ttt gag aaa        96
Val Gly Met Gly Thr Val Asn Gly Leu Leu Asp Glu Leu Phe Glu Lys
             20                  25                  30 aac gtg ctg aac cag gag gag atg gag aga gta aaa tgt gaa aac gct       144
Asn Val Leu Asn Gln Glu Glu Met Glu Arg Val Lys Cys Glu Asn Ala
         35                  40                  45 acc gtt atg gac aag gcc cga gct ctg atc gac agc gtc ctg cgg aaa       192
Thr Val Met Asp Lys Ala Arg Ala Leu Ile Asp Ser Val Leu Arg Lys
     50                  55                  60 ggg cca cgg gcg tgc cag atc ttt atc tgt cac atc tgt gag gaa gac       240
Gly Pro Arg Ala Cys Gln Ile Phe Ile Cys His Ile Cys Glu Glu Asp
 65                  70                  75                  80 acc cac ctt gca gag acg ctg ggg ctc tcc tca agc cca caa tct gga       288
Thr His Leu Ala Glu Thr Leu Gly Leu Ser Ser Ser Pro Gln Ser Gly
                 85                  90                  95 aat tct cag aac acc acg gac tct gaa gta gcg ttt cct cct ctt cca       336
```

-continued

```
                Asn Ser Gln Asn Thr Thr Asp Ser Glu Val Ala Phe Pro Pro Leu Pro
                            100                 105                 110 gcc agc gtg aat aac atg cct ggg ccg gct gag cca gaa gaa tct gta        384
Ala Ser Val Asn Asn Met Pro Gly Pro Ala Glu Pro Glu Glu Ser Val
            115                 120                 125 gat gct ctc aag ctt tgt cct cgt gaa aac ttc gtg aaa ctg tgt aaa        432
Asp Ala Leu Lys Leu Cys Pro Arg Glu Asn Phe Val Lys Leu Cys Lys
130                 135                 140 cag agg gct gaa gag atc tac cca ata aag gag aga aag gat cgt act        480
Gln Arg Ala Glu Glu Ile Tyr Pro Ile Lys Glu Arg Lys Asp Arg Thr
145                 150                 155                 160 cgt ctg gct ctc atc ata tgc aat acg acg ttc gat cat ctt tct ctc        528
Arg Leu Ala Leu Ile Ile Cys Asn Thr Thr Phe Asp His Leu Ser Leu
                165                 170                 175 agg aag ggg gct gac ctt gac gtt gca ggg atg agg agg ctg ctt aca        576
Arg Lys Gly Ala Asp Leu Asp Val Ala Gly Met Arg Arg Leu Leu Thr
            180                 185                 190 gac ctt ggc tac agt gtg cac ata aaa gag gaa ctc act gct aag gac        624
Asp Leu Gly Tyr Ser Val His Ile Lys Glu Glu Leu Thr Ala Lys Asp
        195                 200                 205 atg gaa tca gag ctg agg gca ttt gct gcc cgt cca gag cac aag tcc        672
Met Glu Ser Glu Leu Arg Ala Phe Ala Ala Arg Pro Glu His Lys Ser
210                 215                 220 tcg gac agc aca ttc ctg gtg ttc atg tct cat ggc atc ctg agt gga        720
Ser Asp Ser Thr Phe Leu Val Phe Met Ser His Gly Ile Leu Ser Gly
225                 230                 235                 240 atc tgt ggg acg aag tac agc gct gaa gga gac cca gat gta ttg gct        768
Ile Cys Gly Thr Lys Tyr Ser Ala Glu Gly Asp Pro Asp Val Leu Ala
                245                 250                 255 tat gac acc atc ttc cag att ttc aac aac cgc aac tgc ctt agt cta        816
Tyr Asp Thr Ile Phe Gln Ile Phe Asn Asn Arg Asn Cys Leu Ser Leu
                260                 265                 270 aag gac aag ccc aag gtc atc atc gtc cag gcc tgc aga ggt gaa aat        864
Lys Asp Lys Pro Lys Val Ile Ile Val Gln Ala Cys Arg Gly Glu Asn
            275                 280                 285 ttg ggg gaa ctg ttg atc agt gac tct cca gcg gcc cca atg gac agc        912
Leu Gly Glu Leu Leu Ile Ser Asp Ser Pro Ala Ala Pro Met Asp Ser
        290                 295                 300 act tca cag atg ggt agc agc ctt tca cag gtg ggt gac aac cta gag        960
Thr Ser Gln Met Gly Ser Ser Leu Ser Gln Val Gly Asp Asn Leu Glu
305                 310                 315                 320 gac gac gcc att tac aag gtc cac gtg gag aag gac ttc atc gct ttc       1008
Asp Asp Ala Ile Tyr Lys Val His Val Glu Lys Asp Phe Ile Ala Phe
                325                 330                 335 tgc tcc tcg acc cca cat cat gtg tct tgg aga gac gtg aac aag gga       1056
Cys Ser Ser Thr Pro His His Val Ser Trp Arg Asp Val Asn Lys Gly
            340                 345                 350 tct ctc ttc att aca caa ctc atc acg tgc ttc caa aag tat tcg tgg       1104
Ser Leu Phe Ile Thr Gln Leu Ile Thr Cys Phe Gln Lys Tyr Ser Trp
        355                 360                 365 tgc ttt cat ctg gag gaa gta ttt cgg aag gta caa cag tca ttt gaa       1152
Cys Phe His Leu Glu Glu Val Phe Arg Lys Val Gln Gln Ser Phe Glu
370                 375                 380 aaa cca aat gtt aga gcc cag atg ccc acc att gaa cga cta tcc atg       1200
Lys Pro Asn Val Arg Ala Gln Met Pro Thr Ile Glu Arg Leu Ser Met
385                 390                 395                 400 aca aga tgt ttc tac ctc ttc cca gga cat taa                           1233
Thr Arg Cys Phe Tyr Leu Phe Pro Gly His
                405                 410
```

<210> SEQ ID NO 15
<211> LENGTH: 410
<212> TYPE: PRT
<213> ORGANISM: Felis catus

<400> SEQUENCE: 15

```
Met Ala Asp Lys Val Leu Lys Glu Lys Arg Lys Gln Phe Ile Asn Ser
1               5                   10                  15

Val Gly Met Gly Thr Val Asn Gly Leu Leu Asp Glu Leu Phe Glu Lys
            20                  25                  30

Asn Val Leu Asn Gln Glu Glu Met Glu Arg Val Lys Cys Glu Asn Ala
        35                  40                  45

Thr Val Met Asp Lys Ala Arg Ala Leu Ile Asp Ser Val Leu Arg Lys
    50                  55                  60

Gly Pro Arg Ala Cys Gln Ile Phe Ile Cys His Ile Cys Glu Glu Asp
65                  70                  75                  80

Thr His Leu Ala Glu Thr Leu Gly Leu Ser Ser Pro Gln Ser Gly
                85                  90                  95

Asn Ser Gln Asn Thr Thr Asp Ser Glu Val Ala Phe Pro Pro Leu Pro
            100                 105                 110

Ala Ser Val Asn Asn Met Pro Gly Pro Ala Glu Pro Glu Glu Ser Val
        115                 120                 125

Asp Ala Leu Lys Leu Cys Pro Arg Glu Asn Phe Val Lys Leu Cys Lys
    130                 135                 140

Gln Arg Ala Glu Glu Ile Tyr Pro Ile Lys Glu Arg Lys Asp Arg Thr
145                 150                 155                 160

Arg Leu Ala Leu Ile Ile Cys Asn Thr Thr Phe Asp His Leu Ser Leu
                165                 170                 175

Arg Lys Gly Ala Asp Leu Asp Val Ala Gly Met Arg Arg Leu Leu Thr
            180                 185                 190

Asp Leu Gly Tyr Ser Val His Ile Lys Glu Glu Leu Thr Ala Lys Asp
        195                 200                 205

Met Glu Ser Glu Leu Arg Ala Phe Ala Ala Arg Pro Glu His Lys Ser
    210                 215                 220

Ser Asp Ser Thr Phe Leu Val Phe Met Ser His Gly Ile Leu Ser Gly
225                 230                 235                 240

Ile Cys Gly Thr Lys Tyr Ser Ala Glu Gly Asp Pro Asp Val Leu Ala
                245                 250                 255

Tyr Asp Thr Ile Phe Gln Ile Phe Asn Asn Arg Asn Cys Leu Ser Leu
            260                 265                 270

Lys Asp Lys Pro Lys Val Ile Ile Val Gln Ala Cys Arg Gly Glu Asn
        275                 280                 285

Leu Gly Glu Leu Leu Ile Ser Asp Ser Pro Ala Ala Pro Met Asp Ser
    290                 295                 300

Thr Ser Gln Met Gly Ser Ser Leu Ser Gln Val Gly Asp Asn Leu Glu
305                 310                 315                 320

Asp Asp Ala Ile Tyr Lys Val His Val Glu Lys Asp Phe Ile Ala Phe
                325                 330                 335

Cys Ser Ser Thr Pro His His Val Ser Trp Arg Asp Val Asn Lys Gly
            340                 345                 350

Ser Leu Phe Ile Thr Gln Leu Ile Thr Cys Phe Gln Lys Tyr Ser Trp
        355                 360                 365

Cys Phe His Leu Glu Glu Val Phe Arg Lys Val Gln Gln Ser Phe Glu
    370                 375                 380

Lys Pro Asn Val Arg Ala Gln Met Pro Thr Ile Glu Arg Leu Ser Met
```

```
                385                 390                 395                 400

Thr Arg Cys Phe Tyr Leu Phe Pro Gly His
                405                 410

<210> SEQ ID NO 16
<211> LENGTH: 1233
<212> TYPE: DNA
<213> ORGANISM: Felis catus

<400> SEQUENCE: 16
ttaatgtcct gggaagaggt agaaacatct tgtcatggat agtcgttcaa tggtgggcat      60
ctgggctcta acatttggtt tttcaaatga ctgttgtacc ttccgaaata cttcctccag     120
atgaaagcac cacgaatact tttggaagca cgtgatgagt tgtgtaatga agagagatcc     180
cttgttcacg tctctccaag acacatgatg tggggtcgag gagcagaaag cgatgaagtc     240
cttctccacg tggaccttgt aaatggcgtc gtcctctagg ttgtcaccca cctgtgaaag     300
gctgctaccc atctgtgaag tgctgtccat tggggccgct ggagagtcac tgatcaacag     360
ttcccccaaa ttttcacctc tgcaggcctg gacgatgatg accttgggct tgtccttag     420 actaaggcag ttgcggttgt tgaaaatctg aagatggtg tcataagcca atacatctgg      480
gtctccttca gcgctgtact tcgtcccaca gattccactc aggatgccat gagacatgaa     540
caccaggaat gtgctgtccg aggacttgtg ctctggacgg gcagcaaatg ccctcagctc     600
tgattccatg tccttagcag tgagttcctc ttttatgtgc acactgtagc caaggtctgt     660
aagcagcctc ctcatccctg caacgtcaag gtcagccccc ttcctgagag aaagatgatc     720
gaacgtcgta ttgcatatga tgagagccag acgagtacga tcctttctct cctttattgg     780
gtagatctct tcagccctct gtttacacag tttcacgaag ttttcacgag acaaagctt      840 gagagcatct acagattctt ctggctcagc cggcccaggc atgttattca cgctggctgg     900
aagaggagga aacgctactt cagagtccgt ggtgttctga aatttccag attgtgggct      960 tgaggagagc cccagcgtct ctgcaaggtg ggtgtcttcc tcacagatgt gacagataaa    1020
gatctggcac gcccgtggcc ctttccgcag gacgctgtcg atcagagctc gggccttgtc    1080
cataacggta gcgttttcac attttactct ctccatctcc tcctggttca gcacgttttt    1140
ctcaaagagt tcatccagca agccgttgac cgtccccatg ccgactgagt tgatgaactg    1200
cttcctcttc tccttcagga ccttgtcggc cat                                 1233

<210> SEQ ID NO 17
<211> LENGTH: 526
<212> TYPE: DNA
<213> ORGANISM: Felis catus
<220> FEATURE:
<221> NAME/KEY: CDS
<222> LOCATION: (18)..(524)

<400> SEQUENCE: 17
ggcacgagca aaaagcc atg gcc gac aag gat ctg aag ggc aag agg aag          50
                   Met Ala Asp Lys Asp Leu Lys Gly Lys Arg Lys
                    1               5                  10 cag ttc atc aac tca gtc ggc atg ggg acg gtc aac ggc ttg ctg gat        98
Gln Phe Ile Asn Ser Val Gly Met Gly Thr Val Asn Gly Leu Leu Asp
            15                  20                  25 gaa ctc ttt gag aaa aac gtg ctg aac cag gag gag atg gag aga gta       146
Glu Leu Phe Glu Lys Asn Val Leu Asn Gln Glu Glu Met Glu Arg Val
        30                  35                  40 aaa tgt gaa aac gct acc gtt atg gac aag gcc cga gct ctg atc gac       194
Lys Cys Glu Asn Ala Thr Val Met Asp Lys Ala Arg Ala Leu Ile Asp
```

```
              45                  50                  55
agc gtc ctg cgg aaa ggg cca cgg gcg tgc cag atc ttt atc tgt cac      242
Ser Val Leu Arg Lys Gly Pro Arg Ala Cys Gln Ile Phe Ile Cys His
 60                  65                  70                  75 atc tgt gag gaa gac acc cac ctt gca gag acg ctg ggg ctc tcc tca      290
Ile Cys Glu Glu Asp Thr His Leu Ala Glu Thr Leu Gly Leu Ser Ser
                 80                  85                  90 agc cca caa tct gga aat tct cag aac acc acg gac tct gaa gta gcg      338
Ser Pro Gln Ser Gly Asn Ser Gln Asn Thr Thr Asp Ser Glu Val Ala
             95                 100                 105 ttt cct cct ctt cca gcc agc gtg aat aac atg cct ggg ccg gct gag      386
Phe Pro Pro Leu Pro Ala Ser Val Asn Asn Met Pro Gly Pro Ala Glu
        110                 115                 120 cca gaa gaa tct gta gat gct ctc aag ctt tgt cct cgt gaa aac ttc      434
Pro Glu Glu Ser Val Asp Ala Leu Lys Leu Cys Pro Arg Glu Asn Phe
    125                 130                 135 gtg aaa ctg tgt aaa cag agg gct gaa gag atc tac cca ata aag gag      482
Val Lys Leu Cys Lys Gln Arg Ala Glu Glu Ile Tyr Pro Ile Lys Glu
140                 145                 150                 155 aga aag gat cgt act cgt ctg gct ctc atc ata tgc aat acg ac           526
Arg Lys Asp Arg Thr Arg Leu Ala Leu Ile Ile Cys Asn Thr
                160                 165

<210> SEQ ID NO 18
<211> LENGTH: 169
<212> TYPE: PRT
<213> ORGANISM: Felis catus

<400> SEQUENCE: 18

Met Ala Asp Lys Asp Leu Lys Gly Lys Arg Lys Gln Phe Ile Asn Ser
 1               5                  10                  15

Val Gly Met Gly Thr Val Asn Gly Leu Leu Asp Glu Leu Phe Glu Lys
                20                  25                  30

Asn Val Leu Asn Gln Glu Glu Met Glu Arg Val Lys Cys Glu Asn Ala
             35                  40                  45

Thr Val Met Asp Lys Ala Arg Ala Leu Ile Asp Ser Val Leu Arg Lys
         50                  55                  60

Gly Pro Arg Ala Cys Gln Ile Phe Ile Cys His Ile Cys Glu Glu Asp
 65                  70                  75                  80

Thr His Leu Ala Glu Thr Leu Gly Leu Ser Ser Pro Gln Ser Gly
                 85                  90                  95

Asn Ser Gln Asn Thr Thr Asp Ser Glu Val Ala Phe Pro Pro Leu Pro
            100                 105                 110

Ala Ser Val Asn Asn Met Pro Gly Pro Ala Glu Pro Glu Glu Ser Val
        115                 120                 125

Asp Ala Leu Lys Leu Cys Pro Arg Glu Asn Phe Val Lys Leu Cys Lys
    130                 135                 140

Gln Arg Ala Glu Glu Ile Tyr Pro Ile Lys Glu Arg Lys Asp Arg Thr
145                 150                 155                 160

Arg Leu Ala Leu Ile Ile Cys Asn Thr
                165

<210> SEQ ID NO 19
<211> LENGTH: 526
<212> TYPE: DNA
<213> ORGANISM: Felis catus

<400> SEQUENCE: 19
gtcgtattgc atatgatgag agccagacga gtacgatcct ttctctcctt tattgggtag    60
```

```
atctcttcag ccctctgttt acacagtttc acgaagtttt cacgaggaca aagcttgaga    120
gcatctacag attcttctgg ctcagccggc ccaggcatgt tattcacgct ggctggaaga    180
ggaggaaacg ctacttcaga gtccgtggtg ttctgagaat tccagattg tgggcttgag     240 gagagcccca gcgtctctgc aaggtgggtg tcttcctcac agatgtgaca gataaagatc    300
tggcacgccc gtggcccttt ccgcaggacg ctgtcgatca gagctcgggc cttgtccata    360
acggtagcgt tttcacattt tactctctcc atctcctcct ggttcagcac gttttttctca   420 aagagttcat ccagcaagcc gttgaccgtc cccatgccga ctgagttgat gaactgcttc    480
ctcttgccct tcagatcctt gtcggccatg gcttttttgct cgtgcc                  526
```

```
<210> SEQ ID NO 20
<211> LENGTH: 500
<212> TYPE: DNA
<213> ORGANISM: Felis catus
<220> FEATURE:
<221> NAME/KEY: CDS
<222> LOCATION: (3)..(362)
<220> FEATURE:
<221> NAME/KEY: misc_feature
<222> LOCATION: (473)..(473)
<223> OTHER INFORMATION: n = unknown

<400> SEQUENCE: 20 gg gaa ctg ttg atc agt gac tct cca gcg gcc cca atg gac agc act       47
   Glu Leu Leu Ile Ser Asp Ser Pro Ala Ala Pro Met Asp Ser Thr
   1               5                  10                  15 tca cag atg ggt agc agc ctt tca cag gtg ggt gac aac cta gag gac      95
Ser Gln Met Gly Ser Ser Leu Ser Gln Val Gly Asp Asn Leu Glu Asp
               20                  25                  30 gac gcc att tac aag gtc cac gtg gag aag gac ttc atc gct ttc tgc     143
Asp Ala Ile Tyr Lys Val His Val Glu Lys Asp Phe Ile Ala Phe Cys
           35                  40                  45 tcc tcg acc cca cat cat gtg tct tgg aga gac gtg aac aag gga tct    191
Ser Ser Thr Pro His His Val Ser Trp Arg Asp Val Asn Lys Gly Ser
       50                  55                  60 ctc ttc att aca caa ctc atc acg tgc ttc caa aag tat tcg tgg tgc    239
Leu Phe Ile Thr Gln Leu Ile Thr Cys Phe Gln Lys Tyr Ser Trp Cys
65                  70                  75 ttt cat ctg gag gaa gta ttt cgg aag gta caa cag tca ttt gaa aaa    287
Phe His Leu Glu Glu Val Phe Arg Lys Val Gln Gln Ser Phe Glu Lys
80                  85                  90                  95 cca aat gtt aga gcc cag atg ccc acc att gaa cga cta tcc atg aca    335
Pro Asn Val Arg Ala Gln Met Pro Thr Ile Glu Arg Leu Ser Met Thr
               100                 105                 110 aga tac ttc tat ctc ttc cct ggc aat tgaaaatagc aatcatgggc          382
Arg Tyr Phe Tyr Leu Phe Pro Gly Asn
           115                 120 agtccagccc ttcttgacca acttggaaaa gtaccttagc tagcacaaca cactcattta    442
acgtttggta tctcaataaa aatgaaaaca nctaaaaaaa aaaaaaaaaa aaaaaaaa      500
```

```
<210> SEQ ID NO 21
<211> LENGTH: 120
<212> TYPE: PRT
<213> ORGANISM: Felis catus

<400> SEQUENCE: 21

Glu Leu Leu Ile Ser Asp Ser Pro Ala Ala Pro Met Asp Ser Thr Ser
1               5                  10                  15

Gln Met Gly Ser Ser Leu Ser Gln Val Gly Asp Asn Leu Glu Asp Asp
```

```
                 20                  25                  30
Ala Ile Tyr Lys Val His Val Glu Lys Asp Phe Ile Ala Phe Cys Ser
            35                  40                  45

Ser Thr Pro His His Val Ser Trp Arg Asp Val Asn Lys Gly Ser Leu
 50                  55                  60

Phe Ile Thr Gln Leu Ile Thr Cys Phe Gln Lys Tyr Ser Trp Cys Phe
 65                  70                  75                  80

His Leu Glu Glu Val Phe Arg Lys Val Gln Gln Ser Phe Glu Lys Pro
                85                  90                  95

Asn Val Arg Ala Gln Met Pro Thr Ile Glu Arg Leu Ser Met Thr Arg
            100                 105                 110

Tyr Phe Tyr Leu Phe Pro Gly Asn
            115                 120

<210> SEQ ID NO 22
<211> LENGTH: 500
<212> TYPE: DNA
<213> ORGANISM: Felis catus
<220> FEATURE:
<221> NAME/KEY: misc_feature
<222> LOCATION: (28)..(28)
<223> OTHER INFORMATION: n = unknown

<400> SEQUENCE: 22
tttttttttt ttttttttt tttttagntg ttttcatttt tattgagata ccaaacgtta      60
aatgagtgtg ttgtgctagc taaggtactt ttccaagttg gtcaagaagg gctggactgc    120
ccatgattgc tattttcaat tgccagggaa gagatagaag tatcttgtca tggatagtcg    180
ttcaatggtg ggcatctggg ctctaacatt tggttttca  aatgactgtt gtaccttccg    240
aaatacttcc tccagatgaa agcaccacga atactttgg  aagcacgtga tgagttgtgt    300
aatgaagaga gatcccttgt tcacgtctct ccaagacaca tgatgtgggg tcgaggagca    360
gaaagcgatg aagtccttct ccacgtggac cttgtaaatg gcgtcgtcct ctaggttgtc    420
acccacctgt gaaaggctgc tacccatctg tgaagtgctg tccattgggg ccgctggaga    480
gtcactgatc aacagttccc                                                500

<210> SEQ ID NO 23
<211> LENGTH: 1230
<212> TYPE: DNA
<213> ORGANISM: Felis catus
<220> FEATURE:
<221> NAME/KEY: CDS
<222> LOCATION: (1)..(1230)

<400> SEQUENCE: 23 atg gcc gac aag gat ctg aag ggc aag agg aag cag ttc atc aac tca     48
Met Ala Asp Lys Asp Leu Lys Gly Lys Arg Lys Gln Phe Ile Asn Ser
 1               5                  10                  15 gtc ggc atg ggg acg gtc aac ggc ttg ctg gat gaa ctc ttt gag aaa     96
Val Gly Met Gly Thr Val Asn Gly Leu Leu Asp Glu Leu Phe Glu Lys
                20                  25                  30 aac gtg ctg aac cag gag gag atg gag aga gta aaa tgt gaa aac gct    144
Asn Val Leu Asn Gln Glu Glu Met Glu Arg Val Lys Cys Glu Asn Ala
            35                  40                  45 acc gtt atg gac aag gcc cga gct ctg atc gac agc gtc ctg cgg aaa    192
Thr Val Met Asp Lys Ala Arg Ala Leu Ile Asp Ser Val Leu Arg Lys
 50                  55                  60 ggg cca cgg gcg tgc cag atc ttt atc tgt cac atc tgt gag gaa gac    240
Gly Pro Arg Ala Cys Gln Ile Phe Ile Cys His Ile Cys Glu Glu Asp
 65                  70                  75                  80
```

-continued

| | | |
|---|---|---|
| acc cac ctt gca gag acg ctg ggg ctc tcc tca agc cca caa tct gga<br>Thr His Leu Ala Glu Thr Leu Gly Leu Ser Ser Ser Pro Gln Ser Gly<br>                          85                          90                        95 | 288 |
| aat tct cag aac acc acg gac tct gaa gta gcg ttt cct cct ctt cca<br>Asn Ser Gln Asn Thr Thr Asp Ser Glu Val Ala Phe Pro Pro Leu Pro<br>                          100                          105                        110 | 336 |
| gcc agc gtg aat aac atg cct ggg ccg gct gag cca gaa gaa tct gta<br>Ala Ser Val Asn Asn Met Pro Gly Pro Ala Glu Pro Glu Glu Ser Val<br>                          115                          120                        125 | 384 |
| gat gct ctc aag ctt tgt cct cgt gaa aac ttc gtg aaa ctg tgt aaa<br>Asp Ala Leu Lys Leu Cys Pro Arg Glu Asn Phe Val Lys Leu Cys Lys<br>130                        135                        140 | 432 |
| cag agg gct gaa gag atc tac cca ata aag gag aga aag gat cgt act<br>Gln Arg Ala Glu Glu Ile Tyr Pro Ile Lys Glu Arg Lys Asp Arg Thr<br>145                        150                        155                        160 | 480 |
| cgt ctg gct ctc atc ata tgc aat acg acg ttc gat cat ctt tct ctc<br>Arg Leu Ala Leu Ile Ile Cys Asn Thr Thr Phe Asp His Leu Ser Leu<br>                          165                          170                        175 | 528 |
| agg aag ggg gct gac ctt gac gtt gca ggg atg agg agg ctg ctt aca<br>Arg Lys Gly Ala Asp Leu Asp Val Ala Gly Met Arg Arg Leu Leu Thr<br>                          180                          185                        190 | 576 |
| gac ctt ggc tac agt gtg cac ata aaa gag gaa ctc act gct aag gac<br>Asp Leu Gly Tyr Ser Val His Ile Lys Glu Glu Leu Thr Ala Lys Asp<br>                          195                          200                        205 | 624 |
| atg gaa tca gag ctg agg gca ttt gct gcc cgt cca gag cac aag tcc<br>Met Glu Ser Glu Leu Arg Ala Phe Ala Ala Arg Pro Glu His Lys Ser<br>          210                        215                        220 | 672 |
| tcg gac agc aca ttc ctg gtg ttc atg tct cat ggc atc ctg agt gga<br>Ser Asp Ser Thr Phe Leu Val Phe Met Ser His Gly Ile Leu Ser Gly<br>225                        230                        235                        240 | 720 |
| atc tgt ggg acg aag tac agc gct gaa gga gac cca gat gta ttg gct<br>Ile Cys Gly Thr Lys Tyr Ser Ala Glu Gly Asp Pro Asp Val Leu Ala<br>                          245                          250                        255 | 768 |
| tat gac acc atc ttc cag att ttc aac aac cgc aac tgc ctt agt cta<br>Tyr Asp Thr Ile Phe Gln Ile Phe Asn Asn Arg Asn Cys Leu Ser Leu<br>                          260                          265                        270 | 816 |
| aag gac aag ccc aag gtc atc atc gtc cag gcc tgc aga ggt gaa aat<br>Lys Asp Lys Pro Lys Val Ile Ile Val Gln Ala Cys Arg Gly Glu Asn<br>                          275                          280                        285 | 864 |
| ttg ggg gaa ctg ttg atc agt gac tct cca gcg gcc cca atg gac agc<br>Leu Gly Glu Leu Leu Ile Ser Asp Ser Pro Ala Ala Pro Met Asp Ser<br>          290                        295                        300 | 912 |
| act tca cag atg ggt agc agc ctt tca cag gtg ggt gac aac cta gag<br>Thr Ser Gln Met Gly Ser Ser Leu Ser Gln Val Gly Asp Asn Leu Glu<br>305                        310                        315                        320 | 960 |
| gac gac gcc att tac aag gtc cac gtg gag aag gac ttc atc gct ttc<br>Asp Asp Ala Ile Tyr Lys Val His Val Glu Lys Asp Phe Ile Ala Phe<br>                          325                          330                        335 | 1008 |
| tgc tcc tcg acc cca cat cat gtg tct tgg aga gac gtg aac aag gga<br>Cys Ser Ser Thr Pro His His Val Ser Trp Arg Asp Val Asn Lys Gly<br>                          340                          345                        350 | 1056 |
| tct ctc ttc att aca caa ctc atc acg tgc ttc caa aag tat tcg tgg<br>Ser Leu Phe Ile Thr Gln Leu Ile Thr Cys Phe Gln Lys Tyr Ser Trp<br>                          355                          360                        365 | 1104 |
| tgc ttt cat ctg gag gaa gta ttt cgg aag gta caa cag tca ttt gaa<br>Cys Phe His Leu Glu Glu Val Phe Arg Lys Val Gln Gln Ser Phe Glu<br>          370                        375                        380 | 1152 |
| aaa cca aat gtt aga gcc cag atg ccc acc att gaa cga cta tcc atg<br>Lys Pro Asn Val Arg Ala Gln Met Pro Thr Ile Glu Arg Leu Ser Met<br>385                        390                        395                        400 | 1200 |

```
aca aga tac ttc tat ctc ttc cct ggc aat                            1230
Thr Arg Tyr Phe Tyr Leu Phe Pro Gly Asn
            405                 410
```

<210> SEQ ID NO 24
<211> LENGTH: 410
<212> TYPE: PRT
<213> ORGANISM: Felis catus

<400> SEQUENCE: 24

```
Met Ala Asp Lys Asp Leu Lys Gly Lys Arg Lys Gln Phe Ile Asn Ser
1               5                   10                  15

Val Gly Met Gly Thr Val Asn Gly Leu Leu Asp Glu Leu Phe Glu Lys
            20                  25                  30

Asn Val Leu Asn Gln Glu Glu Met Glu Arg Val Lys Cys Glu Asn Ala
        35                  40                  45

Thr Val Met Asp Lys Ala Arg Ala Leu Ile Asp Ser Val Leu Arg Lys
    50                  55                  60

Gly Pro Arg Ala Cys Gln Ile Phe Ile Cys His Ile Cys Glu Glu Asp
65                  70                  75                  80

Thr His Leu Ala Glu Thr Leu Gly Leu Ser Ser Pro Gln Ser Gly
            85                  90                  95

Asn Ser Gln Asn Thr Thr Asp Ser Glu Val Ala Phe Pro Pro Leu Pro
            100                 105                 110

Ala Ser Val Asn Asn Met Pro Gly Pro Ala Glu Pro Glu Ser Val
        115                 120                 125

Asp Ala Leu Lys Leu Cys Pro Arg Glu Asn Phe Val Lys Leu Cys Lys
130                 135                 140

Gln Arg Ala Glu Glu Ile Tyr Pro Ile Lys Glu Arg Lys Asp Arg Thr
145                 150                 155                 160

Arg Leu Ala Leu Ile Ile Cys Asn Thr Thr Phe Asp His Leu Ser Leu
                165                 170                 175

Arg Lys Gly Ala Asp Leu Asp Val Ala Gly Met Arg Arg Leu Leu Thr
            180                 185                 190

Asp Leu Gly Tyr Ser Val His Ile Lys Glu Glu Leu Thr Ala Lys Asp
        195                 200                 205

Met Glu Ser Glu Leu Arg Ala Phe Ala Ala Arg Pro Glu His Lys Ser
    210                 215                 220

Ser Asp Ser Thr Phe Leu Val Phe Met Ser His Gly Ile Leu Ser Gly
225                 230                 235                 240

Ile Cys Gly Thr Lys Tyr Ser Ala Glu Gly Asp Pro Asp Val Leu Ala
                245                 250                 255

Tyr Asp Thr Ile Phe Gln Ile Phe Asn Asn Arg Asn Cys Leu Ser Leu
            260                 265                 270

Lys Asp Lys Pro Lys Val Ile Val Gln Ala Cys Arg Gly Glu Asn
        275                 280                 285

Leu Gly Glu Leu Leu Ile Ser Asp Ser Pro Ala Ala Pro Met Asp Ser
    290                 295                 300

Thr Ser Gln Met Gly Ser Ser Leu Ser Gln Val Gly Asp Asn Leu Glu
305                 310                 315                 320

Asp Asp Ala Ile Tyr Lys Val His Val Glu Lys Asp Phe Ile Ala Phe
                325                 330                 335

Cys Ser Ser Thr Pro His His Val Ser Trp Arg Asp Val Asn Lys Gly
            340                 345                 350

Ser Leu Phe Ile Thr Gln Leu Ile Thr Cys Phe Gln Lys Tyr Ser Trp
```

```
                    355                 360                 365
Cys Phe His Leu Glu Glu Val Phe Arg Lys Val Gln Gln Ser Phe Glu
            370                 375                 380

Lys Pro Asn Val Arg Ala Gln Met Pro Thr Ile Glu Arg Leu Ser Met
385                 390                 395                 400

Thr Arg Tyr Phe Tyr Leu Phe Pro Gly Asn
                405                 410

<210> SEQ ID NO 25
<211> LENGTH: 1230
<212> TYPE: DNA
<213> ORGANISM: Felis catus

<400> SEQUENCE: 25
attgccaggg aagagataga agtatcttgt catggatagt cgttcaatgg tgggcatctg      60
ggctctaaca tttggttttt caaatgactg ttgtaccttc gaaatactt cctccagatg     120 aaagcaccac gaatactttt ggaagcacgt gatgagttgt gtaatgaaga gagatccctt     180
gttcacgtct ctccaagaca catgatgtgg ggtcgaggag cagaaagcga tgaagtcctt     240
ctccacgtgg accttgtaaa tggcgtcgtc tctaggttg tcacccacct gtgaaaggct      300
gctacccatc tgtgaagtgc tgtccattgg ggccgctgga gagtcactga tcaacagttc     360
ccccaaattt tcacctctgc aggcctggac gatgatgacc ttgggcttgt cctttagact     420
aaggcagttg cggttgttga aaatctggaa gatggtgtca taagccaata catctgggtc     480
tccttcagcg ctgtacttcg tcccacagat tccactcagg atgccatgag acatgaacac     540
caggaatgtg ctgtccgagg acttgtgctc tggacgggca gcaaatgccc tcagctctga     600
ttccatgtcc ttagcagtga gttcctcttt tatgtgcaca ctgtagccaa ggtctgtaag     660
cagcctcctc atccctgcaa cgtcaaggtc agccccttc ctgagagaaa gatgatcgaa      720
cgtcgtattg catatgatga gagccagacg agtacgatcc tttctctcct ttattgggta     780
gatctcttca gccctctgtt tacacagttt cacgaagttt tcacgaggac aaagcttgag     840
agcatctaca gattcttctg gctcagccgg cccaggcatg ttattcacgc tggctggaag     900
aggaggaaac gctacttcag agtccgtggt gttctgagaa tttccagatt gtgggcttga     960
ggagagcccc agcgtctctg caaggtgggt gtcttcctca cagatgtgac agataaagat    1020
ctggcacgcc cgtggcccttt tccgcaggac gctgtcgatc agagctcggg ccttgtccat    1080
aacggtagcg tttttcacatt ttactctctc catctcctcc tggttcagca cgttttttctc    1140 aaagagttca tccagcaagc cgttgaccgt ccccatgccg actgagttga tgaactgctt    1200
cctcttgccc ttcagatcct tgtcggccat                                     1230

<210> SEQ ID NO 26
<211> LENGTH: 921
<212> TYPE: DNA
<213> ORGANISM: Felis catus
<220> FEATURE:
<221> NAME/KEY: CDS
<222> LOCATION: (1)..(921)

<400> SEQUENCE: 26 ata tgg gaa ctg gag aaa aac gtt tat gtt gta gag ttg gac tgg cac        48
Ile Trp Glu Leu Glu Lys Asn Val Tyr Val Val Glu Leu Asp Trp His
1                5                  10                  15 cct gat gcc ccc gga gaa atg gtg gtc ctc acc tgc aat act cct gaa        96
Pro Asp Ala Pro Gly Glu Met Val Val Leu Thr Cys Asn Thr Pro Glu
                20                  25                  30
```

```
gaa gat gac atc acc tgg acc tct gac cag agc agt gaa gtc cta ggc      144
Glu Asp Asp Ile Thr Trp Thr Ser Asp Gln Ser Ser Glu Val Leu Gly
         35                  40                  45 tct ggt aaa act ctg acc atc caa gtc aaa gaa ttt gca gat gct ggc      192
Ser Gly Lys Thr Leu Thr Ile Gln Val Lys Glu Phe Ala Asp Ala Gly
 50                  55                  60 cag tat acc tgt cat aaa gga ggc gag gtt ctg agc cat tcg ttc ctc      240
Gln Tyr Thr Cys His Lys Gly Gly Glu Val Leu Ser His Ser Phe Leu
 65                  70                  75                  80 ctg ata cac aaa aag gaa gat gga att tgg tcc act gat atc tta agg      288
Leu Ile His Lys Lys Glu Asp Gly Ile Trp Ser Thr Asp Ile Leu Arg
             85                  90                  95 gaa cag aaa gaa tcc aaa aat aag atc ttt cta aaa tgt gag gca aag      336
Glu Gln Lys Glu Ser Lys Asn Lys Ile Phe Leu Lys Cys Glu Ala Lys
            100                 105                 110 aat tat tct gga cgt ttc acc tgc tgg tgg ctg acg gca atc agt acc      384
Asn Tyr Ser Gly Arg Phe Thr Cys Trp Trp Leu Thr Ala Ile Ser Thr
                115                 120                 125 gat ttg aaa ttc act gtc aaa agc agc aga ggc tcc tct gac ccc caa      432
Asp Leu Lys Phe Thr Val Lys Ser Ser Arg Gly Ser Ser Asp Pro Gln
130                 135                 140 gag gtg act tgt gga gca gcg aca ctc tca gca gag aag gtc aga gtg      480
Glu Val Thr Cys Gly Ala Ala Thr Leu Ser Ala Glu Lys Val Arg Val
145                 150                 155                 160 gac aac agg gat tat aag aag tac aca gtg gag tgt cag gag ggc agt      528
Asp Asn Arg Asp Tyr Lys Lys Tyr Thr Val Glu Cys Gln Glu Gly Ser
                165                 170                 175 gcc tgc ccg gct gcc gag gag agc cta ccc att gaa gtc gtg gtg gac      576
Ala Cys Pro Ala Ala Glu Glu Ser Leu Pro Ile Glu Val Val Val Asp
            180                 185                 190 gct att cac aag ctc aag tac gaa aac tac acc agc agc ttc ttc atc      624
Ala Ile His Lys Leu Lys Tyr Glu Asn Tyr Thr Ser Ser Phe Phe Ile
        195                 200                 205 agg gac atc atc aaa ccg gac cca ccc aag aac ctg caa ctg aag cca      672
Arg Asp Ile Ile Lys Pro Asp Pro Pro Lys Asn Leu Gln Leu Lys Pro
210                 215                 220 tta aaa aat tct cgg cat gtg gaa gtg agc tgg gaa tac cct gac acc      720
Leu Lys Asn Ser Arg His Val Glu Val Ser Trp Glu Tyr Pro Asp Thr
225                 230                 235                 240 tgg agc acc cca cat tcc tac ttc tcc tta aca ttt ggc gta cag gtc      768
Trp Ser Thr Pro His Ser Tyr Phe Ser Leu Thr Phe Gly Val Gln Val
                245                 250                 255 cag ggc aag aac aac aga gaa aag aaa gac aga ctc tcc gtg gac aag      816
Gln Gly Lys Asn Asn Arg Glu Lys Lys Asp Arg Leu Ser Val Asp Lys
            260                 265                 270 acc tca gcc aag gtc gtg tgc cac aag gat gcc aag atc cgc gtg caa      864
Thr Ser Ala Lys Val Val Cys His Lys Asp Ala Lys Ile Arg Val Gln
        275                 280                 285 gcc aga gac cgc tac tat agc tca tcc tgg agc aac tgg gca tcc gtg      912
Ala Arg Asp Arg Tyr Tyr Ser Ser Ser Trp Ser Asn Trp Ala Ser Val
    290                 295                 300 tcc tgc agt                                                          921
Ser Cys Ser
305
```

<210> SEQ ID NO 27
<211> LENGTH: 307
<212> TYPE: PRT
<213> ORGANISM: Felis catus

<400> SEQUENCE: 27

```
Ile Trp Glu Leu Glu Lys Asn Val Tyr Val Val Glu Leu Asp Trp His
1               5                   10                  15

Pro Asp Ala Pro Gly Glu Met Val Val Leu Thr Cys Asn Thr Pro Glu
            20                  25                  30

Glu Asp Asp Ile Thr Trp Thr Ser Asp Gln Ser Ser Glu Val Leu Gly
        35                  40                  45

Ser Gly Lys Thr Leu Thr Ile Gln Val Lys Glu Phe Ala Asp Ala Gly
    50                  55                  60

Gln Tyr Thr Cys His Lys Gly Gly Glu Val Leu Ser His Ser Phe Leu
65              70                  75                  80

Leu Ile His Lys Lys Glu Asp Gly Ile Trp Ser Thr Asp Ile Leu Arg
                85                  90                  95

Glu Gln Lys Glu Ser Lys Asn Lys Ile Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Thr Val Lys Ser Ser Arg Gly Ser Ser Asp Pro Gln
    130                 135                 140

Glu Val Thr Cys Gly Ala Ala Thr Leu Ser Ala Glu Lys Val Arg Val
145                 150                 155                 160

Asp Asn Arg Asp Tyr Lys Lys Tyr Thr Val Glu Cys Gln Glu Gly Ser
                165                 170                 175

Ala Cys Pro Ala Ala Glu Glu Ser Leu Pro Ile Glu Val Val Val Asp
            180                 185                 190

Ala Ile His Lys Leu Lys Tyr Glu Asn Tyr Thr Ser Ser Phe Phe Ile
        195                 200                 205

Arg Asp Ile Ile Lys Pro Asp Pro Pro Lys Asn Leu Gln Leu Lys Pro
    210                 215                 220

Leu Lys Asn Ser Arg His Val Glu Val Ser Trp Glu Tyr Pro Asp Thr
225                 230                 235                 240

Trp Ser Thr Pro His Ser Tyr Phe Ser Leu Thr Phe Gly Val Gln Val
                245                 250                 255

Gln Gly Lys Asn Asn Arg Glu Lys Lys Asp Arg Leu Ser Val Asp Lys
            260                 265                 270

Thr Ser Ala Lys Val Val Cys His Lys Asp Ala Lys Ile Arg Val Gln
        275                 280                 285

Ala Arg Asp Arg Tyr Tyr Ser Ser Ser Trp Ser Asn Trp Ala Ser Val
    290                 295                 300

Ser Cys Ser
305

<210> SEQ ID NO 28
<211> LENGTH: 921
<212> TYPE: DNA
<213> ORGANISM: Felis catus

<400> SEQUENCE: 28
actgcaggac acggatgccc agttgctcca ggatgagcta tagtagcggt ctctggcttg      60
cacgcggatc ttggcatcct tgtggcacac gaccttggct gaggtcttgt ccacggagag     120
tctgtctttc ttttctctgt tgttcttgcc ctggacctgt acgccaaatg ttaaggagaa     180
gtaggaatgt ggggtgctcc aggtgtcagg gtattcccag ctcacttcca catgccgaga     240 atttttaat ggcttcagtt gcaggttctt gggtgggtcc ggtttgatga tgtccctgat     300
gaagaagctg ctggtgtagt tttcgtactt gagcttgtga atagcgtcca ccacgacttc     360
```

-continued

```
aatgggtagg ctctcctcgg cagccgggca ggcactgccc tcctgacact ccactgtgta      420
cttcttataa tccctgttgt ccactctgac cttctctgct gagagtgtcg ctgctccaca      480
agtcacctct tgggggtcag aggagcctct gctgcttttg acagtgaatt tcaaatcggt      540
actgattgcc gtcagccacc agcaggtgaa acgtccagaa taattctttg cctcacattt      600
tagaaagatc ttattttgg attctttctg ttcccttaag atatcagtgg accaaattcc      660
atcttccttt ttgtgtatca ggaggaacga atggctcaga acctcgcctc ctttatgaca      720
ggtatactgg ccagcatctg caaattcttt gacttggatg gtcagagttt taccagagcc      780
taggacttca ctgctctggt cagaggtcca ggtgatgtca tcttcttcag gagtattgca      840
ggtgaggacc accatttctc cggggcatc agggtgccag tccaactcta caacataaac      900
gtttttctcc agttcccata t                                                921

<210> SEQ ID NO 29
<211> LENGTH: 987
<212> TYPE: DNA
<213> ORGANISM: Felis catus
<220> FEATURE:
<221> NAME/KEY: CDS
<222> LOCATION: (1)..(987)

<400> SEQUENCE: 29 atg cat cct cag cag ttg gtc atc gcc tgg ttt tcc ctg gtt ttg ctg        48
Met His Pro Gln Gln Leu Val Ile Ala Trp Phe Ser Leu Val Leu Leu
1               5                  10                  15 gca cct ccc ctc atg gcc ata tgg gaa ctg gag aaa aac gtt tat gtt        96
Ala Pro Pro Leu Met Ala Ile Trp Glu Leu Glu Lys Asn Val Tyr Val
            20                  25                  30 gta gag ttg gac tgg cac cct gat gcc ccc gga gaa atg gtg gtc ctc       144
Val Glu Leu Asp Trp His Pro Asp Ala Pro Gly Glu Met Val Val Leu
        35                  40                  45 acc tgc aat act cct gaa gaa gat gac atc acc tgg acc tct gac cag       192
Thr Cys Asn Thr Pro Glu Glu Asp Asp Ile Thr Trp Thr Ser Asp Gln
    50                  55                  60 agc agt gaa gtc cta ggc tct ggt aaa act ctg acc atc caa gtc aaa       240
Ser Ser Glu Val Leu Gly Ser Gly Lys Thr Leu Thr Ile Gln Val Lys
65                  70                  75                  80 gaa ttt gca gat gct ggc cag tat acc tgt cat aaa gga ggc gag gtt       288
Glu Phe Ala Asp Ala Gly Gln Tyr Thr Cys His Lys Gly Gly Glu Val
                85                  90                  95 ctg agc cat tcg ttc ctc ctg ata cac aaa aag gaa gat gga att tgg       336
Leu Ser His Ser Phe Leu Leu Ile His Lys Lys Glu Asp Gly Ile Trp
            100                 105                 110 tcc act gat atc tta agg gaa cag aaa gaa tcc aaa aat aag atc ttt       384
Ser Thr Asp Ile Leu Arg Glu Gln Lys Glu Ser Lys Asn Lys Ile Phe
        115                 120                 125 cta aaa tgt gag gca aag aat tat tct gga cgt ttc acc tgc tgg tgg       432
Leu Lys Cys Glu Ala Lys Asn Tyr Ser Gly Arg Phe Thr Cys Trp Trp
    130                 135                 140 ctg acg gca atc agt acc gat ttg aaa ttc act gtc aaa agc agc aga       480
Leu Thr Ala Ile Ser Thr Asp Leu Lys Phe Thr Val Lys Ser Ser Arg
145                 150                 155                 160 ggc tcc tct gac ccc caa ggg gtg act tgt gga gca gcg aca ctc tca       528
Gly Ser Ser Asp Pro Gln Gly Val Thr Cys Gly Ala Ala Thr Leu Ser
                165                 170                 175 gca gag aag gtc aga gtg gac aac agg gat tat aag aag tac aca gtg       576
Ala Glu Lys Val Arg Val Asp Asn Arg Asp Tyr Lys Lys Tyr Thr Val
            180                 185                 190 gag tgt cag gag ggc agt gcc tgc ccg gct gcc gag gag agc cta ccc       624
Glu Cys Gln Glu Gly Ser Ala Cys Pro Ala Ala Glu Glu Ser Leu Pro
```

```
Glu Cys Gln Glu Gly Ser Ala Cys Pro Ala Ala Glu Glu Ser Leu Pro
            195                 200                 205 att gaa gtc gtg gtg gac gct att cac aag ctc aag tac gaa aac tac      672
Ile Glu Val Val Val Asp Ala Ile His Lys Leu Lys Tyr Glu Asn Tyr
    210                 215                 220 acc agc agc ttc ttc atc agg gac atc atc aaa ccg gac cca ccc aag      720
Thr Ser Ser Phe Phe Ile Arg Asp Ile Ile Lys Pro Asp Pro Pro Lys
225                 230                 235                 240 aac ctg caa ctg aag cca tta aaa aat tct cgg cat gtg gaa gtg agc      768
Asn Leu Gln Leu Lys Pro Leu Lys Asn Ser Arg His Val Glu Val Ser
            245                 250                 255 tgg gaa tac cct gac acc tgg agc acc cca cat tcc tac ttc tcc tta      816
Trp Glu Tyr Pro Asp Thr Trp Ser Thr Pro His Ser Tyr Phe Ser Leu
        260                 265                 270 aca ttt ggc gta cag gtc cag ggc aag aac aac aga gaa aag aaa gac      864
Thr Phe Gly Val Gln Val Gln Gly Lys Asn Asn Arg Glu Lys Lys Asp
            275                 280                 285 aga ctc tcc gtg gac aag acc tca gcc aag gtc gtg tgc cac aag gat      912
Arg Leu Ser Val Asp Lys Thr Ser Ala Lys Val Val Cys His Lys Asp
290                 295                 300 gcc aag atc cgc gtg caa gcc aga gac cgc tac tat agc tca tcc tgg      960
Ala Lys Ile Arg Val Gln Ala Arg Asp Arg Tyr Tyr Ser Ser Ser Trp
305                 310                 315                 320 agc aac tgg gca tcc gtg tcc tgc agt                                  987
Ser Asn Trp Ala Ser Val Ser Cys Ser
            325

<210> SEQ ID NO 30
<211> LENGTH: 329
<212> TYPE: PRT
<213> ORGANISM: Felis catus

<400> SEQUENCE: 30

Met His Pro Gln Gln Leu Val Ile Ala Trp Phe Ser Leu Val Leu Leu
1               5                   10                  15

Ala Pro Pro Leu Met Ala Ile Trp Glu Leu Glu Lys Asn Val Tyr Val
            20                  25                  30

Val Glu Leu Asp Trp His Pro Asp Ala Pro Gly Glu Met Val Val Leu
        35                  40                  45

Thr Cys Asn Thr Pro Glu Glu Asp Asp Ile Thr Trp Thr Ser Asp Gln
    50                  55                  60

Ser Ser Glu Val Leu Gly Ser Gly Lys Thr Leu Thr Ile Gln Val Lys
65                  70                  75                  80

Glu Phe Ala Asp Ala Gly Gln Tyr Thr Cys His Lys Gly Gly Glu Val
                85                  90                  95

Leu Ser His Ser Phe Leu Leu Ile His Lys Lys Glu Asp Gly Ile Trp
            100                 105                 110

Ser Thr Asp Ile Leu Arg Glu Gln Lys Glu Ser Lys Asn Lys Ile Phe
        115                 120                 125

Leu Lys Cys Glu Ala Lys Asn Tyr Ser Gly Arg Phe Thr Cys Trp Trp
    130                 135                 140

Leu Thr Ala Ile Ser Thr Asp Leu Lys Phe Thr Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Lys Val Arg Val Asp Asn Arg Asp Tyr Lys Lys Tyr Thr Val
            180                 185                 190

Glu Cys Gln Glu Gly Ser Ala Cys Pro Ala Ala Glu Glu Ser Leu Pro
```

```
                195                 200                 205
Ile Glu Val Val Asp Ala Ile His Lys Leu Lys Tyr Glu Asn Tyr
    210                 215                 220

Thr Ser Ser Phe Phe Ile Arg Asp Ile Ile Lys Pro Asp Pro Lys
225                 230                 235                 240

Asn Leu Gln Leu Lys Pro Leu Lys Asn Ser Arg His Val Glu Val Ser
                245                 250                 255

Trp Glu Tyr Pro Asp Thr Trp Ser Thr Pro His Ser Tyr Phe Ser Leu
                260                 265                 270

Thr Phe Gly Val Gln Val Gln Gly Lys Asn Asn Arg Glu Lys Lys Asp
                275                 280                 285

Arg Leu Ser Val Asp Lys Thr Ser Ala Lys Val Val Cys His Lys Asp
    290                 295                 300

Ala Lys Ile Arg Val Gln Ala Arg Asp Arg Tyr Tyr Ser Ser Ser Trp
305                 310                 315                 320

Ser Asn Trp Ala Ser Val Ser Cys Ser
                325

<210> SEQ ID NO 31
<211> LENGTH: 987
<212> TYPE: DNA
<213> ORGANISM: Felis catus

<400> SEQUENCE: 31
actgcaggac acggatgccc agttgctcca ggatgagcta tagtagcggt ctctggcttg     60
cacgcggatc ttggcatcct tgtggcacac gaccttggct gaggtcttgt ccacggagag    120
tctgtctttc ttttctctgt tgttcttgcc ctggacctgt acgccaaatg ttaaggagaa    180
gtaggaatgt ggggtgctcc agtgtcaggg tattcccag ctcacttcca catgccgaga    240 atttttttaat ggcttcagtt gcaggttctt gggtgggtcc ggtttgatga tgtccctgat    300
gaagaagctg ctggtgtagt tttcgtactt gagcttgtga atagcgtcca ccacgacttc    360
aatgggtagg ctctcctcgg cagccgggca ggcactgccc tcctgacact ccactgtgta    420
cttcttataa tccctgttgt ccactctgac ctttctctgct gagagtgtcg ctgctccaca    480
agtcacccct tgggggtcag aggagcctct gctgcttttg acagtgaatt tcaaatcggt    540
actgattgcc gtcagccacc agcaggtgaa acgtccagaa taattctttg cctcacattt    600
tagaaagatc ttattttttgg attctttctg ttcccttaag atatcagtgg accaaattcc    660
atcttccttt ttgtgtatca ggaggaacga atggctcaga acctcgcctc ctttatgaca    720
ggtatactgg ccagcatctg caaattcttt gacttggatg gtcagagttt taccagagcc    780
taggacttca ctgctctggt cagaggtcca ggtgatgtca tcttcttcag gagtattgca    840
ggtgaggacc accatttctc cgggggcatc agggtgccag tccaactcta caacataaac    900 gttttttctcc agttcccata tggccatgag gggaggtgcc agcaaaacca gggaaaacca    960
ggcgatgacc aactgctgag gatgcat                                        987

<210> SEQ ID NO 32
<211> LENGTH: 666
<212> TYPE: DNA
<213> ORGANISM: Felis catus
<220> FEATURE:
<221> NAME/KEY: CDS
<222> LOCATION: (1)..(666)

<400> SEQUENCE: 32 atg tgc ccg ccg cgt ggc ctc ctc ctt gta acc atc ctg gtc ctg tta     48
```

```
Met Cys Pro Pro Arg Gly Leu Leu Leu Val Thr Ile Leu Val Leu Leu
1               5                   10                  15 aac cac ctg gac cac ctc agt ttg gcc agg aac ctc ccc aca ccc aca        96
Asn His Leu Asp His Leu Ser Leu Ala Arg Asn Leu Pro Thr Pro Thr
            20                  25                  30 cca agc cca gga atg ttc cag tgc ctc aac cac tcc caa acc ctg ctg       144
Pro Ser Pro Gly Met Phe Gln Cys Leu Asn His Ser Gln Thr Leu Leu
        35                  40                  45 cga gcc atc agc aac acg ctt cag aag gcc aga caa act cta gaa ttt       192
Arg Ala Ile Ser Asn Thr Leu Gln Lys Ala Arg Gln Thr Leu Glu Phe
    50                  55                  60 tac tcc tgc act tcc gaa gag att gat cat gaa gat atc aca aaa gat       240
Tyr Ser Cys Thr Ser Glu Glu Ile Asp His Glu Asp Ile Thr Lys Asp
65                  70                  75                  80 aaa acc agc aca gtg gag gcc tgc tta cca ctg gaa tta acc atg aat       288
Lys Thr Ser Thr Val Glu Ala Cys Leu Pro Leu Glu Leu Thr Met Asn
                85                  90                  95 gag agt tgc ctg gct tcc aga gag atc tct ctg ata act aat ggg agt       336
Glu Ser Cys Leu Ala Ser Arg Glu Ile Ser Leu Ile Thr Asn Gly Ser
            100                 105                 110 tgc ctg gcc tcc aga aag acc tct ttt atg acg acc ctg tgc ctt agc       384
Cys Leu Ala Ser Arg Lys Thr Ser Phe Met Thr Thr Leu Cys Leu Ser
        115                 120                 125 agt atc tat gag gac ttg aag atg tac cag gtg gag ttc aag gcc atg       432
Ser Ile Tyr Glu Asp Leu Lys Met Tyr Gln Val Glu Phe Lys Ala Met
    130                 135                 140 aat gca aag ctg tta atg gat cct aaa agg cag atc ttt ctg gat caa       480
Asn Ala Lys Leu Leu Met Asp Pro Lys Arg Gln Ile Phe Leu Asp Gln
145                 150                 155                 160 aac atg ctg aca gct att gat gag ctg tta cag gcc ctg aat gtc aac       528
Asn Met Leu Thr Ala Ile Asp Glu Leu Leu Gln Ala Leu Asn Val Asn
                165                 170                 175 agt gtg act gtg cca cag aac tcc tcc ctg gaa gaa ccg gat ttt tat       576
Ser Val Thr Val Pro Gln Asn Ser Ser Leu Glu Glu Pro Asp Phe Tyr
            180                 185                 190 aaa act aaa atc aag ctc tgc ata ctt ctt cat gct ttc aga att cgt       624
Lys Thr Lys Ile Lys Leu Cys Ile Leu Leu His Ala Phe Arg Ile Arg
        195                 200                 205 gca gtg acc atc aat aga atg atg agc tat ctg aat gct tcc               666
Ala Val Thr Ile Asn Arg Met Met Ser Tyr Leu Asn Ala Ser
    210                 215                 220

<210> SEQ ID NO 33
<211> LENGTH: 222
<212> TYPE: PRT
<213> ORGANISM: Felis catus

<400> SEQUENCE: 33

Met Cys Pro Pro Arg Gly Leu Leu Leu Val Thr Ile Leu Val Leu Leu
1               5                   10                  15

Asn His Leu Asp His Leu Ser Leu Ala Arg Asn Leu Pro Thr Pro Thr
            20                  25                  30

Pro Ser Pro Gly Met Phe Gln Cys Leu Asn His Ser Gln Thr Leu Leu
        35                  40                  45

Arg Ala Ile Ser Asn Thr Leu Gln Lys Ala Arg Gln Thr Leu Glu Phe
    50                  55                  60

Tyr Ser Cys Thr Ser Glu Glu Ile Asp His Glu Asp Ile Thr Lys Asp
65                  70                  75                  80

Lys Thr Ser Thr Val Glu Ala Cys Leu Pro Leu Glu Leu Thr Met Asn
                85                  90                  95
```

```
Glu Ser Cys Leu Ala Ser Arg Glu Ile Ser Leu Ile Thr Asn Gly Ser
            100                 105                 110
Cys Leu Ala Ser Arg Lys Thr Ser Phe Met Thr Thr Leu Cys Leu Ser
        115                 120                 125
Ser Ile Tyr Glu Asp Leu Lys Met Tyr Gln Val Glu Phe Lys Ala Met
    130                 135                 140
Asn Ala Lys Leu Leu Met Asp Pro Lys Arg Gln Ile Phe Leu Asp Gln
145                 150                 155                 160
Asn Met Leu Thr Ala Ile Asp Glu Leu Leu Gln Ala Leu Asn Val Asn
                165                 170                 175
Ser Val Thr Val Pro Gln Asn Ser Ser Leu Glu Glu Pro Asp Phe Tyr
            180                 185                 190
Lys Thr Lys Ile Lys Leu Cys Ile Leu Leu His Ala Phe Arg Ile Arg
        195                 200                 205
Ala Val Thr Ile Asn Arg Met Met Ser Tyr Leu Asn Ala Ser
    210                 215                 220
```

<210> SEQ ID NO 34
<211> LENGTH: 666
<212> TYPE: DNA
<213> ORGANISM: Felis catus

<400> SEQUENCE: 34

```
ggaagcattc agatagctca tcattctatt gatggtcact gcacgaattc tgaaagcatg    60
aagaagtatg cagagcttga ttttagtttt ataaaaatcc ggttcttcca gggaggagtt   120
ctgtggcaca gtcacactgt tgacattcag ggcctgtaac agctcatcaa tagctgtcag   180
catgttttga tccagaaaga tctgcctttt aggatccatt aacagctttg cattcatggc   240
cttgaactcc acctggtaca tcttcaagtc ctcatagata ctgctaaggc acagggtcgt   300
cataaaagag gtctttctgg aggccaggca actcccatta gttatcagag agatctctct   360
ggaagccagg caactctcat tcatggttaa ttccagtggt aagcaggcct ccactgtgct   420
ggttttatct tttgtgatat cttcatgatc aatctcttcg gaagtgcagg agtaaaattc   480
tagagtttgt ctggccttct gaagcgtgtt gctgatggct cgcagcaggg tttgggagtg   540
gttgaggcac tggaacattc ctgggcttgg tgtgggtgtg gggaggttcc tggccaaact   600
gaggtggtcc aggtggttta acaggaccag gatggttaca aggaggaggc cacgcggcgg   660
gcacat                                                              666
```

<210> SEQ ID NO 35
<211> LENGTH: 591
<212> TYPE: DNA
<213> ORGANISM: Felis catus
<220> FEATURE:
<221> NAME/KEY: CDS
<222> LOCATION: (1)..(591)

<400> SEQUENCE: 35

```
agg aac ctc ccc aca ccc aca cca agc cca gga atg ttc cag tgc ctc    48
Arg Asn Leu Pro Thr Pro Thr Pro Ser Pro Gly Met Phe Gln Cys Leu
1               5                   10                  15 aac cac tcc caa acc ctg ctg cga gcc atc agc aac acg ctt cag aag    96
Asn His Ser Gln Thr Leu Leu Arg Ala Ile Ser Asn Thr Leu Gln Lys
            20                  25                  30 gcc aga caa act cta gaa ttt tac tcc tgc act tcc gaa gag att gat   144
Ala Arg Gln Thr Leu Glu Phe Tyr Ser Cys Thr Ser Glu Glu Ile Asp
        35                  40                  45
```

```
cat gaa gat atc aca aaa gat aaa acc agc aca gtg gag gcc tgc tta    192
His Glu Asp Ile Thr Lys Asp Lys Thr Ser Thr Val Glu Ala Cys Leu
     50                  55                  60 cca ctg gaa tta acc atg aat gag agt tgc ctg gct tcc aga gag atc    240
Pro Leu Glu Leu Thr Met Asn Glu Ser Cys Leu Ala Ser Arg Glu Ile
 65                  70                  75                  80 tct ctg ata act aat ggg agt tgc ctg gcc tcc aga aag acc tct ttt    288
Ser Leu Ile Thr Asn Gly Ser Cys Leu Ala Ser Arg Lys Thr Ser Phe
                 85                  90                  95 atg acg acc ctg tgc ctt agc agt atc tat gag gac ttg aag atg tac    336
Met Thr Thr Leu Cys Leu Ser Ser Ile Tyr Glu Asp Leu Lys Met Tyr
                100                 105                 110 cag gtg gag ttc aag gcc atg aat gca aag ctg tta atg gat cct aaa    384
Gln Val Glu Phe Lys Ala Met Asn Ala Lys Leu Leu Met Asp Pro Lys
            115                 120                 125 agg cag atc ttt ctg gat caa aac atg ctg aca gct att gat gag ctg    432
Arg Gln Ile Phe Leu Asp Gln Asn Met Leu Thr Ala Ile Asp Glu Leu
        130                 135                 140 tta cag gcc ctg aat gtc aac agt gtg act gtg cca cag aac tcc tcc    480
Leu Gln Ala Leu Asn Val Asn Ser Val Thr Val Pro Gln Asn Ser Ser
145                 150                 155                 160 ttg gaa gaa ccg gat ttt tat aaa act aaa atc aag ctc tgc ata ctt    528
Leu Glu Glu Pro Asp Phe Tyr Lys Thr Lys Ile Lys Leu Cys Ile Leu
                165                 170                 175 ctt cat gct ttc aga att cgt gca gtg acc atc aat aga atg atg agc    576
Leu His Ala Phe Arg Ile Arg Ala Val Thr Ile Asn Arg Met Met Ser
                180                 185                 190 tat ctg aat gct tcc                                                591
Tyr Leu Asn Ala Ser
        195

<210> SEQ ID NO 36
<211> LENGTH: 197
<212> TYPE: PRT
<213> ORGANISM: Felis catus

<400> SEQUENCE: 36

Arg Asn Leu Pro Thr Pro Thr Pro Ser Pro Gly Met Phe Gln Cys Leu
 1               5                  10                  15

Asn His Ser Gln Thr Leu Leu Arg Ala Ile Ser Asn Thr Leu Gln Lys
            20                  25                  30

Ala Arg Gln Thr Leu Glu Phe Tyr Ser Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Met Asn Glu Ser Cys Leu Ala Ser Arg Glu Ile
 65                  70                  75                  80

Ser Leu Ile Thr Asn Gly Ser Cys Leu Ala Ser Arg Lys Thr Ser Phe
                 85                  90                  95

Met Thr Thr Leu Cys Leu Ser Ser Ile Tyr Glu Asp Leu Lys Met Tyr
                100                 105                 110

Gln Val Glu Phe Lys Ala Met Asn Ala Lys Leu Leu Met Asp Pro Lys
            115                 120                 125

Arg Gln Ile Phe Leu Asp Gln Asn Met Leu Thr Ala Ile Asp Glu Leu
        130                 135                 140

Leu Gln Ala Leu Asn Val Asn Ser Val Thr Val Pro Gln Asn Ser Ser
145                 150                 155                 160

Leu Glu Glu Pro Asp Phe Tyr Lys Thr Lys Ile Lys Leu Cys Ile Leu
                165                 170                 175
```

Leu His Ala Phe Arg Ile Arg Ala Val Thr Ile Asn Arg Met Met Ser
            180                 185                 190

Tyr Leu Asn Ala Ser
        195

<210> SEQ ID NO 37
<211> LENGTH: 591
<212> TYPE: DNA
<213> ORGANISM: Felis catus

<400> SEQUENCE: 37

```
ggaagcattc agatagctca tcattctatt gatggtcact gcacgaattc tgaaagcatg      60
aagaagtatg cagagcttga ttttagtttt ataaaaatcc ggttcttcca aggaggagtt     120
ctgtggcaca gtcacactgt tgacattcag ggcctgtaac agctcatcaa tagctgtcag     180
catgttttga tccagaaaga tctgcctttt aggatccatt aacagctttg cattcatggc     240
cttgaactcc acctggtaca tcttcaagtc ctcatagata ctgctaaggc acagggtcgt     300
cataaaagag gtctttctgg aggccaggca actcccatta gttatcagag agatctctct     360
ggaagccagg caactctcat tcatggttaa ttccagtggt aagcaggcct ccactgtgct     420
ggttttatct tttgtgatat cttcatgatc aatctcttcg gaagtgcagg agtaaaattc     480
tagagtttgt ctggccttct gaagcgtgtt gctgatggct cgcagcaggg tttgggagtg     540
gttgaggcac tggaacattc ctgggcttgg tgtgggtgtg gggaggttcc t              591
```

<210> SEQ ID NO 38
<211> LENGTH: 1599
<212> TYPE: DNA
<213> ORGANISM: Felis catus
<220> FEATURE:
<221> NAME/KEY: CDS
<222> LOCATION: (1)..(1599)

<400> SEQUENCE: 38

```
atg cat cct cag cag ttg gtc atc gcc tgg ctt tcc ctg gtt ttg ctg       48
Met His Pro Gln Gln Leu Val Ile Ala Trp Leu Ser Leu Val Leu Leu
1               5                   10                  15 gca cct ccc ctc atg gcc ata tgg gaa ctg gag aaa aac gtt tat gtt       96
Ala Pro Pro Leu Met Ala Ile Trp Glu Leu Glu Lys Asn Val Tyr Val
            20                  25                  30 gta gag ttg gac tgg cac cct gat gcc ccc gga gaa atg gtg gtc ctc      144
Val Glu Leu Asp Trp His Pro Asp Ala Pro Gly Glu Met Val Val Leu
        35                  40                  45 acc tgc aat act cct gaa gaa gat gac atc acc tgg acc tct gac cag      192
Thr Cys Asn Thr Pro Glu Glu Asp Asp Ile Thr Trp Thr Ser Asp Gln
    50                  55                  60 agc agt gaa gtc cta ggc tct ggt aaa act ctg acc atc caa gtc aaa      240
Ser Ser Glu Val Leu Gly Ser Gly Lys Thr Leu Thr Ile Gln Val Lys
65                  70                  75                  80 gaa ttt gca gat gct ggc cag tat acc tgt cat aaa gga ggc gag gtt      288
Glu Phe Ala Asp Ala Gly Gln Tyr Thr Cys His Lys Gly Gly Glu Val
                85                  90                  95 ctg agc cat tcg ttc ctc ctg ata cac aaa aag gaa gat gga att tgg      336
Leu Ser His Ser Phe Leu Leu Ile His Lys Lys Glu Asp Gly Ile Trp
            100                 105                 110 tcc act gat atc tta agg gaa cag aaa gaa tcc aaa aat aag atc ttt      384
Ser Thr Asp Ile Leu Arg Glu Gln Lys Glu Ser Lys Asn Lys Ile Phe
        115                 120                 125 cta aaa tgt gag gca aag aat tat tct gga cgt ttc acc tgc tgg tgg      432
Leu Lys Cys Glu Ala Lys Asn Tyr Ser Gly Arg Phe Thr Cys Trp Trp
```

```
            130                 135                 140
ctg acg gca atc agt acc gat ttg aaa ttc act gtc aaa agc agc aga    480
Leu Thr Ala Ile Ser Thr Asp Leu Lys Phe Thr Val Lys Ser Ser Arg
145                 150                 155                 160 ggc tcc tct gac ccc caa gag gtg act tgt gga gca gcg aca ctc tca    528
Gly Ser Ser Asp Pro Gln Glu Val Thr Cys Gly Ala Ala Thr Leu Ser
                165                 170                 175 gca gag aag gtc aga gtg gac aac agg gat tat aag aag tac aca gtg    576
Ala Glu Lys Val Arg Val Asp Asn Arg Asp Tyr Lys Lys Tyr Thr Val
            180                 185                 190 gag tgt cag gag ggc agt gcc tgc ccg gct gcc gag gag agc cta ccc    624
Glu Cys Gln Glu Gly Ser Ala Cys Pro Ala Ala Glu Glu Ser Leu Pro
        195                 200                 205 att gaa gtc gtg gtg gac gct att cac aag ctc aag tac gaa aac tac    672
Ile Glu Val Val Val Asp Ala Ile His Lys Leu Lys Tyr Glu Asn Tyr
    210                 215                 220 acc agc agc ttc ttc atc agg gac atc atc aaa ccg gac cca ccc aag    720
Thr Ser Ser Phe Phe Ile Arg Asp Ile Ile Lys Pro Asp Pro Pro Lys
225                 230                 235                 240 aac ctg caa ctg aag cca tta aaa aat tct cgg cat gtg gaa gtg agc    768
Asn Leu Gln Leu Lys Pro Leu Lys Asn Ser Arg His Val Glu Val Ser
                245                 250                 255 tgg gaa tac cct gac acc tgg agc acc cca cat tcc tac ttc tcc tta    816
Trp Glu Tyr Pro Asp Thr Trp Ser Thr Pro His Ser Tyr Phe Ser Leu
            260                 265                 270 aca ttt ggc gta cag gtc cag ggc aag aac aac aga gaa aag aaa gac    864
Thr Phe Gly Val Gln Val Gln Gly Lys Asn Asn Arg Glu Lys Lys Asp
        275                 280                 285 aga ctc tcc gtg gac aag acc tca gcc aag gtc gtg tgc cac aag gat    912
Arg Leu Ser Val Asp Lys Thr Ser Ala Lys Val Val Cys His Lys Asp
    290                 295                 300 gcc aag atc cgc gtg caa gcc aga gac cgc tac tat agc tca tcc tgg    960
Ala Lys Ile Arg Val Gln Ala Arg Asp Arg Tyr Tyr Ser Ser Ser Trp
305                 310                 315                 320 agc aac tgg gca tcc gtg tcc tgc agt ggt ggc ggt ggc ggc gga tct   1008
Ser Asn Trp Ala Ser Val Ser Cys Ser Gly Gly Gly Gly Gly Gly Ser
                325                 330                 335 aga aac ttg cca acc cct act cca tcc ccg ggg atg ttc cag tgc ctc   1056
Arg Asn Leu Pro Thr Pro Thr Pro Ser Pro Gly Met Phe Gln Cys Leu
            340                 345                 350 aac cac tcc caa acc ctg ctg cga gcc atc agc aac acg ctt cag aag   1104
Asn His Ser Gln Thr Leu Leu Arg Ala Ile Ser Asn Thr Leu Gln Lys
        355                 360                 365 gcc aga caa act cta gaa ttt tac tcc tgc act tcc gaa gag att gat   1152
Ala Arg Gln Thr Leu Glu Phe Tyr Ser Cys Thr Ser Glu Glu Ile Asp
    370                 375                 380 cat gaa gat atc aca aaa gat aaa acc agc aca gtg gag gcc tgc tta   1200
His Glu Asp Ile Thr Lys Asp Lys Thr Ser Thr Val Glu Ala Cys Leu
385                 390                 395                 400 cca ctg gaa tta acc atg aat gag agt tgc ctg gct tcc aga gag atc   1248
Pro Leu Glu Leu Thr Met Asn Glu Ser Cys Leu Ala Ser Arg Glu Ile
                405                 410                 415 tct ctg ata act aat ggg agt tgc ctg gcc tcc aga aag acc tct ttt   1296
Ser Leu Ile Thr Asn Gly Ser Cys Leu Ala Ser Arg Lys Thr Ser Phe
            420                 425                 430 atg acg acc ctg tgc ctt agc agt atc tat gag gac ttg aag atg tac   1344
Met Thr Thr Leu Cys Leu Ser Ser Ile Tyr Glu Asp Leu Lys Met Tyr
        435                 440                 445 cag gtg gag ttc aag gcc atg aat gca aag ctg tta atg gat cct aaa   1392
Gln Val Glu Phe Lys Ala Met Asn Ala Lys Leu Leu Met Asp Pro Lys
```

-continued

```
             450                 455                 460
agg cag atc ttt ctg gat caa aac atg ctg aca gct att gat gag ctg    1440
Arg Gln Ile Phe Leu Asp Gln Asn Met Leu Thr Ala Ile Asp Glu Leu
465                 470                 475                 480 tta cag gcc ctg aat gtc aac agt gtg act gtg cca cag aac tcc tcc    1488
Leu Gln Ala Leu Asn Val Asn Ser Val Thr Val Pro Gln Asn Ser Ser
                485                 490                 495 ttg gaa gaa ccg gat ttt tat aaa act aaa atc aag ctc tgc ata ctt    1536
Leu Glu Glu Pro Asp Phe Tyr Lys Thr Lys Ile Lys Leu Cys Ile Leu
            500                 505                 510 ctt cat gct ttc aga att cgt gca gtg acc atc aat aga atg atg agc    1584
Leu His Ala Phe Arg Ile Arg Ala Val Thr Ile Asn Arg Met Met Ser
        515                 520                 525 tat ctg aat gct tcc                                                1599
Tyr Leu Asn Ala Ser
    530

<210> SEQ ID NO 39
<211> LENGTH: 533
<212> TYPE: PRT
<213> ORGANISM: Felis catus

<400> SEQUENCE: 39

Met His Pro Gln Gln Leu Val Ile Ala Trp Leu Ser Leu Val Leu Leu
1               5                   10                  15

Ala Pro Pro Leu Met Ala Ile Trp Glu Leu Glu Lys Asn Val Tyr Val
            20                  25                  30

Val Glu Leu Asp Trp His Pro Asp Ala Pro Gly Glu Met Val Val Leu
        35                  40                  45

Thr Cys Asn Thr Pro Glu Glu Asp Asp Ile Thr Trp Thr Ser Asp Gln
50                  55                  60

Ser Ser Glu Val Leu Gly Ser Gly Lys Thr Leu Thr Ile Gln Val Lys
65                  70                  75                  80

Glu Phe Ala Asp Ala Gly Gln Tyr Thr Cys His Lys Gly Gly Glu Val
                85                  90                  95

Leu Ser His Ser Phe Leu Leu Ile His Lys Lys Glu Asp Gly Ile Trp
            100                 105                 110

Ser Thr Asp Ile Leu Arg Glu Gln Lys Glu Ser Lys Asn Lys Ile Phe
        115                 120                 125

Leu Lys Cys Glu Ala Lys Asn Tyr Ser Gly Arg Phe Thr Cys Trp Trp
130                 135                 140

Leu Thr Ala Ile Ser Thr Asp Leu Lys Phe Thr Val Lys Ser Ser Arg
145                 150                 155                 160

Gly Ser Ser Asp Pro Gln Glu Val Thr Cys Gly Ala Ala Thr Leu Ser
                165                 170                 175

Ala Glu Lys Val Arg Val Asp Asn Arg Asp Tyr Lys Lys Tyr Thr Val
            180                 185                 190

Glu Cys Gln Glu Gly Ser Ala Cys Pro Ala Ala Glu Glu Ser Leu Pro
        195                 200                 205

Ile Glu Val Val Val Asp Ala Ile His Lys Leu Lys Tyr Glu Asn Tyr
210                 215                 220

Thr Ser Ser Phe Phe Ile Arg Asp Ile Ile Lys Pro Asp Pro Pro Lys
225                 230                 235                 240

Asn Leu Gln Leu Lys Pro Leu Lys Asn Ser Arg His Val Glu Val Ser
                245                 250                 255

Trp Glu Tyr Pro Asp Thr Trp Ser Thr Pro His Ser Tyr Phe Ser Leu
            260                 265                 270
```

Thr Phe Gly Val Gln Val Gln Gly Lys Asn Asn Arg Glu Lys Lys Asp
            275                 280                 285

Arg Leu Ser Val Asp Lys Thr Ser Ala Lys Val Val Cys His Lys Asp
        290                 295                 300

Ala Lys Ile Arg Val Gln Ala Arg Asp Arg Tyr Tyr Ser Ser Ser Trp
305                 310                 315                 320

Ser Asn Trp Ala Ser Val Ser Cys Ser Gly Gly Gly Gly Gly Gly Ser
                325                 330                 335

Arg Asn Leu Pro Thr Pro Thr Pro Ser Pro Gly Met Phe Gln Cys Leu
            340                 345                 350

Asn His Ser Gln Thr Leu Leu Arg Ala Ile Ser Asn Thr Leu Gln Lys
        355                 360                 365

Ala Arg Gln Thr Leu Glu Phe Tyr Ser Cys Thr Ser Glu Glu Ile Asp
    370                 375                 380

His Glu Asp Ile Thr Lys Asp Lys Thr Ser Thr Val Glu Ala Cys Leu
385                 390                 395                 400

Pro Leu Glu Leu Thr Met Asn Glu Ser Cys Leu Ala Ser Arg Glu Ile
                405                 410                 415

Ser Leu Ile Thr Asn Gly Ser Cys Leu Ala Ser Arg Lys Thr Ser Phe
            420                 425                 430

Met Thr Thr Leu Cys Leu Ser Ser Ile Tyr Glu Asp Leu Lys Met Tyr
        435                 440                 445

Gln Val Glu Phe Lys Ala Met Asn Ala Lys Leu Leu Met Asp Pro Lys
    450                 455                 460

Arg Gln Ile Phe Leu Asp Gln Asn Met Leu Thr Ala Ile Asp Glu Leu
465                 470                 475                 480

Leu Gln Ala Leu Asn Val Asn Ser Val Thr Val Pro Gln Asn Ser Ser
                485                 490                 495

Leu Glu Glu Pro Asp Phe Tyr Lys Thr Lys Ile Lys Leu Cys Ile Leu
            500                 505                 510

Leu His Ala Phe Arg Ile Arg Ala Val Thr Ile Asn Arg Met Met Ser
        515                 520                 525

Tyr Leu Asn Ala Ser
    530

<210> SEQ ID NO 40
<211> LENGTH: 1599
<212> TYPE: DNA
<213> ORGANISM: Felis catus

<400> SEQUENCE: 40
ggaagcattc agatagctca tcattctatt gatggtcact gcacgaattc tgaaagcatg      60
aagaagtatg cagagcttga ttttagtttt ataaaaatcc ggttcttcca aggaggagtt     120
ctgtggcaca gtcacactgt tgacattcag ggcctgtaac agctcatcaa tagctgtcag     180
catgttttga tccagaaaga tctgcctttt aggatccatt aacagctttg cattcatggc     240
cttgaactcc acctggtaca tcttcaagtc ctcatagata ctgctaaggc acagggtcgt     300
cataaaagag gtctttctgg aggccaggca actcccatta gttatcagag atctctct      360 ggaagccagg caactctcat tcatggttaa ttccagtggt aagcaggcct ccactgtgct     420
ggttttatct tttgtgatat cttcatgatc aatctcttcg gaagtgcagg agtaaaattc     480
tagagtttgt ctggccttct gaagcgtgtt gctgatggct cgcagcaggg tttgggagtg     540
gttgaggcac tggaacatcc ccggggatgg agtaggggtt ggcaagtttc tagatccgcc     600

-continued

```
gccaccgcca ccactgcagg acacggatgc ccagttgctc caggatgagc tatagtagcg    660
gtctctggct tgcacgcgga tcttggcatc cttgtggcac acgaccttgg ctgaggtctt    720
gtccacggag agtctgtctt tcttttctct gttgttcttg ccctggacct gtacgccaaa    780
tgttaaggag aagtaggaat gtggggtgct ccaggtgtca gggtattccc agctcacttc    840
cacatgccga gaatttttta atggcttcag ttgcaggttc ttgggtgggt ccggtttgat    900
gatgtccctg atgaagaagc tgctggtgta gttttcgtac ttgagcttgt gaatagcgtc    960
caccacgact tcaatgggta ggctctcctc ggcagccggg caggcactgc cctcctgaca   1020
ctccactgtg tacttcttat aatcccgtgtt gtccactctg accttctctg ctgagagtgt   1080
cgctgctcca caagtcacct cttggggggtc agaggagcct ctgctgcttt tgacagtgaa   1140
tttcaaatcg gtactgattg ccgtcagcca ccagcaggtg aaacgtccag aataattctt   1200
tgcctcacat tttagaaaga tcttattttt ggattctttc tgttccctta agatatcagt   1260
ggaccaaatt ccatcttcct ttttgtgtat caggaggaac gaatggctca gaacctcgcc   1320
tcctttatga caggtatact ggccagcatc tgcaaattct ttgacttgga tggtcagagt   1380
tttaccagag cctaggactt cactgctctg gtcagaggtc caggtgatgt catcttcttc   1440
aggagtattg caggtgagga ccaccatttc tccgggggca tcagggtgcc agtccaactc   1500
tacaacataa acgttttttct ccagttccca tatggccatg aggggaggtg ccagcaaaac   1560
cagggaaagc caggcgatga ccaactgctg aggatgcat                           1599
```

<210> SEQ ID NO 41
<211> LENGTH: 576
<212> TYPE: DNA
<213> ORGANISM: Felis catus

<400> SEQUENCE: 41

```
aattcttgtt ttgaacagtg aacattatgg acttatcccc attttcatcc ttttttttca     60
aaatgagttt gaaaagatct ttctcttttt cacaagctag aaagtacccc ttgtacaatg    120
aagactcaaa ttgtatctta tcatcatgtc ctggaacact tctctgaaag aatatgatgt    180
catttccttc atcattgata ctctcaggag gactcatttc cttaaaggaa ataattttgt    240
tctcacagga gagagtagac atggtcttat aattcacaga gatggttact gccagacctc    300
tagtgaggct atctttatac atatatatga taaaattcagt ccggggtgca ttatctgtac    360
agtcagaatc aggcatatcc tcaaacacag gttgatctcc ctggttaatg aagagaactt    420
ggtcgttcaa gttcgtaag attgagagtt tatgttcaag cttgccaaag taatctgtt     480 ccaggttttc atcactgtca gctacaaagt aaagtgtatt gtcaataaat ttcattccca    540
caaagttgat gcaatcatct actggtatag cagtca                              576
```

<210> SEQ ID NO 42

<400> SEQUENCE: 42

000

<210> SEQ ID NO 43
<211> LENGTH: 1533
<212> TYPE: DNA
<213> ORGANISM: Felis catus
<220> FEATURE:
<221> NAME/KEY: CDS
<222> LOCATION: (1)..(1533)

<400> SEQUENCE: 43

| | | | | | | | | | | | | | | | |
|---|---|---|---|---|---|---|---|---|---|---|---|---|---|---|---|
| ata | tgg | gaa | ctg | gag | aaa | aac | gtt | tat | gtt | gta | gag | ttg | gac | tgg | cac | 48 |
| Ile | Trp | Glu | Leu | Glu | Lys | Asn | Val | Tyr | Val | Val | Glu | Leu | Asp | Trp | His | |
| 1 | | | | 5 | | | | | 10 | | | | | 15 | | |

| cct | gat | gcc | ccc | gga | gaa | atg | gtg | gtc | ctc | acc | tgc | aat | act | cct | gaa | 96 |
| Pro | Asp | Ala | Pro | Gly | Glu | Met | Val | Val | Leu | Thr | Cys | Asn | Thr | Pro | Glu | |
| | | | 20 | | | | | 25 | | | | | 30 | | | |

| gaa | gat | gac | atc | acc | tgg | acc | tct | gac | cag | agc | agt | gaa | gtc | cta | ggc | 144 |
| Glu | Asp | Asp | Ile | Thr | Trp | Thr | Ser | Asp | Gln | Ser | Ser | Glu | Val | Leu | Gly | |
| | | 35 | | | | | 40 | | | | | 45 | | | | |

| tct | ggt | aaa | act | ctg | acc | atc | caa | gtc | aaa | gaa | ttt | gca | gat | gct | ggc | 192 |
| Ser | Gly | Lys | Thr | Leu | Thr | Ile | Gln | Val | Lys | Glu | Phe | Ala | Asp | Ala | Gly | |
| | 50 | | | | | 55 | | | | | 60 | | | | | |

| cag | tat | acc | tgt | cat | aaa | gga | ggc | gag | gtt | ctg | agc | cat | tcg | ttc | ctc | 240 |
| Gln | Tyr | Thr | Cys | His | Lys | Gly | Gly | Glu | Val | Leu | Ser | His | Ser | Phe | Leu | |
| 65 | | | | | 70 | | | | | 75 | | | | | 80 | |

| ctg | ata | cac | aaa | aag | gaa | gat | gga | att | tgg | tcc | act | gat | atc | tta | agg | 288 |
| Leu | Ile | His | Lys | Lys | Glu | Asp | Gly | Ile | Trp | Ser | Thr | Asp | Ile | Leu | Arg | |
| | | | | 85 | | | | | 90 | | | | | 95 | | |

| gaa | cag | aaa | gaa | tcc | aaa | aat | aag | atc | ttt | cta | aaa | tgt | gag | gca | aag | 336 |
| Glu | Gln | Lys | Glu | Ser | Lys | Asn | Lys | Ile | Phe | Leu | Lys | Cys | Glu | Ala | Lys | |
| | | | 100 | | | | | 105 | | | | | 110 | | | |

| aat | tat | tct | gga | cgt | ttc | acc | tgc | tgg | tgg | ctg | acg | gca | atc | agt | acc | 384 |
| Asn | Tyr | Ser | Gly | Arg | Phe | Thr | Cys | Trp | Trp | Leu | Thr | Ala | Ile | Ser | Thr | |
| | | 115 | | | | | 120 | | | | | 125 | | | | |

| gat | ttg | aaa | ttc | act | gtc | aaa | agc | agc | aga | ggc | tcc | tct | gac | ccc | caa | 432 |
| Asp | Leu | Lys | Phe | Thr | Val | Lys | Ser | Ser | Arg | Gly | Ser | Ser | Asp | Pro | Gln | |
| | 130 | | | | | 135 | | | | | 140 | | | | | |

| gag | gtg | act | tgt | gga | gca | gcg | aca | ctc | tca | gca | gag | aag | gtc | aga | gtg | 480 |
| Glu | Val | Thr | Cys | Gly | Ala | Ala | Thr | Leu | Ser | Ala | Glu | Lys | Val | Arg | Val | |
| 145 | | | | | 150 | | | | | 155 | | | | | 160 | |

| gac | aac | agg | gat | tat | aag | aag | tac | aca | gtg | gag | tgt | cag | gag | ggc | agt | 528 |
| Asp | Asn | Arg | Asp | Tyr | Lys | Lys | Tyr | Thr | Val | Glu | Cys | Gln | Glu | Gly | Ser | |
| | | | | 165 | | | | | 170 | | | | | 175 | | |

| gcc | tgc | ccg | gct | gcc | gag | gag | agc | cta | ccc | att | gaa | gtc | gtg | gtg | gac | 576 |
| Ala | Cys | Pro | Ala | Ala | Glu | Glu | Ser | Leu | Pro | Ile | Glu | Val | Val | Val | Asp | |
| | | | 180 | | | | | 185 | | | | | 190 | | | |

| gct | att | cac | aag | ctc | aag | tac | gaa | aac | tac | acc | agc | agc | ttc | ttc | atc | 624 |
| Ala | Ile | His | Lys | Leu | Lys | Tyr | Glu | Asn | Tyr | Thr | Ser | Ser | Phe | Phe | Ile | |
| | | 195 | | | | | 200 | | | | | 205 | | | | |

| agg | gac | atc | atc | aaa | ccg | gac | cca | ccc | aag | aac | ctg | caa | ctg | aag | cca | 672 |
| Arg | Asp | Ile | Ile | Lys | Pro | Asp | Pro | Pro | Lys | Asn | Leu | Gln | Leu | Lys | Pro | |
| | 210 | | | | | 215 | | | | | 220 | | | | | |

| tta | aaa | aat | tct | cgg | cat | gtg | gaa | gtg | agc | tgg | gaa | tac | cct | gac | acc | 720 |
| Leu | Lys | Asn | Ser | Arg | His | Val | Glu | Val | Ser | Trp | Glu | Tyr | Pro | Asp | Thr | |
| 225 | | | | | 230 | | | | | 235 | | | | | 240 | |

| tgg | agc | acc | cca | cat | tcc | tac | ttc | tcc | tta | aca | ttt | ggc | gta | cag | gtc | 768 |
| Trp | Ser | Thr | Pro | His | Ser | Tyr | Phe | Ser | Leu | Thr | Phe | Gly | Val | Gln | Val | |
| | | | | 245 | | | | | 250 | | | | | 255 | | |

| cag | ggc | aag | aac | aac | aga | gaa | aag | aaa | gac | aga | ctc | tcc | gtg | gac | aag | 816 |
| Gln | Gly | Lys | Asn | Asn | Arg | Glu | Lys | Lys | Asp | Arg | Leu | Ser | Val | Asp | Lys | |
| | | | 260 | | | | | 265 | | | | | 270 | | | |

| acc | tca | gcc | aag | gtc | gtg | tgc | cac | aag | gat | gcc | aag | atc | cgc | gtg | caa | 864 |
| Thr | Ser | Ala | Lys | Val | Val | Cys | His | Lys | Asp | Ala | Lys | Ile | Arg | Val | Gln | |
| | | 275 | | | | | 280 | | | | | 285 | | | | |

| gcc | aga | gac | cgc | tac | tat | agc | tca | tcc | tgg | agc | aac | tgg | gca | tcc | gtg | 912 |
| Ala | Arg | Asp | Arg | Tyr | Tyr | Ser | Ser | Ser | Trp | Ser | Asn | Trp | Ala | Ser | Val | |
| | 290 | | | | | 295 | | | | | 300 | | | | | |

| tcc | tgc | agt | ggt | ggc | ggt | ggc | ggc | gga | tct | aga | aac | ttg | cca | acc | cct | 960 |
| Ser | Cys | Ser | Gly | Gly | Gly | Gly | Gly | Gly | Ser | Arg | Asn | Leu | Pro | Thr | Pro | |
| 305 | | | | | 310 | | | | | 315 | | | | | 320 | |

```
act cca tcc ccg ggg atg ttc cag tgc ctc aac cac tcc caa acc ctg      1008
Thr Pro Ser Pro Gly Met Phe Gln Cys Leu Asn His Ser Gln Thr Leu
            325                 330                 335 ctg cga gcc atc agc aac acg ctt cag aag gcc aga caa act cta gaa      1056
Leu Arg Ala Ile Ser Asn Thr Leu Gln Lys Ala Arg Gln Thr Leu Glu
            340                 345                 350 ttt tac tcc tgc act tcc gaa gag att gat cat gaa gat atc aca aaa      1104
Phe Tyr Ser Cys Thr Ser Glu Glu Ile Asp His Glu Asp Ile Thr Lys
            355                 360                 365 gat aaa acc agc aca gtg gag gcc tgc tta cca ctg gaa tta acc atg      1152
Asp Lys Thr Ser Thr Val Glu Ala Cys Leu Pro Leu Glu Leu Thr Met
370                 375                 380 aat gag agt tgc ctg gct tcc aga gag atc tct ctg ata act aat ggg      1200
Asn Glu Ser Cys Leu Ala Ser Arg Glu Ile Ser Leu Ile Thr Asn Gly
385                 390                 395                 400 agt tgc ctg gcc tcc aga aag acc tct ttt atg acg acc ctg tgc ctt      1248
Ser Cys Leu Ala Ser Arg Lys Thr Ser Phe Met Thr Thr Leu Cys Leu
                405                 410                 415 agc agt atc tat gag gac ttg aag atg tac cag gtg gag ttc aag gcc      1296
Ser Ser Ile Tyr Glu Asp Leu Lys Met Tyr Gln Val Glu Phe Lys Ala
                420                 425                 430 atg aat gca aag ctg tta atg gat cct aaa agg cag atc ttt ctg gat      1344
Met Asn Ala Lys Leu Leu Met Asp Pro Lys Arg Gln Ile Phe Leu Asp
            435                 440                 445 caa aac atg ctg aca gct att gat gag ctg tta cag gcc ctg aat gtc      1392
Gln Asn Met Leu Thr Ala Ile Asp Glu Leu Leu Gln Ala Leu Asn Val
450                 455                 460 aac agt gtg act gtg cca cag aac tcc tcc ttg gaa gaa ccg gat ttt      1440
Asn Ser Val Thr Val Pro Gln Asn Ser Ser Leu Glu Glu Pro Asp Phe
465                 470                 475                 480 tat aaa act aaa atc aag ctc tgc ata ctt ctt cat gct ttc aga att      1488
Tyr Lys Thr Lys Ile Lys Leu Cys Ile Leu Leu His Ala Phe Arg Ile
                485                 490                 495 cgt gca gtg acc atc aat aga atg atg agc tat ctg aat gct tcc          1533
Arg Ala Val Thr Ile Asn Arg Met Met Ser Tyr Leu Asn Ala Ser
                500                 505                 510
```

<210> SEQ ID NO 44
<211> LENGTH: 511
<212> TYPE: PRT
<213> ORGANISM: Felis catus

<400> SEQUENCE: 44

```
Ile Trp Glu Leu Glu Lys Asn Val Tyr Val Glu Leu Asp Trp His
1               5                   10                  15

Pro Asp Ala Pro Gly Glu Met Val Val Leu Thr Cys Asn Thr Pro Glu
                20                  25                  30

Glu Asp Asp Ile Thr Trp Thr Ser Asp Gln Ser Ser Glu Val Leu Gly
            35                  40                  45

Ser Gly Lys Thr Leu Thr Ile Gln Val Lys Glu Phe Ala Asp Ala Gly
        50                  55                  60

Gln Tyr Thr Cys His Lys Gly Gly Glu Val Leu Ser His Ser Phe Leu
65                  70                  75                  80

Leu Ile His Lys Lys Glu Asp Gly Ile Trp Ser Thr Asp Ile Leu Arg
                85                  90                  95

Glu Gln Lys Glu Ser Lys Asn Lys Ile Phe Leu Lys Cys Glu Ala Lys
            100                 105                 110

Asn Tyr Ser Gly Arg Phe Thr Cys Trp Trp Leu Thr Ala Ile Ser Thr
        115                 120                 125
```

```
Asp Leu Lys Phe Thr Val Lys Ser Ser Arg Gly Ser Ser Asp Pro Gln
130                 135                 140

Glu Val Thr Cys Gly Ala Ala Thr Leu Ser Ala Glu Lys Val Arg Val
145                 150                 155                 160

Asp Asn Arg Asp Tyr Lys Lys Tyr Thr Val Glu Cys Gln Glu Gly Ser
                165                 170                 175

Ala Cys Pro Ala Ala Glu Glu Ser Leu Pro Ile Glu Val Val Val Asp
            180                 185                 190

Ala Ile His Lys Leu Lys Tyr Glu Asn Tyr Thr Ser Ser Phe Phe Ile
        195                 200                 205

Arg Asp Ile Ile Lys Pro Asp Pro Lys Asn Leu Gln Leu Lys Pro
210                 215                 220

Leu Lys Asn Ser Arg His Val Glu Val Ser Trp Glu Tyr Pro Asp Thr
225                 230                 235                 240

Trp Ser Thr Pro His Ser Tyr Phe Ser Leu Thr Phe Gly Val Gln Val
                245                 250                 255

Gln Gly Lys Asn Asn Arg Glu Lys Lys Asp Arg Leu Ser Val Asp Lys
            260                 265                 270

Thr Ser Ala Lys Val Val Cys His Lys Asp Ala Lys Ile Arg Val Gln
        275                 280                 285

Ala Arg Asp Arg Tyr Tyr Ser Ser Ser Trp Ser Asn Trp Ala Ser Val
290                 295                 300

Ser Cys Ser Gly Gly Gly Gly Gly Ser Arg Asn Leu Pro Thr Pro
305                 310                 315                 320

Thr Pro Ser Pro Gly Met Phe Gln Cys Leu Asn His Ser Gln Thr Leu
                325                 330                 335

Leu Arg Ala Ile Ser Asn Thr Leu Gln Lys Ala Arg Gln Thr Leu Glu
            340                 345                 350

Phe Tyr Ser Cys Thr Ser Glu Glu Ile Asp His Glu Asp Ile Thr Lys
        355                 360                 365

Asp Lys Thr Ser Thr Val Glu Ala Cys Leu Pro Leu Glu Leu Thr Met
370                 375                 380

Asn Glu Ser Cys Leu Ala Ser Arg Glu Ile Ser Leu Ile Thr Asn Gly
385                 390                 395                 400

Ser Cys Leu Ala Ser Arg Lys Thr Ser Phe Met Thr Thr Leu Cys Leu
                405                 410                 415

Ser Ser Ile Tyr Glu Asp Leu Lys Met Tyr Gln Val Glu Phe Lys Ala
            420                 425                 430

Met Asn Ala Lys Leu Leu Met Asp Pro Lys Arg Gln Ile Phe Leu Asp
        435                 440                 445

Gln Asn Met Leu Thr Ala Ile Asp Glu Leu Leu Gln Ala Leu Asn Val
450                 455                 460

Asn Ser Val Thr Val Pro Gln Asn Ser Ser Leu Glu Glu Pro Asp Phe
465                 470                 475                 480

Tyr Lys Thr Lys Ile Lys Leu Cys Ile Leu Leu His Ala Phe Arg Ile
                485                 490                 495

Arg Ala Val Thr Ile Asn Arg Met Met Ser Tyr Leu Asn Ala Ser
            500                 505                 510

<210> SEQ ID NO 45
<211> LENGTH: 1533
<212> TYPE: DNA
<213> ORGANISM: Felis catus

<400> SEQUENCE: 45
```

-continued

```
ggaagcattc agatagctca tcattctatt gatggtcact gcacgaattc tgaaagcatg      60
aagaagtatg cagagcttga ttttagtttt ataaaaatcc ggttcttcca aggaggagtt     120
ctgtggcaca gtcacactgt tgacattcag ggcctgtaac agctcatcaa tagctgtcag     180
catgttttga tccagaaaga tctgcctttt aggatccatt aacagctttg cattcatggc     240
cttgaactcc acctggtaca tcttcaagtc ctcatagata ctgctaaggc acagggtcgt     300
cataaaagag gtctttctgg aggccaggca actcccatta gttatcagag agatctctct     360
ggaagccagg caactctcat tcatggttaa ttccagtggt aagcaggcct ccactgtgct     420
ggttttatct tttgtgatat cttcatgatc aatctcttcg gaagtgcagg agtaaaattc     480
tagagtttgt ctggccttct gaagcgtgtt gctgatggct cgcagcaggg tttgggagtg     540
gttgaggcac tggaacatcc ccggggatgg agtaggggtt ggcaagtttc tagatccgcc     600
gccaccgcca ccactgcagg acacggatgc ccagttgctc caggatgagc tatagtagcg     660
gtctctggct tgcacgcgga tcttggcatc cttgtggcac acgaccttgg ctgaggtctt     720
gtccacggag agtctgtctt tcttttctct gttgttcttg ccctggacct gtacgccaaa     780
tgttaaggag aagtaggaat gtggggtgct ccaggtgtca gggtattccc agctcacttc     840
cacatgccga gaattttta atggcttcag ttgcaggttc ttgggtgggt ccggtttgat     900
gatgtccctg atgaagaagc tgctggtgta gttttcgtac ttgagcttgt gaatagcgtc     960
caccacgact tcaatgggta ggctctcctc ggcagccggg caggcactgc cctcctgaca    1020
ctccactgtg tacttcttat aatccctgtt gtccactctg accttctctg ctgagagtgt    1080
cgctgctcca caagtcacct cttggggggtc agaggagcct ctgctgcttt tgacagtgaa    1140
tttcaaatcg gtactgattg ccgtcagcca ccagcaggtg aaacgtccag aataattctt    1200
tgcctcacat tttagaaaga tcttattttt ggattctttc tgttcccta agatatcagt     1260 ggaccaaatt ccatcttcct ttttgtgtat caggaggaac gaatggctca gaacctcgcc    1320
tcctttatga caggtatact ggccagcatc tgcaaattct ttgacttgga tggtcagagt    1380
tttaccagag cctaggactt cactgctctg gtcagaggtc caggtgatgt catcttcttc    1440
aggagtattg caggtgagga ccaccatttc tccgggggca tcagggtgcc agtccaactc    1500
tacaacataa acgttttttct ccagttccca tat                                1533
```

<210> SEQ ID NO 46
<211> LENGTH: 666
<212> TYPE: DNA
<213> ORGANISM: Canis familiaris
<220> FEATURE:
<221> NAME/KEY: CDS
<222> LOCATION: (1)..(666)

<400> SEQUENCE: 46

```
atg tgc ccg ccg cgc ggc ctc ctc ctt gtg acc atc ctg gtc ctg cta       48
Met Cys Pro Pro Arg Gly Leu Leu Leu Val Thr Ile Leu Val Leu Leu
1               5                   10                  15 agc cac ctg gac cac ctt act tgg gcc agg agc ctc ccc aca gcc tca       96
Ser His Leu Asp His Leu Thr Trp Ala Arg Ser Leu Pro Thr Ala Ser
            20                  25                  30 ccg agc cca gga ata ttc cag tgc ctc aac cac tcc caa aac ctg ctg      144
Pro Ser Pro Gly Ile Phe Gln Cys Leu Asn His Ser Gln Asn Leu Leu
        35                  40                  45 aga gcc gtc agc aac acg ctt cag aag gcc aga caa act cta gaa tta      192
Arg Ala Val Ser Asn Thr Leu Gln Lys Ala Arg Gln Thr Leu Glu Leu
    50                  55                  60 tat tcc tgc act tcc gaa gag att gat cat gaa gat atc aca aag gat      240
```

```
Tyr Ser Cys Thr Ser Glu Glu Ile Asp His Glu Asp Ile Thr Lys Asp
65                  70                  75                  80 aaa acc agc aca gtg gag gcc tgc tta cca ctg gaa tta acc atg aat     288
Lys Thr Ser Thr Val Glu Ala Cys Leu Pro Leu Glu Leu Thr Met Asn
                85                  90                  95 gag agt tgc ctg gct tcc aga gag atc tct ttg ata act aac ggg agt     336
Glu Ser Cys Leu Ala Ser Arg Glu Ile Ser Leu Ile Thr Asn Gly Ser
            100                 105                 110 tgc ctg gcc tct gga aag gcc tct ttt atg acg gtc ctg tgc ctt agc     384
Cys Leu Ala Ser Gly Lys Ala Ser Phe Met Thr Val Leu Cys Leu Ser
        115                 120                 125 agc atc tat gag gac ttg aag atg tac cag atg gaa ttc aag gcc atg     432
Ser Ile Tyr Glu Asp Leu Lys Met Tyr Gln Met Glu Phe Lys Ala Met
130                 135                 140 aac gca aag ctt tta atg gat ccc aag agg cag atc ttt ctg gat caa     480
Asn Ala Lys Leu Leu Met Asp Pro Lys Arg Gln Ile Phe Leu Asp Gln
145                 150                 155                 160 aac atg ctg aca gct atc gat gag ctg tta cag gcc ctg aat ttc aac     528
Asn Met Leu Thr Ala Ile Asp Glu Leu Leu Gln Ala Leu Asn Phe Asn
                165                 170                 175 agt gtg act gtg cca cag aaa tcc tcc ctt gaa gag ccg gat ttt tat     576
Ser Val Thr Val Pro Gln Lys Ser Ser Leu Glu Glu Pro Asp Phe Tyr
            180                 185                 190 aaa act aaa atc aag ctc tgc ata ctt ctt cat gct ttc aga att cgt     624
Lys Thr Lys Ile Lys Leu Cys Ile Leu Leu His Ala Phe Arg Ile Arg
        195                 200                 205 gcg gtg acc atc gat aga atg atg agt tat ctg aat tct tcc                 666
Ala Val Thr Ile Asp Arg Met Met Ser Tyr Leu Asn Ser Ser
210                 215                 220

<210> SEQ ID NO 47
<211> LENGTH: 222
<212> TYPE: PRT
<213> ORGANISM: Canis familiaris

<400> SEQUENCE: 47

Met Cys Pro Pro Arg Gly Leu Leu Val Thr Ile Leu Val Leu Leu
1               5                   10                  15

Ser His Leu Asp His Leu Thr Trp Ala Arg Ser Leu Pro Thr Ala Ser
                20                  25                  30

Pro Ser Pro Gly Ile Phe Gln Cys Leu Asn His Ser Gln Asn Leu Leu
            35                  40                  45

Arg Ala Val Ser Asn Thr Leu Gln Lys Ala Arg Gln Thr Leu Glu Leu
        50                  55                  60

Tyr Ser Cys Thr Ser Glu Glu Ile Asp His Glu Asp Ile Thr Lys Asp
65                  70                  75                  80

Lys Thr Ser Thr Val Glu Ala Cys Leu Pro Leu Glu Leu Thr Met Asn
                85                  90                  95

Glu Ser Cys Leu Ala Ser Arg Glu Ile Ser Leu Ile Thr Asn Gly Ser
            100                 105                 110

Cys Leu Ala Ser Gly Lys Ala Ser Phe Met Thr Val Leu Cys Leu Ser
        115                 120                 125

Ser Ile Tyr Glu Asp Leu Lys Met Tyr Gln Met Glu Phe Lys Ala Met
130                 135                 140

Asn Ala Lys Leu Leu Met Asp Pro Lys Arg Gln Ile Phe Leu Asp Gln
145                 150                 155                 160

Asn Met Leu Thr Ala Ile Asp Glu Leu Leu Gln Ala Leu Asn Phe Asn
                165                 170                 175
```

```
Ser Val Thr Val Pro Gln Lys Ser Ser Leu Glu Glu Pro Asp Phe Tyr
            180                 185                 190

Lys Thr Lys Ile Lys Leu Cys Ile Leu Leu His Ala Phe Arg Ile Arg
        195                 200                 205

Ala Val Thr Ile Asp Arg Met Met Ser Tyr Leu Asn Ser Ser
        210                 215                 220

<210> SEQ ID NO 48
<211> LENGTH: 666
<212> TYPE: DNA
<213> ORGANISM: Canis familiaris

<400> SEQUENCE: 48
ggaagaattc agataactca tcattctatc gatggtcacc gcacgaattc tgaaagcatg      60
aagaagtatg cagagcttga ttttagtttt ataaaaatcc ggctcttcaa gggaggattt     120
ctgtggcaca gtcacactgt tgaaattcag ggcctgtaac agctcatcga tagctgtcag     180
catgttttga tccagaaaga tctgcctctt gggatccatt aaaagctttg cgttcatggc     240
cttgaattcc atctggtaca tcttcaagtc ctcatagatg ctgctaaggc acaggaccgt     300
cataaaagag gcctttccag aggccaggca actcccgtta gttatcaaag agatctctct     360
ggaagccagg caactctcat tcatggttaa ttccagtggt aagcaggcct ccactgtgct     420
ggttttatcc tttgtgatat cttcatgatc aatctcttcg gaagtgcagg aatataattc     480
tagagtttgt ctggccttct gaagcgtgtt gctgacggct ctcagcaggt tttgggagtg     540
gttgaggcac tggaatattc ctgggctcgg tgaggctgtg gggaggctcc tggcccaagt     600
aaggtggtcc aggtggctta gcaggaccag gatggtcaca aggaggaggc cgcgcggcgg     660
gcacat                                                                666

<210> SEQ ID NO 49
<211> LENGTH: 591
<212> TYPE: DNA
<213> ORGANISM: Canis familiaris
<220> FEATURE:
<221> NAME/KEY: CDS
<222> LOCATION: (1)..(591)

<400> SEQUENCE: 49 agg agc ctc ccc aca gcc tca ccg agc cca gga ata ttc cag tgc ctc      48
Arg Ser Leu Pro Thr Ala Ser Pro Ser Pro Gly Ile Phe Gln Cys Leu
1               5                   10                  15 aac cac tcc caa aac ctg ctg aga gcc gtc agc aac acg ctt cag aag      96
Asn His Ser Gln Asn Leu Leu Arg Ala Val Ser Asn Thr Leu Gln Lys
            20                  25                  30 gcc aga caa act cta gaa tta tat tcc tgc act tcc gaa gag att gat     144
Ala Arg Gln Thr Leu Glu Leu Tyr Ser Cys Thr Ser Glu Glu Ile Asp
        35                  40                  45 cat gaa gat atc aca aag gat aaa acc agc aca gtg gag gcc tgc tta     192
His Glu Asp Ile Thr Lys Asp Lys Thr Ser Thr Val Glu Ala Cys Leu
    50                  55                  60 cca ctg gaa tta acc atg aat gag agt tgc ctg gct tcc aga gag atc     240
Pro Leu Glu Leu Thr Met Asn Glu Ser Cys Leu Ala Ser Arg Glu Ile
65                  70                  75                  80 tct ttg ata act aac ggg agt tgc ctg gcc tct gga aag gcc tct ttt     288
Ser Leu Ile Thr Asn Gly Ser Cys Leu Ala Ser Gly Lys Ala Ser Phe
                85                  90                  95 atg acg gtc ctg tgc ctt agc agc atc tat gag gac ttg aag atg tac     336
Met Thr Val Leu Cys Leu Ser Ser Ile Tyr Glu Asp Leu Lys Met Tyr
            100                 105                 110
```

```
cag atg gaa ttc aag gcc atg aac gca aag ctt tta atg gat ccc aag      384
Gln Met Glu Phe Lys Ala Met Asn Ala Lys Leu Leu Met Asp Pro Lys
        115                 120                 125 agg cag atc ttt ctg gat caa aac atg ctg aca gct atc gat gag ctg      432
Arg Gln Ile Phe Leu Asp Gln Asn Met Leu Thr Ala Ile Asp Glu Leu
130                 135                 140 tta cag gcc ctg aat ttc aac agt gtg act gtg cca cag aaa tcc tcc      480
Leu Gln Ala Leu Asn Phe Asn Ser Val Thr Val Pro Gln Lys Ser Ser
145                 150                 155                 160 ctt gaa gag ccg gat ttt tat aaa act aaa atc aag ctc tgc ata ctt      528
Leu Glu Glu Pro Asp Phe Tyr Lys Thr Lys Ile Lys Leu Cys Ile Leu
                165                 170                 175 ctt cat gct ttc aga att cgt gcg gtg acc atc gat aga atg atg agt      576
Leu His Ala Phe Arg Ile Arg Ala Val Thr Ile Asp Arg Met Met Ser
            180                 185                 190 tat ctg aat tct tcc                                                   591
Tyr Leu Asn Ser Ser
        195

<210> SEQ ID NO 50
<211> LENGTH: 197
<212> TYPE: PRT
<213> ORGANISM: Canis familiaris

<400> SEQUENCE: 50

Arg Ser Leu Pro Thr Ala Ser Pro Ser Pro Gly Ile Phe Gln Cys Leu
1               5                   10                  15

Asn His Ser Gln Asn Leu Leu Arg Ala Val Ser Asn Thr Leu Gln Lys
            20                  25                  30

Ala Arg Gln Thr Leu Glu Leu Tyr Ser Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Met Asn Glu Ser Cys Leu Ala Ser Arg Glu Ile
65                  70                  75                  80

Ser Leu Ile Thr Asn Gly Ser Cys Leu Ala Ser Gly Lys Ala Ser Phe
                85                  90                  95

Met Thr Val Leu Cys Leu Ser Ser Ile Tyr Glu Asp Leu Lys Met Tyr
            100                 105                 110

Gln Met Glu Phe Lys Ala Met Asn Ala Lys Leu Leu Met Asp Pro Lys
        115                 120                 125

Arg Gln Ile Phe Leu Asp Gln Asn Met Leu Thr Ala Ile Asp Glu Leu
    130                 135                 140

Leu Gln Ala Leu Asn Phe Asn Ser Val Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Met Met Ser
            180                 185                 190

Tyr Leu Asn Ser Ser
        195

<210> SEQ ID NO 51
<211> LENGTH: 591
<212> TYPE: DNA
<213> ORGANISM: Canis familiaris

<400> SEQUENCE: 51
ggaagaattc agataactca tcattctatc gatggtcacc gcacgaattc tgaaagcatg    60
```

```
aagaagtatg cagagcttga ttttagtttt ataaaaatcc ggctcttcaa gggaggattt      120
ctgtggcaca gtcacactgt tgaaattcag ggcctgtaac agctcatcga tagctgtcag      180
catgttttga tccagaaaga tctgcctctt gggatccatt aaaagctttg cgttcatggc      240
cttgaattcc atctggtaca tcttcaagtc ctcatagatg ctgctaaggc acaggaccgt      300
cataaaagag gcctttccag aggccaggca actcccgtta gttatcaaag agatctctct      360
ggaagccagg caactctcat tcatggttaa ttccagtggt aagcaggcct ccactgtgct      420
ggttttatcc tttgtgatat cttcatgatc aatctcttcg gaagtgcagg aatataattc      480
tagagtttgt ctggccttct gaagcgtgtt gctgacggct ctcagcaggt tttgggagtg      540
gttgaggcac tggaatattc ctgggctcgg tgaggctgtg gggaggctcc t              591
```

```
<210> SEQ ID NO 52
<211> LENGTH: 921
<212> TYPE: DNA
<213> ORGANISM: Canis familiaris
<220> FEATURE:
<221> NAME/KEY: CDS
<222> LOCATION: (1)..(921)

<400> SEQUENCE: 52 ata tgg gaa ctg gag aaa gat gtt tat gtt gta gag ttg gac tgg cac      48
Ile Trp Glu Leu Glu Lys Asp Val Tyr Val Val Glu Leu Asp Trp His
1               5                   10                  15 cct gat gcc ccc gga gaa atg gtg gtc ctc acc tgc cat acc cct gaa      96
Pro Asp Ala Pro Gly Glu Met Val Val Leu Thr Cys His Thr Pro Glu
                20                  25                  30 gaa gat gac atc act tgg acc tca gcg cag agc agt gaa gtc cta ggt      144
Glu Asp Asp Ile Thr Trp Thr Ser Ala Gln Ser Ser Glu Val Leu Gly
            35                  40                  45 tct ggt aaa act ctg acc atc caa gtc aaa gaa ttt gga gat gct ggc      192
Ser Gly Lys Thr Leu Thr Ile Gln Val Lys Glu Phe Gly Asp Ala Gly
        50                  55                  60 cag tat acc tgc cat aaa gga ggc aag gtt ctg agc cgc tca ctc ctg      240
Gln Tyr Thr Cys His Lys Gly Gly Lys Val Leu Ser Arg Ser Leu Leu
65                  70                  75                  80 ttg att cac aaa aaa gaa gat gga att tgg tcc act gat atc tta aag      288
Leu Ile His Lys Lys Glu Asp Gly Ile Trp Ser Thr Asp Ile Leu Lys
                85                  90                  95 gaa cag aaa gaa tcc aaa aat aag atc ttt ctg aaa tgt gag gca aag      336
Glu Gln Lys Glu Ser Lys Asn Lys Ile Phe Leu Lys Cys Glu Ala Lys
                100                 105                 110 aat tat tct gga cgt ttc aca tgc tgg tgg ctg acg gca atc agt act      384
Asn Tyr Ser Gly Arg Phe Thr Cys Trp Trp Leu Thr Ala Ile Ser Thr
            115                 120                 125 gat ttg aaa ttc agt gtc aaa agt agc aga ggc ttc tct gac ccc caa      432
Asp Leu Lys Phe Ser Val Lys Ser Ser Arg Gly Phe Ser Asp Pro Gln
        130                 135                 140 ggg gtg aca tgt gga gca gtg aca ctt tca gca gag agg gtc aga gtg      480
Gly Val Thr Cys Gly Ala Val Thr Leu Ser Ala Glu Arg Val Arg Val
145                 150                 155                 160 gac aac agg gat tat aag aag tac aca gtg gag tgt cag gag ggc agt      528
Asp Asn Arg Asp Tyr Lys Lys Tyr Thr Val Glu Cys Gln Glu Gly Ser
                165                 170                 175 gcc tgc ccc tct gcc gag gag agc cta ccc atc gag gtc gtg gtg gat      576
Ala Cys Pro Ser Ala Glu Glu Ser Leu Pro Ile Glu Val Val Val Asp
            180                 185                 190 gct att cac aag ctc aag tat gaa aac tac acc agc agc ttc ttc atc      624
Ala Ile His Lys Leu Lys Tyr Glu Asn Tyr Thr Ser Ser Phe Phe Ile
```

-continued

```
                195                 200                 205
aga gac atc atc aaa cca gac cca ccc aca aac ctg cag ctg aag cca      672
Arg Asp Ile Ile Lys Pro Asp Pro Pro Thr Asn Leu Gln Leu Lys Pro
    210                 215                 220 ttg aaa aat tct cgg cac gtg gag gtc agc tgg gaa tac ccc gac acc      720
Leu Lys Asn Ser Arg His Val Glu Val Ser Trp Glu Tyr Pro Asp Thr
225                 230                 235                 240 tgg agc acc cca cat tcc tac ttc tcc ctg aca ttt tgc ata cag gcc      768
Trp Ser Thr Pro His Ser Tyr Phe Ser Leu Thr Phe Cys Ile Gln Ala
                245                 250                 255 cag ggc aag aac aat aga gaa aag aaa gat aga ctc tgc gtg gac aag      816
Gln Gly Lys Asn Asn Arg Glu Lys Lys Asp Arg Leu Cys Val Asp Lys
            260                 265                 270 acc tca gcc aag gtc gtg tgc cac aag gat gcc aag atc cgc gtg caa      864
Thr Ser Ala Lys Val Val Cys His Lys Asp Ala Lys Ile Arg Val Gln
        275                 280                 285 gcc cga gac cgc tac tat agt tca tcc tgg agc gac tgg gca tct gtg      912
Ala Arg Asp Arg Tyr Tyr Ser Ser Ser Trp Ser Asp Trp Ala Ser Val
    290                 295                 300 tcc tgc agt                                                          921
Ser Cys Ser
305

<210> SEQ ID NO 53
<211> LENGTH: 307
<212> TYPE: PRT
<213> ORGANISM: Canis familiaris

<400> SEQUENCE: 53

Ile Trp Glu Leu Glu Lys Asp Val Tyr Val Glu Leu Asp Trp His
1               5                   10                  15

Pro Asp Ala Pro Gly Glu Met Val Val Leu Thr Cys His Thr Pro Glu
                20                  25                  30

Glu Asp Asp Ile Thr Trp Thr Ser Ala Gln Ser Ser Glu Val Leu Gly
            35                  40                  45

Ser Gly Lys Thr Leu Thr Ile Gln Val Lys Glu Phe Gly Asp Ala Gly
        50                  55                  60

Gln Tyr Thr Cys His Lys Gly Gly Lys Val Leu Ser Arg Ser Leu Leu
65                  70                  75                  80

Leu Ile His Lys Lys Glu Asp Gly Ile Trp Ser Thr Asp Ile Leu Lys
                85                  90                  95

Glu Gln Lys Glu Ser Lys Asn Lys Ile Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Ser Val Lys Ser Ser Arg Gly Phe Ser Asp Pro Gln
    130                 135                 140

Gly Val Thr Cys Gly Ala Val Thr Leu Ser Ala Glu Arg Val Arg Val
145                 150                 155                 160

Asp Asn Arg Asp Tyr Lys Lys Tyr Thr Val Glu Cys Gln Glu Gly Ser
                165                 170                 175

Ala Cys Pro Ser Ala Glu Glu Ser Leu Pro Ile Glu Val Val Val Asp
            180                 185                 190

Ala Ile His Lys Leu Lys Tyr Glu Asn Tyr Thr Ser Ser Phe Phe Ile
        195                 200                 205

Arg Asp Ile Ile Lys Pro Asp Pro Pro Thr Asn Leu Gln Leu Lys Pro
    210                 215                 220
```

-continued

```
Leu Lys Asn Ser Arg His Val Glu Val Ser Trp Glu Tyr Pro Asp Thr
225                 230                 235                 240

Trp Ser Thr Pro His Ser Tyr Phe Ser Leu Thr Phe Cys Ile Gln Ala
            245                 250                 255

Gln Gly Lys Asn Asn Arg Glu Lys Lys Asp Arg Leu Cys Val Asp Lys
        260                 265                 270

Thr Ser Ala Lys Val Val Cys His Lys Asp Ala Lys Ile Arg Val Gln
    275                 280                 285

Ala Arg Asp Arg Tyr Tyr Ser Ser Ser Trp Ser Asp Trp Ala Ser Val
290                 295                 300

Ser Cys Ser
305

<210> SEQ ID NO 54
<211> LENGTH: 921
<212> TYPE: DNA
<213> ORGANISM: Canis familiaris

<400> SEQUENCE: 54
actgcaggac acagatgccc agtcgctcca ggatgaacta tagtagcggt ctcgggcttg      60
cacgcggatc ttggcatcct tgtggcacac gaccttggct gaggtcttgt ccacgcagag     120
tctatctttc ttttctctat tgttcttgcc ctgggcctgt atgcaaaatg tcagggagaa     180
gtaggaatgt ggggtgctcc aggtgtcggg gtattcccag ctgacctcca cgtgccgaga     240 attttttcaat ggcttcagct gcaggttttgt gggtgggtct ggtttgatga tgtctctgat    300
gaagaagctg ctggtgtagt tttcatactt gagcttgtga atagcatcca ccacgacctc     360
gatgggtagg ctctcctcgg cagaggggca ggcactgccc tcctgacact ccactgtgta     420
cttcttataa tccctgttgt ccactctgac cctctctgct gaaagtgtca ctgctccaca     480
tgtcacccct tgggggtcag agaagcctct gctactttttg acactgaatt tcaaatcagt    540
actgattgcc gtcagccacc agcatgtgaa acgtccagaa taattctttg cctcacattt     600
cagaaagatc ttattttttgg attctttctg ttcctttaag atatcagtgg accaaattcc    660
atcttctttt ttgtgaatca acaggagtga gcggctcaga accttgcctc ctttatggca    720
ggtatactgg ccagcatctc caaattcttt gacttggatg gtcagagttt taccagaacc    780
taggacttca ctgctctgcg ctgaggtcca agtgatgtca tcttcttcag ggtatggca     840 ggtgaggacc accatttctc cgggggcatc agggtgccag tccaactcta acataaac      900 atctttctcc agttcccata t                                               921

<210> SEQ ID NO 55
<211> LENGTH: 985
<212> TYPE: DNA
<213> ORGANISM: Felis catus
<220> FEATURE:
<221> NAME/KEY: CDS
<222> LOCATION: (1)..(984)

<400> SEQUENCE: 55 atg cat cct cag cag ttg gtc atc gcc tgg ttt tcc ctg gtt ttg ctg       48
Met His Pro Gln Gln Leu Val Ile Ala Trp Phe Ser Leu Val Leu Leu
1               5                   10                  15 gca cct ccc ctc atg gcc ata tgg gaa ctg gag aaa aac gtt tat gtt       96
Ala Pro Pro Leu Met Ala Ile Trp Glu Leu Glu Lys Asn Val Tyr Val
                20                  25                  30 gta gag ttg gac tgg cac cct gat gcc ccc gga gaa atg gtg gtc ctc      144
Val Glu Leu Asp Trp His Pro Asp Ala Pro Gly Glu Met Val Val Leu
            35                  40                  45
```

| | | |
|---|---|---|
| acc tgc aat act cct gaa gaa gat gac atc acc tgg acc tct gac cag<br>Thr Cys Asn Thr Pro Glu Glu Asp Asp Ile Thr Trp Thr Ser Asp Gln<br>50                    55                    60 | | 192 |
| agc agt gaa gtc cta ggc tct ggt aaa act ctg acc atc caa gtc aaa<br>Ser Ser Glu Val Leu Gly Ser Gly Lys Thr Leu Thr Ile Gln Val Lys<br>65                  70                   75                 80 | | 240 |
| gaa ttt gca gat gct ggc cag tat acc tgt cat aaa gga ggc gag gtt<br>Glu Phe Ala Asp Ala Gly Gln Tyr Thr Cys His Lys Gly Gly Glu Val<br>                    85                     90                     95 | | 288 |
| ctg agc cat tcg ttc ctc ctg ata cac aaa aag gaa gat gga att tgg<br>Leu Ser His Ser Phe Leu Leu Ile His Lys Lys Glu Asp Gly Ile Trp<br>                100                   105                   110 | | 336 |
| tcc act gat atc tta agg gaa cag aaa gaa tcc aaa aat aag atc ttt<br>Ser Thr Asp Ile Leu Arg Glu Gln Lys Glu Ser Lys Asn Lys Ile Phe<br>             115                   120                   125 | | 384 |
| cta aaa tgt gag gca aag aat tat tct gga cgt ttc acc tgc tgg tgg<br>Leu Lys Cys Glu Ala Lys Asn Tyr Ser Gly Arg Phe Thr Cys Trp Trp<br>130                   135                   140 | | 432 |
| ctg acg gca atc agt acc gat ttg aaa ttc act gtc aaa agc agc aga<br>Leu Thr Ala Ile Ser Thr Asp Leu Lys Phe Thr Val Lys Ser Ser Arg<br>145                   150                   155                   160 | | 480 |
| ggc tcc tct gac ccc caa ggg gtg act tgt gga gca gcg aca ctc tca<br>Gly Ser Ser Asp Pro Gln Gly Val Thr Cys Gly Ala Ala Thr Leu Ser<br>                           165                   170                   175 | | 528 |
| gca gag aag gtc aga gtg gac aac agg gat tat aag aag tac aca gtg<br>Ala Glu Lys Val Arg Val Asp Asn Arg Asp Tyr Lys Lys Tyr Thr Val<br>                    180                   185                   190 | | 576 |
| gag tgt cag gag ggc agt gcc tgc ccg gct gcc gag gag agc cta ccc<br>Glu Cys Gln Glu Gly Ser Ala Cys Pro Ala Ala Glu Glu Ser Leu Pro<br>             195                   200                   205 | | 624 |
| att gaa gtc gtg gtg gac gct att cac aag ctc aag tac gaa aac tac<br>Ile Glu Val Val Val Asp Ala Ile His Lys Leu Lys Tyr Glu Asn Tyr<br>210                   215                   220 | | 672 |
| acc agc agc ttc ttc atc agg gac atc atc aaa ccg gac cca ccc aag<br>Thr Ser Ser Phe Phe Ile Arg Asp Ile Ile Lys Pro Asp Pro Pro Lys<br>225                   230                   235                   240 | | 720 |
| aac ctg caa ctg aag cca tta aaa aat tct cgg cat gtg gaa gtg agc<br>Asn Leu Gln Leu Lys Pro Leu Lys Asn Ser Arg His Val Glu Val Ser<br>                         245                   250                   255 | | 768 |
| tgg gaa tac cct gac acc tgg agc acc cca cat tcc tac ttc tcc tta<br>Trp Glu Tyr Pro Asp Thr Trp Ser Thr Pro His Ser Tyr Phe Ser Leu<br>                    260                   265                   270 | | 816 |
| aca ttt ggc gta cag gtc cag ggc aag aac aac aga gaa aag aaa gac<br>Thr Phe Gly Val Gln Val Gln Gly Lys Asn Asn Arg Glu Lys Lys Asp<br>             275                   280                   285 | | 864 |
| aga ctc tcc gtg gac aag acc tca gcc aag gtc gtg tgc cac aag gat<br>Arg Leu Ser Val Asp Lys Thr Ser Ala Lys Val Val Cys His Lys Asp<br>290                   295                   300 | | 912 |
| gcc aag atc cgc gtg caa gcc aga gac cgc tac tat agc tca tcc tgg<br>Ala Lys Ile Arg Val Gln Ala Arg Asp Arg Tyr Tyr Ser Ser Ser Trp<br>305                   310                   315                   320 | | 960 |
| agc aac tgg gca tcc gtg tcc tgc a<br>Ser Asn Trp Ala Ser Val Ser Cys<br>                         325 | | 985 |

<210> SEQ ID NO 56
<211> LENGTH: 328
<212> TYPE: PRT
<213> ORGANISM: Felis catus

<400> SEQUENCE: 56

```
Met His Pro Gln Gln Leu Val Ile Ala Trp Phe Ser Leu Val Leu Leu
1               5                   10                  15

Ala Pro Pro Leu Met Ala Ile Trp Glu Leu Glu Lys Asn Val Tyr Val
                20                  25                  30

Val Glu Leu Asp Trp His Pro Asp Ala Pro Gly Glu Met Val Val Leu
            35                  40                  45

Thr Cys Asn Thr Pro Glu Glu Asp Asp Ile Thr Trp Thr Ser Asp Gln
        50                  55                  60

Ser Ser Glu Val Leu Gly Ser Gly Lys Thr Leu Thr Ile Gln Val Lys
65                  70                  75                  80

Glu Phe Ala Asp Ala Gly Gln Tyr Thr Cys His Lys Gly Gly Glu Val
                    85                  90                  95

Leu Ser His Ser Phe Leu Leu Ile His Lys Lys Glu Asp Gly Ile Trp
                100                 105                 110

Ser Thr Asp Ile Leu Arg Glu Gln Lys Glu Ser Lys Asn Lys Ile Phe
            115                 120                 125

Leu Lys Cys Glu Ala Lys Asn Tyr Ser Gly Arg Phe Thr Cys Trp Trp
130                 135                 140

Leu Thr Ala Ile Ser Thr Asp Leu Lys Phe Thr Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Lys Val Arg Val Asp Asn Arg Asp Tyr Lys Lys Tyr Thr Val
            180                 185                 190

Glu Cys Gln Glu Gly Ser Ala Cys Pro Ala Ala Glu Glu Ser Leu Pro
        195                 200                 205

Ile Glu Val Val Val Asp Ala Ile His Lys Leu Lys Tyr Glu Asn Tyr
            210                 215                 220

Thr Ser Ser Phe Phe Ile Arg Asp Ile Ile Lys Pro Asp Pro Pro Lys
225                 230                 235                 240

Asn Leu Gln Leu Lys Pro Leu Lys Asn Ser Arg His Val Glu Val Ser
                245                 250                 255

Trp Glu Tyr Pro Asp Thr Trp Ser Thr Pro His Ser Tyr Phe Ser Leu
            260                 265                 270

Thr Phe Gly Val Gln Val Gln Gly Lys Asn Asn Arg Glu Lys Lys Asp
        275                 280                 285

Arg Leu Ser Val Asp Lys Thr Ser Ala Lys Val Val Cys His Lys Asp
            290                 295                 300

Ala Lys Ile Arg Val Gln Ala Arg Asp Arg Tyr Tyr Ser Ser Ser Trp
305                 310                 315                 320

Ser Asn Trp Ala Ser Val Ser Cys
                325

<210> SEQ ID NO 57
<211> LENGTH: 985
<212> TYPE: DNA
<213> ORGANISM: Felis catus

<400> SEQUENCE: 57
tgcaggacac ggatgcccag ttgctccagg atgagctata gtagcggtct ctggcttgca     60
cgcggatctt ggcatccttg tggcacacga ccttggctga ggtcttgtcc acggagagtc    120
tgtctttctt ttctctgttg ttcttgccct ggacctgtac gccaaatgtt aaggagaagt    180
aggaatgtgg ggtgctccag gtgtcagggt attcccagct cacttccaca tgccgagaat    240
```

-continued

```
ttttttaatgg cttcagttgc aggttcttgg gtgggtccgg tttgatgatg tccctgatga        300
agaagctgct ggtgtagttt tcgtacttga gcttgtgaat agcgtccacc acgacttcaa        360
tgggtaggct ctcctcggca gccgggcagg cactgccctc ctgacactcc actgtgtact        420
tcttataatc cctgttgtcc actctgacct tctctgctga gagtgtcgct gctccacaag        480
tcaccccttg ggggtcagag gagcctctgc tgcttttgac agtgaatttc aaatcggtac        540
tgattgccgt cagccaccag caggtgaaac gtccagaata attctttgcc tcacatttta        600
gaaagatctt attttgggat tctttctgtt cccttaagat atcagtggac caaattccat        660
cttcctttt gtgtatcagg aggaacgaat ggctcagaac ctcgcctcct ttatgacagg         720
tatactggcc agcatctgca aattctttga cttggatggt cagagttta ccagagccta         780
ggacttcact gctctggtca gaggtccagg tgatgtcatc ttcttcagga gtattgcagg        840
tgaggaccac catttctccg ggggcatcag ggtgccagtc caactctaca acataaacgt        900
ttttctccag ttcccatatg gccatgaggg gaggtgccag caaaaccagg gaaaaccagg        960
cgatgaccaa ctgctgagga tgcat                                              985
```

<210> SEQ ID NO 58
<211> LENGTH: 987
<212> TYPE: DNA
<213> ORGANISM: Canis familiaris
<220> FEATURE:
<221> NAME/KEY: CDS
<222> LOCATION: (1)..(987)

<400> SEQUENCE: 58

```
atg cac cct cag cag ttg gtc atc tcc tgg ttt tcc ctc gtt ttg ctg         48
Met His Pro Gln Gln Leu Val Ile Ser Trp Phe Ser Leu Val Leu Leu
1               5                   10                  15 gcg tct ccc ctc atg gcc ata tgg gaa ctg gag aaa gat gtt tat gtt         96
Ala Ser Pro Leu Met Ala Ile Trp Glu Leu Glu Lys Asp Val Tyr Val
                20                  25                  30 gta gag ttg gac tgg cac cct gat gcc ccc gga gaa atg gtg gtc ctc         144
Val Glu Leu Asp Trp His Pro Asp Ala Pro Gly Glu Met Val Val Leu
            35                  40                  45 acc tgc cat acc cct gaa gaa gat gac atc act tgg acc tca gcg cag         192
Thr Cys His Thr Pro Glu Glu Asp Asp Ile Thr Trp Thr Ser Ala Gln
        50                  55                  60 agc agt gaa gtc cta ggt tct ggt aaa act ctg acc atc caa gtc aaa         240
Ser Ser Glu Val Leu Gly Ser Gly Lys Thr Leu Thr Ile Gln Val Lys
65                  70                  75                  80 gaa ttt gga gat gct ggc cag tat acc tgc cat aaa gga ggc aag gtt         288
Glu Phe Gly Asp Ala Gly Gln Tyr Thr Cys His Lys Gly Gly Lys Val
                85                  90                  95 ctg agc cgc tca ctc ctg ttg att cac aaa aaa gaa gat gga att tgg         336
Leu Ser Arg Ser Leu Leu Leu Ile His Lys Lys Glu Asp Gly Ile Trp
            100                 105                 110 tcc act gat atc tta aag gaa cag aaa gaa tcc aaa aat aag atc ttt         384
Ser Thr Asp Ile Leu Lys Glu Gln Lys Glu Ser Lys Asn Lys Ile Phe
        115                 120                 125 ctg aaa tgt gag gca aag aat tat tct gga cgt ttc aca tgc tgg tgg         432
Leu Lys Cys Glu Ala Lys Asn Tyr Ser Gly Arg Phe Thr Cys Trp Trp
    130                 135                 140 ctg acg gca atc agt act gat ttg aaa ttc agt gtc aaa agt agc aga         480
Leu Thr Ala Ile Ser Thr Asp Leu Lys Phe Ser Val Lys Ser Ser Arg
145                 150                 155                 160 ggc ttc tct gac ccc caa ggg gtg aca tgt gga gca gtg aca ctt tca         528
Gly Phe Ser Asp Pro Gln Gly Val Thr Cys Gly Ala Val Thr Leu Ser
                165                 170                 175
```

```
gca gag agg gtc aga gtg gac aac agg gat tat aag aag tac aca gtg      576
Ala Glu Arg Val Arg Val Asp Asn Arg Asp Tyr Lys Lys Tyr Thr Val
        180                 185                 190 gag tgt cag gag ggc agt gcc tgc ccc tct gcc gag gag agc cta ccc      624
Glu Cys Gln Glu Gly Ser Ala Cys Pro Ser Ala Glu Glu Ser Leu Pro
            195                 200                 205 atc gag gtc gtg gtg gat gct att cac aag ctc aag tat gaa aac tac      672
Ile Glu Val Val Val Asp Ala Ile His Lys Leu Lys Tyr Glu Asn Tyr
210                 215                 220 acc agc agc ttc ttc atc aga gac atc atc aaa cca gac cca ccc aca      720
Thr Ser Ser Phe Phe Ile Arg Asp Ile Ile Lys Pro Asp Pro Pro Thr
225                 230                 235                 240 aac ctg cag ctg aag cca ttg aaa aat tct cgg cac gtg gag gtc agc      768
Asn Leu Gln Leu Lys Pro Leu Lys Asn Ser Arg His Val Glu Val Ser
                245                 250                 255 tgg gaa tac ccc gac acc tgg agc acc cca cat tcc tac ttc tcc ctg      816
Trp Glu Tyr Pro Asp Thr Trp Ser Thr Pro His Ser Tyr Phe Ser Leu
            260                 265                 270 aca ttt tgc ata cag gcc cag ggc aag aac aat aga gaa aag aaa gat      864
Thr Phe Cys Ile Gln Ala Gln Gly Lys Asn Asn Arg Glu Lys Lys Asp
        275                 280                 285 aga ctc tgc gtg gac aag acc tca gcc aag gtc gtg tgc cac aag gat      912
Arg Leu Cys Val Asp Lys Thr Ser Ala Lys Val Val Cys His Lys Asp
290                 295                 300 gcc aag atc cgc gtg caa gcc cga gac cgc tac tat agt tca tcc tgg      960
Ala Lys Ile Arg Val Gln Ala Arg Asp Arg Tyr Tyr Ser Ser Ser Trp
305                 310                 315                 320 agc gac tgg gca tct gtg tca tgc agt                                  987
Ser Asp Trp Ala Ser Val Ser Cys Ser
            325

<210> SEQ ID NO 59
<211> LENGTH: 329
<212> TYPE: PRT
<213> ORGANISM: Canis familiaris

<400> SEQUENCE: 59

Met His Pro Gln Gln Leu Val Ile Ser Trp Phe Ser Leu Val Leu Leu
1               5                   10                  15

Ala Ser Pro Leu Met Ala Ile Trp Glu Leu Glu Lys Asp Val Tyr Val
            20                  25                  30

Val Glu Leu Asp Trp His Pro Asp Ala Pro Gly Glu Met Val Val Leu
        35                  40                  45

Thr Cys His Thr Pro Glu Glu Asp Asp Ile Thr Trp Thr Ser Ala Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Lys Val
                85                  90                  95

Leu Ser Arg Ser Leu Leu Ile His Lys Lys Glu Asp Gly Ile Trp
            100                 105                 110

Ser Thr Asp Ile Leu Lys Glu Gln Lys Glu Ser Lys Asn Lys Ile Phe
        115                 120                 125

Leu Lys Cys Glu Ala Lys Asn Tyr Ser Gly Arg Phe Thr Cys Trp Trp
    130                 135                 140

Leu Thr Ala Ile Ser Thr Asp Leu Lys Phe Ser Val Lys Ser Ser Arg
145                 150                 155                 160

Gly Phe Ser Asp Pro Gln Gly Val Thr Cys Gly Ala Val Thr Leu Ser
```

```
                     165                 170                 175
Ala Glu Arg Val Arg Val Asp Asn Arg Asp Tyr Lys Lys Tyr Thr Val
            180                 185                 190

Glu Cys Gln Glu Gly Ser Ala Cys Pro Ser Ala Glu Glu Ser Leu Pro
        195                 200                 205

Ile Glu Val Val Asp Ala Ile His Lys Leu Lys Tyr Glu Asn Tyr
    210                 215                 220

Thr Ser Ser Phe Phe Ile Arg Asp Ile Ile Lys Pro Asp Pro Pro Thr
225                 230                 235                 240

Asn Leu Gln Leu Lys Pro Leu Lys Asn Ser Arg His Val Glu Val Ser
                245                 250                 255

Trp Glu Tyr Pro Asp Thr Trp Ser Thr Pro His Ser Tyr Phe Ser Leu
            260                 265                 270

Thr Phe Cys Ile Gln Ala Gln Gly Lys Asn Asn Arg Glu Lys Lys Asp
        275                 280                 285

Arg Leu Cys Val Asp Lys Thr Ser Ala Lys Val Cys His Lys Asp
    290                 295                 300

Ala Lys Ile Arg Val Gln Ala Arg Asp Arg Tyr Tyr Ser Ser Ser Trp
305                 310                 315                 320

Ser Asp Trp Ala Ser Val Ser Cys Ser
                325
```

<210> SEQ ID NO 60
<211> LENGTH: 987
<212> TYPE: DNA
<213> ORGANISM: Canis familiaris

<400> SEQUENCE: 60

| | | | | | |
|---|---|---|---|---|---|
| actgcatgac | acagatgccc | agtcgctcca | ggatgaacta | tagtagcggt | ctcgggcttg | 60 |
| cacgcggatc | ttggcatcct | tgtggcacac | gaccttggct | gaggtcttgt | ccacgcagag | 120 |
| tctatctttc | ttttctctat | tgttcttgcc | ctgggcctgt | atgcaaaatg | tcagggagaa | 180 |
| gtaggaatgt | ggggtgctcc | aggtgtcggg | gtattcccag | ctgacctcca | cgtgccgaga | 240 |
| attttttcaat | ggcttcagct | gcaggtttgt | gggtgggtct | ggtttgatga | tgtctctgat | 300 |
| gaagaagctg | ctggtgtagt | tttcatactt | gagcttgtga | atagcatcca | ccacgacctc | 360 |
| gatgggtagg | ctctcctcgg | cagaggggca | ggcactgccc | tcctgacact | ccactgtgta | 420 |
| cttcttataa | tccctgttgt | ccactctgac | cctctctgct | gaaagtgtca | ctgctccaca | 480 |
| tgtcacccct | tggggtcag | agaagcctct | gctactttg | acactgaatt | tcaaatcagt | 540 |
| actgattgcc | gtcagccacc | agcatgtgaa | acgtccagaa | taattctttg | cctcacattt | 600 |
| cagaaagatc | ttattttgg | attctttctg | ttcctttaag | atatcagtgg | accaaattcc | 660 |
| atcttctttt | ttgtgaatca | acaggagtga | gcggctcaga | accttgcctc | ctttatggca | 720 |
| ggtatactgg | ccagcatctc | caaattcttt | gacttggatg | gtcagagttt | taccagaacc | 780 |
| taggacttca | ctgctctgcg | ctgaggtcca | agtgatgtca | tcttcttcag | ggtatggca | 840 |
| ggtgaggacc | accatttctc | cggggggcatc | agggtgccag | tccaactcta | caacataaac | 900 |
| atctttctcc | agttcccata | tggccatgag | gggagacgcc | agcaaaacga | gggaaaacca | 960 |
| ggagatgacc | aactgctgag | ggtgcat | | | | 987 |

<210> SEQ ID NO 61
<211> LENGTH: 1599
<212> TYPE: DNA
<213> ORGANISM: Canis familiaris
<220> FEATURE:

<221> NAME/KEY: CDS
<222> LOCATION: (1)..(1599)

<400> SEQUENCE: 61

```
atg cac cct cag cag ttg gtc atc tcc tgg ttt tcc ctc gtt ttg ctg      48
Met His Pro Gln Gln Leu Val Ile Ser Trp Phe Ser Leu Val Leu Leu
1               5                   10                  15 gcg tct ccc ctc atg gcc ata tgg gaa ctg gag aaa gat gtt tat gtt      96
Ala Ser Pro Leu Met Ala Ile Trp Glu Leu Glu Lys Asp Val Tyr Val
            20                  25                  30 gta gag ttg gac tgg cac cct gat gcc ccc gga gaa atg gtg gtc ctc     144
Val Glu Leu Asp Trp His Pro Asp Ala Pro Gly Glu Met Val Val Leu
        35                  40                  45 acc tgc cat acc cct gaa gaa gat gac atc act tgg acc tca gcg cag     192
Thr Cys His Thr Pro Glu Glu Asp Asp Ile Thr Trp Thr Ser Ala Gln
    50                  55                  60 agc agt gaa gtc cta ggt tct ggt aaa act ctg acc atc caa gtc aaa     240
Ser Ser Glu Val Leu Gly Ser Gly Lys Thr Leu Thr Ile Gln Val Lys
65                  70                  75                  80 gaa ttt gga gat gct ggc cag tat acc tgc cat aaa gga ggc aag gtt     288
Glu Phe Gly Asp Ala Gly Gln Tyr Thr Cys His Lys Gly Gly Lys Val
                85                  90                  95 ctg agc cgc tca ctc ctg ttg att cac aaa aaa gaa gat gga att tgg     336
Leu Ser Arg Ser Leu Leu Leu Ile His Lys Lys Glu Asp Gly Ile Trp
            100                 105                 110 tcc act gat atc tta aag gaa cag aaa gaa tcc aaa aat aag atc ttt     384
Ser Thr Asp Ile Leu Lys Glu Gln Lys Glu Ser Lys Asn Lys Ile Phe
        115                 120                 125 ctg aaa tgt gag gca aag aat tat tct gga cgt ttc aca tgc tgg tgg     432
Leu Lys Cys Glu Ala Lys Asn Tyr Ser Gly Arg Phe Thr Cys Trp Trp
    130                 135                 140 ctg acg gca atc agt act gat ttg aaa ttc agt gtc aaa agt agc aga     480
Leu Thr Ala Ile Ser Thr Asp Leu Lys Phe Ser Val Lys Ser Ser Arg
145                 150                 155                 160 ggc ttc tct gac ccc caa ggg gtg aca tgt gga gca gtg aca ctt tca     528
Gly Phe Ser Asp Pro Gln Gly Val Thr Cys Gly Ala Val Thr Leu Ser
                165                 170                 175 gca gag agg gtc aga gtg gac aac agg gat tat aag aag tac aca gtg     576
Ala Glu Arg Val Arg Val Asp Asn Arg Asp Tyr Lys Lys Tyr Thr Val
            180                 185                 190 gag tgt cag gag ggc agt gcc tgc ccc tct gcc gag gag agc cta ccc     624
Glu Cys Gln Glu Gly Ser Ala Cys Pro Ser Ala Glu Glu Ser Leu Pro
        195                 200                 205 atc gag gtc gtg gtg gat gct att cac aag ctc aag tat gaa aac tac     672
Ile Glu Val Val Val Asp Ala Ile His Lys Leu Lys Tyr Glu Asn Tyr
    210                 215                 220 acc agc agc ttc ttc atc aga gac atc atc aaa cca gac cca ccc aca     720
Thr Ser Ser Phe Phe Ile Arg Asp Ile Ile Lys Pro Asp Pro Pro Thr
225                 230                 235                 240 aac ctg cag ctg aag cca ttg aaa aat tct cgg cac gtg gag gtc agc     768
Asn Leu Gln Leu Lys Pro Leu Lys Asn Ser Arg His Val Glu Val Ser
                245                 250                 255 tgg gaa tac ccc gac acc tgg agc acc cca cat tcc tac ttc tcc ctg     816
Trp Glu Tyr Pro Asp Thr Trp Ser Thr Pro His Ser Tyr Phe Ser Leu
            260                 265                 270 aca ttt tgc ata cag gcc cag ggc aag aac aat aga gaa aag aaa gat     864
Thr Phe Cys Ile Gln Ala Gln Gly Lys Asn Asn Arg Glu Lys Lys Asp
        275                 280                 285 aga ctc tgc gtg gac aag acc tca gcc aag gtc gtg tgc cac aag gat     912
Arg Leu Cys Val Asp Lys Thr Ser Ala Lys Val Val Cys His Lys Asp
    290                 295                 300
```

```
gcc aag atc cgc gtg caa gcc cga gac cgc tac tat agt tca tcc tgg      960
Ala Lys Ile Arg Val Gln Ala Arg Asp Arg Tyr Tyr Ser Ser Ser Trp
305                 310                 315                 320 agc gac tgg gca tct gtg tca tgc agt ggt ggc ggt ggc ggc gga tct     1008
Ser Asp Trp Ala Ser Val Ser Cys Ser Gly Gly Gly Gly Gly Gly Ser
                325                 330                 335 aga aac ttg cca acc cct act cca tcc ccg ggt atg ttc caa tgt ttg     1056
Arg Asn Leu Pro Thr Pro Thr Pro Ser Pro Gly Met Phe Gln Cys Leu
            340                 345                 350 aac cac tcc caa acc ttg ttg aga gcc gtc agc aac acg ctt cag aag     1104
Asn His Ser Gln Thr Leu Leu Arg Ala Val Ser Asn Thr Leu Gln Lys
        355                 360                 365 gcc aga caa act cta gaa tta tat tcc tgc act tcc gaa gag att gat     1152
Ala Arg Gln Thr Leu Glu Leu Tyr Ser Cys Thr Ser Glu Glu Ile Asp
370                 375                 380 cat gaa gat atc aca aag gat aaa acc agc aca gtg gag gcc tgc tta     1200
His Glu Asp Ile Thr Lys Asp Lys Thr Ser Thr Val Glu Ala Cys Leu
385                 390                 395                 400 cca ctg gaa tta acc atg aat gag agt tgc ctg gct tcc aga gag atc     1248
Pro Leu Glu Leu Thr Met Asn Glu Ser Cys Leu Ala Ser Arg Glu Ile
                405                 410                 415 tct ttg ata act aac ggg agt tgc ctg gcc tct gga aag gcc tct ttt     1296
Ser Leu Ile Thr Asn Gly Ser Cys Leu Ala Ser Gly Lys Ala Ser Phe
            420                 425                 430 atg acg gtc ctg tgc ctt agc agc atc tat gag gac ttg aag atg tac     1344
Met Thr Val Leu Cys Leu Ser Ser Ile Tyr Glu Asp Leu Lys Met Tyr
        435                 440                 445 cag atg gaa ttc aag gcc atg aac gca aag ctt tta atg gat ccc aag     1392
Gln Met Glu Phe Lys Ala Met Asn Ala Lys Leu Leu Met Asp Pro Lys
450                 455                 460 agg cag atc ttt ctg gat caa aac atg ctg aca gct atc gat gag ctg     1440
Arg Gln Ile Phe Leu Asp Gln Asn Met Leu Thr Ala Ile Asp Glu Leu
465                 470                 475                 480 tta cag gcc ctg aat ttc aac agt gtg act gtg cca cag aaa tcc tcc     1488
Leu Gln Ala Leu Asn Phe Asn Ser Val Thr Val Pro Gln Lys Ser Ser
                485                 490                 495 ctt gaa gag ccg gat ttt tat aaa act aaa atc aag ctc tgc ata ctt     1536
Leu Glu Glu Pro Asp Phe Tyr Lys Thr Lys Ile Lys Leu Cys Ile Leu
            500                 505                 510 ctt cat gct ttc aga att cgt gcg gtg acc atc aat aga atg atg tcc     1584
Leu His Ala Phe Arg Ile Arg Ala Val Thr Ile Asn Arg Met Met Ser
        515                 520                 525 tac ttg aac tct tcc                                                 1599
Tyr Leu Asn Ser Ser
    530

<210> SEQ ID NO 62
<211> LENGTH: 533
<212> TYPE: PRT
<213> ORGANISM: Canis familiaris

<400> SEQUENCE: 62

Met His Pro Gln Gln Leu Val Ile Ser Trp Phe Ser Leu Val Leu Leu
1               5                   10                  15

Ala Ser Pro Leu Met Ala Ile Trp Glu Leu Glu Lys Asp Val Tyr Val
            20                  25                  30

Val Glu Leu Asp Trp His Pro Asp Ala Pro Gly Glu Met Val Val Leu
        35                  40                  45

Thr Cys His Thr Pro Glu Glu Asp Asp Ile Thr Trp Thr Ser Ala Gln
    50                  55                  60
```

```
Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Lys Val
                 85                  90                  95

Leu Ser Arg Ser Leu Leu Leu Ile His Lys Lys Glu Asp Gly Ile Trp
            100                 105                 110

Ser Thr Asp Ile Leu Lys Glu Gln Lys Glu Ser Lys Asn Lys Ile Phe
            115                 120                 125

Leu Lys Cys Glu Ala Lys Asn Tyr Ser Gly Arg Phe Thr Cys Trp Trp
130                 135                 140

Leu Thr Ala Ile Ser Thr Asp Leu Lys Phe Ser Val Lys Ser Ser Arg
145                 150                 155                 160

Gly Phe Ser Asp Pro Gln Gly Val Thr Cys Gly Ala Val Thr Leu Ser
                165                 170                 175

Ala Glu Arg Val Arg Val Asp Asn Arg Asp Tyr Lys Lys Tyr Thr Val
            180                 185                 190

Glu Cys Gln Glu Gly Ser Ala Cys Pro Ser Ala Glu Glu Ser Leu Pro
            195                 200                 205

Ile Glu Val Val Val Asp Ala Ile His Lys Leu Lys Tyr Glu Asn Tyr
210                 215                 220

Thr Ser Ser Phe Phe Ile Arg Asp Ile Ile Lys Pro Asp Pro Pro Thr
225                 230                 235                 240

Asn Leu Gln Leu Lys Pro Leu Lys Asn Ser Arg His Val Glu Val Ser
                245                 250                 255

Trp Glu Tyr Pro Asp Thr Trp Ser Thr Pro His Ser Tyr Phe Ser Leu
            260                 265                 270

Thr Phe Cys Ile Gln Ala Gln Gly Lys Asn Asn Arg Glu Lys Lys Asp
            275                 280                 285

Arg Leu Cys Val Asp Lys Thr Ser Ala Lys Val Val Cys His Lys Asp
290                 295                 300

Ala Lys Ile Arg Val Gln Ala Arg Asp Arg Tyr Tyr Ser Ser Ser Trp
305                 310                 315                 320

Ser Asp Trp Ala Ser Val Ser Cys Ser Gly Gly Gly Gly Gly Gly Ser
                325                 330                 335

Arg Asn Leu Pro Thr Pro Thr Pro Ser Pro Gly Met Phe Gln Cys Leu
            340                 345                 350

Asn His Ser Gln Thr Leu Leu Arg Ala Val Ser Asn Thr Leu Gln Lys
            355                 360                 365

Ala Arg Gln Thr Leu Glu Leu Tyr Ser Cys Thr Ser Glu Glu Ile Asp
370                 375                 380

His Glu Asp Ile Thr Lys Asp Lys Thr Ser Thr Val Glu Ala Cys Leu
385                 390                 395                 400

Pro Leu Glu Leu Thr Met Asn Glu Ser Cys Leu Ala Ser Arg Glu Ile
                405                 410                 415

Ser Leu Ile Thr Asn Gly Ser Cys Leu Ala Ser Gly Lys Ala Ser Phe
            420                 425                 430

Met Thr Val Leu Cys Leu Ser Ser Ile Tyr Glu Asp Leu Lys Met Tyr
            435                 440                 445

Gln Met Glu Phe Lys Ala Met Asn Ala Lys Leu Leu Met Asp Pro Lys
450                 455                 460

Arg Gln Ile Phe Leu Asp Gln Asn Met Leu Thr Ala Ile Asp Glu Leu
465                 470                 475                 480

Leu Gln Ala Leu Asn Phe Asn Ser Val Thr Val Pro Gln Lys Ser Ser
```

```
                    485                 490                 495
Leu Glu Glu Pro Asp Phe Tyr Lys Thr Lys Ile Lys Leu Cys Ile Leu
                500                 505                 510

Leu His Ala Phe Arg Ile Arg Ala Val Thr Ile Asn Arg Met Met Ser
            515                 520                 525

Tyr Leu Asn Ser Ser
        530

<210> SEQ ID NO 63
<211> LENGTH: 1599
<212> TYPE: DNA
<213> ORGANISM: Canis familiaris

<400> SEQUENCE: 63
ggaagagttc aagtaggaca tcattctatt gatggtcacc gcacgaattc tgaaagcatg      60
aagaagtatg cagagcttga ttttagtttt ataaaaatcc ggctcttcaa gggaggattt     120
ctgtggcaca gtcacactgt tgaaattcag ggcctgtaac agctcatcga tagctgtcag     180
catgttttga tccagaaaga tctgcctctt gggatccatt aaaagctttg cgttcatggc     240
cttgaattcc atctggtaca tcttcaagtc ctcatagatg ctgctaaggc acaggaccgt     300
cataaaagag gccttTccag aggccaggca actcccgtta gttatcaaag agatctctct     360
ggaagccagg caactctcat tcatggttaa ttccagtggt aagcaggcct ccactgtgct     420
ggttttatcc tttgtgatat cttcatgatc aatctcttcg gaagtgcagg aatataattc     480
tagagtttgt ctggccttct gaagcgtgtt gctgacggct ctcaacaagg tttgggagtg     540
gttcaaacat tggaacatac ccggggatgg agtaggggtt ggcaagtttc tagatccgcc     600
gccaccgcca ccactgcatg acacagatgc ccagtcgctc caggatgaac tatagtagcg     660
gtctcgggct tgcacgcgga tcttggcatc cttgtggcac acgaccttgg ctgaggtctt     720
gtccacgcag agtctatctt tcttttctct attgttcttg ccctgggcct gtatgcaaaa     780
tgtcagggag aagtaggaat gtggggtgct ccaggtgtcg gggtattccc agctgacctc     840
cacgtgccga gaatttttca atggcttcag ctgcaggttt gtgggtgggt ctggtttgat     900
gatgtctctg atgaagaagc tgctggtgta gttttcatac ttgagcttgt gaatagcatc     960
caccacgacc tcgatgggta ggctctcctc ggcagagggg caggcactgc cctcctgaca    1020
ctccactgtg tacttcttat aatccctgtt gtccactctg accctctctg ctgaaagtgt    1080
cactgctcca catgtcaccc cttgggggtc agagaagcct ctgctacttt tgacactgaa    1140
tttcaaatca gtactgattg ccgtcagcca ccagcatgtg aaacgtccag aataattctt    1200
tgcctcacat ttcagaaaga tcttattttt ggattctttc tgttccttta agatatcagt    1260
ggaccaaatt ccatcttctt ttttgtgaat caacaggagt gagcggctca gaaccttgcc    1320
tcctttatgg caggtatact ggccagcatc tccaaattct tgacttgga tggtcagagt    1380 tttaccagaa cctaggactt cactgctctg cgctgaggtc caagtgatgt catcttcttc    1440
aggggtatgg caggtgagga ccaccatttc tccgggggca tcagggtgcc agtccaactc    1500
tacaacataa acatctttct ccagttccca tatggccatg aggggagacg ccagcaaaac    1560
gagggaaaac caggagatga ccaactgctg agggtgcat                          1599

<210> SEQ ID NO 64

<400> SEQUENCE: 64

000
```

<210> SEQ ID NO 65

<400> SEQUENCE: 65

000

<210> SEQ ID NO 66
<211> LENGTH: 1533
<212> TYPE: DNA
<213> ORGANISM: Canis familiaris
<220> FEATURE:
<221> NAME/KEY: CDS
<222> LOCATION: (1)..(1533)

<400> SEQUENCE: 66

| | | | | | | | | | | | | | | | | |
|---|---|---|---|---|---|---|---|---|---|---|---|---|---|---|---|---|
| ata | tgg | gaa | ctg | gag | aaa | gat | gtt | tat | gtt | gta | gag | ttg | gac | tgg | cac | 48 |
| Ile | Trp | Glu | Leu | Glu | Lys | Asp | Val | Tyr | Val | Val | Glu | Leu | Asp | Trp | His | |
| 1 | | | | 5 | | | | | 10 | | | | | 15 | | |
| cct | gat | gcc | ccc | gga | gaa | atg | gtg | gtc | ctc | acc | tgc | cat | acc | cct | gaa | 96 |
| Pro | Asp | Ala | Pro | Gly | Glu | Met | Val | Val | Leu | Thr | Cys | His | Thr | Pro | Glu | |
| | | | 20 | | | | | 25 | | | | | 30 | | | |
| gaa | gat | gac | atc | act | tgg | acc | tca | gcg | cag | agc | agt | gaa | gtc | cta | ggt | 144 |
| Glu | Asp | Asp | Ile | Thr | Trp | Thr | Ser | Ala | Gln | Ser | Ser | Glu | Val | Leu | Gly | |
| | | 35 | | | | | 40 | | | | | 45 | | | | |
| tct | ggt | aaa | act | ctg | acc | atc | caa | gtc | aaa | gaa | ttt | gga | gat | gct | ggc | 192 |
| Ser | Gly | Lys | Thr | Leu | Thr | Ile | Gln | Val | Lys | Glu | Phe | Gly | Asp | Ala | Gly | |
| | 50 | | | | | 55 | | | | | 60 | | | | | |
| cag | tat | acc | tgc | cat | aaa | gga | ggc | aag | gtt | ctg | agc | cgc | tca | ctc | ctg | 240 |
| Gln | Tyr | Thr | Cys | His | Lys | Gly | Gly | Lys | Val | Leu | Ser | Arg | Ser | Leu | Leu | |
| 65 | | | | | 70 | | | | | 75 | | | | | 80 | |
| ttg | att | cac | aaa | aaa | gaa | gat | gga | att | tgg | tcc | act | gat | atc | tta | aag | 288 |
| Leu | Ile | His | Lys | Lys | Glu | Asp | Gly | Ile | Trp | Ser | Thr | Asp | Ile | Leu | Lys | |
| | | | | 85 | | | | | 90 | | | | | 95 | | |
| gaa | cag | aaa | gaa | tcc | aaa | aat | aag | atc | ttt | ctg | aaa | tgt | gag | gca | aag | 336 |
| Glu | Gln | Lys | Glu | Ser | Lys | Asn | Lys | Ile | Phe | Leu | Lys | Cys | Glu | Ala | Lys | |
| | | | 100 | | | | | 105 | | | | | 110 | | | |
| aat | tat | tct | gga | cgt | ttc | aca | tgc | tgg | tgg | ctg | acg | gca | atc | agt | act | 384 |
| Asn | Tyr | Ser | Gly | Arg | Phe | Thr | Cys | Trp | Trp | Leu | Thr | Ala | Ile | Ser | Thr | |
| | | 115 | | | | | 120 | | | | | 125 | | | | |
| gat | ttg | aaa | ttc | agt | gtc | aaa | agt | agc | aga | ggc | ttc | tct | gac | ccc | caa | 432 |
| Asp | Leu | Lys | Phe | Ser | Val | Lys | Ser | Ser | Arg | Gly | Phe | Ser | Asp | Pro | Gln | |
| | 130 | | | | | 135 | | | | | 140 | | | | | |
| ggg | gtg | aca | tgt | gga | gca | gtg | aca | ctt | tca | gca | gag | agg | gtc | aga | gtg | 480 |
| Gly | Val | Thr | Cys | Gly | Ala | Val | Thr | Leu | Ser | Ala | Glu | Arg | Val | Arg | Val | |
| 145 | | | | | 150 | | | | | 155 | | | | | 160 | |
| gac | aac | agg | gat | tat | aag | aag | tac | aca | gtg | gag | tgt | cag | gag | ggc | agt | 528 |
| Asp | Asn | Arg | Asp | Tyr | Lys | Lys | Tyr | Thr | Val | Glu | Cys | Gln | Glu | Gly | Ser | |
| | | | | 165 | | | | | 170 | | | | | 175 | | |
| gcc | tgc | ccc | tct | gcc | gag | gag | agc | cta | ccc | atc | gag | gtc | gtg | gtg | gat | 576 |
| Ala | Cys | Pro | Ser | Ala | Glu | Glu | Ser | Leu | Pro | Ile | Glu | Val | Val | Val | Asp | |
| | | | 180 | | | | | 185 | | | | | 190 | | | |
| gct | att | cac | aag | ctc | aag | tat | gaa | aac | tac | acc | agc | agc | ttc | ttc | atc | 624 |
| Ala | Ile | His | Lys | Leu | Lys | Tyr | Glu | Asn | Tyr | Thr | Ser | Ser | Phe | Phe | Ile | |
| | | 195 | | | | | 200 | | | | | 205 | | | | |
| aga | gac | atc | atc | aaa | cca | gac | cca | ccc | aca | aac | ctg | cag | ctg | aag | cca | 672 |
| Arg | Asp | Ile | Ile | Lys | Pro | Asp | Pro | Pro | Thr | Asn | Leu | Gln | Leu | Lys | Pro | |
| | 210 | | | | | 215 | | | | | 220 | | | | | |
| ttg | aaa | aat | tct | cgg | cac | gtg | gag | gtc | agc | tgg | gaa | tac | ccc | gac | acc | 720 |
| Leu | Lys | Asn | Ser | Arg | His | Val | Glu | Val | Ser | Trp | Glu | Tyr | Pro | Asp | Thr | |
| 225 | | | | | 230 | | | | | 235 | | | | | 240 | |
| tgg | agc | acc | cca | cat | tcc | tac | ttc | tcc | ctg | aca | ttt | tgc | ata | cag | gcc | 768 |
| Trp | Ser | Thr | Pro | His | Ser | Tyr | Phe | Ser | Leu | Thr | Phe | Cys | Ile | Gln | Ala | |

```
               245                 250                 255
cag ggc aag aac aat aga gaa aag aaa gat aga ctc tgc gtg gac aag      816
Gln Gly Lys Asn Asn Arg Glu Lys Lys Asp Arg Leu Cys Val Asp Lys
            260                 265                 270 acc tca gcc aag gtc gtg tgc cac aag gat gcc aag atc cgc gtg caa      864
Thr Ser Ala Lys Val Val Cys His Lys Asp Ala Lys Ile Arg Val Gln
        275                 280                 285 gcc cga gac cgc tac tat agt tca tcc tgg agc gac tgg gca tct gtg      912
Ala Arg Asp Arg Tyr Tyr Ser Ser Ser Trp Ser Asp Trp Ala Ser Val
    290                 295                 300 tca tgc agt ggt ggc ggt ggc ggc gga tct aga aac ttg cca acc cct      960
Ser Cys Ser Gly Gly Gly Gly Gly Gly Ser Arg Asn Leu Pro Thr Pro
305                 310                 315                 320 act cca tcc ccg ggt atg ttc caa tgt ttg aac cac tcc caa acc ttg     1008
Thr Pro Ser Pro Gly Met Phe Gln Cys Leu Asn His Ser Gln Thr Leu
                325                 330                 335 ttg aga gcc gtc agc aac acg ctt cag aag gcc aga caa act cta gaa     1056
Leu Arg Ala Val Ser Asn Thr Leu Gln Lys Ala Arg Gln Thr Leu Glu
            340                 345                 350 tta tat tcc tgc act tcc gaa gag att gat cat gaa gat atc aca aag     1104
Leu Tyr Ser Cys Thr Ser Glu Glu Ile Asp His Glu Asp Ile Thr Lys
        355                 360                 365 gat aaa acc agc aca gtg gag gcc tgc tta cca ctg gaa tta acc atg     1152
Asp Lys Thr Ser Thr Val Glu Ala Cys Leu Pro Leu Glu Leu Thr Met
    370                 375                 380 aat gag agt tgc ctg gct tcc aga gag atc tct ttg ata act aac ggg     1200
Asn Glu Ser Cys Leu Ala Ser Arg Glu Ile Ser Leu Ile Thr Asn Gly
385                 390                 395                 400 agt tgc ctg gcc tct gga aag gcc tct ttt atg acg gtc ctg tgc ctt     1248
Ser Cys Leu Ala Ser Gly Lys Ala Ser Phe Met Thr Val Leu Cys Leu
                405                 410                 415 agc agc atc tat gag gac ttg aag atg tac cag atg gaa ttc aag gcc     1296
Ser Ser Ile Tyr Glu Asp Leu Lys Met Tyr Gln Met Glu Phe Lys Ala
            420                 425                 430 atg aac gca aag ctt tta atg gat ccc aag agg cag atc ttt ctg gat     1344
Met Asn Ala Lys Leu Leu Met Asp Pro Lys Arg Gln Ile Phe Leu Asp
        435                 440                 445 caa aac atg ctg aca gct atc gat gag ctg tta cag gcc ctg aat ttc     1392
Gln Asn Met Leu Thr Ala Ile Asp Glu Leu Leu Gln Ala Leu Asn Phe
    450                 455                 460 aac agt gtg act gtg cca cag aaa tcc tcc ctt gaa gag ccg gat ttt     1440
Asn Ser Val Thr Val Pro Gln Lys Ser Ser Leu Glu Glu Pro Asp Phe
465                 470                 475                 480 tat aaa act aaa atc aag ctc tgc ata ctt ctt cat gct ttc aga att     1488
Tyr Lys Thr Lys Ile Lys Leu Cys Ile Leu Leu His Ala Phe Arg Ile
                485                 490                 495 cgt gcg gtg acc atc aat aga atg atg tcc tac ttg aac tct tcc         1533
Arg Ala Val Thr Ile Asn Arg Met Met Ser Tyr Leu Asn Ser Ser
            500                 505                 510

<210> SEQ ID NO 67
<211> LENGTH: 511
<212> TYPE: PRT
<213> ORGANISM: Canis familiaris

<400> SEQUENCE: 67

Ile Trp Glu Leu Glu Lys Asp Val Tyr Val Glu Leu Asp Trp His
1               5                   10                  15

Pro Asp Ala Pro Gly Glu Met Val Val Leu Thr Cys His Thr Pro Glu
                20                  25                  30
```

-continued

```
Glu Asp Asp Ile Thr Trp Thr Ser Ala Gln Ser Ser Glu Val Leu Gly
             35                  40                  45
Ser Gly Lys Thr Leu Thr Ile Gln Val Lys Glu Phe Gly Asp Ala Gly
 50                  55                  60
Gln Tyr Thr Cys His Lys Gly Lys Val Leu Ser Arg Ser Leu Leu
 65                  70                  75                  80
Leu Ile His Lys Lys Glu Asp Gly Ile Trp Ser Thr Asp Ile Leu Lys
                 85                  90                  95
Glu Gln Lys Glu Ser Lys Asn Lys Ile Phe Leu Lys Cys Glu Ala Lys
                100                 105                 110
Asn Tyr Ser Gly Arg Phe Thr Cys Trp Trp Leu Thr Ala Ile Ser Thr
            115                 120                 125
Asp Leu Lys Phe Ser Val Lys Ser Ser Arg Gly Phe Ser Asp Pro Gln
130                 135                 140
Gly Val Thr Cys Gly Ala Val Thr Leu Ser Ala Glu Arg Val Arg Val
145                 150                 155                 160
Asp Asn Arg Asp Tyr Lys Lys Tyr Thr Val Glu Cys Gln Glu Gly Ser
                165                 170                 175
Ala Cys Pro Ser Ala Glu Glu Ser Leu Pro Ile Glu Val Val Val Asp
            180                 185                 190
Ala Ile His Lys Leu Lys Tyr Glu Asn Tyr Thr Ser Ser Phe Phe Ile
        195                 200                 205
Arg Asp Ile Ile Lys Pro Asp Pro Pro Thr Asn Leu Gln Leu Lys Pro
210                 215                 220
Leu Lys Asn Ser Arg His Val Glu Val Ser Trp Glu Tyr Pro Asp Thr
225                 230                 235                 240
Trp Ser Thr Pro His Ser Tyr Phe Ser Leu Thr Phe Cys Ile Gln Ala
                245                 250                 255
Gln Gly Lys Asn Asn Arg Glu Lys Lys Asp Arg Leu Cys Val Asp Lys
            260                 265                 270
Thr Ser Ala Lys Val Val Cys His Lys Asp Ala Lys Ile Arg Val Gln
        275                 280                 285
Ala Arg Asp Arg Tyr Tyr Ser Ser Ser Trp Ser Asp Trp Ala Ser Val
290                 295                 300
Ser Cys Ser Gly Gly Gly Gly Gly Ser Arg Asn Leu Pro Thr Pro
305                 310                 315                 320
Thr Pro Ser Pro Gly Met Phe Gln Cys Leu Asn His Ser Gln Thr Leu
                325                 330                 335
Leu Arg Ala Val Ser Asn Thr Leu Gln Lys Ala Arg Gln Thr Leu Glu
            340                 345                 350
Leu Tyr Ser Cys Thr Ser Glu Glu Ile Asp His Glu Asp Ile Thr Lys
        355                 360                 365
Asp Lys Thr Ser Thr Val Glu Ala Cys Leu Pro Leu Glu Leu Thr Met
370                 375                 380
Asn Glu Ser Cys Leu Ala Ser Arg Glu Ile Ser Leu Ile Thr Asn Gly
385                 390                 395                 400
Ser Cys Leu Ala Ser Gly Lys Ala Ser Phe Met Thr Val Leu Cys Leu
                405                 410                 415
Ser Ser Ile Tyr Glu Asp Leu Lys Met Tyr Gln Met Glu Phe Lys Ala
            420                 425                 430
Met Asn Ala Lys Leu Leu Met Asp Pro Lys Arg Gln Ile Phe Leu Asp
        435                 440                 445
Gln Asn Met Leu Thr Ala Ile Asp Glu Leu Leu Gln Ala Leu Asn Phe
450                 455                 460
```

-continued

Asn Ser Val Thr Val Pro Gln Lys Ser Ser Leu Glu Glu Pro Asp Phe
465                 470                 475                 480

Tyr Lys Thr Lys Ile Lys Leu Cys Ile Leu Leu His Ala Phe Arg Ile
                485                 490                 495

Arg Ala Val Thr Ile Asn Arg Met Met Ser Tyr Leu Asn Ser Ser
        500                 505                 510

<210> SEQ ID NO 68
<211> LENGTH: 1533
<212> TYPE: DNA
<213> ORGANISM: Canis familiaris

<400> SEQUENCE: 68

| | | | | | |
|---|---|---|---|---|---|
| ggaagagttc | aagtaggaca | tcattctatt | gatggtcacc | gcacgaattc | tgaaagcatg | 60 |
| aagaagtatg | cagagcttga | ttttagtttt | ataaaaatcc | ggctcttcaa | gggaggattt | 120 |
| ctgtggcaca | gtcacactgt | tgaaattcag | ggcctgtaac | agctcatcga | tagctgtcag | 180 |
| catgttttga | tccagaaaga | tctgcctctt | gggatccatt | aaaagctttg | cgttcatggc | 240 |
| cttgaattcc | atctggtaca | tcttcaagtc | ctcatagatg | ctgctaaggc | acaggaccgt | 300 |
| cataaaagag | gcctttccag | aggccaggca | actcccgtta | gttatcaaag | agatctctct | 360 |
| ggaagccagg | caactctcat | tcatggttaa | ttccagtggt | aagcaggcct | ccactgtgct | 420 |
| ggttttatcc | tttgtgatat | cttcatgatc | aatctcttcg | gaagtgcagg | aatataattc | 480 |
| tagagtttgt | ctggccttct | gaagcgtgtt | gctgacggct | ctcaacaagg | tttgggagtg | 540 |
| gttcaaacat | tggaacatac | ccggggatgg | agtaggggtt | ggcaagtttc | tagatccgcc | 600 |
| gccaccgcca | ccactgcatg | acacagatgc | ccagtcgctc | caggatgaac | tatagtagcg | 660 |
| gtctcgggct | tgcacgcgga | tcttggcatc | cttgtggcac | acgaccttgg | ctgaggtctt | 720 |
| gtccacgcag | agtctatctt | tcttttctct | attgttcttg | ccctgggcct | gtatgcaaaa | 780 |
| tgtcagggag | aagtaggaat | gtggggtgct | ccaggtgtcg | gggtattccc | agctgacctc | 840 |
| cacgtgccga | gaattttcta | atggcttcag | ctgcaggttt | gtgggtgggt | ctggtttgat | 900 |
| gatgtctctg | atgaagaagc | tgctggtgta | gttttcatac | ttgagcttgt | gaatagcatc | 960 |
| caccacgacc | tcgatgggta | ggctctcctc | ggcagagggg | caggcactgc | cctcctgaca | 1020 |
| ctccactgtg | tacttcttat | aatcccctgtt | gtccactctg | accctctctg | ctgaaagtgt | 1080 |
| cactgctcca | catgtcaccc | cttggggggtc | agagaagcct | ctgctacttt | tgacactgaa | 1140 |
| tttcaaatca | gtactgattg | ccgtcagcca | ccagcatgtg | aaacgtccag | aataattctt | 1200 |
| tgcctcacat | ttcagaaaga | tcttattttt | ggattctttc | tgttccttta | agatatcagt | 1260 |
| ggaccaaatt | ccatcttctt | ttttgtgaat | caacaggagt | gagcggctca | gaaccttgcc | 1320 |
| tcctttatgg | caggtatact | ggccagcatc | tccaaattct | ttgacttgga | tggtcagagt | 1380 |
| tttaccagaa | cctaggactt | cactgctctg | cgctgaggtc | caagtgatgt | catcttcttc | 1440 |
| aggggtatgg | caggtgagga | ccaccatttc | tccgggggca | tcagggtgcc | agtccaactc | 1500 |
| tacaacataa | acatctttct | ccagttccca | tat | | | 1533 |

<210> SEQ ID NO 69
<211> LENGTH: 30
<212> TYPE: DNA
<213> ORGANISM: Artificial Sequence
<220> FEATURE:
<223> OTHER INFORMATION: Synthetic Primer

<400> SEQUENCE: 69

```
gccaagctcg aaattaaccc tcactaaagg                                    30

<210> SEQ ID NO 70
<211> LENGTH: 28
<212> TYPE: DNA
<213> ORGANISM: Artificial sequence
<220> FEATURE:
<223> OTHER INFORMATION: Synthetic Primer

<400> SEQUENCE: 70
cgacggccag tgaattgtaa tacgactc                                      28

<210> SEQ ID NO 71
<211> LENGTH: 31
<212> TYPE: DNA
<213> ORGANISM: Artificial sequence
<220> FEATURE:
<223> OTHER INFORMATION: Synthetic Primer

<400> SEQUENCE: 71
agtgatgaag gcctggaatc agattacttt g                                  31

<210> SEQ ID NO 72
<211> LENGTH: 32
<212> TYPE: DNA
<213> ORGANISM: Artificial sequence
<220> FEATURE:
<223> OTHER INFORMATION: Synthetic Primer

<400> SEQUENCE: 72
atggcctgga acacttctct gaaagaatat ga                                 32

<210> SEQ ID NO 73
<211> LENGTH: 30
<212> TYPE: DNA
<213> ORGANISM: Artificial sequence
<220> FEATURE:
<223> OTHER INFORMATION: Synthetic Primer

<400> SEQUENCE: 73
aactattgag cacagggata aagatgactg                                    30

<210> SEQ ID NO 74
<211> LENGTH: 33
<212> TYPE: DNA
<213> ORGANISM: Artificial sequence
<220> FEATURE:
<223> OTHER INFORMATION: Synthetic Primer

<400> SEQUENCE: 74
aatatctaat tcttgttttg aacagtgaac att                                33

<210> SEQ ID NO 75
<211> LENGTH: 36
<212> TYPE: DNA
<213> ORGANISM: Artificial sequence
<220> FEATURE:
<223> OTHER INFORMATION: Synthetic Primer

<400> SEQUENCE: 75
tatgccggct actttggcaa gcttgaacat aaactc                             36

<210> SEQ ID NO 76
<211> LENGTH: 37
<212> TYPE: DNA
<213> ORGANISM: Artificial sequence
<220> FEATURE:
```

<223> OTHER INFORMATION: Synthetic Primer

<400> SEQUENCE: 76
ggcctcgagc taattcttgt tttgaacagt gaacatt            37

<210> SEQ ID NO 77
<211> LENGTH: 28
<212> TYPE: DNA
<213> ORGANISM: Artificial sequence
<220> FEATURE:
<223> OTHER INFORMATION: Synthetic Primer

<400> SEQUENCE: 77
atggccgaca aggtcctgaa ggagaaga                      28

<210> SEQ ID NO 78
<211> LENGTH: 33
<212> TYPE: DNA
<213> ORGANISM: Artificial sequence
<220> FEATURE:
<223> OTHER INFORMATION: Synthetic Primer

<400> SEQUENCE: 78
ttaatgtcct gggaagaggt agaaacatct tgt                33

<210> SEQ ID NO 79
<211> LENGTH: 26
<212> TYPE: DNA
<213> ORGANISM: Artificial sequence
<220> FEATURE:
<223> OTHER INFORMATION: Synthetic Primer

<400> SEQUENCE: 79
tcaagcccac aatctggaaa ttctca                        26

<210> SEQ ID NO 80
<211> LENGTH: 26
<212> TYPE: DNA
<213> ORGANISM: Artificial sequence
<220> FEATURE:
<223> OTHER INFORMATION: Synthetic Primer

<400> SEQUENCE: 80
ctggagagtc actgatcaac agttcc                        26

<210> SEQ ID NO 81
<211> LENGTH: 36
<212> TYPE: DNA
<213> ORGANISM: Artificial sequence
<220> FEATURE:
<223> OTHER INFORMATION: Synthetic Primer

<400> SEQUENCE: 81
acaaggatcc accatggccg acaaggatct gaaggg             36

<210> SEQ ID NO 82
<211> LENGTH: 39
<212> TYPE: DNA
<213> ORGANISM: Artificial sequence
<220> FEATURE:
<223> OTHER INFORMATION: Synthetic Primer

<400> SEQUENCE: 82
cgcctctaga cctcaattgc cagggaagag atagaagta          39

<210> SEQ ID NO 83

```
<211> LENGTH: 60
<212> TYPE: DNA
<213> ORGANISM: Artificial sequence
<220> FEATURE:
<223> OTHER INFORMATION: Synthetic Primer

<400> SEQUENCE: 83
ctgcagtggt ggcggtggcg gcggatctag aaacttgcca acccctactc catccccggg    60

<210> SEQ ID NO 84
<211> LENGTH: 60
<212> TYPE: DNA
<213> ORGANISM: Artificial sequence
<220> FEATURE:
<223> OTHER INFORMATION: Synthetic Primer

<400> SEQUENCE: 84
cccggggatg gagtaggggt tggcaagttt ctagatccgc cgccaccgcc accactgcag    60

<210> SEQ ID NO 85
<211> LENGTH: 28
<212> TYPE: DNA
<213> ORGANISM: Artificial sequence
<220> FEATURE:
<223> OTHER INFORMATION: Synthetic Primer

<400> SEQUENCE: 85
atgcatcctc agcagttggt catcgcct                                       28

<210> SEQ ID NO 86
<211> LENGTH: 25
<212> TYPE: DNA
<213> ORGANISM: Artificial sequence
<220> FEATURE:
<223> OTHER INFORMATION: Synthetic Primer

<400> SEQUENCE: 86
tgcaggacac ggatgcccag ttgct                                          25

<210> SEQ ID NO 87
<211> LENGTH: 37
<212> TYPE: DNA
<213> ORGANISM: Artificial sequence
<220> FEATURE:
<223> OTHER INFORMATION: Synthetic Primer

<400> SEQUENCE: 87
acaggtacca tgcatcctca gcagttggtc atcgcct                             37

<210> SEQ ID NO 88
<211> LENGTH: 25
<212> TYPE: DNA
<213> ORGANISM: Artificial sequence
<220> FEATURE:
<223> OTHER INFORMATION: Synthetic Primer

<400> SEQUENCE: 88
ctaactgcag gacacggatg cccag                                          25

<210> SEQ ID NO 89
<211> LENGTH: 19
<212> TYPE: DNA
<213> ORGANISM: Artificial sequence
<220> FEATURE:
<223> OTHER INFORMATION: Synthetic Primer

<400> SEQUENCE: 89
```

```
atgtgcccgc cgcgtggcc                                              19
```

<210> SEQ ID NO 90
<211> LENGTH: 27
<212> TYPE: DNA
<213> ORGANISM: Artificial sequence
<220> FEATURE:
<223> OTHER INFORMATION: Synthetic Primer

<400> SEQUENCE: 90

```
ctaggaagca ttcagatagc tcatcat                                     27
```

<210> SEQ ID NO 91
<211> LENGTH: 39
<212> TYPE: DNA
<213> ORGANISM: Artificial sequence
<220> FEATURE:
<223> OTHER INFORMATION: Synthetic Primer

<400> SEQUENCE: 91

```
tatgacccgg ggatgttcca gtgcctcaac cactcccaa                        39
```

<210> SEQ ID NO 92
<211> LENGTH: 41
<212> TYPE: DNA
<213> ORGANISM: Artificial sequence
<220> FEATURE:
<223> OTHER INFORMATION: Synthetic Primer

<400> SEQUENCE: 92

```
atgactgcgg ccgcctagga agcattcaga tagctcatca t                     41
```

<210> SEQ ID NO 93
<211> LENGTH: 20
<212> TYPE: DNA
<213> ORGANISM: Artificial sequence
<220> FEATURE:
<223> OTHER INFORMATION: Synthetic Primer

<400> SEQUENCE: 93

```
ccatcctggt cctgctaagc                                             20
```

<210> SEQ ID NO 94
<211> LENGTH: 22
<212> TYPE: DNA
<213> ORGANISM: Artificial sequence
<220> FEATURE:
<223> OTHER INFORMATION: Synthetic Primer

<400> SEQUENCE: 94

```
ccatctggta catcttcaag tc                                          22
```

<210> SEQ ID NO 95
<211> LENGTH: 38
<212> TYPE: DNA
<213> ORGANISM: Artificial sequence
<220> FEATURE:
<223> OTHER INFORMATION: Synthetic Primer

<400> SEQUENCE: 95

```
aaaaaacccg ggtatgttcc aatgtttcaa ccactccc                         38
```

<210> SEQ ID NO 96
<211> LENGTH: 51
<212> TYPE: DNA
<213> ORGANISM: Artificial sequence
<220> FEATURE:

<223> OTHER INFORMATION: Synthetic Primer

<400> SEQUENCE: 96
gcggccgctc gagttaggaa gagttcaagt aggacatcat tctattgatg g         51

<210> SEQ ID NO 97
<211> LENGTH: 22
<212> TYPE: DNA
<213> ORGANISM: Artificial sequence
<220> FEATURE:
<223> OTHER INFORMATION: Synthetic Primer

<400> SEQUENCE: 97
cttaaaggaa cagaaagaat cc                                          22

<210> SEQ ID NO 98
<211> LENGTH: 19
<212> TYPE: DNA
<213> ORGANISM: Artificial sequence
<220> FEATURE:
<223> OTHER INFORMATION: Synthetic Primer

<400> SEQUENCE: 98
ggtattccca gctgacctc                                              19

<210> SEQ ID NO 99
<211> LENGTH: 37
<212> TYPE: DNA
<213> ORGANISM: Artificial sequence
<220> FEATURE:
<223> OTHER INFORMATION: Synthetic Primer

<400> SEQUENCE: 99
cataggtacc atgcaccctc agcagttggt catctcc                          37

<210> SEQ ID NO 100
<211> LENGTH: 29
<212> TYPE: DNA
<213> ORGANISM: Artificial sequence
<220> FEATURE:
<223> OTHER INFORMATION: Synthetic Primer

<400> SEQUENCE: 100
atctaaatgc atgacacaga tgcccagtc                                   29

<210> SEQ ID NO 101
<211> LENGTH: 561
<212> TYPE: DNA
<213> ORGANISM: Felis catus
<220> FEATURE:
<221> NAME/KEY: CDS
<222> LOCATION: (1)..(561)

<400> SEQUENCE: 101 ggg atg ttc cag tgc ctc aac cac tcc caa acc ctg ctg cga gcc atc      48
Gly Met Phe Gln Cys Leu Asn His Ser Gln Thr Leu Leu Arg Ala Ile
1               5                   10                  15 agc aac acg ctt cag aag gcc aga caa act cta gaa ttt tac tcc tgc      96
Ser Asn Thr Leu Gln Lys Ala Arg Gln Thr Leu Glu Phe Tyr Ser Cys
            20                  25                  30 act tcc gaa gag att gat cat gaa gat atc aca aaa gat aaa acc agc     144
Thr Ser Glu Glu Ile Asp His Glu Asp Ile Thr Lys Asp Lys Thr Ser
        35                  40                  45 aca gtg gag gcc tgc tta cca ctg gaa tta acc atg aat gag agt tgc     192
Thr Val Glu Ala Cys Leu Pro Leu Glu Leu Thr Met Asn Glu Ser Cys
    50                  55                  60

```
ctg gct tcc aga gag atc tct ctg ata act aat ggg agt tgc ctg gcc      240
Leu Ala Ser Arg Glu Ile Ser Leu Ile Thr Asn Gly Ser Cys Leu Ala
 65                  70                  75                  80 tcc aga aag acc tct ttt atg acg acc ctg tgc ctt agc agt atc tat      288
Ser Arg Lys Thr Ser Phe Met Thr Thr Leu Cys Leu Ser Ser Ile Tyr
                 85                  90                  95 gag gac ttg aag atg tac cag gtg gag ttc aag gcc atg aat gca aag      336
Glu Asp Leu Lys Met Tyr Gln Val Glu Phe Lys Ala Met Asn Ala Lys
            100                 105                 110 ctg tta atg gat cct aaa agg cag atc ttt ctg gat caa aac atg ctg      384
Leu Leu Met Asp Pro Lys Arg Gln Ile Phe Leu Asp Gln Asn Met Leu
        115                 120                 125 aca gct att gat gag ctg tta cag gcc ctg aat gtc aac agt gtg act      432
Thr Ala Ile Asp Glu Leu Leu Gln Ala Leu Asn Val Asn Ser Val Thr
    130                 135                 140 gtg cca cag aac tcc tcc ctg gaa gaa ccg gat ttt tat aaa act aaa      480
Val Pro Gln Asn Ser Ser Leu Glu Glu Pro Asp Phe Tyr Lys Thr Lys
145                 150                 155                 160 atc aag ctc tgc ata ctt ctt cat gct ttc aga att cgt gca gtg acc      528
Ile Lys Leu Cys Ile Leu Leu His Ala Phe Arg Ile Arg Ala Val Thr
                165                 170                 175 atc aat aga atg atg agc tat ctg aat gct tcc                          561
Ile Asn Arg Met Met Ser Tyr Leu Asn Ala Ser
            180                 185

<210> SEQ ID NO 102
<211> LENGTH: 187
<212> TYPE: PRT
<213> ORGANISM: Felis catus

<400> SEQUENCE: 102

Gly Met Phe Gln Cys Leu Asn His Ser Gln Thr Leu Leu Arg Ala Ile
 1               5                  10                  15

Ser Asn Thr Leu Gln Lys Ala Arg Gln Thr Leu Glu Phe Tyr Ser Cys
                20                  25                  30

Thr Ser Glu Glu Ile Asp His Glu Asp Ile Thr Lys Asp Lys Thr Ser
            35                  40                  45

Thr Val Glu Ala Cys Leu Pro Leu Glu Leu Thr Met Asn Glu Ser Cys
    50                  55                  60

Leu Ala Ser Arg Glu Ile Ser Leu Ile Thr Asn Gly Ser Cys Leu Ala
 65                  70                  75                  80

Ser Arg Lys Thr Ser Phe Met Thr Thr Leu Cys Leu Ser Ser Ile Tyr
                 85                  90                  95

Glu Asp Leu Lys Met Tyr Gln Val Glu Phe Lys Ala Met Asn Ala Lys
            100                 105                 110

Leu Leu Met Asp Pro Lys Arg Gln Ile Phe Leu Asp Gln Asn Met Leu
        115                 120                 125

Thr Ala Ile Asp Glu Leu Leu Gln Ala Leu Asn Val Asn Ser Val Thr
    130                 135                 140

Val Pro Gln Asn Ser Ser Leu Glu Glu Pro Asp Phe Tyr Lys Thr Lys
145                 150                 155                 160

Ile Lys Leu Cys Ile Leu Leu His Ala Phe Arg Ile Arg Ala Val Thr
                165                 170                 175

Ile Asn Arg Met Met Ser Tyr Leu Asn Ala Ser
            180                 185

<210> SEQ ID NO 103
<211> LENGTH: 561
```

-continued

```
<212> TYPE: DNA
<213> ORGANISM: Felis catus

<400> SEQUENCE: 103
ggaagcattc agatagctca tcattctatt gatggtcact gcacgaattc tgaaagcatg    60
aagaagtatg cagagcttga ttttagtttt ataaaaatcc ggttcttcca gggaggagtt   120
ctgtggcaca gtcacactgt tgacattcag ggcctgtaac agctcatcaa tagctgtcag   180
catgttttga tccagaaaga tctgcctttt aggatccatt aacagctttg cattcatggc   240
cttgaactcc acctggtaca tcttcaagtc ctcatagata ctgctaaggc acagggtcgt   300
cataaaagag gtctttctgg aggccaggca actcccatta gttatcagag atctctct    360 ggaagccagg caactctcat tcatggttaa ttccagtggt aagcaggcct ccactgtgct   420
ggttttatct tttgtgatat cttcatgatc aatctcttcg gaagtgcagg agtaaaattc   480
tagagtttgt ctggccttct gaagcgtgtt gctgatggct cgcagcaggg tttgggagtg   540
gttgaggcac tggaacatcc c                                             561

<210> SEQ ID NO 104
<211> LENGTH: 1455
<212> TYPE: DNA
<213> ORGANISM: Canis familiaris
<220> FEATURE:
<221> NAME/KEY: CDS
<222> LOCATION: (232)..(897)

<400> SEQUENCE: 104
ggcacgaggc aaaccccgcg ggcccagctc cacgtgtcac cgagaagctg atgtagagag    60
agacagagag agaaagcaag ccggacaccg gagtcccggg aaagtcctgg cgcgcctcgg   120
gccaattata aaaatgtgac ccccggggtc ggcctcccac cgccgccctc ccctgccgcg   180
tccgcagtcc gcgtccagcg cccgccgggg tccacgcagc gcccgcccag c atg tgc   237
                                                        Met Cys
                                                          1 ccg ccg cgc ggc ctc ctc ctt gtg acc atc ctg gtc ctg cta agc cac   285
Pro Pro Arg Gly Leu Leu Leu Val Thr Ile Leu Val Leu Leu Ser His
          5                  10                  15 ctg gac cac ctt act tgg gcc agg agc ctc ccc aca gcc tca ccg agc   333
Leu Asp His Leu Thr Trp Ala Arg Ser Leu Pro Thr Ala Ser Pro Ser
 20                  25                  30 cca gga ata ttc cag tgc ctc aac cac tcc caa aac ctg ctg aga gcc   381
Pro Gly Ile Phe Gln Cys Leu Asn His Ser Gln Asn Leu Leu Arg Ala
 35                  40                  45                  50 gtc agc aac acg ctt cag aag gcc aga caa act cta gaa tta tat tcc   429
Val Ser Asn Thr Leu Gln Lys Ala Arg Gln Thr Leu Glu Leu Tyr Ser
              55                  60                  65 tgc act tcc gaa gag att gat cat gaa gat atc aca aag gat aaa acc   477
Cys Thr Ser Glu Glu Ile Asp His Glu Asp Ile Thr Lys Asp Lys Thr
         70                  75                  80 agc aca gtg gag gcc tgc tta cca ctg gaa tta acc atg aat gag agt   525
Ser Thr Val Glu Ala Cys Leu Pro Leu Glu Leu Thr Met Asn Glu Ser
     85                  90                  95 tgc ctg gct tcc aga gag atc tct ttg ata act aac ggg agt tgc ctg   573
Cys Leu Ala Ser Arg Glu Ile Ser Leu Ile Thr Asn Gly Ser Cys Leu
100                 105                 110 gcc tct gga aag gcc tct ttt atg acg gtc ctg tgc ctt agc agc atc   621
Ala Ser Gly Lys Ala Ser Phe Met Thr Val Leu Cys Leu Ser Ser Ile
115                 120                 125                 130 tat gag gac ttg aag atg tac cag atg gaa ttc aag gcc atg aac gca   669
Tyr Glu Asp Leu Lys Met Tyr Gln Met Glu Phe Lys Ala Met Asn Ala
```

```
                         135                 140                 145
aag ctt tta atg gat ccc aag agg cag atc ttt ctg gat caa aac atg    717
Lys Leu Leu Met Asp Pro Lys Arg Gln Ile Phe Leu Asp Gln Asn Met
            150                 155                 160 ctg aca gct atc gat gag ctg tta cag gcc ctg aat ttc aac agt gtg    765
Leu Thr Ala Ile Asp Glu Leu Leu Gln Ala Leu Asn Phe Asn Ser Val
        165                 170                 175 act gtg cca cag aaa tcc tcc ctt gaa gag ccg gat ttt tat aaa act    813
Thr Val Pro Gln Lys Ser Ser Leu Glu Glu Pro Asp Phe Tyr Lys Thr
    180                 185                 190 aaa atc aag ctc tgc ata ctt ctt cat gct ttc aga att cgt gcg gtg    861
Lys Ile Lys Leu Cys Ile Leu Leu His Ala Phe Arg Ile Arg Ala Val
195                 200                 205                 210 acc atc gat aga atg atg agt tat ctg aat tct tcc taaaaagctg         907
Thr Ile Asp Arg Met Met Ser Tyr Leu Asn Ser Ser
                215                 220 aggtctctct cgactttaaa gtcattccta taaaaatgtg aacccaaaag aattttcat   967 aagataggg ttaagaacca gggaggggg gcttgacct ggtcctactt aagctagtac   1027
gataattctc atgcttgttt acattagttg ccactcaaat tttgaaagat gtgactgtta 1087 tatcccacac gatgcctttg accaagtata tttcacattt actatggata agttaagtgt 1147 tcgtgagcaa attgctaaag aggaaaaatg tcctcaccga acatgttttt attttcctt  1207 taatagaaga gcaagacttt ataagctatt tctgtaccaa actgtttgta gaaacaaaca 1267 ctcaagcata atttatttaa aaatacttat ttatataatt ttgtgttcat gaaagcatgt 1327 gaattaattt atatttattt atgttatatt tattaaagta tttattatca agtggatttg 1387 ggatatctta tgttctaaaa ataaaatgat tgagtagaaa aaaaaaaaaa aaaaaaaaa  1447 aaaaaaaa                                                          1455

<210> SEQ ID NO 105
<211> LENGTH: 222
<212> TYPE: PRT
<213> ORGANISM: Canis familiaris

<400> SEQUENCE: 105

Met Cys Pro Pro Arg Gly Leu Leu Val Thr Ile Leu Val Leu Leu
1               5                   10                  15

Ser His Leu Asp His Leu Thr Trp Ala Arg Ser Leu Pro Thr Ala Ser
            20                  25                  30

Pro Ser Pro Gly Ile Phe Gln Cys Leu Asn His Ser Gln Asn Leu Leu
        35                  40                  45

Arg Ala Val Ser Asn Thr Leu Gln Lys Ala Arg Gln Thr Leu Glu Leu
    50                  55                  60

Tyr Ser Cys Thr Ser Glu Glu Ile Asp His Glu Asp Ile Thr Lys Asp
65                  70                  75                  80

Lys Thr Ser Thr Val Glu Ala Cys Leu Pro Leu Glu Leu Thr Met Asn
                85                  90                  95

Glu Ser Cys Leu Ala Ser Arg Glu Ile Ser Leu Ile Thr Asn Gly Ser
            100                 105                 110

Cys Leu Ala Ser Gly Lys Ala Ser Phe Met Thr Val Leu Cys Leu Ser
        115                 120                 125

Ser Ile Tyr Glu Asp Leu Lys Met Tyr Gln Met Glu Phe Lys Ala Met
    130                 135                 140

Asn Ala Lys Leu Leu Met Asp Pro Lys Arg Gln Ile Phe Leu Asp Gln
145                 150                 155                 160
```

Asn Met Leu Thr Ala Ile Asp Glu Leu Leu Gln Ala Leu Asn Phe Asn
            165                 170                 175

Ser Val Thr Val Pro Gln Lys Ser Ser Leu Glu Glu Pro Asp Phe Tyr
            180                 185                 190

Lys Thr Lys Ile Lys Leu Cys Ile Leu Leu His Ala Phe Arg Ile Arg
            195                 200                 205

Ala Val Thr Ile Asp Arg Met Met Ser Tyr Leu Asn Ser Ser
    210                 215                 220

<210> SEQ ID NO 106
<211> LENGTH: 1455
<212> TYPE: DNA
<213> ORGANISM: Canis familiaris

<400> SEQUENCE: 106

| | | | | | |
|---|---|---|---|---|---|
| tttttttttt | tttttttttt | tttttttttt | tctactcaat | catttatttt | ttagaacata | 60 |
| agatatccca | aatccacttg | ataataaata | ctttaataaa | tataacataa | ataaatataa | 120 |
| attaattcac | atgctttcat | gaacacaaaa | ttatataaat | aagtattttt | aaataaatta | 180 |
| tgcttgagtg | tttgtttcta | caaacagttt | ggtacagaaa | tagcttataa | agtcttgctc | 240 |
| ttctattaaa | gggaaaataa | aaacatgttc | ggtgaggaca | ttttcctct | ttagcaattt | 300 |
| gctcacgaac | acttaactta | tccatagtaa | atgtgaaata | tacttggtca | aaggcatcgt | 360 |
| gtgggatata | acagtcacat | ctttcaaaat | ttgagtggca | actaatgtaa | acaagcatga | 420 |
| gaattatcgt | actagcttaa | gtaggaccag | gtcaagccac | cccctccctg | gttcttaacc | 480 |
| cctatcttat | gaaaaattct | tttgggttca | cattttata | ggaatgactt | taaagtcgag | 540 |
| agagacctca | gcttttagg | aagaattcag | ataactcatc | attctatcga | tggtcaccgc | 600 |
| acgaattctg | aaagcatgaa | gaagtatgca | gagcttgatt | ttagttttat | aaaaatccgg | 660 |
| ctcttcaagg | gaggatttct | gtggcacagt | cacactgttg | aaattcaggg | cctgtaacag | 720 |
| ctcatcgata | gctgtcagca | tgttttgatc | cagaaagatc | tgcctcttgg | gatccattaa | 780 |
| aagctttgcg | ttcatggcct | tgaattccat | ctggtacatc | ttcaagtcct | catagatgct | 840 |
| gctaaggcac | aggaccgtca | taaaagaggc | ctttccagag | gccaggcaac | tcccgttagt | 900 |
| tatcaaagag | atctctctgg | aagccaggca | actctcattc | atggttaatt | ccagtggtaa | 960 |
| gcaggcctcc | actgtgctgg | ttttatcctt | tgtgatatct | tcatgatcaa | tctcttcgga | 1020 |
| agtgcaggaa | tataattcta | gagtttgtct | ggccttctga | agcgtgttgc | tgacggctct | 1080 |
| cagcaggttt | tgggagtggt | tgaggcactg | gaatattcct | gggctcggtg | aggctgtggg | 1140 |
| gaggctcctg | gcccaagtaa | ggtggtccag | gtggcttagc | aggaccagga | tggtcacaag | 1200 |
| gaggaggccg | cgcggcgggc | acatgctggg | cgggcgctgc | gtggaccccg | gcgggcgctg | 1260 |
| gacgcggact | gcggacgcgg | caggggaggg | cggcggtggg | aggccgaccc | gggggtcac | 1320 |
| atttttataa | ttggcccgag | gcgcgccagg | actttcccgg | gactccggtg | tccggccttgc | 1380 |
| tttctctctc | tgtctctctc | tacatcagct | tctcggtgac | acgtggagct | gggcccgcgg | 1440 |
| ggtttgcctc | gtgcc | | | | | 1455 |

<210> SEQ ID NO 107
<211> LENGTH: 2267
<212> TYPE: DNA
<213> ORGANISM: Canis familiaris
<220> FEATURE:
<221> NAME/KEY: CDS
<222> LOCATION: (154)..(1140)

<400> SEQUENCE: 107

```
ggcacgaggc aacttggaca agtcagtttc tagtttaagt ttccatccaa aagctcggta      60
ggagtagggt atataagctc cagtagcagt agcagcagca gcaggagact ccgtttcaga     120
cccagggaac cttgcagcct ggccagaagc aag atg cat cct cag cag ttg gtc     174
                                    Met His Pro Gln Gln Leu Val
                                     1               5 atc tcc tgg ttt tcc ctc gtt ttg ctg gcg tct ccc ctc atg gcc ata      222
Ile Ser Trp Phe Ser Leu Val Leu Leu Ala Ser Pro Leu Met Ala Ile
         10                  15                  20 tgg gaa ctg gag aaa gat gtt tat gtt gta gag ttg gac tgg cac cct      270
Trp Glu Leu Glu Lys Asp Val Tyr Val Val Glu Leu Asp Trp His Pro
     25                  30                  35 gat gcc ccc gga gaa atg gtg gtc ctc acc tgc cat acc cct gaa gaa      318
Asp Ala Pro Gly Glu Met Val Val Leu Thr Cys His Thr Pro Glu Glu
 40                  45                  50                  55 gat gac atc act tgg acc tca gcg cag agc agt gaa gtc cta ggt tct      366
Asp Asp Ile Thr Trp Thr Ser Ala Gln Ser Ser Glu Val Leu Gly Ser
                 60                  65                  70 ggt aaa act ctg acc atc caa gtc aaa gaa ttt gga gat gct ggc cag      414
Gly Lys Thr Leu Thr Ile Gln Val Lys Glu Phe Gly Asp Ala Gly Gln
         75                  80                  85 tat acc tgc cat aaa gga ggc aag gtt ctg agc cgc tca ctc ctg ttg      462
Tyr Thr Cys His Lys Gly Gly Lys Val Leu Ser Arg Ser Leu Leu Leu
     90                  95                 100 att cac aaa aaa gaa gat gga att tgg tcc act gat atc tta aag gaa      510
Ile His Lys Lys Glu Asp Gly Ile Trp Ser Thr Asp Ile Leu Lys Glu
105                 110                 115 cag aaa gaa tcc aaa aat aag atc ttt ctg aaa tgt gag gca aag aat      558
Gln Lys Glu Ser Lys Asn Lys Ile Phe Leu Lys Cys Glu Ala Lys Asn
120                 125                 130                 135 tat tct gga cgt ttc aca tgc tgg tgg ctg acg gca atc agt act gat      606
Tyr Ser Gly Arg Phe Thr Cys Trp Trp Leu Thr Ala Ile Ser Thr Asp
                140                 145                 150 ttg aaa ttc agt gtc aaa agt agc aga ggc ttc tct gac ccc caa ggg      654
Leu Lys Phe Ser Val Lys Ser Ser Arg Gly Phe Ser Asp Pro Gln Gly
        155                 160                 165 gtg aca tgt gga gca gtg aca ctt tca gca gag agg gtc aga gtg gac      702
Val Thr Cys Gly Ala Val Thr Leu Ser Ala Glu Arg Val Arg Val Asp
    170                 175                 180 aac agg gat tat aag aag tac aca gtg gag tgt cag gag ggc agt gcc      750
Asn Arg Asp Tyr Lys Lys Tyr Thr Val Glu Cys Gln Glu Gly Ser Ala
185                 190                 195 tgc ccc tct gcc gag gag agc cta ccc atc gag gtc gtg gtg gat gct      798
Cys Pro Ser Ala Glu Glu Ser Leu Pro Ile Glu Val Val Val Asp Ala
200                 205                 210                 215 att cac aag ctc aag tat gaa aac tac acc agc agc ttc ttc atc aga      846
Ile His Lys Leu Lys Tyr Glu Asn Tyr Thr Ser Ser Phe Phe Ile Arg
                220                 225                 230 gac atc atc aaa cca gac cca ccc aca aac ctg cag ctg aag cca ttg      894
Asp Ile Ile Lys Pro Asp Pro Pro Thr Asn Leu Gln Leu Lys Pro Leu
        235                 240                 245 aaa aat tct cgg cac gtg gag gtc agc tgg gaa tac ccc gac acc tgg      942
Lys Asn Ser Arg His Val Glu Val Ser Trp Glu Tyr Pro Asp Thr Trp
    250                 255                 260 agc acc cca cat tcc tac ttc tcc ctg aca ttt tgc ata cag gcc cag      990
Ser Thr Pro His Ser Tyr Phe Ser Leu Thr Phe Cys Ile Gln Ala Gln
265                 270                 275 ggc aag aac aat aga gaa aag aaa gat aga ctc tgc gtg gac aag acc     1038
Gly Lys Asn Asn Arg Glu Lys Lys Asp Arg Leu Cys Val Asp Lys Thr
280                 285                 290                 295
```

-continued

```
tca gcc aag gtc gtg tgc cac aag gat gcc aag atc cgc gtg caa gcc      1086
Ser Ala Lys Val Val Cys His Lys Asp Ala Lys Ile Arg Val Gln Ala
            300                 305                 310 cga gac cgc tac tat agt tca tcc tgg agc gac tgg gca tct gtg tcc      1134
Arg Asp Arg Tyr Tyr Ser Ser Ser Trp Ser Asp Trp Ala Ser Val Ser
        315                 320                 325 tgc agt taggttccac ccccaggatg aatcttggag ggaaagtgga agatattatg       1190
Cys Ser caaaattttc taaggacaca ttgaagaggc tccaaaagtt attttctgcc taattttctt    1250
tttgtaaagg gtcattattg tgtcttcgca atattttta catttaaatg ccaaatgccc     1310
actgaaacaa tcagctactt tatttataga ttttcagcta gcaggctgcc actgacctta    1370
atgctattta aatatttaag taattatgt atttattaat ttattgttat tgaacacttg     1430
tgtgccaaga tatattgtat gtttcatacc ctcaggacct gatctgtaag gaataggccc    1490
tattatgcaa aatgtgaatt tatgtgttat ttatactgac aactttcaa gcaagaatgt     1550 atcatttta tgacaaccag tgagcacaca atattatgat gccagcacca taatatattt    1610
gtgatggatg ggaacacaga ggtagttaaa tagagacatg gagacacgaa tccatttgag    1670
aagtttctgg agacggagat gttagatcct gtatccataa agacttcctt gcggtggtgt    1730
tgataaagca attcagggcc acttgcattt taagcaagt ttagttttg gatgcctgaa      1790 tttagaaaga cctgagacaa ataactcaaa ttgagattca gcttcagcca ccttgccagt    1850
ccccatcccc atctatctgt aagtcattgg agagtgaccc agggacactg taagtgtctg    1910
gaagtaaaaa ggtcttatga tccaagaggg agaaccaaca tggccaagca caaaaaattg    1970
tcagaatttc cagctgctcc ttaatagcca ggcaaaaaaa gcacatggat gcaagaaaa     2030 tggtcaagaa ttgcttactg gacagcgcaa gtgaacctga ctggtggatg tgaccagaaa    2090
gtgccaatcg ctgaggtgct acttttaagt aatgaatgtg ctttctgtaa agtgatttca    2150
tttcttttct gtttacttat ttgttttgc attctgacaa tgcactaata aaatataac      2210 tcttgtttgc aataataaaa aaaaaaaa aaaaaaaaa aaaaaaa                     2267
```

<210> SEQ ID NO 108
<211> LENGTH: 329
<212> TYPE: PRT
<213> ORGANISM: Canis familiaris

<400> SEQUENCE: 108

```
Met His Pro Gln Gln Leu Val Ile Ser Trp Phe Ser Leu Val Leu Leu
1               5                   10                  15

Ala Ser Pro Leu Met Ala Ile Trp Glu Leu Glu Lys Asp Val Tyr Val
            20                  25                  30

Val Glu Leu Asp Trp His Pro Asp Ala Pro Gly Glu Met Val Val Leu
        35                  40                  45

Thr Cys His Thr Pro Glu Glu Asp Asp Ile Thr Trp Thr Ser Ala Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Lys Val
                85                  90                  95

Leu Ser Arg Ser Leu Leu Leu Ile His Lys Lys Glu Asp Gly Ile Trp
            100                 105                 110

Ser Thr Asp Ile Leu Lys Glu Gln Lys Glu Ser Lys Asn Lys Ile Phe
        115                 120                 125
```

```
Leu Lys Cys Glu Ala Lys Asn Tyr Ser Gly Arg Phe Thr Cys Trp Trp
    130                 135                 140
Leu Thr Ala Ile Ser Thr Asp Leu Lys Phe Ser Val Lys Ser Ser Arg
145                 150                 155                 160
Gly Phe Ser Asp Pro Gln Gly Val Thr Cys Gly Ala Val Thr Leu Ser
                165                 170                 175
Ala Glu Arg Val Arg Val Asp Asn Arg Asp Tyr Lys Lys Tyr Thr Val
            180                 185                 190
Glu Cys Gln Glu Gly Ser Ala Cys Pro Ser Ala Glu Glu Ser Leu Pro
        195                 200                 205
Ile Glu Val Val Val Asp Ala Ile His Lys Leu Lys Tyr Glu Asn Tyr
    210                 215                 220
Thr Ser Ser Phe Phe Ile Arg Asp Ile Ile Lys Pro Asp Pro Pro Thr
225                 230                 235                 240
Asn Leu Gln Leu Lys Pro Leu Lys Asn Ser Arg His Val Glu Val Ser
                245                 250                 255
Trp Glu Tyr Pro Asp Thr Trp Ser Thr Pro His Ser Tyr Phe Ser Leu
            260                 265                 270
Thr Phe Cys Ile Gln Ala Gln Gly Lys Asn Asn Arg Glu Lys Lys Asp
        275                 280                 285
Arg Leu Cys Val Asp Lys Thr Ser Ala Lys Val Val Cys His Lys Asp
    290                 295                 300
Ala Lys Ile Arg Val Gln Ala Arg Asp Arg Tyr Tyr Ser Ser Ser Trp
305                 310                 315                 320
Ser Asp Trp Ala Ser Val Ser Cys Ser
                325

<210> SEQ ID NO 109
<211> LENGTH: 2267
<212> TYPE: DNA
<213> ORGANISM: Canis familiaris

<400> SEQUENCE: 109
tttttttttt tttttttttt tttttttttt tttttttttt tattattgca aacaagagtt      60
atatttttat tagtgcattg tcagaatgca aaaacaaata agtaaacaga aagaaatga     120
aatcacttta cagaaagcac attcattact taaaagtagc acctcagcga ttggcacttt     180
ctggtcacat ccaccagtca ggttcacttg cgctgtccag taagcaattc ttgaccattt     240
tctttgcatc catgtgcttt ttttgcctgg ctattaagga gcagctggaa attctgacaa     300
tttttttgtgc ttggccatgt tggttctccc tcttggatca taagaccttt ttacttccag    360
acacttacag tgtccctggg tcactctcca atgacttaca gatagatggg gatggggact     420
ggcaaggtgg ctgaagctga atctcaattt gagttatttg tctcaggtct ttctaaattc     480
aggcatccaa aaactaaact tgcttaaaaa tgcaagtggc cctgaattgc tttatcaaca     540
ccaccgcaag gaagtcttta tggatacagg atctaacatc tccgtctcca gaaacttctc     600
aaatggattc gtgtctccat gtctctattt aactacctct gtgttcccat ccatcacaaa     660
tatattatgg tgctggcatc ataatattgt gtgctcactg gttgtcataa aaatgataca     720
ttcttgcttg aaaagttgtc agtataaata acacataaat tcacattttg cataataggg     780
cctattcctt acagatcagg tcctgagggt atgaaacata caatatatct ggcacacaa      840
gtgttcaata acaataaatt aataaataca taaattactt aaatatttaa atagcattaa     900
ggtcagtggc agcctgctag ctgaaaatct ataaataaag tagctgattg tttcagtggg     960
catttggcat ttaaatgtaa aaaatattgc gaagacacaa taatgaccct ttacaaaaag    1020
```

-continued

```
aaaattaggc agaaaataac ttttggagcc tcttcaatgt gtccttagaa aattttgcat    1080
aatatcttcc actttccctc caagattcat cctgggggtg gaacctaact gcaggacaca    1140
gatgcccagt cgctccagga tgaactatag tagcggtctc gggcttgcac gcggatcttg    1200
gcatccttgt ggcacacgac cttggctgag gtcttgtcca cgcagagtct atctttcttt    1260
tctctattgt tcttgccctg ggcctgtatg caaaatgtca gggagaagta ggaatgtggg    1320
gtgctccagg tgtcgggta ttcccagctg acctccacgt gccgagaatt tttcaatggc    1380
ttcagctgca ggtttgtggg tgggtctggt ttgatgatgt ctctgatgaa gaagctgctg    1440
gtgtagtttt catacttgag cttgtgaata gcatccacca cgacctcgat gggtaggctc    1500
tcctcggcag aggggcaggc actgccctcc tgacactcca ctgtgtactt cttataatcc    1560
ctgttgtcca ctctgaccct ctctgctgaa agtgtcactg ctccacatgt cacccttgg    1620 gggtcagaga agcctctgct acttttgaca ctgaatttca aatcagtact gattgccgtc    1680
agccaccagc atgtgaaacg tccagaataa ttctttgcct cacatttcag aaagatctta    1740
tttttggatt ctttctgttc ctttaagata tcagtggacc aaattccatc ttcttttttg    1800
tgaatcaaca ggagtgagcg gctcagaacc ttgcctcctt tatggcaggt atactggcca    1860
gcatctccaa attctttgac ttggatggtc agagttttac cagaacctag gacttcactg    1920
ctctgcgctg aggtccaagt gatgtcatct tcttcagggg tatggcaggt gaggaccacc    1980
atttctccgg gggcatcagg gtgccagtcc aactctacaa cataaacatc tttctccagt    2040
tcccatatgg ccatgagggg agacgccagc aaaacgaggg aaaaccagga gatgaccaac    2100
tgctgaggat gcatcttgct tctggccagg ctgcaaggtt ccctgggtct gaaacggagt    2160
ctcctgctgc tgctgctact gctactggag cttatatacc ctactcctac cgagcttttg    2220
gatggaaact taaactagaa actgacttgt ccaagttgcc tcgtgcc                 2267
```

<210> SEQ ID NO 110
<211> LENGTH: 7
<212> TYPE: PRT
<213> ORGANISM: Artificial
<220> FEATURE:
<223> OTHER INFORMATION: Synthetic Linker

<400> SEQUENCE: 110

Gly Gly Gly Gly Gly Gly Ser
1               5

<210> SEQ ID NO 111
<211> LENGTH: 10
<212> TYPE: PRT
<213> ORGANISM: Felis catus

<400> SEQUENCE: 111

Arg Asn Leu Pro Thr Pro Thr Pro Ser Pro
1               5                   10